United States Patent
Yang et al.

(10) Patent No.: US 11,579,149 B2
(45) Date of Patent: Feb. 14, 2023

(54) HIPPO PATHWAY BIOLUMINESCENT BIOSENSOR

(71) Applicant: Queen's University at Kingston, Kingston (CA)

(72) Inventors: Xiaolong Yang, Kingston (CA); Taha Azad, Kingston (CA); Kazem Nouri, Kingston (CA)

(73) Assignee: Queen's University at Kingston, Kingston (CA)

( * ) Notice: Subject to any disclaimer, the term of this patent is extended or adjusted under 35 U.S.C. 154(b) by 649 days.

(21) Appl. No.: 16/177,691

(22) Filed: Nov. 1, 2018

(65) Prior Publication Data

US 2019/0256887 A1 Aug. 22, 2019

Related U.S. Application Data

(60) Provisional application No. 62/580,186, filed on Nov. 1, 2017.

(51) Int. Cl.
| | |
|---|---|
| *C12Q 1/66* | (2006.01) |
| *G01N 33/58* | (2006.01) |
| *C07K 14/47* | (2006.01) |
| *C07K 14/435* | (2006.01) |
| *C12N 9/02* | (2006.01) |

(52) U.S. Cl.
CPC ....... *G01N 33/582* (2013.01); *C07K 14/4702* (2013.01); *C12Q 1/66* (2013.01); *C07K 14/43563* (2013.01); *C07K 2319/61* (2013.01); *C07K 2319/71* (2013.01); *C12N 9/0069* (2013.01); *C12Y 113/12013* (2013.01)

(58) Field of Classification Search
CPC .......................... C12Q 1/66; C12Y 13/12013
See application file for complete search history.

(56) References Cited

U.S. PATENT DOCUMENTS

| | | | |
|---|---|---|---|
| 5,670,356 | A | 9/1997 | Sherf et al. |
| 6,406,856 | B1 | 6/2002 | Glover et al. |
| 7,442,518 | B2 | 10/2008 | Piwnica-Worms et al. |
| 7,678,893 | B2 | 3/2010 | Barsova et al. |
| 7,906,282 | B2 | 3/2011 | Wood et al. |
| 8,609,342 | B2 | 12/2013 | Iida et al. |
| 9,464,313 | B2 | 10/2016 | Lavoie et al. |
| 9,500,654 | B2 | 11/2016 | Tao et al. |
| 9,797,890 | B2 * | 10/2017 | Dixon .................. A61K 51/08 |
| 2012/0190039 | A1 | 7/2012 | Lavoie et al. |

FOREIGN PATENT DOCUMENTS

| | | |
|---|---|---|
| WO | WO00/14271 | 3/2000 |
| WO | WO2005/015161 A2 | 2/2005 |

OTHER PUBLICATIONS

Leach, J. P. et al., "Hippo pathway deficiency reverses systolic heart failure after infarction", Nature 550, pp. 260-264 (2017).
Pfleger, C. M., "The Hippo Pathway: A Master Regulatory Network Important in Development and Dysregulated in Disease", Curr. Top. Dev. Biol. 123, pp. 181-228 (2017).
Mo, J. S., "The role of extracellular biophysical cues in modulating the Hippo-YAP pathway", BMB Rep. 50, pp. 71-78 (2017).
Zhang, Y. et al., "A growing role for the Hippo signaling pathway in the heart", J. Mol. Med. (Berl) 95, pp. 465-472 (2017).
Janse van Rensburg, H. J. et al., "The roles of the Hippo pathway in cancer metastasis", Cell. Signal. 28, pp. 1761-1772 (2016).
Meng, Z., et al., "Mechanisms of Hippo pathway regulation", Genes Dev. 30, pp. 1-17 (2016).
Maugeri-Sacca, M. et al., "Hippo pathway and breast cancer stem cells", Crit. Rev. Oncol. Hematol. 99, pp. 115-122 (2016).
Yu, F. X., et al., "Hippo Pathway in Organ Size Control, Tissue Homeostasis, and Cancer", Cell 163, pp. 811-828 (2015).
Zhao, Y. et al., "The Hiopo pathway in chemotherapeutic drug resistance", Int. J. Cancer 137, pp. 2767-2773 (2015).
Hao, Y., et al., "Tumor suppressor LATS1 is a negative regulator of oncogene YAP", J. Biol. Chem. 283, pp. 5496-5509 (2008).
Zhao, B. et al., "TEAD mediates YAP-dependent gene induction and growth control", Genes Dev. 22, pp. 1962-1971 (2008).
Zhao, B. et al., "Inactivation of YAP oncoprotein by the Hippo pathway is involved in cell contact inhibition and tissue growth control", Genes Dev. 21, pp. 2747-2761 (2007).
Lei, Q. Y. et al., "TAZ promotes cell proliferation and epithelial-mesenchymal transition and is inhibited by the hippo pathway", Mol. Cell. Biol. 28, pp. 2426-2436 (2008).
Chan, E. H. et al., "The Ste20-like kinase Mst2 activates the human large tumor suppressor kinase Lats1", Oncogene 24, pp. 2076-2086 (2005).

* cited by examiner

Primary Examiner — Karen Cochrane Carlson
(74) Attorney, Agent, or Firm — Stephen J. Scribner

(57) ABSTRACT

Bioluminescent biosensors useful for monitoring and/or quantifying, in vitro or in vivo, activity of the Hippo signaling pathway. The biosensors monitor LATS kinase activity or YAP-TEAD interaction. The biosensors may be used in methods for monitoring and/or quantifying in real-time, in vitro or in vivo, activity of the Hippo signaling pathway, wherein the activity may be LATS kinase activity and/or YAP-TEAD interaction. The biosensors may be provided in kits for monitoring and/or quantifying in real-time, in vitro or in vivo, activity of the Hippo signaling pathway, wherein the activity may be LATS kinase activity and/or YAP-TEAD interaction.

14 Claims, 19 Drawing Sheets

Specification includes a Sequence Listing.

LgBiT coding
region

5'...CCATCAACAGTGGAGTTCCGGTGGTGGGGGAGCGGGAGGTGGAGGTCGAGCGGGGAATTC

NheI   BglII   XbaI                   XhoI               SacI                     EcoRI

AGTCTAAGCTAGCAGATCTTCTAGAGTCGGGGCGGCCGCC...3'

FseI

Fig. 5A

BglII  NheI                                      SacI     EcoRI           XhoI

5'...TAAAGCCACCAGATCTGCTAGCGATGCGCTAAGTGGAGGTCAGGGAGGTCAAGGAGGTCGAGCGGAGCGGTGGCGG

SgfI                                                 SmBiT

GAGCGGGAGGTGGAGGGTCGAGGTCAGGTGTCAACCGGCTACCGGCTGTTCGAGGACAGATTCTGTAA...3'

Fig. 5B

BglII
... AGA TCT CGA TCC CGC GAA ATT AAT ACG ACT CAC TAT AGG GGA ATT GTG AGC GGA TAA CAA TTC CCC TCT AGA AAT AAT TTT GTT TAA CTT TAA GAA GGA GAT
                                                     T7 promoter                                                 lac operator                                               rbs NdeI     NheI                                                           T7 tag                                  BamHI  EcoRI   SacI                           SalI          HindIII NotI            XhoI              His tag
ATA CAT ATG GCT AGC ATG ACT GGT GGA CAG CAA ATG GGT CGG GAT CCG AAT TCG AGC TCC GTC GAC AAG CTT GCG GCC GCA CTC GAG CAC CAC CAC CAC CAC CAC TGA
            M   A   S   M   T   G   G   Q   Q   M   G   R   D   P   N   S   S   S   V   D   K   L   A   A   A   L   E   H   H   H   H   H   H  Stop BlpI
GAT CCG GCT GCT AAC AAA GCC CGA AAG GAA GCT GAG TTG GCT GCT GCC ACC GCT GAG CAA TAA CTA GCA TAA CCC CTT GGG GCC TCT AAA CGG GTC TTG AGG GGT TTT TTG ...
                                                                                                                            T7 terminator

| Column 1 | Column 2 | Column 3 |
|---|---|---|
| DMSO | DMSO | DMSO |
| SC 514 | PHA 665752 | Arctigenin |
| BI 78D3 | CGK 733 | SB 415286 |
| Compound 401 | IMD 0354 | SB 216763 |
| SD 208 | Ryuvidine | SB 431542 |
| BIO | PD 198306 | KU 55933 |
| GSK 650394 | TCS 359 | Purvalanol B |
| Naphthyl PP1 | SB 218078 | Purvalanol A |
| SU 5416 | TPCA-1 | SP 600125 |
| Iressa | DEBC | SU 4312 |
| GW 843682X | Ki 8751 | PP 2 |
| DMSO | DMSO | DMSO |
| DMSO | DMSO | DMSO |
| FPA 124 | IKK 16 | Terreic acid |
| H 89 | ZM 306416 | SB 203580 |
| EO 1428 | ZM 323881 | PP 1 |
| D 4476 | ER 27319 maleate | GW 5074 |
| NU 7026 | ZM 447439 | ZM 39923 |
| PI 828 | Arcyriaflavin A | ZM 449829 |
| PQ 401 | CGP 53353 | ZM 336372 |
| CGP 57380 | BIBX 1382 | LFM-A13 |
| LY 364947 | HA 1100 | Olomoucine |
| PD 407824 | Hexabromocyclo | SB 202190 |
| DMSO | DMSO | DMSO |
| DMSO | DMSO | DMSO |
| PHA 665752 | TBB | Y-27632 |
| CGK 733 | Ro 08-2750 | PD 98059 |
| IMD 0354 | GW 583340 | U0126 |
| Ryuvidine | GW 441756 | LY 294002 |
| PD 198306 | API-2 | Genistein |
| TCS 359 | Aminopurvalanol | GF 109203X |
| SB 218078 | Ro 31-8220 | Fasudil |
| TPCA-1 | SL 327 | NH 125 |
| DEBC | SB 239063 | ML9 |
| Ki 8751 | NSC 693868 | AG 490 |
| DMSO | DMSO | DMSO |

Fig. 17B

HIPPO PATHWAY BIOLUMINESCENT BIOSENSOR

REFERENCE TO AN ELECTRONIC SEQUENCE LISTING

The contents of the electronic sequence listing (16177691sequencelistingST25-2.txt; size: 180 kB; date of creation: Aug. 19, 2022) is herein incorporated by reference in its entirety.

RELATED APPLICATION

This application claims the benefit of the filing date of Application No. 62/580,186, filed Nov. 1, 2017, the contents of which are incorporated herein by reference in their entirety.

FIELD

This invention relates to bioluminescent biosensors for non-invasively monitoring and/or quantifying in real-time, in vitro or in vivo, activity of the Hippo signaling pathway.

BACKGROUND

Detailed understanding of biochemical pathways will elucidate signaling mechanisms in physiological and pathological processes, yielding insight into approaches for controlling, treating, and preventing many diseases. The ability to gain such insight is severely limited by the complexity of such pathways and the difficulty in monitoring the activity of key components once identified.

The Hippo pathway is a signaling cascade that plays important roles in development (e.g., organ size control, 3D body shape, and early embryo development), cancer (tumorigenesis, metastasis, drug resistance, and immune evasion), regeneration medicine (stem cell renewal and differentiation and tissue homeostasis/regeneration), heart development and disease (cardiomyocyte proliferation and heart infarction/cardiac injury) and in the neuronal system (neural fate and dendrite tiling)[1-9]. Dysregulation of the Hippo pathway is frequently observed in human cancers. When Hippo signaling is activated by upstream regulators, MST1/2 serine/threonine (S/T) kinases (mammalian homologs of *Drosophila* Hippo) phosphorylate/activate LATS1/2 kinases which subsequently phosphorylate/inactivate their downstream effectors, transcriptional co-activator Yes-associated protein (YAP) and its paralog transcriptional co-activator with PDZ-binding motif (TAZ). S127-phosphorylated YAP (YAP-pS127) or S89-phosphorylated TAZ (TAZ-pS89) bind to cytoplasmic protein 14-3-3 and are prevented from binding to transcription factor TEAD to trans-activate downstream gene targets in the nucleus (e.g., CTGF, CYR61, FGF1, etc.)[10-14]. Although a few regulatory factors of the Hippo pathway have been uncovered (actin dynamics, cell matrix stiffness, cell-cell contact, and lysophosphatidic acid (LPA)[3, 6], comprehensive regulator screens have been technically limited. An absence of available tools precludes measuring the dynamics and activity of the Hippo pathway core components in a quantitative, high-throughput and non-invasive manner.

SUMMARY

One aspect of the invention relates to a luminescent biosensor, comprising: one or more fragments of firefly or NanoBiT luciferase or a functional equivalent thereof; at least one fragment of human YAP or a functional equivalent thereof; and at least one vector.

In one embodiment, the biosensor comprises: a first construct comprising an N-terminal luciferase fragment (Nluc) or a functional equivalent thereof fused to the at least one YAP fragment; a second construct comprising a C-terminal luciferase fragment (Cluc) or a functional equivalent thereof fused to human cytoplasmic 14-3-3 protein or a functional equivalent thereof; wherein the first construct and the second construct are on separate vectors; wherein LATS-dependent phosphorylation of the at least one YAP fragment leads to binding with the human cytoplasmic 14-3-3 protein, which results in binding of Nluc and Cluc to produce luminescence.

In one embodiment, the biosensor comprises Nluc luciferase amino acids 1-416 of SEQ ID NO:6 or a functional equivalent thereof; Cluc luciferase amino acids 394-550 of SEQ ID NO:6 or a functional equivalent thereof; and YAP fragment including 15 amino acids (residues 120-134; SEQ ID NO:7) or a functional equivalent thereof.

In one embodiment, the biosensor comprises a single construct including: an N-terminal luciferase fragment (Nluc) or a functional equivalent thereof fused to the at least one YAP fragment; and a C-terminal luciferase fragment (Cluc) or a functional equivalent thereof fused to human cytoplasmic 14-3-3 protein; wherein LATS-dependent phosphorylation of the at least one YAP fragment leads to a conformational change and binding of Nluc and Cluc to produce luminescence.

In one embodiment, the biosensor comprises Nluc luciferase amino acids 1-416 of SEQ ID NO:6 or a functional equivalent thereof; Cluc luciferase amino acids 394-550 of SEQ ID NO:6 or a functional equivalent thereof; and YAP fragment including 15 amino acids (residues 120-134; SEQ ID NO:7) or a functional equivalent thereof.

In one embodiment, the biosensor comprises a single construct including a luciferase engineered at the C-terminal fused to the one or more YAP fragment; wherein LATS-dependent phosphorylation of the one or more YAP fragment modulates luciferase activity to increase luminescence. In one embodiment, the luciferase is engineered at the C-terminal consisting of amino acids 1-544 (SEQ ID NO:6) or a functional equivalent thereof.

In one embodiment, the biosensor comprises a first construct comprising a LgBiT luciferase fragment or a functional equivalent thereof fused to the at least one YAP fragment or a functional equivalent thereof a second construct comprising a SmBiT luciferase fragment or a functional equivalent thereof fused to human cytoplasmic 14-3-3 protein or a functional equivalent thereof; wherein the first construct and the second construct are on separate vectors; wherein binding of the at least one YAP fragment with the human cytoplasmic 14-3-3 protein and leads to binding of LgBiT and SmBiT to produce luminescence. In one embodiment, the biosensor comprises YAP fragment including 15 amino acids (residues 120-134; SEQ ID NO:7) or a functional equivalent thereof.

In one embodiment, the biosensor comprises: a first construct comprising a LgBiT luciferase fragment or a functional equivalent thereof fused to the at least one YAP fragment or a functional equivalent thereof; a second construct comprising a SmBiT luciferase fragment or a functional equivalent thereof fused to a TEAD fragment or a functional equivalent thereof, or a first construct comprising a LgBiT luciferase fragment or a functional equivalent thereof fused to a TEAD fragment or a functional equivalent thereof; a second construct comprising a SmBiT luciferase fragment or a functional equivalent thereof fused to the at least one YAP fragment or a functional equivalent thereof; wherein the first construct and the second construct are on separate vectors; wherein interaction of the at least one YAP fragment with the TEAD fragment leads to binding of LgBiT and SmBiT to produce luminescence.

In one embodiment, the biosensor comprises: YAP fragment comprising amino acids 50-171 of SEQ ID NO:2 or a functional equivalent thereof; and TAED fragment comprising amino acids 194-411 of SEQ ID NO:50 or a functional equivalent thereof.

Another aspect of the invention relates to a method, comprising: non-invasively monitoring and/or quantifying in real-time, in vitro or in vivo, activity of the Hippo signaling pathway, comprising transfecting a cell with a luminescent biosensor as described herein, and detecting luminescence; wherein an intensity of the luminescence is indicative of amount of activity of the Hippo signaling pathway.

Another aspect of the invention relates to a method for monitoring and/or quantifying activity of the Hippo signaling pathway, comprising: treating a cell with a luminescent biosensor as described herein; and detecting luminescence of the treated cell; wherein an intensity of the luminescence is indicative of amount of activity of the Hippo signaling pathway. In one embodiment, an intensity of the luminescence is indicative of amount of LATS kinase activity in the Hippo signaling pathway. In one embodiment, an intensity of the luminescence is indicative of amount of YAP-TEAD interaction in the Hippo signaling pathway. In one embodiment, treating a cell comprises transfecting a cell with the luminescent biosensor. In one embodiment, treating a cell comprises lysing the cell and combining a cell lysate with the luminescent biosensor.

In one embodiment, the method comprises: non-invasively monitoring and/or quantifying in real-time, in vitro or in vivo, activity of LATS kinase, comprising transfecting the cell with a luminescent biosensor as described herein, and detecting luminescence; wherein an intensity of the luminescence is indicative of amount of LATS kinase activity in the Hippo signaling pathway.

In one embodiment, the method comprises: non-invasively monitoring and/or quantifying in real-time, in vitro or in vivo, YAP-TEAD interaction, comprising transfecting the cell with a luminescent biosensor as described herein, and detecting luminescence; wherein an intensity of the luminescence is indicative of amount of YAP-TEAD interaction in the Hippo signaling pathway.

Another aspect of the invention relates to a method, comprising: monitoring and/or quantifying activity of one or more proteins of the Hippo signaling pathway, comprising combining the one or more proteins with a luminescent biosensor as described herein and at least one substance, and detecting luminescence of the luminescent biosensor; wherein an intensity of the luminescence is indicative of effect of the at least one substance on activity of the one or more proteins of the Hippo signaling pathway.

In various embodiments of the above method, the at least one substance is selected from a chemical compound such as a small molecule inhibitor (e.g., molecular weight below about 500 Daltons), a large molecule inhibitor (e.g., molecular weight above about 500 Daltons), a biological agent (e.g., antibody), protein, polypeptide, peptide, DNA aptamer, microRNA, interfering RNA (shRNA, siRNA), a sugar, lipid, glycoprotein, and glycolipid.

Another aspect of the invention relates to a method for monitoring and/or quantifying activity of the Hippo signaling pathway in a biological sample obtained from a subject, comprising: treating cells of the biological sample with at least one reagent comprising the a luminescent biosensor as described herein; and detecting luminescence of the treated biological sample; wherein an intensity of the luminescence is indicative of amount of activity of the Hippo signaling pathway. In one embodiment, an intensity of the luminescence is indicative of amount of LATS kinase activity in the Hippo signaling pathway. In one embodiment, an intensity of the luminescence is indicative of amount of YAP-TEAD interaction in the Hippo signaling pathway. In various embodiments, the biological sample comprises at least one of tissue and blood. In one embodiment, the biological sample comprises blood. In one embodiment, an intensity of the luminescence is indicative of the cells being cancer cells.

Another aspect of the invention relates to a kit, comprising: a luminescent biosensor as described herein; at least one reagent; and, optionally, instructions for using the kit.

BRIEF DESCRIPTION OF THE DRAWINGS

For a greater understanding of the invention, and to show more clearly how it may be carried into effect, embodiments will be described, by way of example, with reference to the accompanying drawings, wherein.

Figure 3A:
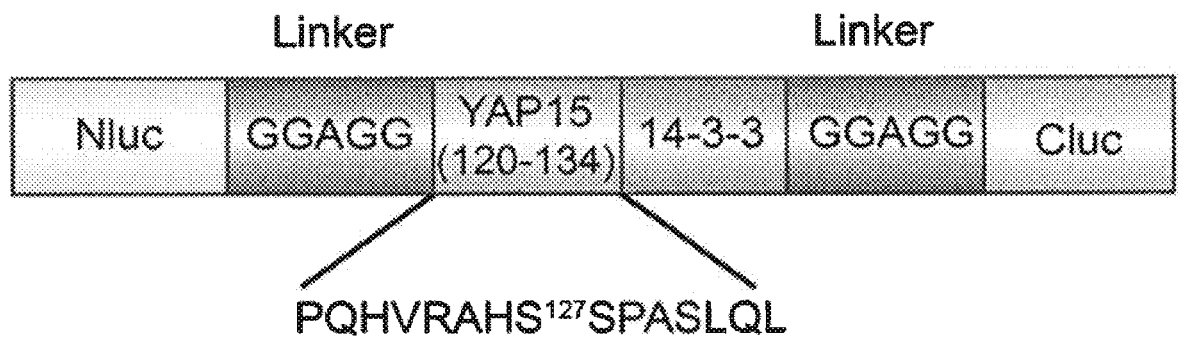

FIG. 3A is a schematic diagram showing the domain structure of a LATS intramolecular biosensor based on SEQ ID NOs:6, 7, 73, according to one embodiment.

Figure 3B:
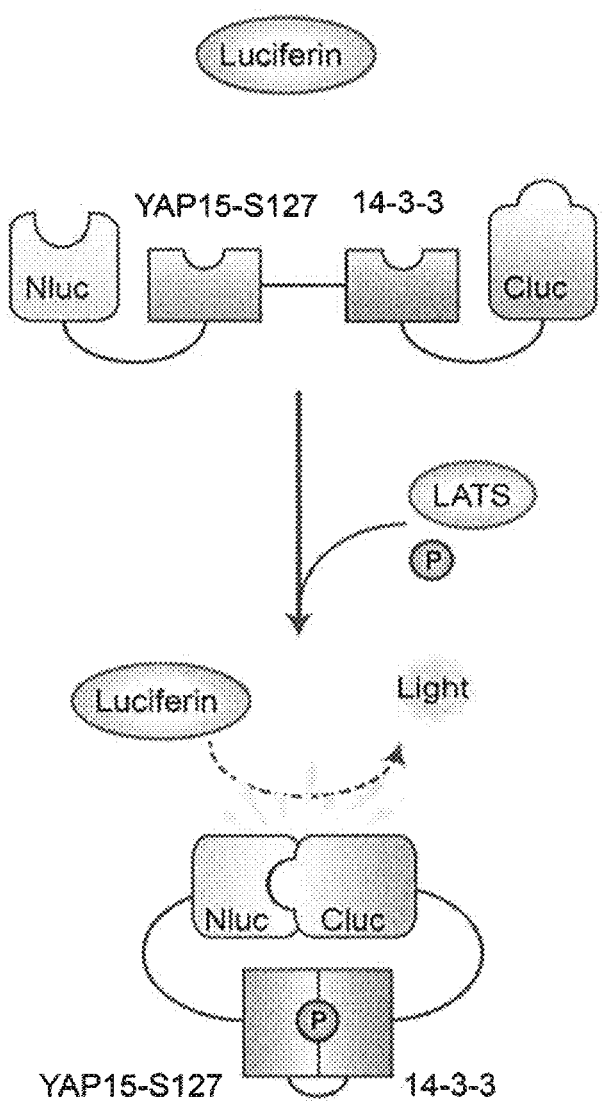

FIG. 3B is a schematic diagram showing the mechanism by which a LATS intramolecular biosensor determines LATS kinase activity.

Figure 3C:
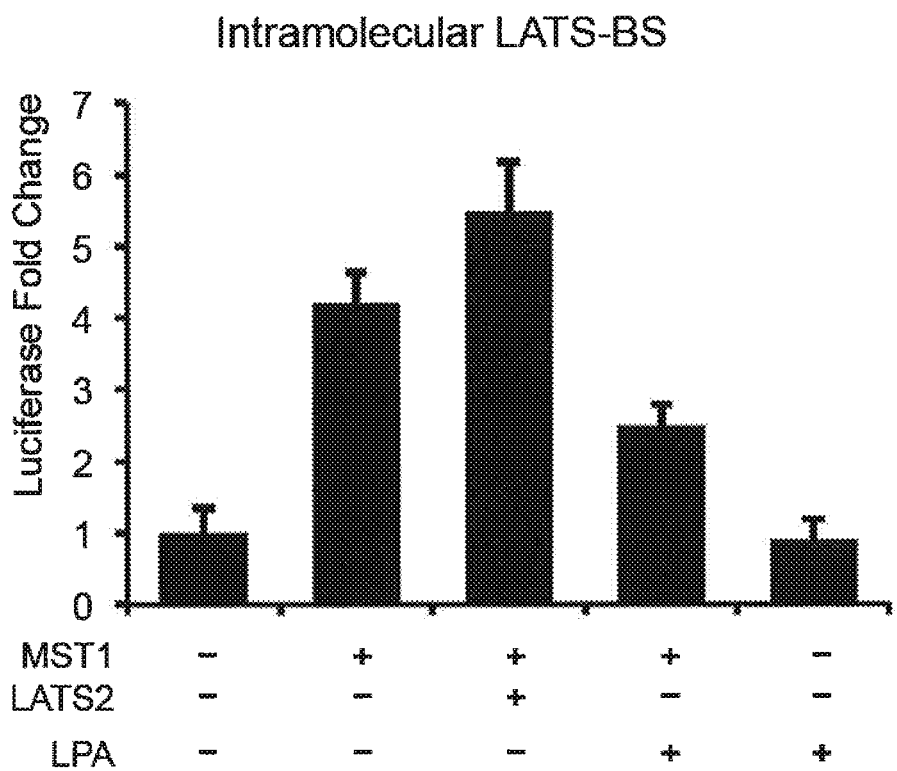

FIG. 3C is a bar chart showing results of a validation study of an intramolecular LATS biosensor according to the embodiment of FIG. 3A.

Figure 4A:
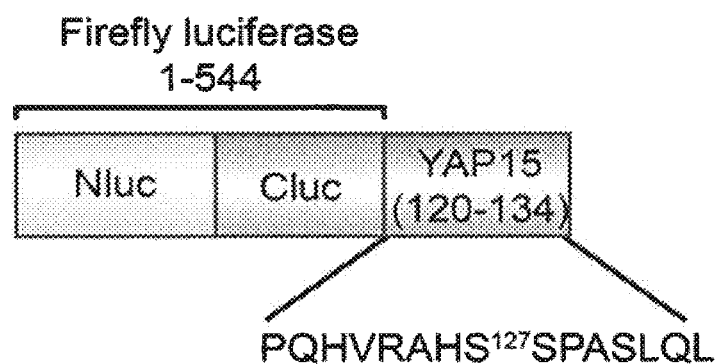

FIG. 4A is a schematic diagram showing the domain structure of an engineered LATS biosensor based on SEQ ID NOs:6, 7, according to one embodiment.

Figure 4B:
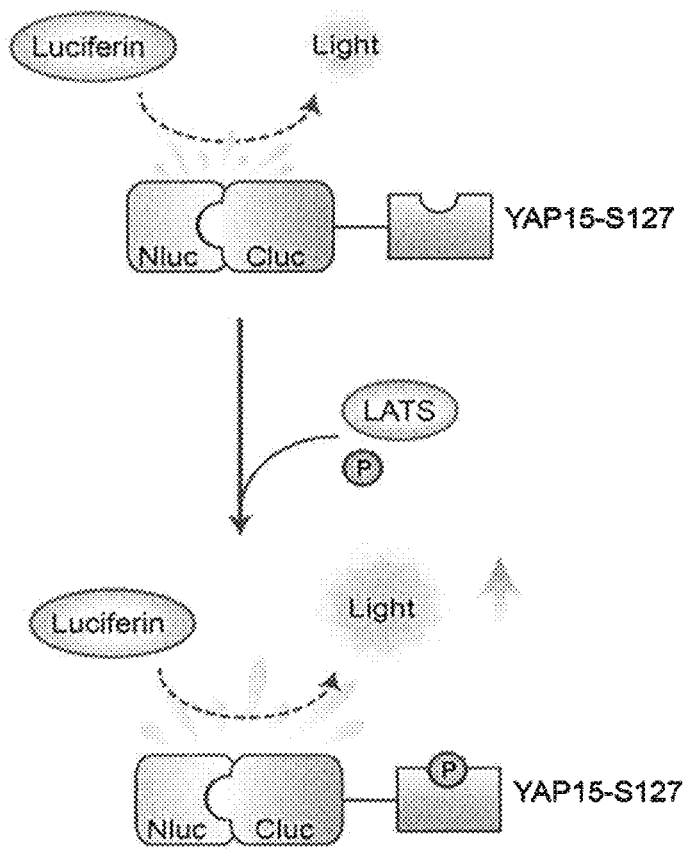

FIG. 4B is a schematic diagram showing the mechanism by which an engineered LATS biosensor determines LATS kinase activity.

Figure 4C:
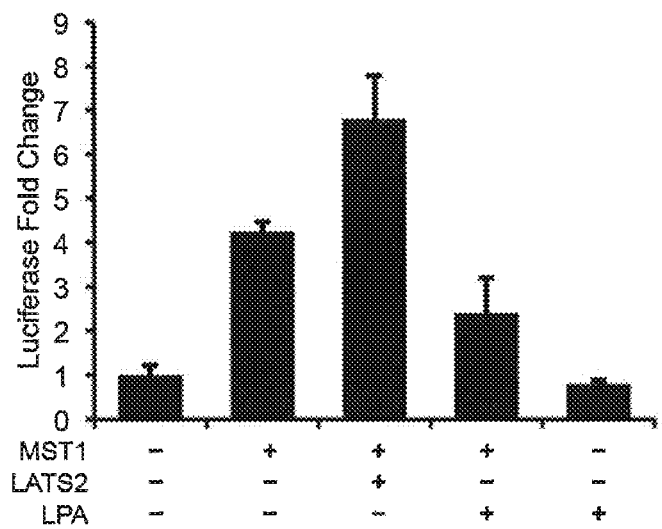

FIG. 4C is a bar chart showing results of a validation study of an engineered LATS biosensor according to the embodiment of FIG. 4A.

FIGS. 5A-5D show diagrams of multiple cloning sites of vectors (pBiT1.1-N [TK/LgBiT; 5A]; pBiT2.1-C [TK/SmBiT; 5B]; pET16b (5C)) and domain structures of constructs (5D) used to make NanoBiT (NanoLuc) biosensors based on Nluc and CLuc (SEQ ID NO:6), YAP15 (SEQ ID NO:7), LgBiT (SEQ ID NO:52), SmBiT (SEQ ID NO:54), and 14-3-3 (SEQ ID NO:4), according to embodiments of the invention.

Figure 6:
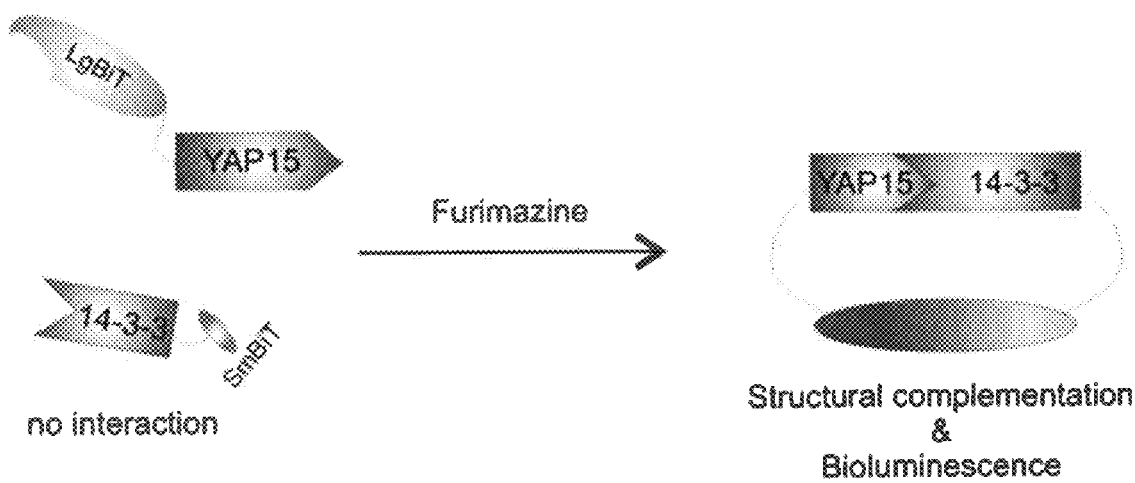

FIG. 6 is a schematic diagram showing an overview of a NanoBiT interaction system of a LATS NanoBiT biosensor according to an embodiment of the invention.

Figure 7:
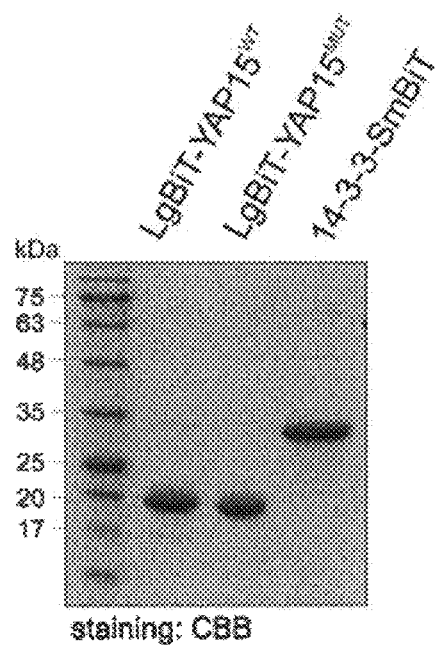

FIG. 7 shows a coomassie brilliant blue (CBB) stained SDS-PAGE of purified proteins for a LATS NanoBiT biosensor.

Figure 8A:
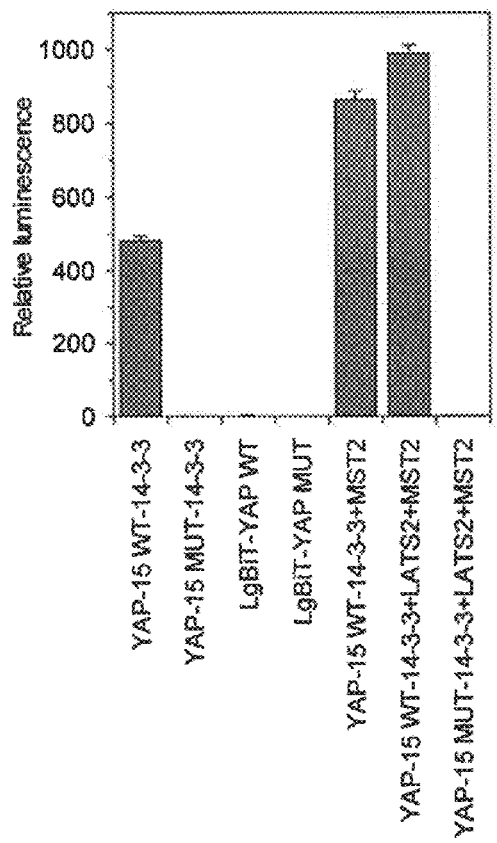

FIG. 8A shows results of a NanoBiT biosensor assay of overexpressed LgBiT-YAP15 WT and mutant (MUT) and 14-3-3-SmBiT in HEK293T cells as relative luminescence to YAP15MUT-14-3-3.

Figure 8B:
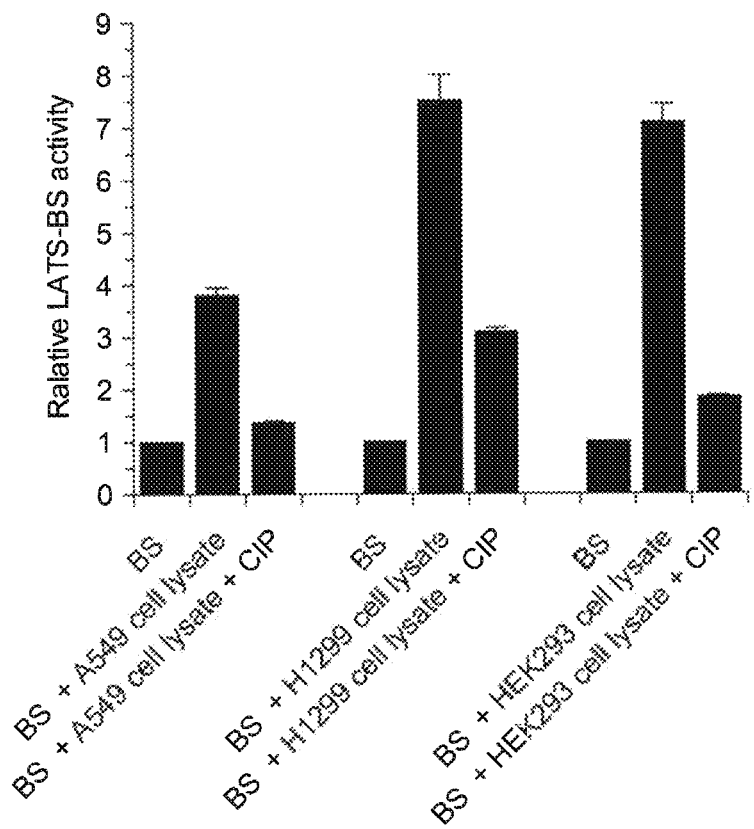

FIG. 8B shows results of a NanoBiT LATS biosensor assay for cancer cells.

Figure 8C:
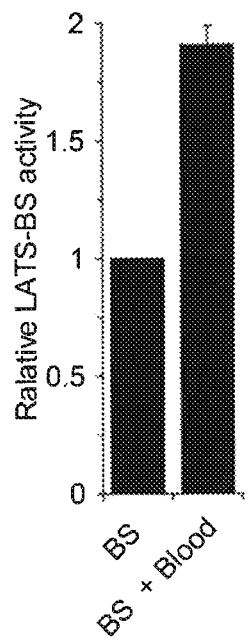

FIG. 8C shows results of a NanoBiT LATS biosensor assay for blood.

Figure 9:
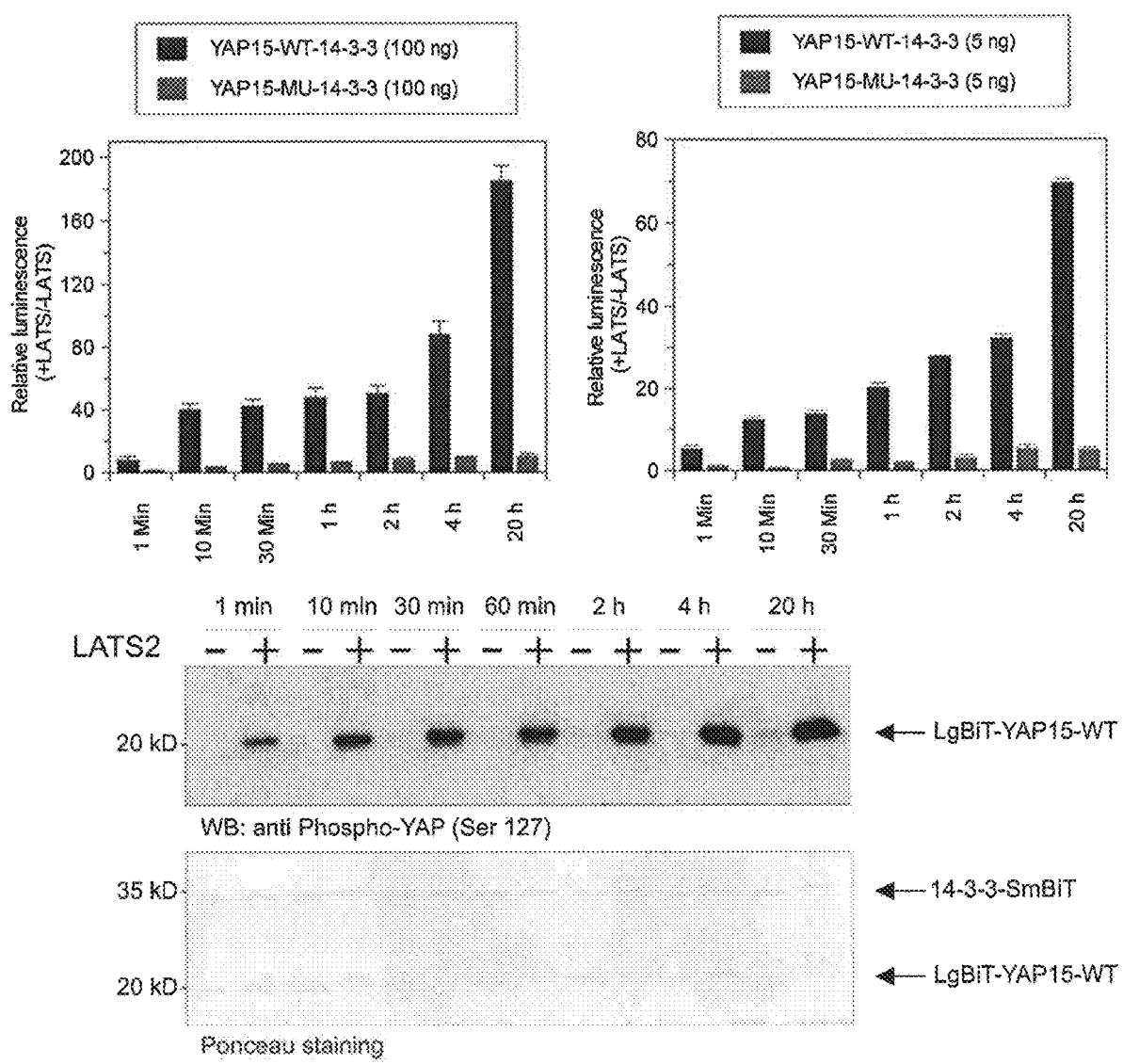

FIG. 9 shows results of an in vitro NanoBiT biosensor assay using purified LgBiT-YAP15 (WT and mutant), 14-3-3-SmBiT, and LATS2 kinase; upper panel shows the result of the NanoBiT assay for YAP15WT or mutant at two different concentrations of biosensor (5 and 100 ng) as a ratio of luminescence signal at different time points; lower panel shows immunoblotting analysis and ponceau staining of the respective samples with 100 ng of biosensor.

Figure 10:
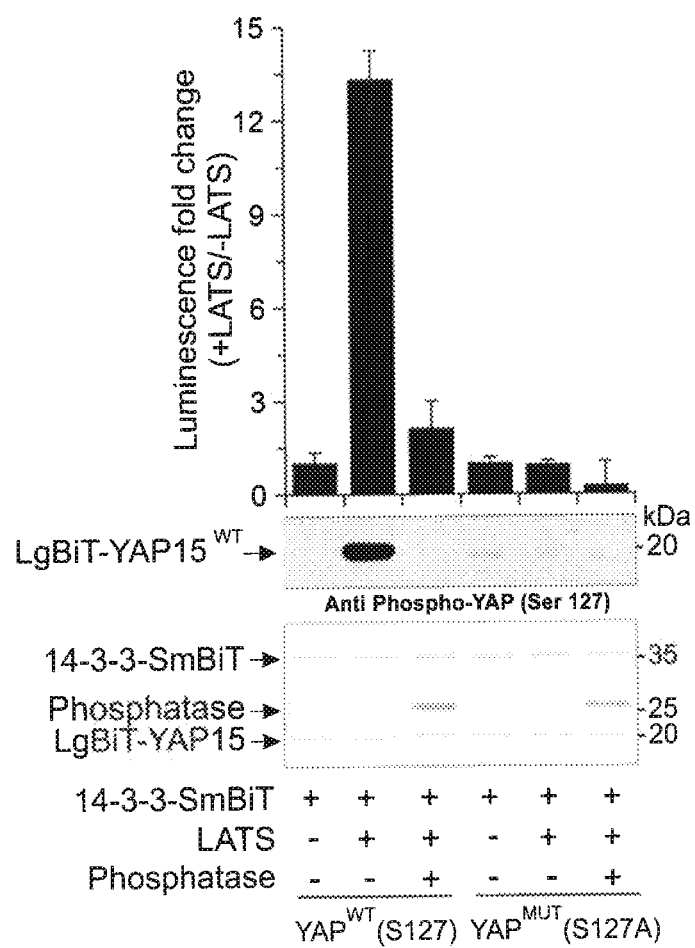

FIG. 10 shows the results of a kinase assay with purified proteins; upper panel shows the NanoBiT LATS biosensor assay for YAP15 WT and mutant (100 ng) with and without lambda phosphatase after 30 min; the lower panels show the relative immunoblotting and Ponceau staining for the respective samples.

Figure 11:
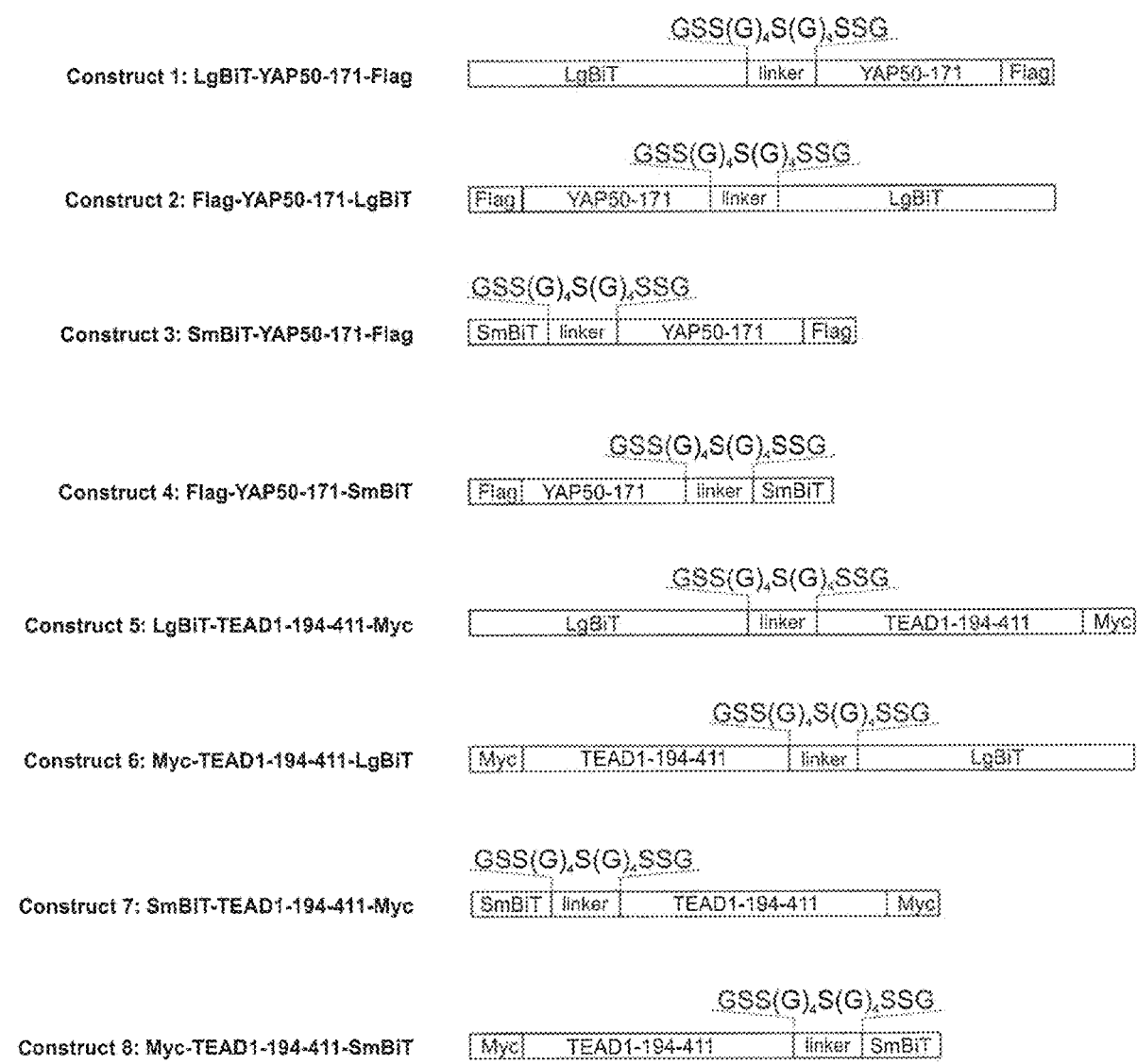

FIG. 11 shows diagrams of domain structures of eight constructs used to make a YAP-TEAD biosensor based on LgBiT (SEQ ID NO:52), SmBiT (SEQ ID NO:54), YAP50-171 (SEQ ID NO:2), and TEAD1-194-411 (SEQ ID NO:50), according to one embodiment.

Figure 12:
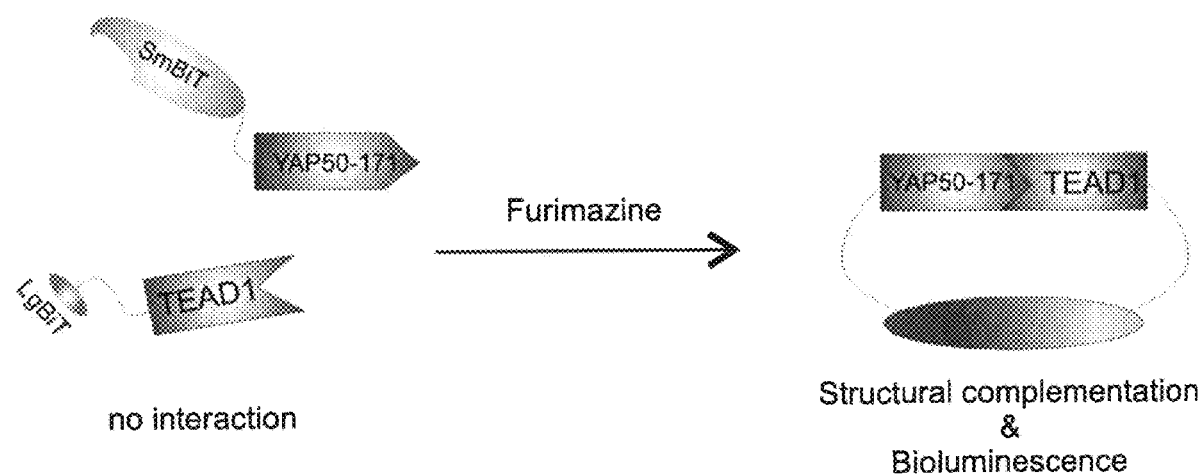

FIG. 12 shows a schematic overview of a NanoBiT interaction system of a YAP-TEAD NanoBiT biosensor according to an embodiment of the invention.

Figure 13:
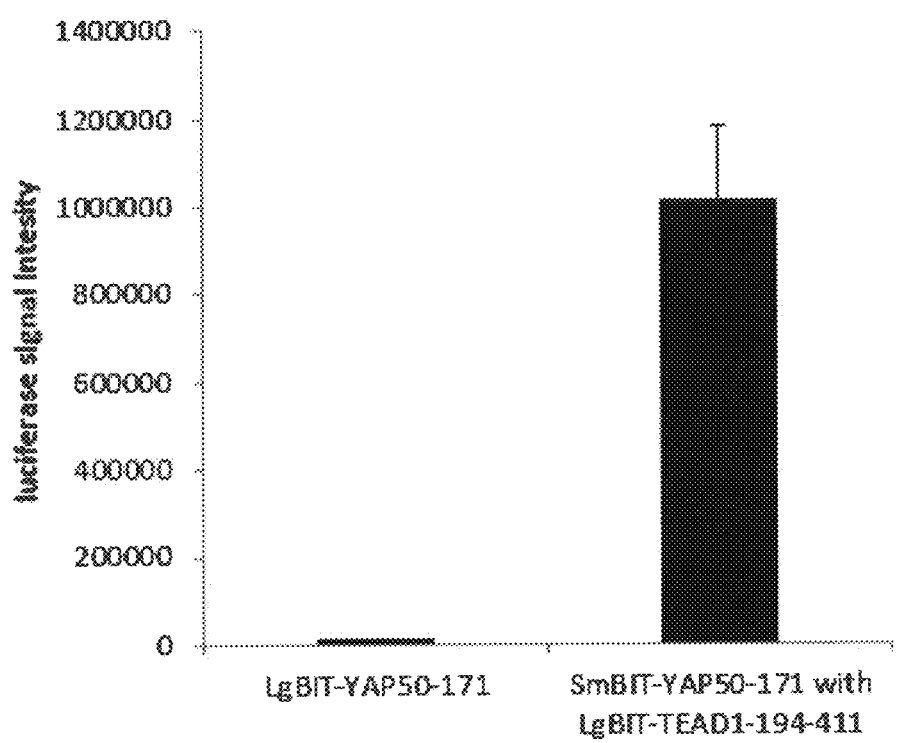

FIG. 13 shows the results of an assay of overexpressed YAP50-171 of SEQ ID NO:2 and TEAD1-194-411 of SEQ ID NO:50 in HEK293T cells lysed with passive lysis buffer, for a biosensor with a combination of SmBiT-YAP50-171 (SEQ ID NO:2) and LgBiT-TEAD1-194-411 of SEQ ID NO:50 constructs.

Figure 14:
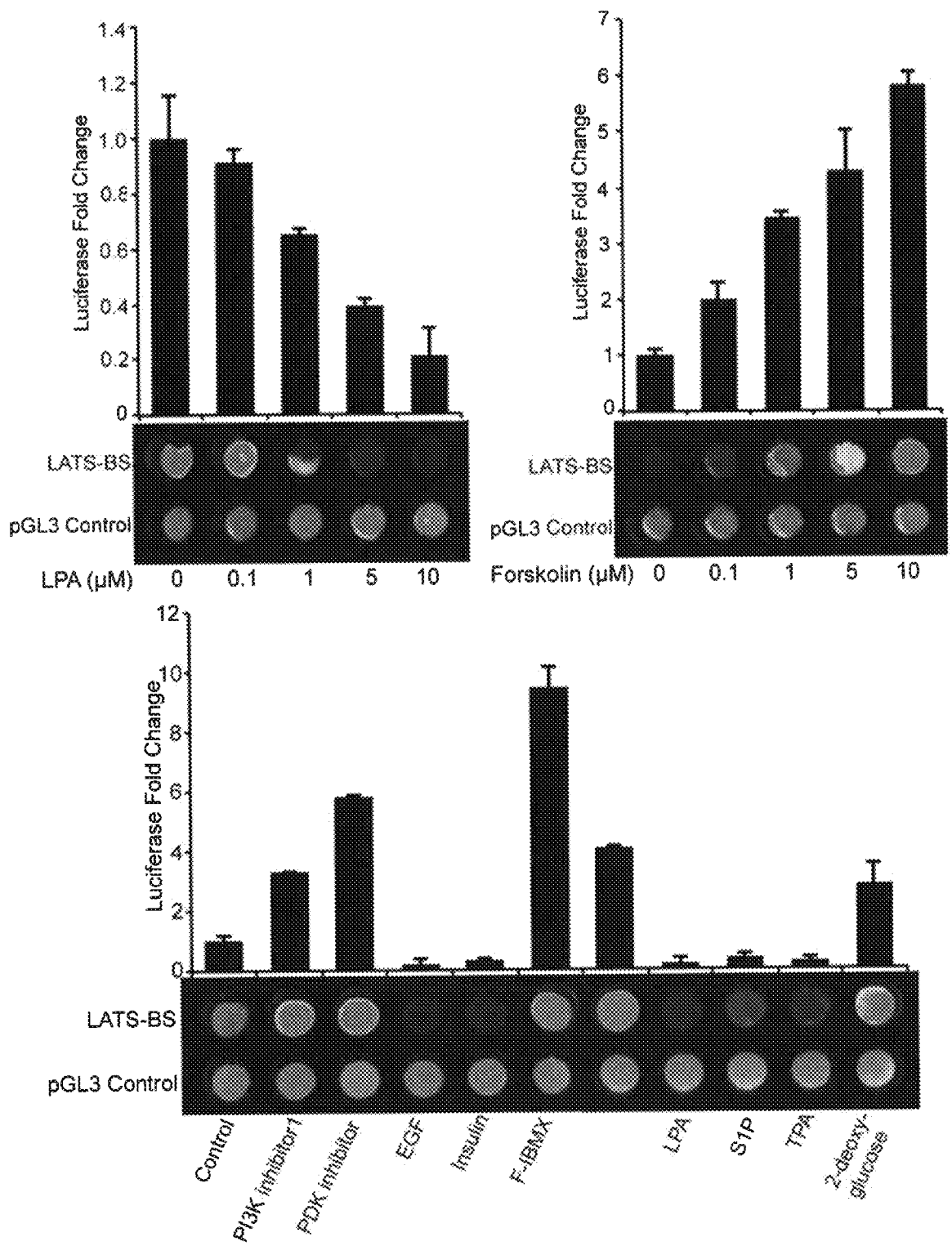

FIG. 14 shows the results of an assay for analyzing LATS kinase activity under various stimuli regulating Hippo signaling by live cell luciferase imaging, using an intermolecular LATS-BS as described herein.

Figure 15:
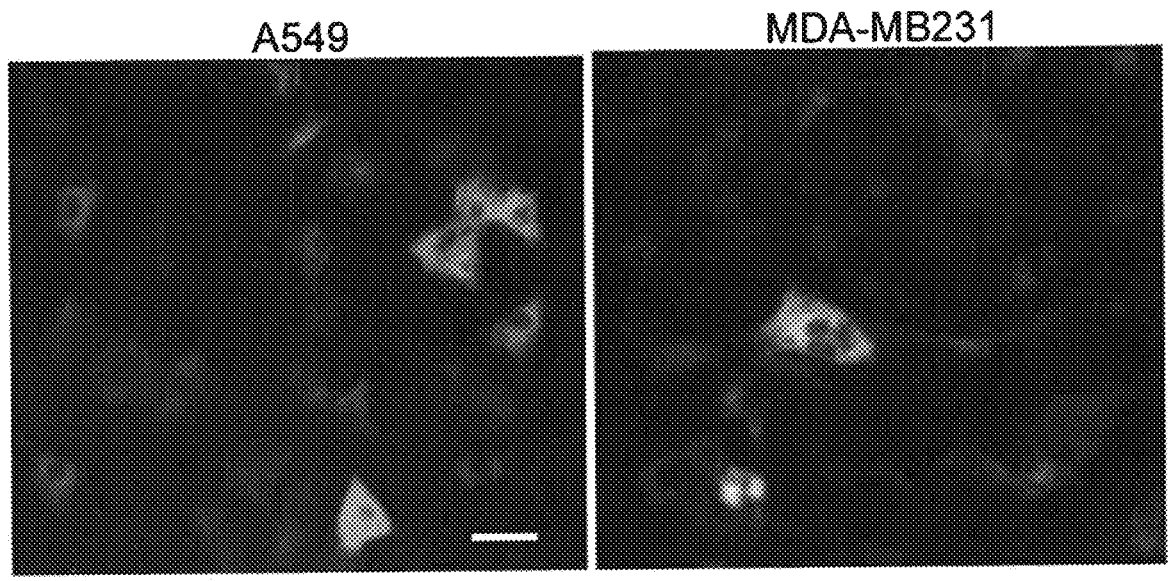

FIG. 15 is a photomicrograph showing the results of an experiment to determine subcellular LATS kinase activity using an intermolecular LATS-BS as described herein, obtained by bioluminescent microscopy.

Figure 16:
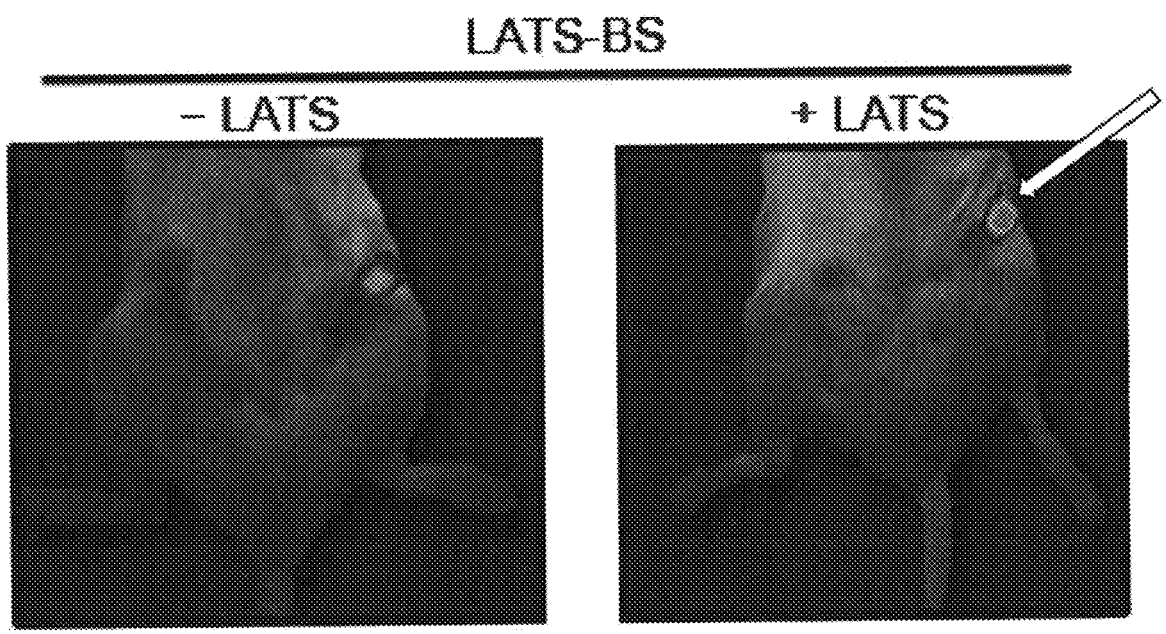

FIG. 16 is a photograph showing LATS kinase activity in mice by in vivo luciferase imaging, using an intermolecular LATS-BS as described herein.

Figure 17A:
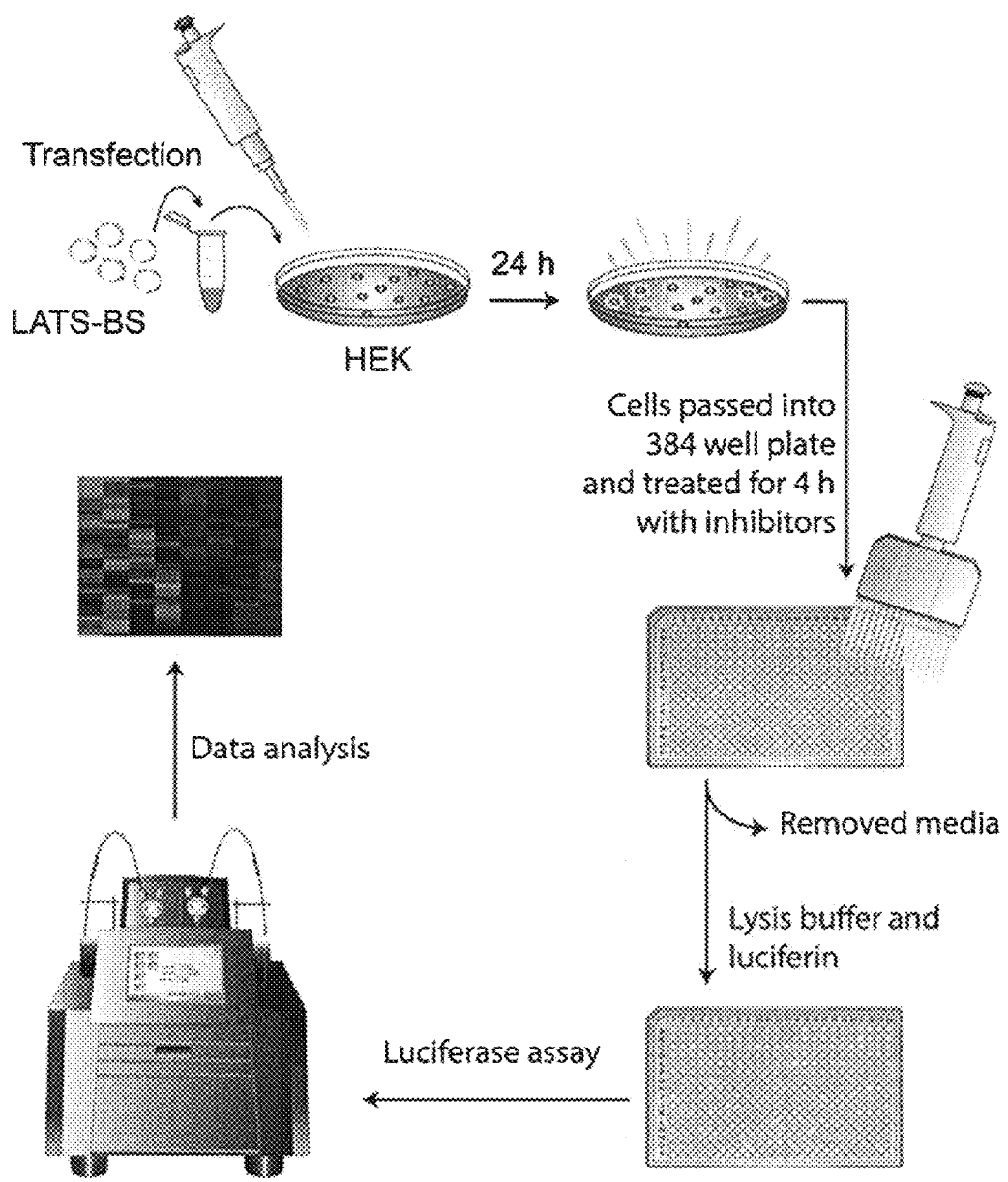

FIG. 17A is a schematic diagram showing a method for a screening assay, and FIG. 17B shows the results of a screening assay for identifying novel regulators of LATS using an intermolecular LATS-BS as described herein and a kinase inhibitor screen.

DETAILED DESCRIPTION OF EMBODIMENTS

In practicing the embodiments described herein, many conventional techniques in cell biology, molecular biology, protein biochemistry, immunology, and bacteriology are used. These techniques are well-known in the art and are provided in any number of available publications, such as Current Protocols in Molecular Biology, Vols. I-III, Ausubel, Ed. (1997); Sambrook et al., Molecular Cloning: A Laboratory Manual, Second Ed. (Cold Spring Harbor Laboratory Press, Cold Spring Harbor, N.Y., 1989). Unless specifically defined herein, all technical and scientific terms used herein generally have the same meaning as commonly understood by one of ordinary skill in the art to which this invention belongs.

One aspect of the invention relates to bioluminescence-based biosensor constructs that non-invasively monitor real-time in vitro and in vive activity of LATS kinase, the central player of the Hippo signaling pathway. A LATS biosensor (LATS-BS) as described herein quantifies LATS kinase activity by split luciferase assay, a bioluminescence-based technique that non-invasively monitors protein-protein interactions in vitro and in vive in real-time with accurate quantification, high sensitivity, and excellent reproducibility. Embodiments of the biosensor constructs include fragments of firefly (Photinus sp., e.g., Photinus pyralis) or NanoBiT (also referred to as NanoLuc) luciferase and human YAP1. Some embodiments include human cytoplasmic protein 14-3-3 or a fragment thereof.

Another aspect of the invention relates to a method for non-invasively monitoring real-time in vitro and in vivo activity of LATS kinase. In various embodiments, the method includes using a LATS biosensor as described herein to quantify LATS kinase activity. The embodiments provide a bioluminescence-based technique for monitoring LATS kinase activity with accurate quantification, high sensitivity, and excellent reproducibility (see Examples for details).

A third aspect of the invention relates to bioluminescent biosensor constructs and methods for non-invasively monitoring YAP-TEAD interaction, a critical step in regulation of downstream target by the Hippo pathway. Embodiments of the biosensor constructs include fragments of NanoBiT luciferase and fragments of human YAP1 and TEAD1, or functional equivalents thereof, and provide a bioluminescent-based technique for monitoring YAP and TEAD interactions both in vitro and in vivo with high sensitivity, stability, and reproducibility.

At least eight isoforms of YAP1 are known. SEQ ID NO:1 shows the full human YAP2L isoform mRNA (accession number: AB567720) and SEQ ID NO:2 shows the amino acid sequence. The fragments used in the embodiments described herein were obtained from the YAP2L isoform of YAP1 (SEQ ID NO:2). However, the fragments used in the embodiments described herein may be obtained from any of the isoforms, or may be functional equivalents thereof. In this disclosure, the terms "YAP1" and "YAP" are used interchangeably to refer to an isoform of YAP1. SEQ ID NO:3 shows the full human 14-3-3 protein theta mRNA (accession number: P27348) and SEQ ID NO:4 shows the amino acid sequence. SEQ ID NO:5 shows the full length firefly luciferase mRNA and SEQ ID NO:6 shows the luciferase protein.

Since LATS phosphorylates S127 on YAP1 and cytoplasmic protein 14-3-3 binds specifically to phosphorylated but not un-phosphorylated S127-YAP, embodiments were constructed for monitoring LATS kinase activity by measuring the pS127-YAP/14-3-3 interaction.

Figure 1A:
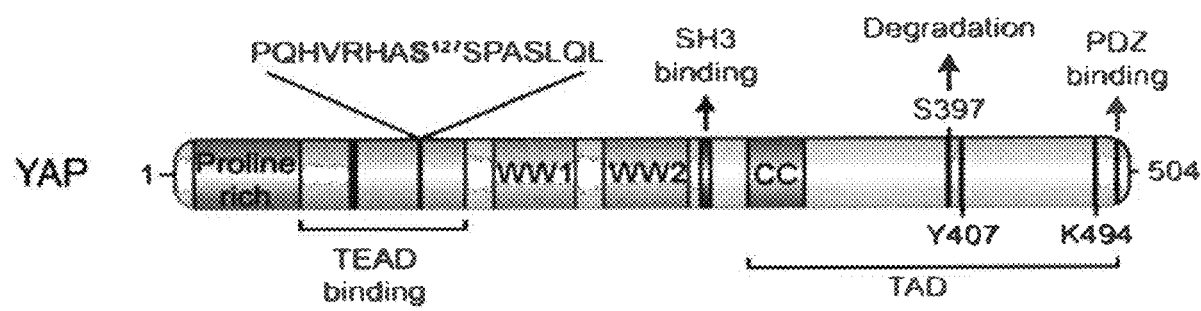
FIG. 1A is a schematic diagram of YAP1 protein structure (SEQ ID NO:2) showing LATS phosphorylation site (S127) and the surrounding 15 amino acid sequence (YAP15; SEQ ID NO:7).

In various embodiments, a LATS-BS includes a minimal YAP1 fragment that interacts with 14-3-3 in a phosphorylation-dependent manner. The full length YAP1 protein was not used to avoid confounding signals by post-translational modifications of YAP1 by other upstream regulators. In one embodiment, the minimal YAP1 fragment includes 15 amino acids (YAP15) surrounding the S127 LATS phosphorylation site (amino acids 120-134; SEQ ID NO:7; FIG. 1A). Functional equivalents may be used, such as other sizes of YAP1 fragments, such as, for example, longer (e.g., 16-20 amino acids) or shorter (e.g., 12-14 amino acids) surrounding the S127 (SEQ ID NO:2). Embodiments may include a YAP fragment with a HxRxxS motif (SEQ ID NO:71). Since H, R, and S residues but not other amino acids in the HxRxxS motif (SEQ ID NO:71) on the YAP fragment are essential for LATS biosensor function (see, e.g., FIG. 2D), variants of YAP fragments with changes of amino acids other than H/R/S may also be used. Larger fragments (e.g., 20-100 amino acids) may result in confounding signals.

Figure 1B:
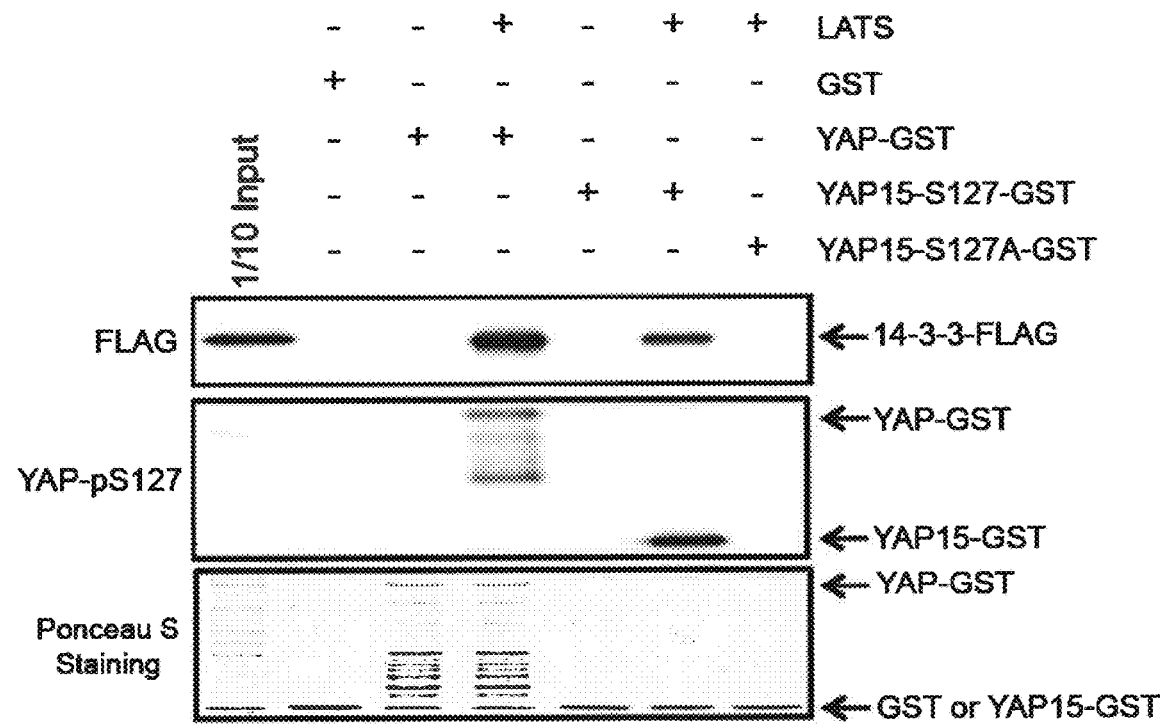
FIG. 1B is a western blot for GST pulldown assays showing results confirming that YAP15 is sufficient for interaction with cytoplasmic protein 14-3-3 in vitro.

Minimal YAP1 fragments were tested for interaction with 14-3-3 after phosphorylation by LATS2 kinase. Using in vitro GST-pulldown assays, it was found that like full-length YAP-GST, YAP15-GST could directly bind to 14-3-3 after LATS phosphorylation while a phosphorylation-mutant YAP15-S127A-GST (A, alanine) could not. FIG. 1B shows that YAP15 is sufficient for interaction with 14-3-3 in vitro. To collect the data, GST-tagged full length YAP (YAP-GST), YAP15 with wild type sequence (YAP15-S127-GST), or mutant YAP15 that cannot be phosphorylated by LATS (YAP15-S127A-GST) was purified from bacterial cells and 1 μg of GST fusion protein was incubated for 20 minutes at 30° C. with recombinant LATS kinase. 100 μg of cell lysate from human embryonic kidney cells (HEK293) transiently expressing 14-3-3-Flag was added and YAP or YAP15-S127 or YAP15-S127A/14-3-3 binding was assessed by GST pull-down with protein S-agarose beads, followed by western blot with anti-Flag (14-3-3-Flag) and anti-YAP-pS127 antibodies. The membrane was stained with Ponceau S to visualize the fusion proteins.

Since the TEAD family consists of four members, other TEADs (TEAD2-4) may also be used to replace TEAD1 to make biosensors similar to the YAP-TEAD1 biosensor. Throughout this disclosure, "TEAD1" and "TEAD" are used interchangeably to refer to any one of the TEAD family members.

In the following descriptions of various embodiments of the biosensor, references to sequences and sequence listings are made. Those of ordinary skill in the art will readily appreciate that the invention is not limited to the specific sequences described, as many variants are possible without departing from the invention. For example, substitutions, mutations, deletions, and/or additions of one or more nucleotides or amino acids may be made, or may occur, without substantial effect on functional properties of a biosensor. Such a functional equivalent may have, for example, 60%, or 70%, or 80%, or 90%, or more sequence identity with a sequence described herein. Such functional equivalents are intended to be included in the embodiments of the invention.

1. LATS Biosensor 1.1 Intermolecular Biosensor

Figure 2A:
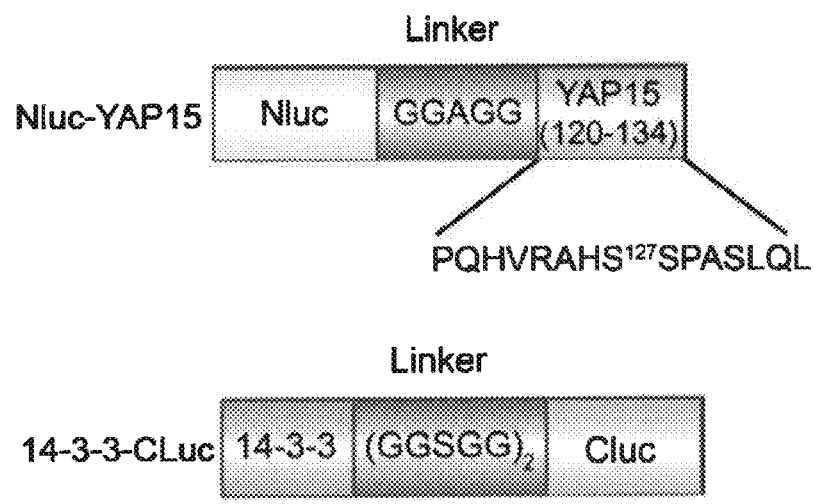
FIG. 2A shows schematic diagrams of domain structures of a LATS intermolecular biosensor, referred to as Nluc-YAP15 (upper; SEQ ID NOs:6, 7) and 14-3-3-Cluc (lower; SEQ ID NOs:4, 6), according to an embodiment of the invention.

The biosensor was made by overlapping PCR using firefly luciferase as a template. YAP15 and 14-3-3 were fused with N-terminal and C-terminal luciferase fragments (Nluc and Cluc), respectively, to create a LATS-B S. As shown in FIG. 2A, for Nluc-YAP15, firefly luciferase amino acids 1-416 (N-luciferase, Nluc) (SEQ ID NO: 6) were fused to the N-terminal of YAP15 (120-134; SEQ ID NO:7) separated by a glycine/alanine linker (GGAGG; SEQ ID NO:73); and for 14-3-3-Clue, luciferase amino acids 394-550 (C-luciferase, Cluc; SEQ ID NO:6) were fused to the C-terminal of 14-3-3 (SEQ ID NO: 4) separated by a glycine/serine linker (GGSGGGGSGG; SEQ ID NO:74). Biosensors were cloned into the BamHI/NotI sites of the pcDNA3.1/hygro (+) vector (SEQ ID NO:9, purchased from Invitrogen, Dublin, Ireland). Primers are shown in SEQ ID NOs:10-16. The full length sequences for Nluc-YAP15 and 14-3-3-Clue in pcDNA3.1/hygro (+) vector are given in SEQ ID NOs:57 and 58, respectively, wherein the underlined portions are the main constructs and the rest is the vector.

Figure 2B:
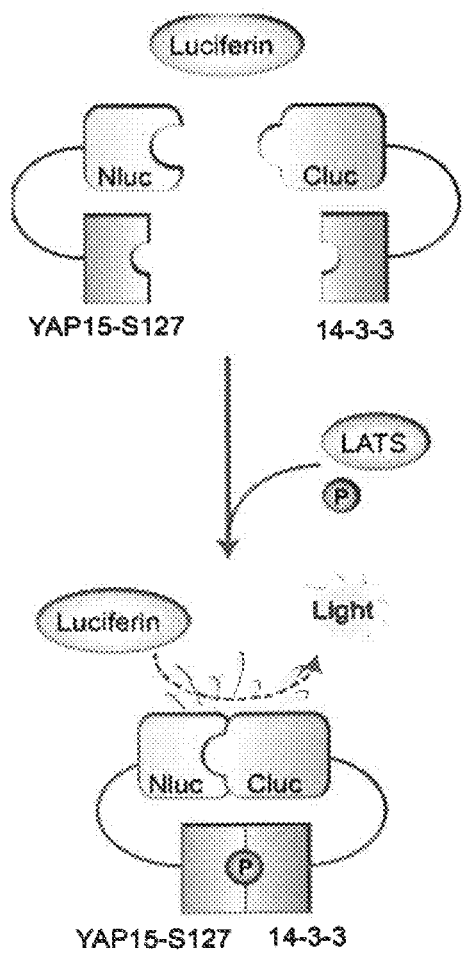
FIG. 2B is a schematic diagram showing the mechanism by which a LATS intermolecular biosensor determines LATS kinase activity.

The mechanism of action for how the LATS-BS determines LATS kinase activity is shown in FIG. 2B. At baseline, there is no interaction between YAP15 and 14-3-3 so the LATS-BS shows minimal bioluminescence activity. However, LATS-dependent phosphorylation of YAP15-S127 leads to 14-3-3 binding, luciferase complementation, and high bioluminescence signal.

Figure 2C:
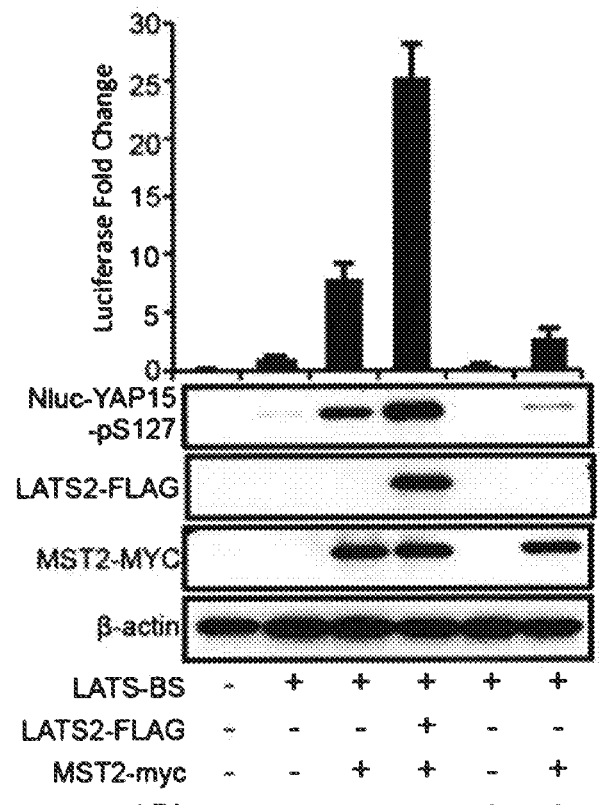
FIG. 2C shows experimental results validating LATS intermolecular biosensor activity, where biosensor activity or NLuc-YAP15-S127 phosphorylation status were determined in HEK293 cells 48 hours after transfection by luciferase assay or western blot, respectively. Data are presented as mean±SD, n=3.

In a validation study, LATS-BS was transfected alone or together with LATS2 or/and MST2 into HEK293 cells and biosensor activity or NLuc-YAP15-S127 phosphorylation status were determined 48 hours after transfection by luciferase assay or western blot, respectively. As depicted in FIG. 2C, HEK293 cells transfected with LATS-BS alone had low luciferase activity and this was correlated with a low degree of Nluc-YAP15-S127 phosphorylation. Co-transfection of LATS-BS with MST2 was associated with increases in both Nluc-YAP-S127 phosphorylation and luciferase activity, and this effect was suppressed with lysophosphatidic acid (LPA), an inhibitor of the Hippo pathway. For lysophosphatidic acid (LPA) treatment, cells were stimulated with 10 μM LPA for 1 hour before collection (n=3). LATS-BS co-expression with both MST2 and LATS2 was correlated with further increases in Nluc-YAP15-S127 phosphorylation and luciferase activity. Collectively, these observations are consistent with a model where MST2 activates LATS2, which phosphorylates Nluc-YAP15-S127, leading to binding with Cluc-14-3-3 and reconstitution of active luciferase.

Figure 2D:
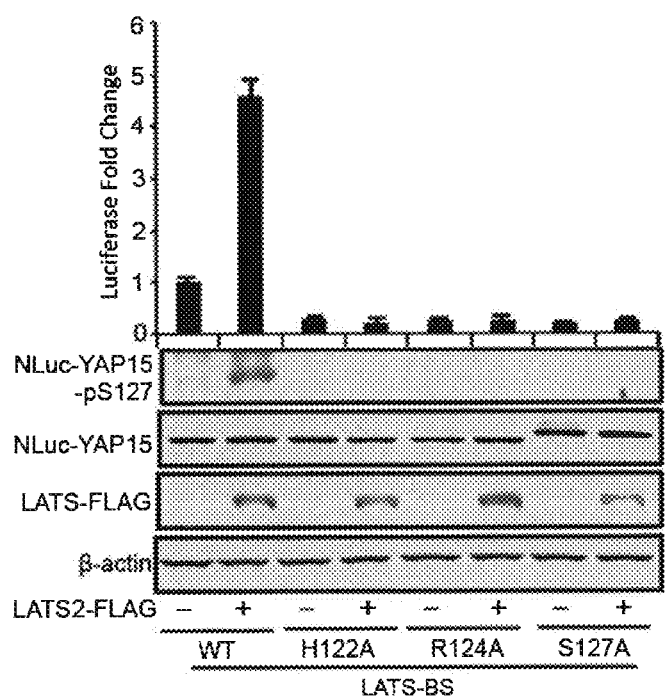
FIG. 2D shows experimental results confirming that a LATS intermolecular biosensor responds specifically to LATS kinase activity, by mutation of the LATS kinase consensus motif (HXRXXS/T; H, histidine; R, arginine; X, any amino acid; S, serine; T, threonine; SEQ ID NOs:71, 72) in Nluc-YAP15 (SEQ ID NOs:7, 8). Data are presented as mean±SD, n=3.
Figure 2E:
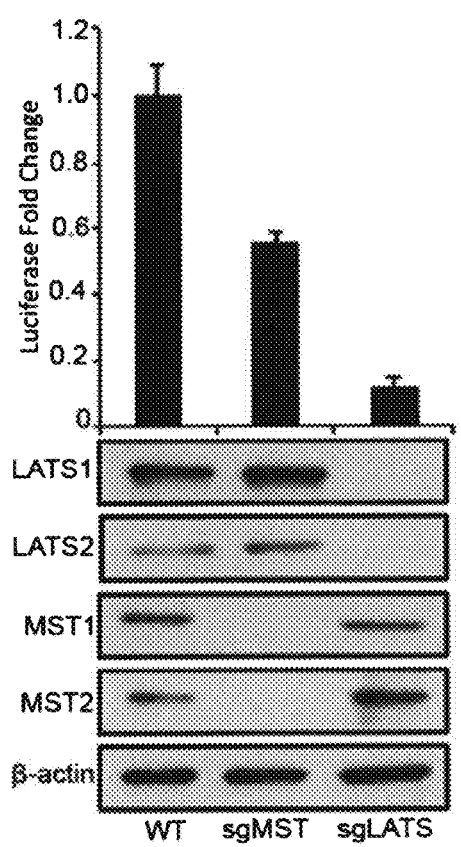
FIG. 2E shows experimental results confirming that LATS intermolecular biosensor activity is reduced by MST or LATS knockout. Data are presented as mean±SD, n=3.
Figure 2F:
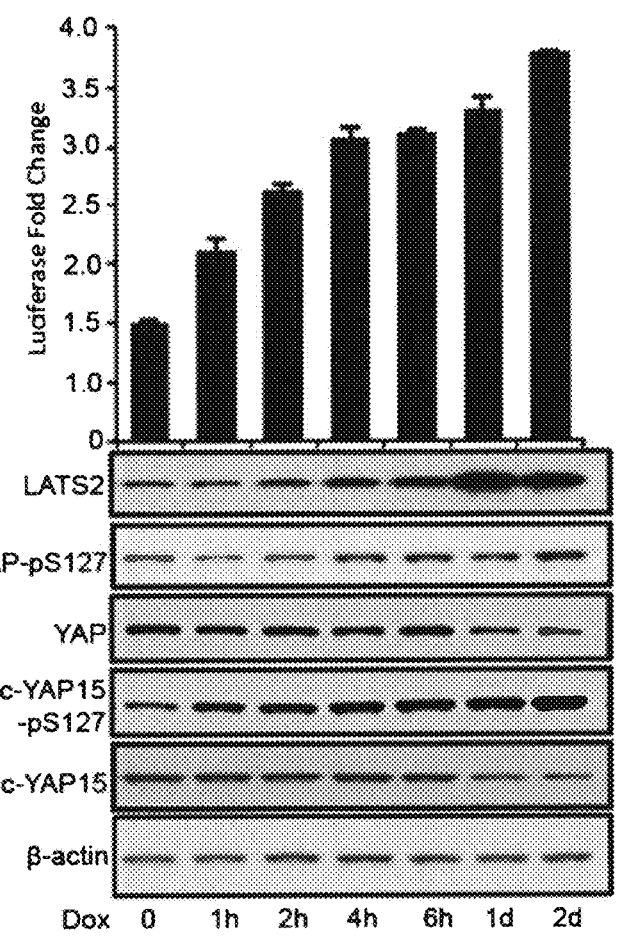
FIG. 2F shows experimental results confirming that LATS intermolecular biosensor can be stably expressed to detect LATS kinase activity, wherein biosensor activity and phosphorylation status were monitored in a HEK293A cell line with doxycycline (Dox)-inducible LATS2 overexpression and stable LATS biosensor (LATS-BS) expression, and biosensor activity and phosphorylation status of endogenous YAP (YAP-pS127) and Nluc-YA15P-S127 (Nluc-YAP15- pS127) were determined at the indicated times by luciferase assay and western blot, respectively. Data are presented as mean±SD, n=3.

To further validate the biosensor construct model, conserved residues (H, histidine; R, arginine; S) within the LATS consensus phosphorylation motif (HxRxxS/T; x, any amino acid; SEQ ID NOs: 71, 72) on Nluc-YAP15-S127 were mutated to A (H122A, R124A, and S127A). Each individual mutation completely abolished Nluc-YAP15-S127 phosphorylation and LATS-BS luciferase activity, as shown in FIG. 2D. In addition, the basal LATS-BS signal was reduced by knockout of endogenous MST1/2 in HEK293A (50% reduction) or more dramatically by LATS1/2 knockout (HO % reduction), as shown in FIG. 2E. LATS-BS was transfected into CRISPR-Cas9-generated LATS1/2 or MST1/2 knockout HEK293A and basal biosensor activity was determined 48 hours after transfection (n=3). Furthermore, inducible expression of LATS2 in HEK293A cells stably expressing LATS-BS showed that the levels of LATS2 are correlated with the level of endogenous YAP-pS127, Nluc-YAP15-pS127 as well as with LATS-BS activity, as shown in FIG. 2F. Biosensor activity and phosphorylation status were monitored in a HEK293A cell line with doxycycline (Dox)-inducible LATS2 overexpression and stable LATS-BS expression. Cells were treated with 1 μg/mL Dox for the indicated times and biosensor activity and phosphorylation status of endogenous YAP (YAP-pS127) and Nluc-YA15P-S127 (Nluc-YAP15-pS127) were determined by luciferase assay and western blot, respectively (n=3).

This LATS biosensor was also used to examine LATS kinase activity in living cells and mice and to perform a screening assay for regulators of LATS (see details in Examples).

1.2 Intramolecular Biosensor

An intramolecular biosensor was made by overlapping PCR using firefly luciferase as a template. In one embodiment, firefly luciferase amino acids 1-416 (N-luciferase, Nluc; SEQ ID NO:6) were fused to the N-terminal of YAP15 (120-134) (SEQ ID NO:7) separated by a glycine/alanine linker (GGAGG; SEQ ID NO:73). Within the same open reading frame, luciferase amino acids 394-550 (C-luciferase, Cluc; SEQ ID NO:6) were fused to the C-terminal of 14-3-3 separated by a glycine/alanine linker. For this biosensor, LATS phosphorylates YAP15-5127 to cause a conformational change in the intramolecular LATS-BS, leading to luciferase complementation and detectable biosensor activity. Primers are shown in SEQ ID NOs:10, 16, 17, and 18.

The domain structure is shown in FIG. 3A and the mechanism of action for how the LATS-BS determines LATS kinase activity is shown in FIG. 3B. At baseline, there is no interaction between YAP15 and 14-3-3 so the LATS-BS shows minimal bioluminescence activity. However, LATS-dependent phosphorylation of YAP15-S127 leads to 14-3-3 binding, luciferase complementation, and high bioluminescence signal.

To validate the intramolecular biosensor, the biosensor was transfected alone or together with LATS2 or/and MST2 into HEK293 cells and biosensor activity was determined 48 hours after transfection by luciferase assay. For LPA treatment, cells were stimulated with 10 μM LPA, an inhibitor of the Hippo pathway, for 1 hour before collection (n=3). Results are shown in FIG. 3C.

13 Engineered Biosensor

The biosensor was made by overlapping PCR using firefly luciferase as a template. In one embodiment, the C-terminal seven amino acids from firefly luciferase were removed to create Eng-luc (544 amino acids). This construct was fused to the N-terminal of YAP15 (amino acids 120-134; SEQ ID NO:7). This brings the luciferase site in close proximity to YAP15-5127 such that LATS-dependent phosphorylation of YAP-S127 modulates luciferase activity directly. Primers are shown in SEQ ID NOs:10 and 19.

The domain structure of the Eng-luc LATS biosensor according to one embodiment is shown in FIG. 4A and the mechanism of action for how the biosensor determines LATS kinase activity is shown in FIG. 4B.

For validation of the Eng-luc LATS-BS, the biosensor was transfected alone or together with LATS2 or/and MST2 into HEK293 cells and biosensor activity was determined 48 hours after transfection by luciferase assay. For LPA treatment, cells were stimulated with 10 μM LPA for 1 hour before collection (n=3). Results are shown in FIG. 4C.

1.4. NanoBiT Biosensor

For this biosensor YAP15 (aa 120-134; SEQ ID NO:7) and 14-3-3 full length (aa 1-245; SEQ ID NO:4) were used. As shown in FIG. 7-10, a YAP15 mutant was used as a negative control in these experiments.

To clone YAP15 and 14-3-3 in NanoBiT (also referred to as NanoLuc) vectors (purchased from Promega Corporation, Madison, Wis., U.S.A.), primers with EcoR1 and Bglll restriction sites were used. For the LgBiT-YAP15 construct, primers shown in SEQ ID NOs:20-23 were used. For the 14-3-3-SmBiT construct, primers shown in SEQ ID NOs: 24-25 were used.

In the case of YAP15WT (S127; SEQ ID NO:7) and mutant (A127; SEQ ID NO:8), primers with EcoR1 and Bglll flanking ends were annealed first and then they were ligated into digested pBiT 1.1 N (TK-LgBiT) vector (SEQ ID NO:26; purchased from Promega Corporation) with N-terminal LgBiT domain. FIG. 5A shows the multiple cloning site. For making the 14-3-3-SmBiT construct, in order to amplify 14-3-3 gene, standard PCR using the above mentioned primers was done by using 14-3-3 as a template. PCR product was digested using EcoR1 and Bglll restriction enzymes and was ligated into pBiT 2.1 C (TK-SmBiT; purchased from Promega Corporation) (SEQ ID NO:27) with SmBiT (11 amino acid) sequence at the C-terminus. FIG. 5B shows the multiple cloning site.

To make LgBiT-YAP15 (WT and mutant) and 14-3-3-SmBiT constructs for protein expression and purification in *E. coli*, the primers shown in SEQ ID NOs:28-30 were used for the LgBiT-YAP15 construct, and the primers shown in SEQ ID NOs:31-32 were used for the 14-3-3-SmBiT construct. For PCR, LgBiT-YAP15 and 14-3-3-SmBiT in NanoBiT vectors were used as template. pET16b vector (SEQ ID NO:33; purchased from Novagen (Millipore (Canada) Ltd., Etobicoke, Canada) was used for overexpression of LgBiT-YAP15 (WT and mutant) and 14-3-3-SmBiT as His-tagged proteins. FIG. 5C shows the multiple cloning site.

Figure 5D:
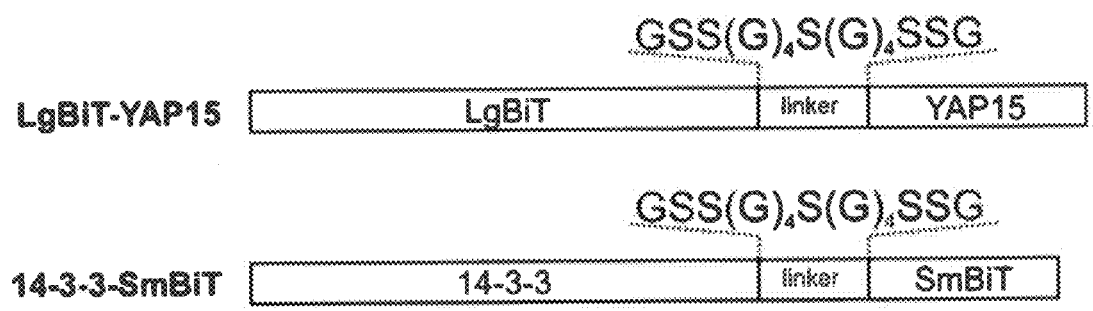

FIG. 5D shows a schematic representation of the LgBiT-YAP15 and 14-3-3-SmBiT constructs. SEQ ID NOs:59, 60, 61, and 62 give the full length sequences for LgBiT-YAP15 in pBiT 1.1 N vector, 14-3-3-LgBiT in pBiT2.1-C vector, LgBiT-YAP15 in pET16b vector, and SmBiT in pET16b vector, respectively, wherein the underlined portions are the main constructs and the rest is the vector.

FIG. 6 is a schematic diagram showing an overview of the NanoBiT interaction system. YAP15 and 14-3-3 are fused to LgBiT and SmBiT, respectively. Interaction of purified fusion proteins or overexpressed proteins in the cells leads to structural complementation of LgBiT with SmBiT that consequently generates a functional enzyme with bright luminescence.

For protein expression, the *E. coli* strain CodonPlus (DE3)-RIPL was transformed and used to purify the respective proteins. *E. coli* with the respective construct were grown until an OD600 value of 0.6-0.8 and then induced with 0.3 mM isopropyl-β-D-thiogalactopyranoside (IPTG) overnight at 20° C. Protein purification was carried out by incubating cells at 4° C. with DNase I (10 μg/ml) followed by cell lysis by sonication. Bacterial lysates were centrifuged to collect soluble fractions and His-tagged proteins were purified from the supernatant via Ni-affinity purification. After eluting and concentrating, proteins were subjected to dialysis against standard buffer containing 30 mM Tris-HCl, pH 7.5, 150 mM NaCl, 5 mM MgCl2, and 2 mM DTT. All purified proteins were analyzed by SDS-PAGE and stored at −80° C. FIG. 7 shows coomassie brilliant blue (CBB) stained SDS-PAGE of purified proteins for the biosensor.

NanoBiT Assay for YAP15-14-3-3 in Cells.

A NanoBiT assay was prepared for YAP15-14-3-3 in cells. HEK293T cells ($3\times10^5$) were transfected using Polyjet transfection reagent according to the manufacturer's instructions in 12-well plates by using 250 ng of each plasmid DNA per transfection. After 48 h the cells were lysed with passive lysis buffer and the NanoBiT assay of overexpressed LgBiT-YAP15 WT and mutant and 14-3-3-SmBiT was performed. Relative luminescence to YAP15MUT-14-3-3 was determined as shown in FIG. 8A.

NanoBiT Assay for YAP15-14-3-3 Using Cancer Cells.

Cancer cells (A549, H1299, and HEK293) were treated with okadaic acid for 1 h to activate LATS before lysing with passive lysis buffer. Then, 350 μg cell lysate was untreated or treated with calf intestine phosphatase (CIP) to inactivate the biosensor, followed by LATS pulldown and measurement of LATS kinase activity in vitro using purified LATS BS. As shown in FIG. 8B, the NanoBiT LATS-BS produced a strong signal for all three types of cancer cells.

NanoBiT Assay for YAP15-14-3-3 Using Blood.

Mononuclear cells were separated from fresh human blood and then lysed with passive lysis buffer. Then, 350 μg cell lysate was used to pull-down LATS kinase and measure its activity in vitro using purified NanoBiT LATS-BS. As shown in FIG. 8C, the NanoBiT LATS-BS produced a strong signal.

NanoBiT Assay Using Purified Proteins.

In order to test the LATS NanoBiT biosensor in vitro, a kinase assay was done using purified LgBiT-YAP15 (WT and mutant), 14-3-3-SmBiT and LATS2 as the kinase. The assay was done with two different concentrations of biosensor (100 ng and 5 ng). After 1, 10, 20, 30 min and 1, 2, 4 and 20 h luminescence was measured and also phosphorylation level was checked using WB. Results are shown in FIG. 9. The upper panel shows the result of NanoBiT assay for YAP15WT and mutant at the two different concentrations of biosensor (5 and 100 ng) as a ratio of luminescence signal in the presence to absence of LATS as a kinase in different time points. The lower panel shows immunoblotting analysis and Ponceau staining of the respective samples from the experiment with 100 ng of biosensor.

Kinase Assay with and without Phosphatase.

To confirm that the biosensor is phosphorylation dependent and works through LATS, lambda phosphatase was used and luminescence as well as phosphorylation was determined. The results show that treating with lambda phosphatase abolishes luminescence. In FIG. 10 the upper panel shows the result of an assay for the biosensor with YAP15 WT or mutant (100 ng) with and without lambda phosphatase after 30 min. The Y axis shows the ratio of luminescence in the presence of LATS and in the absence of LATS. The lower panels show the relative immunoblotting and Ponceau staining for the respective samples 2. YAP-TEAD Biosensor YAP transcriptionally activates downstream genes by interacting with the TEAD family of transcription factors (i.e., TEAD1-4). To monitor interaction between YAP and TEAD, a NanoBiT split luciferase biosensor was developed that quantifies YAP1 and TEAD1 interaction. This biosensor is based on a YAP fragment (residues 50-171; SEQ ID NO:2)-TEAD1 fragment (residues 194-411; SEQ ID NO:50) complex, in which YAP wraps around the globular structure of TEAD1. FIG. 12 shows a schematic overview of the NanoBiT interaction system of a YAP-TEAD NanoBiT biosensor as described herein. The YAP1 mRNA and amino acid sequences are given in SEQ ID NOs:1 and 2, respectively. The TEAD1 mRNA and protein sequences are given in SEQ ID NOs:49 and 50, respectively. The Large BiT (LgBiT) mRNA and protein sequences are given in SEQ ID NOs:51 and 52, respectively. The Small BiT (SmBiT) mRNA and protein sequences are given in SEQ ID NOs:53 and 54, respectively. The vectors were pcDNA3.1/hygro(+) (SEQ ID NO:9), pcDNA3.1/hygro(+)-Flag (SEQ ID NO:55), and pcDNA3.1/hygro(+)-Myc (SEQ ID NO:56).

Eight NanoBit split luciferase constructs were made using the primers as listed below. The domain structures of the eight constructs are shown in FIG. 11.

Construct 1:
LgBiT-YAP50-171-Flag (overlapping PCR):
SEQ ID NO:34. B1-Kozak-LgBiT-F primer (41 nucleotides):
SEQ ID NO:35. LgBiT-(GS)-R primer (54 nucleotides):
SEQ ID NO:36. (GS)-YAP50-F primer (69 nucleotides):
SEQ ID NO:37. N1-YAP171-Flag-R primer (63 nucleotides)

Construct 2:
Flag-YAP50-171-LgBiT (overlapping PCR):
SEQ ID NO:38. B1-YAP50-F primer (32 nucleotides):
SEQ ID NO:39. (GS)-YAP171-R primer (68 nucleotides):
SEQ ID NO:40. (GS)-LgBiT-F primer (66 nucleotides):
SEQ ID NO:41. N1-LgBiT-R primer (43 nucleotides):

Construct 3:
SmBiT-YAP50-171-Flag (tandem PCR):
SEQ ID NO:42. B1-Kozak-SmiBiT-(GS)-F primer (98 nucleotides):
SEQ ID NO:36. (GS)-YAP50-F primer (69 nucleotides):
SEQ ID NO:37. N1-YAP171-Flag-R primer (63 nucleotides)

Construct 4:
Flag-YAP50-171-SmBiT (tandem PCR):
SEQ ID NO:38. B1-YAP50-F primer (32 nucleotides)
SEQ ID NO:39. (GS)-YAP171-R primer (68 nucleotides)

SEQ ID NO:43. N1-SmBiT-(GS)-R primer (97 nucleotides):
Construct 5:
LgBiT-TEAD1-194-411-Myc (overlapping PCR):
SEQ ID NO:34. B1-Kozak-LgBiT-F primer (41 nucleotides)
SEQ ID NO:35. LgBiT-(GS)-R primer (54 nucleotides)
SEQ ID NO:44. (GS)-TEAD-194-F primer (73 nucleotides):
SEQ ID NO:45. N1-TEAD411-Myc-R primer (73 nucleotides):
Construct 6:
Myc-TEAD1-194-411-LgBiT (overlapping PCR)
SEQ ID NO:46. B1-TEAD194-F primer (36 nucleotides):
SEQ ID NO:47. GS-TEAD-411-R primer (69 nucleotides):
SEQ ID NO:40. (GS)-LgBiT-F primer (66 nucleotides)
SEQ ID NO:41. N1-LgBiT-R primer (43 nucleotides)
Construct 7:
SmBiT-TEAD1-194-411-Myc (tandem PCR)
SEQ ID NO:42. B1-Kozak-SmiBiT-(GS)-F primer (98 nucleotides)
SEQ ID NO:48. (GS)-TEAD194-F primer (73 nucleotides):
SEQ ID NO:45. N1-TEAD411-Myc-R primer (73 nucleotides)
Construct 8: Myc-TEAD-194-411-SmBiT (tandem PCR)
SEQ ID NO:46. B1-TEAD194-F primer (36 nucleotides)
SEQ ID NO:47. GS-TEAD-411-R primer (69 nucleotides)
SEQ ID NO:43. N1-SmBiT-(GS)-R primer (97 nucleotides)
Cloning.

To make constructs 1 and 5, overlapping PCR was performed using the above primers, and they were inserted into BamH1/Not1 cloning site of pcDNA3.1/hygro. For construct 1, pBiT1.1-N(TK/LgBiT) and full length YAP were used as templates to perform PCR. For construct 5, pBiT1.1-N(TK/LgBiT) and full length TEAD1 were used to perform PCR.

To make constructs 2 and 6, overlapping PCR was performed using the above primers, and they were inserted into BamH1/Not1 cloning site of pcDNA3.1/hygro-Flag/Myc. For construct 2, pBiT1.1-C(TK/LgBiT) and full length YAP were used to perform PCR. For construct 6, pBiT1.1-C(TK/LgBiT) and full length TEAD1 were used to perform PCR.

To make constructs 3 and 7, tandem PCR was performed using the above primers, and they were inserted into BamH1/Not1 cloning site of pcDNA3.1/hygro. For both constructs full length YAP and TEAD1 were used respectively to perform PCR.

To make construct 4 and 8, overlapping PCR was performed using the above primers, and they were inserted into BamH1/Not1 cloning site of pcDNA3.1/hygro-Flag/Myc. For both constructs full length YAP and TEAD1 were used respectively to perform PCR.

SEQ ID NOs:63-70 give the full length sequences for constructs 1-8, respectively, wherein, in each sequence, the underlined portion is the main construct and the rest is the vector.

Validation.

Different combinations of the eight constructs were used in assays in order to find the best orientation for the biosensor. The assays used overexpressed YAP50-171 and TEAD1-194-411 in HEK293T cells lysed with passive lysis buffer. All combinations of SmBiT and LgBiT biosensors worked, but the combination of SmBiT-YAP50-171 and LgBiT-TEAD1-194-411 showed the highest signal and sensitivity (FIG. 13).

Discussion

The embodiments and experiments described herein establish the LATS biosensor embodiments as the first LATS biosensor that can accurately monitor LATS kinase activity and intensity of Hippo signaling in vitro and in vivo, and its use in a new bioluminescence (BLI) method. In addition, the embodiments and experiments described herein establish the YAP-TEAD biosensor embodiments as the first biosensor that can accurately monitor YAP and TEAD interaction, which is essential for elucidating the function of YAP in the Hippo pathway. Although BLI is widely used for reporting promoter activity and imaging tumors in mice, few studies have used it to measure protein function at the cellular level and even fewer studies have examined subcellular protein function using bioluminescence microscopy. The ability to detect LATS kinase activity in individual cells and in blood as provided by the embodiments described herein has applications for evaluating heterogeneous dynamics of LATS kinase activity in cell culture as well as for the real-time monitoring of Hippo signaling responses to various drug treatments, and in applications such as detecting Hippo pathway signaling in biological samples such as tissue and blood obtained from subjects. In particular, the results show that a biosensor as described herein may be useful for detecting cancerous cells in biological samples such as tissue. The results of in vivo experiments in mice further illustrate how LATS-BS embodiments may be used to preclinically examine the effects of a variety of drugs on LATS kinase activity in vivo.

A biosensor as described herein may be provided in a kit to measure the Hippo signaling pathway, for use in vitro and in vivo. For example, a kit may include one or more LATS biosensor such as an intermolecular biosensor, intramolecular biosensor, engineered biosensor, or NanoBiT biosensor, and/or a YAP-TEAD biosensor as described herein, optionally with one or more reagents suitable for using the kit in an assay for a specified biological sample or cell type, and instructions for proper use of the kit. The reagent may be, for example, a reagent appropriate for in vitro use or for in vivo use, a buffer, cell lysis buffer, etc.

Example

The following example provides details of the methods used to make and use an intermolecular LATS biosensor as described herein.

1. Determine activity of purified LATS protein and LATS in cells by in vitro luciferase assay (described above and shown in FIGS. 2C, 2D, 3C, 8, and 13).

2. Determine interaction of YAP and TEAD in cells by in vitro luciferase assay (described above and shown in FIG. 13).

3. Determine LATS kinase activity under various stimuli regulating Hippo signaling by live cell luciferase imaging.

For live cell imaging, LATS-BS or a pGL3-control vector were transfected into HEK293, MDA-MB-231 or A549 cells. After 48 hours, cells were trypsinized and collected in a black, clear bottomed, 96-well plate. 150 µg/mL D-luciferin (D-Luciferin, Potassium Salt, GoldBio #LUCK-250) in media was added to each well 5-10 min before imaging. Exposure time for images was approximately 3 min/plate. Imaging was performed using a LightTools Research system (Synopsys, Ltd., Mountain View, Calif., USA) dark box and a Hamamatsu ORCA-Flash4.0 V2 digital CMOS camera over the course of 20 minutes to establish optimal peak luciferase activity. The bioluminescence of the regions of interest was analyzed for total emission flux using Image-Pro® Plus software (Media Cybernetics, Inc., Rockville, Md., USA).

Experiments were conducted to further validate the LATS intermolecular biosensor and explore potential applications for its use. The LATS-BS responded to numerous signals reported to modulate Hippo pathway activity, including cell confluency, drugs activating Hippo signaling (Forskolin, PI3K inhibitor, PDK inhibitor, F-IBMX, and 2-deoxy-glucose) and Hippo signaling inhibitors (LPA, EGF, Insulin, S1P, and TPA). The LATS-BS is activated by LATS in various cell lines (e.g., A549, MDA-MB231). Notably, in these experiments biosensor activity was measured in both cell lysates and in live cells using luciferase assay and BLI respectively. Collectively, these data illustrate the broad range of potential applications for the LATS-BS in monitoring Hippo pathway activity.

The following compound treatments were used for in vitro luciferase assay and live cells imaging: RAF inhibitor (GW5054, Cayman Chemical, Ann Arbor, Mich., USA), ATR inhibitor (CGK733, Cayman Chemical), PI3K inhibitor 1 (GDC0941, Cayman Chemical), PI3K inhibitor 2 (LY294002, Cayman Chemical), PDK inhibitor (GSK2334470, Cayman Chemical)—10 µM for 4 hours; EGF-100 ng/mL for 1 hour; insulin (Sigma #91077C)—10 µg/ml for 1 hour, F/IBMX (Forskolin, Cayman Chemical/IBMX, Cayman Chemical)—0.1-10 µM for Forskolin and 100 µM for IBMX for 1 hour; L-α-lysophosphatidic acid (LPA) (Sigma #L7260)—0.1-10 µM for 1 hour, sphingosine1-phosphophate (S1P)—1 µM for 1 hour; 12-O-tetradecanoylphorbol-13-acetate (TPA) (#41745; Cell Signaling Technology, Inc., Danvers, Mass., USA)—5 nM for 1 hour; 2-deoxy glucose (#D8375, Sigma-Aldrich Canada Co., Oakville, Ontario, Canada)—25 mM for 1 hour. The results are shown in FIG. 14.

4. Determine subcellular LATS kinase activity by bioluminescent microscopy.

Using the intermolecular LATS-BS, a new method was developed for the Olympus LV200 Bioluminescence Imager, and LATS kinase activity was visualized and quantified at the individual cell level in cancer cell lines. 3.5 mM D-luciferin was added to the media culturing HEK293A, A549 or MDA-MB231 cells stably expressing LATS-BS at 5-10 min before imaging. Images were captured using Olympus LV200 Bioluminescence Imager with exposure times ranging from 30 seconds (HEK293A) to 10 min (MDA-MB-231, A549). The results are shown in FIG. 15. The difference in biosensor signal intensity among individual cells represents altered endogenous LATS kinase activity rather than differential LATS-BS expression levels since only the LATS-phosphorylated fraction of LATS-BS should emit bioluminescence. In addition, data showed that both the levels and subcellular localization of LATS-BS bioluminescence (cytoplasm where LATS is expressed) and GFP (control, nucleus/cytoplasm) were different in the same cell. This technology also allowed comparison of the heterogeneity of LATS kinase activity among cancer cell lines by assessing the distribution of luciferase activity. Further, and of particular significance, using biophotonics BLI, LATS kinase activity was detected in vivo in mice. The subcellular activity of LATS kinase can be also visualized by bioluminescent imaging.

5. Measuring LATS kinase activity in mice by in vivo luciferase imaging.

Further, and of particular significance, using biophotonics BLI, LATS kinase activity was detected in vivo in mice. All mouse procedures were approved by the Queen's University Animal Care Committee (UACC) and performed in accordance with institutional policies. To visualize LATS kinase activity in vivo, 12-week-old female BALB/c mice were anesthetized by exposure to 1-3% isoflurane. 3×106 HEK293 cells transfected with an intermolecular LATS-BS alone (LATS−) or together with LATS (LATS+) were suspended in 100 µL of sterile PBS and injected into the mammary fat pad. Two days after the injection, post-surgery mice received 150 mg/kg of D-luciferin (Cedarlane) dissolved in PBS by intraperitoneal injection. Imaging of ventral view was performed using a LightTools Research system (Encinitas, Calif.) dark box and a Hamamatsu ORCA-Flash4.0 V2 digital CMOS camera over a course of 30 minutes to establish optimal peak luciferase activity. Pseudo-colored parametric overlays of BLI with anatomical reference images were dynamically constructed for each individual animal at comparative time points. The bioluminescence (BLI) of the regions of interest (ROI) was then analyzed for total emission flux using Image Pro Plus software. The results are shown in FIG. 16, where the arrow (right panel) points to the area where high intensity luminescence (red in heatmap) was detected.

6. Identifying novel regulators of LATS by a kinase inhibitor screen.

The intermolecular LATS-BS was used to search for novel kinases regulating Hippo signaling with a small-scale kinase inhibitor screen. The LATS-BS was transfected into HEK293A. Cells were passed into a 384-well plate the following day. 48 hours after transfection, cells were treated with the Tocriscreen Kinase Inhibitor Toolbox (Tocris Bioscience #3514) with each drug administered at 10 µM in DMSO for 4 hours in duplicate. Biosensor activity was then measured by luciferase assay. Fold change ratios were generated by comparing biosensor activity for each drug with that of DMSO-treated controls. The screening schematic and results are shown in FIGS. 17A and 17B, respectively. Of 80 kinase inhibitors screened, six kinase inhibitors activated the biosensor (i.e., inhibitors of VEGFR, MEK, GSK-3, PKB/Akt, EGFR, and CDK) while six inhibitors reduced the biosensor signal (i.e., inhibitors of TrkA, Broad, SYK, ATR/ATM, CHK1, and SGK). From these candidate LATS regulators, VEGFR1/2, GSK-3a/b, CDK4, TrkA, SYK, Broad, and SGK are novel. The screen results were confirmed by luciferase assays using the LATS-BS and an STBS-luciferase reporter that measures the transactivating function of YAP/TAZ32. The kinase inhibitors had the opposite effects on LATS-BS and STBS reporter, suggesting that the screen had identified true regulators of Hippo signaling. It is expected that future large-scale screens using the LATS-BS will identify additional new activators or inhibitors of the Hippo signaling pathway.

All cited publications are incorporated herein by reference in their entirety.

```
Sequences
SEQ ID NO: 1. Human YAP1 (yes-associated protein beta) isoform
2L mRNA (1,401 nucleotides) (accession number: AB567720)
ATGGATCCCGGGCAGCAGCCGCCGCCTCAACCGGCCCCCAGGGCCAAGGGCAGCCGCCTTCGC

AGCCCCCGCAGGGGCAGGGCCCGCCGTCCGGACCCGGGCAACCGGCACCCGCGGCGACCCAGGC
```

-continued

```
GGCGCCGCAGGCACCCCCCGCCGGGCATCAGATCGTGCACGTCCGCGGGGACTCGGAGACCGAC

CTGGAGGCGCTCTTCAACGCCGTCATGAACCCCAAGACGGCCAACGTGCCCCAGACCGTGCCCA

TGAGGCTCCGGAAGCTGCCCGACTCCTTCTTCAAGCCGCCGGAGCCCAAATCCCACTCCCGACA

GGCCAGTACTGATGCAGGCACTGCAGGAGCCCTGACTCCACAGCATGTTCGAGCTCATTCCTCT

CCAGCTTCTCTGCAGTTGGGAGCTGTTTCTCCTGGGACACTGACCCCCACTGGAGTAGTCTCTG

GCCCAGCAGCTACACCCACAGCTCAGCATCTTCGACAGTCTTCTTTTGAGATACCTGATGATGT

ACCTCTGCCAGCAGGTTGGGAGATGGCAAAGACATCTTCTGGTCAGAGATACTTCTTAAATCAC

ATCGATCAGACAACAACATGGCAGGACCCCAGGAAGGCCATGCTGTCCCAGATGAACGTCACAG

CCCCCACCAGTCCACCAGTGCAGCAGAATATGATGAACTCGGCTTCAGCCATGAACCAGAGAAT

CAGTCAGAGTGCTCCAGTGAAACAGCCACCACCCCTGGCTCCCCAGAGCCCACAGGGAGGCGTC

ATGGGTGGCAGCAACTCCAACCAGCAGCAACAGATGCGACTGCAGCAACTGCAGATGGAGAAGG

AGAGGCTGCGGCTGAAACAGCAAGAACTGCTTCGGCAGGCAATGCGGAATATCAATCCCAGCAC

AGCAAATTCTCCAAAATGTCAGGAGTTAGCCCTGCGTAGCCAGTTACCAACACTGGAGCAGGAT

GGTGGGACTCAAAATCCAGTGTCTTCTCCCGGGATGTCTCAGGAATTGAGAACAATGACGACCA

ATAGCTCAGATCCTTTCGTTAACAGTGGCACCTATCACTCTCGAGATGAGAGTACAGACAGTGG

ACTAAGCATGAGCAGCTACAGTGTCCCTCGAACCCCAGATGACTTCCTGAACAGTGTGGATGAG

ATGGATACAGGTGATACTATCAACCAAAGCACCCTGCCCTCACAGCAGAACCGTTTCCCAGACT

ACCTTGAAGCCATTCCTGGGACAAATGTGGACCTTGGAACACTGGAAGGAGATGGAATGAACAT

AGAAGGAGAGGAGCTGATGCCAAGTCTGCAGGAAGCTTTGAGTTCTGACATCCTTAATGACATG

GAGTCTGTTTTGGCTGCCACCAAGCTAGATAAAGAAAGCTTTCTTACATGGTTATAG
```

SEQ ID NO: 2. Human YAP1 isoform 2L protein (504 amino acids)
MDPGQQPPPQPAPQGQGQPPSQPPQGQGPPSGPGQPAPAATQAAPQAPPAGHQIVHVRGDSETD

LEALFNAVMNPKTANVPQTVPMRLRKLPDSFFKPPEPKSHSRQASTDAGTAGALTPQHVRAHSS

PASLQLGAVSPGTLTPTGVVSGPAATPTAQHLRQSSFEIPDDVPLPAGWEMAKTSSGQRYFLNH

IDQTTTWQDPRKAMLSQMNVTAPTSPPVQQNMMNSASGPLPDGWEQAMTQDGEIYYINHKNKTT

SWLDPRLDPRFAMNQRISQSAPVKQPPPLAPQSPQGGVMGGSNSNQQQQMRLQQLQMEKERLRL

KQQELLRQAMRNINPSTANSPKCQELALRSQLPTLEQDGGTQNPVSSPGMSQELRTMTTNSSDP

FLNSGTYHSRDESTDSGLSMSSYSVPRTPDDFLNSVDEMDTGDTINQSTLPSQQNRFPDYLEAI

PGTNVDLGTLEGDGMNIEGEELMPSLQEALSSDILNDMESVLAATKLDKESFLTWL

SEQ ID NO: 3. Human 14-3-3 protein theta mRNA (738 nucleotides)
(accession number: P27348)

```
ATGGAGAAGACTGAGCTGATCCAGAAGGCCAAGCTGGCCGAGCAGGCCGAGCGCTACGACGACA

TGGCCACCTGCATGAAGGCAGTGACCGAGCAGGGCGCCGAGCTGTCCAACGAGGAGCGCAACCT

GCTCTCCGTGGCCTACAAGAACGTGGTCGGGGGCCGCAGGTCCGCCTGGAGGGTCATCTCTAGC

ATCGAGCAGAAGACCGACACCTCCGACAAGAAGTTGCAGCTGATTAAGGACTATCGGGAGAAAG

TGGAGTCCGAGCTGAGATCCATCTGCACCACGGTGCTGGAATTGTTGGATAAATATTTAATAGC

CAATGCAACTAATCCAGAGAGTAAGGTCTTCTATCTGAAAATGAAGGGTGATTACTTCCGGTAC

CTTGCTGAAGTTGCGTGTGGTGATGATCGAAAACAAACGATAGATAATTCCCAAGGAGCTTACC

AAGAGGCATTTGATATAAGCAAGAAAGAGATGCAACCCACACACCCAATCCGCCTGGGGCTTGC

TCTTAACTTTTCTGTATTTTACTATGAGATTCTTAATAACCCAGAGCTTGCCTGCACGCTGGCT

AAAACGGCTTTTGATGAGGCCATTGCTGAACTTGATACACTGAATGAAGACTCATACAAAGACA
```

-continued

GCACCCTCATCATGCAGTTGCTTAGAGACAACCTAACACTTTGGACATCAGACAGTGCAGGAGA

AGAATGTGATGCGGCAGAAGGGGCTGAAAACTAA

SEQ ID NO: 4. Human 14-3-3 protein theta (245 amino acids)
MEKTELIQKAKLAEQAERYDDMATCMKAVTSQGAELSNSERNLLSVAYKNVVGGRRSAWRVISS

IEQKTDTSDKKLQLIKDYREKVESELRSICTTVLELLDKYLIANATHPESKVFYLKMKGDYFRY

LAEVACGDDRKQTIDNSQGAYQEAFDISKKEMQPTHPIRLGLALNFSVFYYEILNNPELACTLA

KTAFDEAIAELDTLNEDSYKDSTLIMQLLRDNLTLWTSDSAGEECDAAEGAEN

SEQ ID NO: 5. Firefly (Photinus pyralis) luciferase mRNA (1,653 nucleotides)
ATGGAAGACGCCAAAAACATAAAGAAAGGCCCGGCGCCATTCTATCCGCTGGAAGATGGAACCG

CTGGAGAGCAACTGCATAAGGCTATGAAGAGATACGCCCTGGTTCCTGGAACAATTGCTTTTAC

AGATGCACATATCGAGGTGGACATCACTTACGCTGAGTACTTCGAAATGTCCGTTCGGTTGGCA

GAAGCTATGAAACGATATGGGCTGAATACAAATCACAGAATCGTCGTATGCAGTGAAAACTCTC

TTCAATTCTTTATGCCGGTGTTGGGCGCGTTATTTATCGGAGTTGCAGTTGCGCCCGCGAACGA

CATTTATAATGAACGTGAATTGCTCAACAGTATGGGCATTTCGCAGCCTACCGTGGTGTTCGTT

TCCAAAAAGGGGTTGCAAAAAATTTTGAACGTGCAAAAAAAGCTCCCAATCATCCAAAAAATTA

TTATCATGGATTCTAAAACGGATTACCAGGGATTTCAGTCGATGTACACGTTCGTCACATCTCA

TCTACCTCCCGGTTTTAATGAATACGATTTTGTGCCAGAGTCCTTCGATAGGGACAAGCAATT

GCACTGATCATGAACTCCTCTGGATCTACTGGTCTGCGTAAAGGTGTCGCTCTGCCTCATAGAA

CTGCCTGCGTGAGATTCTCGCATGCCAGAGATCCTATTTTTGGCAATGAAATCATTCCGGATAC

TGCGATTTTAAGTGTTGTTGCATTCCATCACGGTTTTGGAATGTTTACTACACTCGGATATTTG

ATATGTGGATTTCGAGTCGTCTTAATGTATAGATTTGAAGAAGACCTGTTTCTGAGGAGCCTTC

AGGATTACAAGATTCAAAGTGCGCTGCTGGTGCCAACCCTATTCTCCTTCTTCGCCAAAAGCAC

TCTGATTGACAAATACGATTTATCTAATTTACACGAAATTGCTTCTGGTGGCGCTCCCCTCTCT

AAGGAAGTCGGGGAAGCGGTTGCCAAGAGGTTCCATCTGCCAGGTATCAGGCAAGGATATGGGC

TCACTGAGACTACATCAGCTATTCTGATTACACCCGAGGGGGATGATAAACCGGGCGCGGTCGG

TAAAGTTGTTCCATTTTTTGAAGCGAAGGTTGTGGATCTGGATACCGGGAAAACGCTGGGCGTT

AATCAAAGAGGCGAACTGTGTGTGAGAGGTCCTATGATTATGTCCGGTTATGTAAACAATCCGG

AAGCGACCAACGCCTTGATTGACAAGGATGGATGGCTACATTCTGGAGACATAGCTTACTGGGA

CGAAGACGAACACTTCTTCATCGTTGACCGCCTGAAGTCTCTGATTAAGTACAAAGGCTATCAG

GTGGCTCCCGCTGAATTGGAATCCATCTTGCTCCAACACCCCAACATCTTCGACGCAGGTGTCG

CAGGTCTTCCCGACGATGACGCCGGTGAACTTCCCGCCGCCGTTGTTGTTTGGAGCACGGAAA

GACGATGACGGAAAAAGAGATCGTGGATTACGTCGCCAGTCAAGTAACAACCGCGAAAAAGTTG

CGCGGAGGAGTTGTGTTTGTGGACGAAGTACCGAAAGGTCTTACCGGAAAACTCGACGCAAGAA

AAATCAGAGAGATCCTCATAAAGGCCAAGAAGGGCGGAAAGATCGCCGTGTAA

SEQ ID NO: 6. Firefly (Photinus pyralis) luciferase protein (555 amino acids)
MEDAKNIKKGPAPFYPLEDGTAGEQLHKAMKRYALVPGTIAFTDAHIEVDITYAEYFEMSVRLA

EAMKRYGLNTNHRIVVCSENSLQFFMPVLGALFIGVAVAPANDIYNERELLNSMGISQPTVVFV

SKKGLQKILNVQKKLPIIQKIIIMDSKTDYQGFQSMYTFVTSHLPPGFKEYDFVPESFDRDKTI

ALIMNSSGSTGLPKGVALPHRTACVRFSHARDPIFGNQIIPDTAILSVVPFHHGFGMFTTLGYL

ICGFRVVLMYRFEEELFLRSLQDYKIQSALLVPTLFSFFAKSTLIDKYDLSNLHEIASGGAPLS

KEVGEAVAKRFHLPGIRQGYGLTETTSAILITPEGDDKPGAVGKVVPFFEAKVVDLDTGKTLGV

-continued

NQRGELCVRGPMIMSGYVNNPEATNALIDKDGWLHSGDIAYWDEDEHFFIVDRLKSLIKYKGYQ

VAPAELESILLQHPNIFDAGVAGLPDDDAGELPAAVVVLEKGKTMTEKEIVDYVASQVTTAKKL

RGGVVFVDEVPKGLTGKLDARKIREILIKAKKGGKIAV

SEQ ID NO: 7. YAP15 S127 wildtype (WT) protein fragment (15 amino acids)
PQHVRHASSPASLQL SEQ ID NO: 8. YAP15 A127 mutant protein fragment (15 amino acids)
PQHVRHAASPASLQL SEQ ID NO: 9. pcDNA3.1/hygro(+) vector (5,597 nucleotides)
GACGGATCGGGAGATCTCCCGATCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAA

ATTTAAGCTACAACAAGGCAAGGCTTGACCGACAATTGCATGAAGAATCTGCTTAGCGTTAGGC

GTTTTGCGCTGCTTCGCGATGTACGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGACTCACTATAGGGAGACCCAAGCTGGC

TAGCGTTTAAACTTAAGCTTGGTACCGAGCTCGGATCCACTAGTCCAGTGTGGTGGAATTCTGC

AGATATCCAGCACAGTGGCGGCCGCTCGAGTCTAGAGGGCCCGTTTAAACCCGCTGATCAGCCT

CGACTGTGCCTTCTAGTTGCCAGCCATCTGTTGTTTGCCCCTCCCCCGTGCCTTCCTTGACCCT

GGAAGGTGCCACTCCCACTGTCCTTTCCTAATAAAATGAGGAAATTGCATCGCATTGTCTGAGT

AGGTGTCATTCTATTCTGGGGGGTGGGGTGGGCAGGACAGCAAGGGGGAGGATTGGGAAGACA

ATAGCAGGCATGCTGGGGATGCGGTGGGCTCTATGGCTTCTGAGGCGGAAAGAACCAGCTGGGG

CTCTAGGGGGTATCCCCACGCGCCCTGTAGCGGCGCATTAAGCGCGGCGGGTGTGGTGGTTACG

CGCAGCGTGACCGCTACACTTGCCAGCGCCCTAGCGCCCGCTCCTTTCGCTTTCTTCCCTTCCT

TTCTCGCCACGTTCGCCGGCTTTCCCCGTCAAGCTCTAAATCGGGGGCTCCCTTTAGGGTTCCG

ATTTAGTGCTTTACGGCACCTCGACCCCAAAAAACTTGATTAGGGTGATGGTTCACGTAGTGGG

CCAT0GCCCTGATAGACGGTTTTTCGCCCTTTGACGTTGGAGTCCACGTTCTTTAATAGTGGAC

TCTTGTTCCAAACTGGAACAACACTCAACCCTATCTCGGTCTATTCTTTTGATTTATAAGGGAT

TTTGCCGATTTCGGCCTATTGGTTAAAAAATGAGCTGATTTAACAAAAATTTAACGCGAATTAA

TTCTGTGGAATGTGTGTCAGTTAGGGTGTGGAAAGTCCCCAGGCTCCCCAGCAGGCAGAAGTAT

GCAAAGCATGCATCTCAATTAGTCAGCAACCAGGTGTGGAAAGTCGCCAGGCTCCCCAGCAGGC

AGAAGTATGCAAAGCATGCATCTCAATTAGTCAGCAACCATAGTCCCGCCCCTAACTCCGCCGA

TCCCGCCCCTAACTCCGCCCAGTTCCGCCCATTCTCCGCCCCATGGCTGACTAATTTTTTTTAT

TTATGCAGAGGCCGAGGCCGCCTCTGCCTCTGAGCTATTCCAGAAGTAGTGAGGAGGCTTTTTT

GGAGGCCTAGGCTTTTGCAAAAAGCTCCCGGGAGCTTGTATATCCATTTTCGGATCTGATCAGC

-continued

```
ACGTGATGAAAAAGCCTGAACTCACCGCGACGTCTGTCGAGAAGTTTCTGATCGAAAAGTTCGA

CAGCGTCTCCGACCTGATGCAGCTCTCGGAGGGCGAAGAATCTCGTGCTTTCAGCTTCGATGTA

GGAGGGCGTGGATATGTCCTGCGGGTAAATAGCTGCGCCGATGGTTTCTACAAAGATCGTTATG

TTTATCGGCACTTTGCATCGGCCGCGCTCCCGATTCCGGAAGTGCTTGACATTGGGGAATTCAG

CGAGAGCCTGACCTATTGCATCTCCCGCCGTGCACAGGGTGTCACGTTGCAAGACCTGCCTGAA

ACCGAACTGCCCGCTGTTCTGCAGCCGGTCGCGGAGGCCATGGATGCGATCGCTGCGGCCGATC

TTAGCCAGACGAGCGGGTTCGGCCCATTCGGACCGCAAGGAATCGGTCAATACACTACATGGCG

TGATTTCATATGCGCGATTGCTGATCCCCATGTGTATCACTGGCAAACTGTGATGGACGACACC

GTCAGTGCGTCCGTCGCGCAGGCTCTCGATGAGCTGATGCTTTGGGCCGAGGACTGCCCCGAAG

TCCGGCAGCTCGTGCACGCGGATTTCGGCTCCAACAATGTCCTGACGGACAATGGCCGGATAAC

AGCGGTCATTGACTGGAGCGAGGCGATGTTCGGGGATTCCCAATACGAGGTCGCCAACATGTTC

TTCTGGAGGCCGTGGTTGGCTTGTATGGAGCAGCAGACGCGCTACTTCGAGCGGAGGCATCCGG

AGCTTGCAGGATCGCCGCGGCTCCGGGCGTATATGCTCCGCATTGGTCTTGACCAACTCTATCA

GAGCTTGGTTGACGGCAATTTGGATGATGCAGCTTGGGCGCAGGGTCGATGCGACGGAATCGTC

CGATCCGGAGCCGGGACTGTCGGGCGTACAGAAATCGCCCGCAGAAGCGCGGCCGTGTGGACCG

ATGGCTGTGTAGAAGTACTCGCCGATAGTGGAAAGCGACGCCCCAGCACTCGTCCGAGGGCAAA

GGAATAGCACGTGCTACGAGATTTCGATTCCACCGCCGCCTTCTATGAAAGGTTGGGCTTCGGA

ATCGTTTTCCGGGACGCCGGCTGGATGATCCTCCAGCGCGGGATCTGATGCTGGAGTTCTTCG

CCCACCCCAACTTGTTTATTGCAGCTTATAATGGTTACAAATAAAGCAATAGCATCACAAATTT

CACAAATAAAGCATTTTTTTCACTGCATTCTAGTTGTGGTTTGTCCAAACTCATCAATGTATCT

TATCATGTCTGTATACCGTCGACCTCTAGCTAGAGCTTGGCGTAATCATGGTCATAGCTGTTTC

CTGTGTGAAATTGTTATCCGCTCACAATTCCACACAACATACGAGCCGGAAGCATAAAGTGTAA

AGCCTGGGGTGCCTAATGAGTGAGCTAACTCACATTAATTGCGTTGCGCTCACTGCGCGCTTTC

CAGTCGGGAAACCTGTCGTGCCAGCTGCATTAATGAATCGGCCAACGCGCGGGAGAGGCGGTT

TGCGTATTGGGCGCTCTTCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGGATAACGCA

GGAAAGAACATGTGAGCAAAAGGCCAGCAAAAGGCCAGGAACCGTAAAAAGGGCGCGTTGCTGG

CGTTTTTCCATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCGTGCGCTCT

CCTGTTCCGACCCTGCCGCTTACCGGATACCTGTCCGCCTTTCTCCCTTCGGGAAGCGTGGCGC

TTTCTCATAGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGTCC

AACCCGGTAAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTAGAAGAAC

AGTATTTGGTATCTGCGCTCTGCTGAAGCCAGTTACCTTCGGAAAAAGAGTTGGTAGCTCTTGA

TCCGGCAAACAAACCACCGCTGGTAGCGGTTTTTTTGTTTGCAAGCAGCAGATTACGCGCAGAA

AAAAGGATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCTTTTAAAT

TAAAAATGAAGTTTTAAATCAATCTAAAGTATATATGAGTAAACTTGGTCTGACAGTTACCAAT

GCTTAATCAGTGAGGCACCTATCTCAGCGATCTGTCTATTTCGTTCATCCATAGTTGCCTGACT
```

-continued
CCCCGTCGTGTAGATAACTACGATACGGGAGGGCTTACCATCTGGCCCCAGTGCTGCAATGATA

CCGCGAGACCCACGCTCACCGGCTCCAGATTTATCAGCAATAAACCAGCCAGCCGGAAGGGCCG

AGCGCAGAAGTGGTCCTGCAACTTTATCCGCCTCCATCGAGTCTATTAATTGTTGCCGGGAAGC

TAGAGTAAGTAGTTCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGATCAAGGCGAGTTA

CATGATCCCCATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCTTACTGTCATG

CCATCCGTAAGATGCTTTTCTGTGACTGGTGAGTACTCAACCAAGTCATTCTGAGAATAGTGTA

TGCGGCGACCGAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTACTTTCA

CCAGCGTTTCTGGGTGAGCAAAAACAGGAAGGCAAAATGCCGCAAAAAAGGGAATAAGGGCGAC

ACGGAAATGTTGAATACTCATACTCTTCCTTTTTCAATATTATTGAAGCATTTATCAGGGTTAT

TGTCTCATGAGCGGATACATATTTGAATGTATTTAGAAAAATAAACAAATAGGGGTTCCGCGCA

CATTTCCCCGAAAAGTGCCACCTGAGGTC

SEQ ID NO: 10. B1-Kozak-Nluc-F primer (41 nucleotides)
CTGGATCCGCCGCCACCATGGAAGACGCCAAAAACATG SEQ ID NO: 11. Nluc-416-Yap-15-S127-(GGAGG)-R primer (84 nucleotides)
TTACAACTGCAGAGAAGCTGGAGAGGAATGAGCTCGAACATGCTGTGGGCCTCCAGCTCCTCCT

CCATCCTTGTCAATCAAGGC

SEQ ID NO: 12. N1-Yap-5-Overlapping PCR-R primer (36 nucleotides)
ATGATACTGCGGCCGCTTACAACTGCAGAGAAGCTG SEQ ID NO: 13. B1-Kozak-14-3-3-F primer (38 nucleotides)
CTGGATCCGCCGCCACCATGGAGAAGACTGAGCTGATC SEQ ID NO: 14. (GGGGS)2-14-3-3-R primer (51 nucleotides)
ACTACCTCCTCCTCCACTACCTCCTCCTCCGTTTTCAGCCCCTTCTGCCGC SEQ ID NO: 15. (GGGGS)2-Cluc394-F primer (39 nucleotides)
GGTAGTGGAGGAGGAGGTAGTGGTCCTATGATTATGTCC SEQ ID NO: 16. N1-Cluc-R primer (34 nucleotides)
ATGAAACTGCGGCCGCTTACACGGCGATCTTTCC SEQ ID NO: 17. Nluc398-15-S127-(GGAGG)-R primer (81 nucleotides)
CAACTGCAGAGAAGCTGGAGAGGAATGAGCTCGAACATGCTGTGGGCCTCCAGCTCCTCCCATA

ATCATAGGACCTCTCAC

SEQ ID NO: 18. Yap15-S127-Cluc394-F primer (42 nucleotides)
TCTCCAGCTTCTCTGCAGTTGGGTCCTATGATTATGTCCGGT SEQ ID NO: 19. N1-Yap15-S127-Cluc443 (engineered C-terminus of luciferase)-R primer (86 nucleotides)
ATGAAACTGCGGCCGCTTACAACTGCAGAGAAGCTGGAGAGGAATGAGCTCGAACATGCTGTGG

CTTCTTGGCCTTTATGAGGATC

SEQ ID NO: 20. EcoR1-YAP-S127-BglII-S primer (55 nucleotides)
AATTCACCACAGCATGTTCGAGGTCATTCCTCTCCAGCTTCTCTGCAGTTGTGAA SEQ ID NO: 21. ECoR1-YAP-S127-BglII-AS primer (55 nucleotides)
GATCTTCACAACTGCAGAGAAGCTGGAGAGGAATGAGCTCGAACATGCTGTGGTG SEQ ID NO: 22. EcoR1-YAP-A127-BglII-S primer (55 nucleotides)
AATTCACCACAGCATGTTCGAGCTCATGCGTCTCCAGCTTCTCTGCAGTTGTGAA SEQ ID NO: 23. ECoR1-YAP-A127-BglII-AS primer (55 nucleotides)
GATCTTCACAACTGCAGAGAAGCTGGAGACGCATGAGCTCGAACATGCTGTGGTG -continued SEQ ID NO: 24. BglII-14-3-3-F primer (31 nucleotides)
GGAAGATCTAATGGAGAAGACTGAGCTGATC SEQ ID NO: 25. ECoR1-14-3-3-R primer (34 nucleotides)
CGCCGGAATTCCCGTTTTCAGCCCCTTCTGCCGC SEQ ID NO: 26. pBiT 1.1 N (TK-Larg BiT) whole vector (3,858 nucleotides)
GGCCTAACTGGCCGGTACCTGAGTCTAAATGAGTCTTCGGACCTCGCGGGGCCGCTTAACCGG
TGGTTAGGGTTTGTCTGACGCGGGGGGAGGGGAAGGAACGAAACACTCTCATTCGGAGGCGGC
TCGGGGTTTGGTCTTGGTGGCCACGGGCACGCAGAAGAGCGCCGCGATCCTCTTAAGCACCCCC
CCGCCCTCCGTGGAGGCGGGGGTTTGGTCGGCGGGTGGTAACTGGCGGGCGGCTGACTCGGGCG
GGTCGCGCGCCCCAGAGTGTGACCTTTTCGGTCTGCTCGCAGACCCCCGGGCGGCGCCGCCGCG
GCGGCGACGGGCTCGCTGGGTCCTAGGCTCCATGGGGACCGTATACGTGGACAGGCTCTGGAGC
ATCCGCACGACTGCGGTGATATTAGCGGAGACCTTCTGCGGGACGAGCCGGGTCACGCGGCTGA
CGCGGAGCGTCGGTTGGGCGACAAACAGCAGGACGGGGCACAGGTACACTATCTTGTCACCCGG
AGGCGCGAGGGACTGCAGGAGCTTCAGGGAGTGGCGCAGCTGCTTCATCCCCGTGGCCCGTTGC
TCGCGTTTGCTGGCGGTGTCCCCGGAAGAAATATATTTGCATGTCTTTAGTTCTATGATGACAC
AAACCCCGCCCAGCGTCTTGTCATTGGCGAAGTCGAACACGCAGATGCAGTCGGGGCGGCGCGG
TCCCAGGTCCACTTCGCATATTAAGGTGACGCGTGTGGCCTCGAACACCGAGCGACCCTGCAGC
GACCCGCTTAAAAGCTTGGCAATCCGGTACTGTTGGTAAAGCCACCATGGTCTTCACACTCGAA
GATTTCGTTGGGGACTGGGAACAGACAGCCGCCTACAACCTGGACCAAGTCCTTGAACAGGGAG
GTGTGTCCAGTTTGCTGCAGAATCTCGCCGTGTCCGTAACTCCGATCCAAAGGATTGTCCGGAG
CGGTGAAAATGCCCTGAAGATCGACATCCATGTCATCATCCCGTATGAAGGTCTGAGCGCCGAC
CAAATGGCCCAGATCGAAGAGGTGTTTAAGGTGGTGTACCCTGTGGATGATCATCACTTTAAGG
TGATCCTGCCCTATGGCACACTGGTAATCGACGGGGTTACGCCGAACATGCTGAACTATTTCGG
ACGGCCGTATGAAGGCATCGCCGTGTTCGACGGCAAAAAGATCACTGTAACAGGGACCCTGTGG
AACGGCAACAAAATTATCGACGAGCGCCTGATCACCCCCGACGGCTCCATGCTGTTCCGAGTAA
GCATCAACAGTGGGAGTTCCGGTGGTGGCGGGAGCGGAGGTGGAGGGTCGAGCGGTGGAGCTCA
GGGGAATTCAGTCTAAGCTAGCAGATCTTCTAGAGTCGGGGCGGCCGGCCGCTTCGAGCAGACA
TGATAAGATAGATTGATGAGTTTGGACAAACCACAACTAGAATGCAGTGAAAAAAATGCTTTAT
TTGTGAAATTTGTGATGCTATTGCTTTATTTGTAACCATTATAAGCTGCAATAAACAAGTTAAC
AACAACAATTGCATTCATTTTATGTTTCAGGTTCAGGGGAGGTGTGGGAGGTTTTTTAAAGCA
AGTAAAACCTCTACAAATGTGGTAAAATCGATAAGGATCCGTCGACCGATGCCCTTGAGAGCCT
TCAACCCAGTCAGCTCCTTCCGGTGGGCGCGGGGCATGACTATCGTCGCCGCACTTATGACTGT
CTTCTTTATCATGCAACTCGTAGGACAGGTGCCGGCAGCGCTCTTCCGCTTCCTCGCTCACTGA
CTCGCTGCGCTCGGTCGTTCGGCTGCGGCGAGCGGTATCAGCTCACTCAAAGGCGGTAATACGG
TTATCCACAGAATCAGGGGATAACGCAGGAAAGAACATGTGAGCAAAAGGCCAGCAAAAGGCCA
GGAACCGTAAAAAGGCCGCGTTGCTGGCGTTTTTCCATAGGCTCCGCCCCCCTGACGAGCATCA
CAAAAATCGACGCTCAAGTCAGAGGTGGCGAAACCCGACAGGACTATAAAGATACCAGGCGTTT
CCCCCTGGAAGCTCCCTCGTGCGCTCTCCTGTTCCGACCCTGCCGCTTACCGGATACCTGTCCG
CCTTTCTCCCTTCGGGAAGCGTGGCGCTTTCTCATAGCTCACGCTGTAGGTATCTCAGTTCGGT
GTAGGTCGTTCGCTCCAAGCTGGGCTGTGTGCACGAACCCCCCGTTCAGCCCGACCGCTGCGCC
TTATCCGGTAACTATCGTCTTGAGTCCAACCCGGTAAGACACGACTTATCGCCACTGGCAGCAG
CCACTGGTAACAGGATTAGCAGAGCGAGGTATGTAGGCGGTGCTACAGAGTTCTTGAAGTGGTG

```
GCCTAACTACGGCTACACTAGAAGAACAGTATTTGGTATCTGCGCTCTGCTGAAGCCAGTTACC

TTCGGAAAAAGAGTTGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGATCCTTTGATCTTTTC

TACGGGGTCTGAGGCTCAGTGGAACGAAAAGTCAGGTTAAGGGATTTTGGTCATGAGATTATCA

AAAAGGATCTTCACCTAGATCCTTTTTAAATTAAAAATGAAGTTTTAAATCAATCTAAAGTATA

ATGAGTAAACTTGGTCTGACAGCGGCCGCAAATGCTAAACCACTGCAGTGGTTACCAGTGCTTG

ATCAGTGAGGCACCGATCTCAGCGATCTGCCTATTTCGTTCGTCCATAGTGGCCTGACTCCCCG

TCGTGTAGATCACTAGGATTCGTGAGGGCTTAGCATCAGGCCCCAGCGCAGCAATGATGCCGCG

AGAGCCGCGTTCACCGGCCCCCGATTTGTCAGCAATGAACCAGCCAGCAGGGAGGGCCGAGCGA

AGAAGTGGTCCTGCTACTTTGTCCGCCTCCATCCAGTCTATGAGCTGCTGTCGTGATGCTAGAG

TAAGAAGTTCGCCAGTGAGTAGTTTCCGAAGAGTTGTGGCCATTGCTACTGGCATCGTGGTATC

ACGCTCGTCGTTCGGTATGGCTTCGTTCAACTCTGGTTCCCAGCGGTCAAGCCGGGTCACATGA

TCACCCATATTATGAAGAAATGCAGTCAGCTCCTTAGGGCCTCCGATCGTTGTCAGAAGTAAGT

TGGCCGCGGTGTTGTCGCTCATGGTAATGGCAGCACTACACAATTCTCTTACCGTCATGGCATC

CGTAAGATGCTTTTCCGTGACCGGCGAGTACTCAACCAAGTCGTTTTGTGAGTAGTGTATACGG

CGACCAAGCTGCTCTTGCCCGGCGTGTATACGGGACAACACCGCGCCACATAGCAGTACTTTGA

AAGTGCTCATCATCGGGAATCGTTCTTCGGGGCGGAAAGACTCAAGGATCTTGCCGCTATTGAG

ATCCAGTTCGATATAGCCCACTCTTGCACCCAGTTGATCTTCAGCATCTTTTACTTTCACCAGC

GTTTCGGGGTGTGCAAAAACAGGCAAGCAAAATGCCGCAAAGAAGGGAATGAGTGCGACACGAA

AATGTTGGATGCTCATACTCGTCCTTTTTCAATATTATTGAAGCATTTATGAGGGTTACTAGTA

CGTCTCTCAAGGATAAGTAAGTAATATTAAGGTACGGGAGGTATTGGACAGGCCGCAATAAAAT

ATCTTTATTTTCATTACATCTGTGTGTTGGTTTTTTGTGTGAATCGATAGTACTAACATACGCT

CTCCATCAAAACAAAACGAAACAAAACAAACTAGCAAAATAGGCTGTCCCCAGTGCAAGTGCAG

GTGCCAGAACATTTCTCT

SEQ ID NO: 27. pBiT 2.1 C (TK-SmBiT) whole vector (3,423
nucleotides)
GGCCTAACTGGCCGGTACCTGAGTCTAAATGAGTCTTCGGACCTCGCGGGGCCGCTTAAGCGG

TGGTTAGGGTTTGTCTGACGCGGGGGGAGGGGGAAGGAACGAAACACTCTCATTCGGAGGCGGC

TCGGGGTTTGGTCTTGGTGGCCACGGGCACGCAGAAGAGCGCCGCGATCCTCTTAAGCACCCCC

CCGCCCTCCGTGGAGGCGGGGGTTTGGTCGGCGGGTGGTAACTGGCGGGCCGCTGACTCGGGCG

GGTCGCGCGCCCCAGAGTGTGACCTTTTCGGTCTGCTCGGAGACCCCCGGGCGGCGCCGCCGCG

GCGGCGACGGGCTCGCTGGGTCCTAGGCTCCATGGGACCGTATACGTGGACAGGCTCTGGAGC

ATCCGCACGACTGCGGTGATATTACCGGAGACCTTGTGCGGGACGAGCCGGGTCACGCGGCTGA

CGCGGAGCGTCCGTTGGGCGACAAACACCAGGACGGGGCACAGGTACACTATCTTGTCACCCGG

AGGCGCGAGGGACTGCAGGAGCTTCAGGGAGTGGCGCAGCTGCTTCATCCCCGTGGCCCGTTGC

TCGCGTTTGCTGGCGGTGTCCCCGGAAGAAATATATTTGCATGTCTTTAGTTCTATGATGACAC

AAACCCCGCCCAGCGTCTTGTCATTGGCGAAGTCGAACACGCAGATGCACTCGGGGCGGCGCGG

TCCCAGGTCCACTTCGCATATTAAGGTGACGCGTGTGGCCTCGAACACCGAGCGACCCTGCAGC

GACCCGCTTAAAAGCTTGGCAATCCGGTACTGTGGTAAAGCCACCAGATCTGCTAGCGATCGCC

TAAGTGGGAGCTCAGGGGAATTCTGGCTCGAGCGGTGGTGGCGGGAGCGGAGGTGGAGGGTCGT

CAGGTGTGACCGGCTACCGGCTGTTCGAGGAGATTCTGTAATCTAGAGTCGGGGCGGCCGGCGG
```

```
CTTCGAGCAGACATGATAAGATACATTGATGAGTTTGGACAAACCACAACTAGAATGCAGTGAA
AAAAATGCTTTATTTGTGAAATTTGTGATGCTATTGCTTTATTTGTAACCATTATAAGCTGCAA
TAAACAAGTTAACAACAACAATTGCATTCATTTTATGTTTCAGGTTCAGGGGGAGGTGTGGGAG
GTTTTTTAAAGCAAGTAAAAGCTCTACAAATGTGGTAAAATCGATAAGGATGCGTCGACCGATG
CCCTTGAGAGCCTTCAACCCAGTCAGCTCCTTCCGGTGGGCGCGGGGCATGACTATCGTCGCCG
CAGTTATGACTGTCTTCTTTATCATGCAACTCGTAGGACAGGTGCCGGCAGCGCTCTTCCGCTT
CCTCGCTCACTGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTGAGCAAAAGGC
CAGCAAAAGGCCAGGAACCGTAAAAAGGCCGCGTTGCTGGCGTTTTTCCATAGGCTCCGCCCCC
CTGACGAGCATCACAAAAATCGACGCTCAAGTCAGAGGTGGCGAAACCCGACAGGACTATAAAG
ATACCAGGCGTTTCCCCCTGGAAGCTCCCTCGTGCGCTCTCCTGTTCCGACCCTGCCGCTTACC
GGATACCTGTCCGCCTTTCTCCCTTCGGGAAGCGTGGCGCTTTCTCATAGCTCACGCTGTAGGT
ATCTCAGTTCGGTGTAGGTCGTTCGCTCCAAGCTGGGCTGTGTGCACGAACCCCCCGTTCAGCC
CGACCGCTGCGCCTTATCCGGTAACTATCGTCTTGAGTCCAACCCGGTAAGACACGACTTATCG
CCACTGGCAGCAGCCACTGGTAACAGGATTAGCAGAGCGAGGTATGTAGGCGGTGCTACAGAGT
TCTTGAAGTGGTGGCCTAACTACGGCTACACTAGAAGAACAGTATTTGGTATCTGCGCTCTGCT
GAAGCCAGTTACCTTCGGAAAAAGAGTTGGTAGCTCTTGATCCGGCAAACAAACCACCGCTGGT
AGCGGTGGTTTTTTTGTTTGCAAGCAGCAGATTACGCGCAGAAAAAAAGGATCTCAAGAAGATC
CTTTGATCTTTTCTACGGGGTCTGACGCTCAGTGGAACGAAAACTCACGTTAAGGGATTTTGGT
CATGAGATTATCAAAAAGGATCTTCACCTAGATCCTTTTAAATTAAAAATGAAGTTTTAAATCA
ATCTAAAGTATATATGAGTAAACTTGGTCTGACAGCGGCCGCAAATGCTAAACCACTGCAGTGG
TTACCAGTGCTTGATCAGTGAGGCACCGATCTCAGCGATCTGCCTATTTCGTTCGTCCATAGTG
GCCTGACTCCCCGTCGTGTAGATCACTACGATTCGTGAGGGCTTACCATCAGGCCCCAGCGCAG
CAATGATGCCGCGAGAGCCGCGTTCACCGGCCCCCGATTTGTCAGCAATGAACCAGCCAGCAGG
GAGGGCCGAGCGAAGAAGTGGTCCTGCTACTTTGTCCGCCTCCATCCAGTCTATGAGCTGCTGT
CGTGATGCTAGAGTAAGAAGTTCGCCAGTGAGTAGTTTCCGAAGAGTTGTGGCCATTGCTACTG
GCATGGTGGTATCACGCTCGTCGTTCGGTATGGCTTCGTTCAACTCTGGTTCCCAGCGGTCAAG
CCGGGTCACATGATCACCCATATTATGAAGAAATGCAGTCAGCTCCTTAGGGCCTCCGATCGTT
GTCAGAAGTAAGTTGGCCGCGGTGTTGTCGCTCATGGTAATGGCAGCACTACACAATTCTCTTA
CCGTCATGCCATCCGTAAGATGCTTTTCCGTGACCGGCGAGTACTCAACCAAGTCGTTTTGTGA
GTAGTGTATACGGCGACCAAGCTGCTGTTGCCCGGCGTCTATACGGGACAACACCGCGCCACAT
AGCAGTACTTTGAAAGTGCTCATCATCGGGAATCGTTCTTCGGGGCGGAAAGACTCAAGGATCT
TGCCGCTATTGAGATCCAGTTCGATATAGCCCACTCTTGCACCCAGTTGATCTTCAGCATCTTT
TACTTTCACCAGCGTTTCGGGGTGTGCAAAAACAGGCAAGCAAATGCCGCAAAGAAGGGAATG
AGTGCGACACGAAAATGTTGGATGCTCATACTCGTCCTTTTTCAATATTATTGAAGCATTTATC
AGGGTTACTAGTACGTCTCTCAAGGATAAGTAAGTAATATTAAGGTACGGGAGGTATTGGACAG
GCCGCAATAAAATATCTTTATTTTCATTACATCTGTGTGTTGGTTTTTTGTGTGAATCGATAGT
ACTAACATACGCTCTCCATCAAAACAAAACGAAACAAAACAAACTAGCAAAATAGGCTGTCCCC
AGTGCAAGTGCAGGTGCCAGAACATTTCTCT
```

SEQ ID NO: 28. NdeI-LgBiT-YAP15-F primer (38 nucleotides)
GGAATTCATATGATGGTCTTCACACTCGAAGATTTCGT -continued SEQ ID NO: 29. B1-LgBiT-YAP15-R primer (40 nucleotides)
CGCGGGATCCTTACAACTGCAGAGAAGCTGGAGAGGAATG SEQ ID NO: 30. B1-LgBiT-YAP15A127-R primer (43 nucleotides)
CGCGGGATCCTTACAACTGCAGAGAAGCTGGAGACGCATGAGC SEQ ID NO: 31. NdeI-14-3-3-SmBiT-F primer (38 nucleotides)
GGAATTCATATGATGGAGAAGACTGAGCTGATCCAGAA SEQ ID NO: 32. B1-14-3-3-SmBiT-R primer (40 nucleotides)
CGCGGGATCCTTACAGAATCTCCTCGAACAGCCGGTAGCC SEQ ID NO: 33. pET 16b (6 his N-terminal) whole vector (5,711 nucleotides)
TTCTCATGTTTGACAGCTTATCATCGATAAGCTTTAATGCGGTAGTTTATCACAGTTAAATTGC

TAACGCAGTCAGGCACCGTGTATGAAATCTAACAATGCGCTCATCGTCATCCTCGGCACCGTCA

CCCTGGATGCTGTAGGCATAGGCTTGGTTATGCCGGTACTGCCGGGCCTCTTGCGGGATATCCG

GATATAGTTCCTCCTTTCAGCAAAAAACCCCTCAAGACCCGTTTAGAGGCCCCAAGGGGTTATG

CTAGTTATTGCTCAGCGGTGGCAGCAGCCAACTCAGCTTCCTTTCGGGCTTTGTTAGCAGCCGG

ATCCTCGAGCATATGACGACCTTCGATATGGCCGCTGCTGTGATGATGATGATGATGATGATGA

TGATGGCCCATGGTATATCTCCTTCTTAAAGTTAAACAAAATTATTTCTAGAGGGGAATTGTTA

TCCGCTCACAATTCCCCTATAGTGAGTCGTATTAATTTCGCGGGATCGAGATCTCGATCCTCTA

CGCCGGACGCATCGTGGCCGGCATCACCGGCGCCACAGGTGCGGTTGCTGGCGCCTATATCGCC

GACATCACCGATGGGGAAGATCGGGCTCGCCACTTCGGGCTCATGAGCGCTTGTTTCGCCGTGG

GTATGGTGGCAGGCCCCGTGGCCGGGGACTGTTGGGCGCCATCTCCTTGCATGCACCATTCCT

TGCGGCGGCGGTGCTCAACGGCCTCAACCTACTACTGGGCTGCTTCCTAATGCAGGAGTCGCAT

AAGGGAGAGCGTCGAGATCCCGGACACCATCGAATGGCGCAAAACCTTTCGCGGTATGGCATGA

TAGCGCCCGGAAGAGAGTCAATTCAGGGTGGTGAATGTGAAACCAGTAACGTTATACGATGTCG

CAGAGTATGCCGGTGTCTCTTATCAGACCGTTTCCCGCGTGGTGAACCAGGCCAGCCACGTTTC

TGCGAAAACGCGGGAAAAAGTGGAAGCGGCGATGGCGGAGCTGAATTACATTCCCAACCGCGTG

GCACAACAACTGGCGGGCAAACAGTCGTTGCTGATTGGCGTTGCCACCTCCAGTCTGGCCCTGC

ACGCGCCGTCGCAAATTGTCGCGGCGATTAAATCTCGCGCCGATCAACTGGGTGCCAGCGTGGT

GGTGTCGATGGTAGAACGAAGCGGCGTCGAAGCCTGTAAAGCGGCGGTGCACAATCTTCTCGCG

CAACGCGTCAGTGGGCTGATCATTAACTATCCGCTGGATGACCAGGATGCCATTGCTGTGGAAG

CTGCCTGCACTAATGTTCCGGCGTTATTTCTTGATGTCTCTGACCAGACACCCATCAACAGTAT

TATTTTCTCCCATGAAGACGGTACGCGACTGGGCGTGGAGCATCTGGTCGCATTGGGTCACCAG

CAAATCGCGCTGTTAGCGGGCCCATTAAGTTCTGTCTCGGCGCGTCTGCGTCTGGCTGGCTGGC

ATAAATATCTCACTCGCAATCAAATTCAGCCGATAGCGGAACGGGAAGGCGACTGGAGTGCCAT

GTCCGGTTTTCAACAAACCATGCAAATGCTGAATGAGGGCATCGTTCCCACTGCGATGCTGGTT

GCCAACGATCAGATGGCGCTGGGCGCAATGCGCGCCATTACCGAGTCCGGGCTGCGCGTTGGTG

CGGATATCTCGGTAGTGGGATACGACGATACCGAAGACAGCTCATGTTATATCCCGCCGTTAAC

CACCATCAAACAGGATTTTCGCCTGCTGGGGCAAACCAGCGTGGACCGCTTGCTGCAACTCTCT

CAGGGCCAGGCGGTGAAGGGCAATCAGCTGTTGCCCGTCTCACTGGTGAAAAGAAAAACCACCC

TGGCGCCCAATACGCAAACCGCCTCTCCCCGCGCGTTGGCCGATTCATTAATGCAGCTGGCACG

AGAGGTTTCCCGACTGGAAAGCGGGCAGTGAGCGCAACGCAATTAATGTAAGTTAGCTCACTCA

TTAGGCACCGGGATCTCGACCGATGCCCTTGAGAGCGTTCAACCCAGTCAGCTCCTTCCGGTGG

GCGCGGGGCATGACTATCGTCGCCGCACTTATGACTGTCTTCTTTATCATGCAACTCGTAGGAC

AGGTGCCGGCAGCGCTCTGGGTCATTTTCGGCGAGGACCGCTTTCGCTGGAGCGCGACGATGAT

-continued

```
CGGCCTGTCGCTTGCGGTATTCGGAATCTTGCACGCCCTCGCTCAAGCCTTCGTCACTGGTCCC

GCCACCAAACGTTTCGGCGAGAAGCAGGCCATTATCGCCGGCATGGCGGCCGACGCGCTGGGCT

ACGTCTTGCTGGCGTTCGCGACGCGAGGCTGGATGGCGTTCCCCATTATGATTCTTCTCGCTTC

CGGCGGCATCGGGATGCCCGCGTTGCAGGCCATGCTGTCCAGGCAGGTAGATGACGACCATCAG

GGACAGCTTCAAGGATCGCTCGCGGCTCTTACCAGCCTAACTTCGATCACTGGACCGCTGATCG

TCACGGCGATTTATGCCGCCTCGGCGAGCACATGGAACGGGTTGGCATGGATTGTAGGCGCCGC

CCTATACCTTGTCTGCCTCCCCGCGTTGCGTCGCGGTGCATGGAGCCGGGCCACCTCGACCTGA

ATGGAAGCCGGCGGCACCTCGCTAACGGATTCACCACTCCAAGAATTGGAGCCAATCAATTCTT

GCGGAGAACTGTGAATGCGCAAACCAACCCTTGGCAGAACATATCCATCGCGTCCGCCATCTCC

AGCAGCCGCACGCGGCGCATCTCGGGCAGCGTTGGGTCCTGGCCACGGGTGCGCATGATCGTGC

TCCTGTCGTTGAGGACCCGGCTAGGCTGGCGGGGTTGCCTTACTGGTTAGCAGAATGAATCACC

GATACGCGAGCGAACGTGAAGCGACTGCTGCTGCAAAACGTCTGCGACCTGAGCAACAACATGA

ATGGTCTTCGGTTTCCGTGTTTCGTAAAGTCTGGAAACGCGGAAGTCAGCGCCCTGCACCATTA

TGTTCCGGATCTGCATCGCAGGATGCTGCTGGCTACCCTGTGGAACACCTACATCTGTATTAAC

GAAGCGCTGGCATTGACCCTGAGTGATTTTTCTCTGGTCCCGCCGCATCCATACCGCCAGTTGT

TTACCCTCACAACGTTCCAGTAACCGGGCATGTTCATCATCAGTAACCCGTATCGTGAGCATCC

TCTCTCGTTTCATCGGTATCATTACCCCCATGAACAGAAATCCCCCTTACACGGAGGCATCAGT

GACCAAACAGGAAAAAACCGCGCTTAACATGGCCCGCTTTATCAGAAGCCAGACATTAACGCTT

CTGGAGAAACTCAACGAGCTGGACGCGGATGAACAGGCAGACATCTGTGAATCGCTTCACGACC

ACGCTGATGAGCTTTACCGCAGCTGCCTCGCGCGTTTCGGTGATGACGGTGAAAACCTCTGACA

CATGCAGCTCCCGGAGACGGTCACAGCTTGTCTGTAAGCGGATGCCGGGAGCAGACAAGCCCGT

CAGGGCGCGTCAGCGGGTGTTGGCGGGTGTCGGGGCGCAGCCATGACCCAGTCACGTAGCGATA

GCGGAGTGTATACTGGCTTAACTATGCGGCATCAGAGCAGATTGTACTGAGAGTGCACCATATA

TGCGGTGTGAAATACCGCACAGATGCGTAAGGAGAAAATACCGCATCAGGCGCTGTTCCGGTTC

CTCGCTCACTGACTCGCTGCGCTCGGTCGTTCGGCTGCGGCGAGCGGTATCAGCTCACTCAAAG

GCGGTAATACGGTTATCCACAGAATCAGGGGATAACGCAGGAAAGAACATGTGAGCAAAAGGCC

AGCAAAAGGCCAGGAACCGTAAAAAGGCCGCGTTGCTGGCGTTTTTCCATAGGCTCCGCCCCCC

TGACGAGCATCACAAAAATCGACGCTCAAGTCAGAGGTGGCGAAACCCGACAGGACTATAAAGA

TACCAGGCGTTTCCCCCTGGAAGCTCCCTCGTGCGCTCTCCTGTTCCGACCCTGCCGCTTACCG

GATACCTGTCCGCCTTTCTCCCTTCGGGAAGCGTGGCGCTTTCTCATAGCTCACGCTGTAGGTA

TCTCAGTTCGGTGTAGGTCGTTCGCTCCAAGCTGGGCTGTGTGCACGAACCCCCCGTTCAGCCC

GACCGCTGCGCCTTATCCGGTAAGTATGGTCTTGAGTCCAACCCGGTAAGACACGACTTATCGC

CACTGGCAGCAGCCACTGGTAACAGGATTAGCAGAGCGAGGTATGTAGGCGGTGCTACAGAGTT

CTTGAAGTGGTGGCCTAACTACGGCTACACTAGAAGGACAGTATTTGGTATCTGCGCTCTGCTG

AAGCCAGTTACCTTCGGAAAAAGAGTTGGTAGCTCTTGATCCGGCAAACAAACCACCGCTGGTA

GCGGTGGTTTTTTTGTTTGCAAGCAGCAGATTACGCGCAGAAAAAAAGGATCTCAAGAAGATCC

TTTGATCTTTTCTACGGGGTCTGACGCTCAGTGGAACGAAAACTCACGTTAAGGGATTTTGGTC

ATGAGATTATCAAAAAGGATCTTCACCTAGATCCTTTTAAATTAAAAATGAAGTTTTAAATCAA

TCTAAAGTATATATGAGTAAACTTGGTCTGACAGTTACCAATGCTTAATCAGTGAGGCACCTAT

CTGAGCGATCTGTCTATTTCGTTCATCCATAGTTGCCTGACTGCCCGTCGTGTAGATAACTACG
```

-continued

```
ATACGGGAGGGCTTACCATCTGGCCCCAGTGCTGCAATGATACCGGGAGACCCACGCTCACCGG

CTCCAGATTTATCAGCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAAGTAGTTCGCCAGTT

AATAGTTTGCGCAACGTTGTTGCCATTGCTGCAGGCATCGTGGTGTCACGCTCGTCGTTTGGTA

TGGCTTCATTCAGCTCCGGTTCCCAACGATCAAGGCGAGTTACATGATCCCCCATGTTGTGCAA

AAAAGCGGTTAGCTCCTTCGGTCCTCCGATCGTTGTCAGAAGTAAGTTGGCCGCAGTGTTATCA

CTCATGGTTATGGCAGCACTGCATAATTCTCTTACTGTCATGCCATCCGTAAGATGCTTTTCTG

TGACTGGTGAGTACTCAACCAAGTCATTCTGAGAATAGTGTATGCGGCGACCGAGTTGCTCTTG

CCCGGCGTCAACACGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCGATGTAAC

CCACTCGTGCACCCAACTGATCTTCAGCATCTTTTACTTTCAGCAGCGTTTCTGGGTGAGCAAA

AACAGGAAGGCAAAATGCCGCAAAAAAGGGAATAAGGGCGACACGGAAATGTTGAATACTCATA

CTCTTCCTTTTTCAATATTATTGAAGCATTTATCAGGGTTATTGTCTCATGAGCGGATACATAT

TTGAATGTATTTAGAAAAATAAACAAATAGGGGTTCCGCGCACATTTCCCCGAAAAGTGCCACC

TGACGTCTAAGAAACCATTATTATCATGACATTAACCTATAAAAATAGGCGTATCACGAGGCCC

TTTCGTCTTCAAGAA

SEQ ID NO: 34. B1-Kozak-LgBiT-F primer (41 nucleotides)
CTGGATCCGCCGCCACCATGGTCTTTCACACTCGAAGATTTC SEQ ID NO: 35. LgBiT-(GS)-R primer (54 nucleotides)
ACCGCTCGAGCCTCCACCTCCGCTCCCGCCACCACCGGAACTCCCACTGTTGAT SEQ ID NO: 36. (GS)-YAP50-F primer (69 nucleotides)
GGGAGTTCCGGTGGTGGCGGGAGCGGAGGTGGAGGCTCGAGCGGTGCCGGGCATCAGATCGTGC

ACGTC

SEQ ID NO: 37. N1-YAP171-Flag-R primer (63 nucleotides)
ATGAAACTGCGGCCGCCTTGTCGTCATCGTCTTTGTAGTCTACATCATCAGGTATCTCAAAAG SEQ ID NO: 38. B1-YAP50-F primer (32 nucleotides)
CTGGATCCGCCGGGCATCAGATCGTGCACGTC SEQ ID NO: 39. (GS)-YAP171-R primer (68 nucleotides)
ACCTGACGACCCTCCACCTCCGCTCCCGCCACCACCGCTCGAGCCTACATCATCAGGTATCTCA

AAAG

SEQ ID NO: 40. (GS)-LgBiT-F primer (66 nucleotides)
GGCTCGAGCGGTGGTGGCGGGAGCGGAGGTGGAGGGTCGTCAGGTGTCTTCACACTCGAAGATT

TC

SEQ ID NO: 41. N1-LgBiT-R primer (43 nucleotides)
ATGAAACTGCGGCCGCTTAACTGTTGATGGTTACTCGGAACAG SEQ ID NO: 42. B1-Kozak-SmiBiT-(GS)-F primer (98 nucleotides)
CTGGATCCGCCGCCACCATGGTGACCGGCTACCGGCTGTTCGAGGAGATTCTCGGGAGTTCCGG

TGGTGGCGGGAGCGGAGGTGGAGGCTCGAGCGGT

SEQ ID NO: 43. N1-SmBiT-(GS)-R primer (97 nucleotides)
ATGAAACTGCGGCCGCTTAGAGAATCTCCTCGAACAGCCGGTAGCCGGTCACACCTGACGACCC

TCCACCTCCGCTCCCGCCACCACCGCTCGAGCC

SEQ ID NO: 44. (GS)-TEAD-194-F primer (73 nucleotides)
GGGAGTTCCGGTGGTGGCGGGAGCGGAGGTGGAGGCTCGAGCGGTGAGCCTGCATCGGCCCCAG

CTCCCTCAG

SEQ ID NO: 45. N1-TEAD411-Myc-R primer (73 nucleotides)
ATGAAACTGCGGCCGCTTACAGATCCTCTTCTGAGATGAGTTTTTGTTCATTTGAAACTTCAAA

CACACAGGC
```

-continued

SEQ ID NO: 46. B1-TEAD194-F primer (36 nucleotides)
CTGGATCCGAGCCTGCATCGGCCCCAGCTCCCTCAG SEQ ID NO: 47. GS-TEAD-411-R primer (69 nucleotides)
ACCTGACGACCCTCCACCTCCGCTCCCGCCACCACCGCTCGAGCCATTTGAAACTTCAAACACA

CAGGC

SEQ ID NO: 48. (GS)-TEAD194-F primer (73 nucleotides)
GGGAGTTCCGGTGGTGGCGGGAGCGGAGGTGGAGGCTCGAGCGGTGAGCCTGCATCGGCCCCAG

CTCCCTGAG

SEQ ID NO: 49. TEAD1_HUMAN transcriptional enhancer factor TEF-1
(accession number P28347) mRNA (1,281 nucleotides)
ATTGAGCCCAGCAGCTGGAGCGGCAGTGAGAGCCCTGCCGAAAACATGGAAAGGATGAGTGACT

CTGCAGATAAGCCAATTGACAATGATGCAGAAGGGGTCTGGAGCCCCGACATCGAGCAAACCTT

TCAGGAGGCCCTGGCTATCTATCCACCATGTGGGAGGAGGAAAATCATCTTATCAGACGAAGGC

AAAATGTATGGTAGGAATGAATTGATAGCCAGATACATCAAACTCAGGACAGGCAAGACGAGGA

CCAGAAAACAGGTGTCTAGTCACATTCAGGTTCTTGCCAGAAGGAAATCTCGTGATTTTCATTC

CAAGCTAAAGGATCAGACTGCAAAGGATAAGGCCCTGCAGCACATGGCGGCCATGTCCTCAGCC

CAGATCGTCTCGGCCACTGCGATTCATAAGAAGCTGGGGCTGCCTGGGATTCCACGCCCGACCT

TCCCAGGGGCGCCGGGGTTCTGGCCGGGAATGATTCAAACAGGGCAGCCAGGATCCTCACAAGA

CGTCAAGCCTTTTGTGCAGCAGGCCTACCCCATCCAGCCAGCGGTCACAGCCCCCATTCCAGGG

TTTGAGCCTGCATCGGCCCCAGCTCCCTCAGTCCCTGCCTGGCAAGGTCGCTCCATTGGCACAA

CCAAGCTTCGCCTGGTGGAATTTTCAGCTTTTCTCGAGCAGCAGCGAGACCCAGACTCGTACAA

CAAACACCTCTTCGTGCACATTGGGCATGCCAACCATTCTTACAGTGACCCATTGCTTGAATCA

GTGGACATTCGTCAGATTTATGACAAATTTCCTGAAAAGAAAGGTGGCTTAAAGGAACTGTTTG

GAAAGGGCCCTCAAAATGCCTTCTTCCTCGTAAAATTCTGGGCTGATTTAAACTGCAATATTCA

AGATGATGGTGGGCTTTTTATGGTGTAACCAGTCAGTACGAGAGTTCTGAAAATATGACAGTC

ACCTGTTCCACCAAAGTTTGCTCCTTTGGGAAGCAAGTAGTAGAAAAAGTAGAGACGGAGTATG

CAAGGTTTGAGAATGGCCGATTTGTATACCGAATAAACCGCTCCCCAATGTGTGAATATATGAT

CAACTTCATCCACAAGCTCAAACACTTACCAGAGAAATATATGATGAACAGTGTTTTGGAAAAC

TTCACAATTTTATTGGTGGTAACAAACAGGGATACACAAGAAACTCTACTCTGCATGGCCTGTG

TGTTTGAAGTTTCAAATAGTGAACACGGAGCACAACATCATATTTACAGGCTTGTAAAGGACTG

A

SEQ ID NO: 50. TEAD1_HUMAN protein (426 amino acids)
MEPSSWSGSESPAENMERMSDSADKPIDNDAEGVWSPDIEQSFQEALAIYPPCGRRKIILSDEG

KMYGRNELIARYTKLRTGKTRTRKQVSSHIQVLARRKSRDFHSKLKDQTAKDKALQHMAAMSSA

QIVSATAIHNKLGLPGIPRPTFPGAPGFWPGMIQTGQPGSSQDVKPFVQQAYPIQPAVTAPIPG

FEPASAPAPSVPAWQGRSIGTTKLRLVEFSAFLEQQRDPDSYNKHLFVHIGHANHSYSDPLLES

VDIRQIYDKFPEKKGGLKELFGKGPQNAFFLVKFWADLNCNIQDDAGAFYGVTSQYESSENMTV

TCSTKVCSFGKQVVEKVETEYARFENGRFVYRINRSPMCEYMINFIHKLKHLPEKYMMNSVLEN

FTILLVVTNRDTQETLLCMACVFEVSNSEHGAQHHIYRLVKD

SEQ ID NO: 51. Large BiT (LgBiT) mRNA (477 nucleotides)
ATGGTCTTCACACTCGAAGATTTCGTTGGGGACTGGGAACAGACAGCCGCCTACAACCTGGACC

AAGTCCTTGAACAGGGAGGTGTGTCCAGTTTGCTGCAGAATCTCGCCGTGTCCGTAACTCCGAT

CCAAAGGATTGTCCGGAGCGGTGAAAATGCCCTGAAGATCGACATCCATGTCATCATCCCGTAT

GAAGGTCTGAGCGCCGACCAAATGGCCCAGATCGAAGAGGTGTTTAAGGTGGTGTACCCTGTGG

ATGATCATCACTTTAAGGTGATCCTGCCCTATGGCACACTGGTAATCGACGGGGTTACGCCGAA

CATGCTGAACTATTTCGGACGGCCGTATGAAGGCATCGCCGTGTTCGACGGCAAAAAGATCACT

GTAACAGGGACCCTGTGGAACGGCAACAAAATTATCGACGAGCGCCTGATCACCCCCGACGGCT

CCATGCTGTTCCGAGTAACCATCAACAGT

SEQ ID NO: 52. Large BiT (LgBiT) protein (159 amino acids)
MVFTLEDFVGDWEQTAAYNLDQVLEQGGVSSLLQNLAVSVTPIQRIVRSGENALKIDIHVIIPY

EGLSADQMAQIEEVFKVVYPVDDHHFKVILPYGTLVIDGVTPNMLNYFGRPYSGIAVFDGKKIT

VTGTLWNGNKIIDERLITPDGSMLFRVTINS

SEQ ID NO: 53. Small BiT (SmBiT) mRNA (36 nucleotides)
ATGGTGACCGGCTACCGGCTGTTCGAGGAGATTCTC SEQ ID NO: 54. Small BiT (SmBiT) protein (11 amino acids)
MVTGYRLFEIL SEQ ID NO: 55. pcDNA3.1/hygro(+)-Flag vector (5,490 nucleotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACACAAGGCAAGGCTTGACCGACAATTGCATGAAGAATCTGCTTAGGGTTAGGCG

TTTTGCGCTGCTTCGCGATGTACGGGCCAGATATACGCGTTGACATTGATTATTGACTAGTTAT

TAATAGTAATGAATTACGGGGTCATTAGTTCATAGCCCATATATGGAGTTCCGCGTTACATAAC

TTACGGTAAATGGCCCGCCTGGCTGACCGCCCAACGACCCCGCCCATTGACGTCAATAATGAC

GTATGTTCCCATAGTAACGCCAATAGGGACTTTCCATTGACGTCAATGGGTGGAGTATTTACGG

TAAACTGCCCACTTGGCAGTACATCAAGTGTATCATATGCCAAGTACGCCCCCTATTGACGTCA

ATGACGGTAAATGGCCCGCCTGGCATTATGCCCAGTACATGACCTTATGGGACTTTCCTACTTG

GCAGTACATCTACGTATTAGTCATCGCTATTACCATGGTGATGCGGTTTTGGCAGTACATCAAT

GGGCGTGGATAGCGGTTTGACTCACGGGGATTTCCAAGTCTCCACCCCATTGACGTCAATGGGA

GTTTGTTTTGGCACCAAAATCAACGGGACTTTCCAAAATGTCGTAACAACTCCGCCCCATTGAC

GCAAATGGGCGGTAGGCGTGTACGGTGGGAGGTCTATATAAGCAGAGCTCTCTGGCTAACTAGA

GAACCCACTGCTTACTGGCTTATCGAAATTAATACGACTCACTATAGGGAGACCCAAGCTGGCT

AGCGTTTAAACTTAAGCTTGGTACCATGGACTACAAAGACGATGACGGTGATTATAAAGATCAT

GACATCTACCTGATGTTTCTGGTACTGCCAGGATCCACTAGTCCAGTGTGGTGGAATTCTGCAG

ATATCCAGGACAGTGGCGGCCGCTCGAGTCTAGAGGGCCCGTTTAAACCCGCTGATCAGCCTCG

ACTGTGCCTTCTAGTTGCCAGCCATCTGTTGTTTGCCCCTCCCCCGTGCCTTCCTTGACCCTGG

AAGGTGCCACTCCCACTGTCCTTTCCTAATAAAATGAGGAAATTGCATCGCATTGTCTGAGTAG

GTGTCATTCTATTCTGGGGGGTGGGGTGGGGCAGGACAGCAAGGGGGAGGATTGGGAAGACAAT

AGCAGGCATGCTGGGGATGCGGTGGGCTCTATGGCTTCTGAGGCGGAAAGAACCAGCTGGGGCT

CTAGGGGGTATCCCCACGCGCCCTGTAGCGGCGCATTAAGCGCGGCGGGTGTGGTGGTTACGCG

CAGCGTGACCGCTACACTTGCCAGCGCCCTAGCGCCCGCTCCTTTCGCTTTCTTCCCTTCCTTT

CTCGCCACGTTCGCCGGCTTTCCCCGTCAAGCTCTAAATCGGGGGGTCCCTTTAGGGTTCCGAT

TTAGTGCTTTACGGCACCTCGACCCCAAAAAACTTGATTAGGGTGATGGTTCACGTAGTGGGCC

ATCGCCCTGATAGACGGTTTTTCGCCGTTTGACGTTGGAGTCCACGTTCTTTAATAGTGGACTC

TTGTTCCAAACTGGAACAACACTCAACCCTATCTCGGTCTATTCTTTTGATTTATAAGGGATTT

TGCCGATTTCGGCCTATTGGTTAAAAAATGAGCTGATTTAACAAAAATTTAACGCGAATTAATT

CTGTGGAATGTGTGTCAGTTAGGGTGTGGAAAGTCCCCAGGCTCCCCAGCAGGCAGAAGTATGC

-continued

```
AAAGCATGCATCTCAATTAGTCAGCAACCAGGTGTGGAAAGTCCCCAGGCTCCCCAGCAGGCAG

AAGTATGCAAAGCATGCATCTCAATTAGTCAGCAACCATAGTCCCGCCCCTAACTCCGCCCATC

CCGCCCCTAACTCCGCCCAGTTCCGCCCATTCTCCGCCCCATGGCTGACTAATTTTTTTATTT

ATGCAGAGGCCGAGGCCGCCTCTGCCTCTGAGCTATTCCAGAAGTAGTGAGGAGGCTTTTTTGG

AGGCCTAGGCTTTTGCAAAAAGCTCCCGGGAGCTTGTATATCCATTTTCGGATCTGATCAAGAG

ACAGGATGAGGATCGTTTCGCATGATTGAACAAGATGGATTGCACGCAGGTTCTCCGGCCGCTT

GGGTGGAGAGGCTATTCGGCTATGACTGGGCAGAACAGACAATCGGCTGCTCTGATGCCGCCGT

GTTCCGGCTGTCAGCGCAGGGGCGCCCGGTTCTTTTTGTCAAGACCGACCTGTCCGGTGCCCTG

AATGAACTGCAGGACGAGGCAGCGCGGCTATCGTGGCTGGCCACGACGGGCGTTCCTTGCGCAG

CTGTGCTCGACGTTGTCACTGAAGCGGGAAGGGACTGGCTGCTATTGGGCGAAGTGCCGGGGCA

GGATCTCCTGTCATCTCACCTTGCTCCTGCCGAGAAAGTATCCATCATGGCTGATGCAATGCGG

CGGCTGCATACGCTTGATCCGGCTACCTGCCCATTCGACCACCAAGCGAAACATCGCATCGAGC

GAGCACGTACTCGGATGGAAGCCGGTCTTGTCGATCAGGATGATCTGGACGAAGAGCATCAGGG

GCTCGCGCCAGCCGAACTGTTCGCCAGGCTCAAGGCGCGCATGCCCGACGGCGAGGATCTCGTC

GTGACCCATGGCGATGCCTGCTTGCCGAATATCATGGTGGAAAATGGCCGCTTTTCTGGATTCA

TCGACTGTGGCCGGCTGGGTGTGGCGGACCGCTATCAGGACATAGCGTTGGCTACCCGTGATAT

TGCTGAAGAGCTTGGCGGCGAATGGGCTGACCGCTTCCTCGTGCTTTACGGTATCGCCGCTCCC

GATTCGCAGCGCATCGCCTTCTATCGCCTTCTTGACGAGTTCTTCTGAGCGGGACTCTGGGGTT

CGAAATGACCGACCAAGCGACGCCCAACCTGCCATCACGAGATTTCGATTCCACCGCCGCCTTC

TATGAAAGGTTGGGCTTCGGAATCGTTTTCCGGGACGCCGGCTGGATGATCCTCCAGCGCGGGG

ATCTCATGCTGGAGTTCTTCGCCCACCCCAACTTGTTTATTGCAGCTTATAATGGTTACAAATA

AAGCAATAGCATCACAAATTTCACAAATAAAGCATTTTTTTCACTGCATTCTAGTTGTGGTTTG

TCCAAACTCATCAATGTATCTTATCATGTCTGTATACCGTCGACCTCTAGCTAGAGCTTGGCGT

AATCATGGTCATAGCTGTTTCCTGTGTGAAATTGTTATCCGCTCACAATTCCACACAACATACG

AGCCGGAAGCATAAAGTGTAAAGCCTGGGGTGCCTAATGAGTGAGCTAACTCACATTAATTGCG

TTGCGCTCACTGCCCGCTTTCCAGTCGGGAAACCTGTCGTGCCAGCTGCATTAATGAATCGGCC

AACGCGCGGGGAGAGGCGGTTTGCGTATTGGGCGCTCTTCCGCTTCCTCGCTCACTGACTCGCT

GCGCTCGGTCGTTCGGCTGCGGCGAGCGGTATCAGCTCACTCAAAGGCGGTAATACGGTTATCC

ACAGAATCAGGGGATAACGCAGGAAAGAACATGTGAGCAAAAGGCCAGCAAAAGGCCAGGAACC

GTAAAAAGGCCGCGTTGCTGGCGTTTTTCCATAGGCTCCGCCCCCCTGACGAGCATCACAAAAA

TCGACGCTCAAGTCAGAGGTGGCGAAACCCGACAGGACTATAAAGATACCAGGCGTTTCCCCCT

GGAAGCTCCCTCGTGCGCTCTCCTGTTCCGACCCTGCCGCTTACCGGATACCTGTCCGCCTTTC

CGTTCGCTCCAAGCTGGGCTGTGTGCACGAACCCCCCGTTCAGCCCGACCGCTGCGCCTTATCC

GGTAACTATCGTCTTGAGTCCAACCCGGTAAGACACGACTTATCGCCACTGGCAGCAGCCACTG

GTAACAGGATTAGCAGAGCGAGGTATGTAGGCGGTGCTACAGAGTTCTTGAAGTGGTGGCCTAA

CTACGGCTACACTAGAAGAACAGTATTTGGTATCTGCGCTCTGCTGAAGCCAGTTACCTTCGGA

AAAAGAGTTGGTAGCTCTTGATCCGGCAAACAAACCACCGCTGGTAGCGGTTTTTTTGTTTGCA

AGCAGCAGATTACGCGCAGAAAAAAAGGATCTCAAGAAGATCCTTTGATCTTTTCTACGGGGTC

TGACGCTCAGTGGAACGAAAACTCACGTTAAGGGATTTTGGTCATGAGATTATCAAAAAGGATC

TTCACCTAGATCCTTTTAAATTAAAAATGAAGTTTTAAATCAATCTAAAGTATATATGAGTAAA

CTTGGTCTGACAGTTACCAATGCTTAATCAGTGAGGCACCTATCTCAGCGATCTGTCTATTTCG
```

-continued

TTCATCCATAGTTGCCTGACTCCCCGTCGTGTAGATAACTACGATACGGGAGGGCTTACCATCT

GGCCCCAGTGCTGCAATGATACCGCGAGACCCACGCTCACCGGCTCCAGATTTATCAGCAATAA

ACCAGCCAGCCGGAAGGGCCGAGCGCAGAAGTGGTCCTGCAACTTTATCCGCCTCCATCCAGTC

TATTAATTGTTGCCGGGAAGCTAGAGTAAGTAGTTCGCCAGTTAATAGTTTGCGCAACGTTGTT

GCCATTGCTACAGGCATCGTGGTGTCACGCTCGTCGTTTGGTATGGCTTCATTCAGCTCCGGTT

CCCAACGATCAAGGCGAGTTACATGATCCCCCATGTTGTGCAAAAAAGCGGTTAGCTCCTTCGG

TCCTCCGATCGTTGTCAGAAGTAAGTTGGCCGCAGTGTTATCACTCATGGTTATGGCAGCACTG

CATAATTCTCTTACTGTCATGCCATCCGTAAGATGCTTTTCTGTGACTGGTGAGTACTCAACCA

AGTCATTCTGAGAATAGTGTATGCGGCGACCGAGTTGCTCTTGCCCGGCGTCAATACGGGATAA

TACCGCGCCACATAGCAGAACTTTAAAAGTGCTCATCATTGGAAAACGTTCTTCGGGGCGAAAA

CTCTCAAGGATCTTACCGCTGTTGAGATCCAGTTCGATGTAACCCACTCGTGCACCCAACTGAT

CTTCAGCATCTTTTACTTTCACCAGCGTTTCTGGGTGAGCAAAAACAGGAAGGCAAAATGCCGC

AAAAAAGGGAATAAGGGCGACACGGAAATGTTGAATACTCATACTCTTCCTTTTTCAATATTAT

TGAAGCATTTATCAGGGTTATTGTCTCATGAGCGGATACATATTTGAATGTATTTAGAAAAATA

AACAAATAGGGGTTCCGCGCACATTTCCCCGAAAAGTGCCACCTGACGTC

SEQ ID NO: 56 pcDNA3.1/hygro(+)-Myc vector (5,455 nucleotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGAGGTCTATATAAGCAGAGCTCTCTGGCTAACTAG

AGAACCCACTGCTTACTGGCTTATCGAAATTAATACGACTCACTATAGGGAGACCCAAGCTGGC

TAGCGTTTAAACTTAAGCTTGGTACCATGGAACAAAAACTCATCTCAGAAGAGGATCTGGGATC

CACTAGTCCAGTGTGGTGGAATTCTGCAGATATCCAGCACAGTGGCGGCCGCTCGAGTCTAGAG

GGCCCGTTTAAACCCGCTGATCAGCCTCGACTGTGCCTTCTAGTTGCCAGCCATCTGTTGTTTG

CCCCTCCCCCGTGCCTTCCTTGACCCTGGAAGGTGCCACTCCCACTGTCCTTTCCTAATAAAAT

GAGGAAATTGCATCGCATTGTCTGAGTAGGTGTCATTCTATTCTGGGGGGTGGGGTGGGGCAGG

ACAGCAAGGGGGAGGATTGGGAAGACAATAGCAGGCATGCTGGGGATGCGGTGGGCTCTATGGC

TTCTGAGGCGGAAAGAACCAGCTGGGGCTCTAGGGGGTATCCCCACGCGCCCTGTAGCGGCGCA

TTAAGCGCGGCGGGTGTGGTGGTTACGCGCAGCGTGACCGCTACACTTGCCAGCGCCCTAGCGC

CCGCTCCTTTGGCTTTCTTCCCTTGCTTTCTCGCGACGTTCGCCGGCTTTCCCCGTCAAGCTCT

AAATCGGGGCTCGCTTTAGGGTTCCGATTTAGTGCTTTACGGCACCTCGACCCCAAAAAACTT

GATTAGGGTGATGGTTGACGTAGTGGGCCATCGCCCTGATAGACGGTTTTTCGCCCTTTGACGT

-continued

```
TGGAGTCCACGTTCTTTAATAGTGGACTCTTGTTCCAAACTGGAACAACACTCAACCCTATCTC

GGTCTATTCTTTTGATTTATAAGGGATTTTGCCGATTTCGGCCTATTGGTTAAAAAATGAGCTG

ATTTAACAAAAATTTAACGCGAATTAATTCTGTGGAATGTGTGTCAGTTAGGGTGTGGAAAGTC

CCCAGGCTCCCCAGCAGGCAGAAGTATGCAAAGCATGCATCTCAATTAGTCAGCAACCAGGTGT

GGAAAGTCCCCAGGCTCCCCAGCAGGCAGAAGTATGCAAAGCATGCATCTCAATTAGTCAGCAA

CCATAGTCCCGCCCCTAACTCCGCCCATCCCGCCCCTAACTCCGCCCAGTTCCGCCCATTCTCC

GCCCCATGGCTGACTAATTTTTTTTATTTATGCAGAGGCCGAGGCCGCCTCTGCCTCTGAGCTA

TTCCAGAAGTAGTGAGGAGGCTTTTTTGGAGGCCTAGGCTTTTGCAAAAAGCTCCCGGGAGCTT

GTATATCCATTTTCGGATCTGATCAAGAGACAGGATGAGGATCGTTTCGCATGATTGAAGAAGA

TGGATTGCACGCAGGTTCTCCGGCCGCTTGGGTGGAGAGGCTATTCGGCTATGACTGGGCACAA

CAGACAATCGGCTGCTCTGATGCCGCCGTGTTCCGGCTGTCAGGGCAGGGCGCCCGGTTCTTT

TTGTCAAGACCGACCTGTCCGGTGCCCTGAATGAACTGCAGGACGAGGCAGCGCGGCTATCGTG

GCTGGCCACGACGGGCGTTCCTTGCGCAGCTGTGCTCGACGTTGTCACTGAAGCGGGAAGGGAC

TGGCTGCTATTGGGCGAAGTGCCGGGGCAGGATCTCCTGTCATCTCACCTTGCTCCTGCCGAGA

AAGTATCCATCATGGCTGATGCAATGCGGCGGCTGCATACGCTTGATCCGGCTACCTGCCCATT

CGACCACCAAGCGAAACATCGCATCGAGCGAGCACGTACTCGGATGGAAGCCGGTCTTGTCGAT

CAGGATGATCTGGACGAAGAGCATCAGGGGCTCGCGCCAGCCGAACTGTTCGCCAGGCTCAAGG

CGCGCATGCCCGACGGCGAGGATCTCGTCGTGACCCATGGCGATGCCTGCTTGCCGAATATCAT

GGTGGAAAATGGCCGCTTTTCTGGATTCATCGACTGTGGCCGGCTGGGTGTGGCGGACCGCTAT

CAGGACATAGCGTTGGCTACCCGTGATATTGCTGAAGAGCTTGGCGGCGAATGGGCTGACCGCT

TCCTCGTGCTTTACGGTATCGCCGCTCCCGATTCGCAGCGCATCGCCTTCTATCGCCTTCTTGA

CGAGTTCTTCTGAGCGGGACTCTGGGGTTCGAAATGACCGACCAAGCGACGCCCAACCTGCCAT

CACGAGATTTCGATTCCACCGCCGCCTTCTATGAAAGGTTGGGCTTCGGAATCGTTTTCCGGGA

CGCCGGCTGGATGATCCTGCAGCGCGGGGATCTCATGCTGGAGTTCTTCGCCCACCCCAACTTG

TTTATTGCAGCTTATAATGGTTACAAATAAAGCAATAGCATCACAAATTTCACAAATAAAGCAT

TTTTTTCACTGCATTCTAGTTGTGGTTTGTCCAAACTCATCAATGTATCTTATCATGTCTGTAT

ACCGTCGACGTCTAGCTAGAGCTTGGCGTAATCATGGTCATAGCTGTTTGCTGTGTGAAATTGT

TATCCGCTCACAATTCCACACAACATACGAGCCGGAAGCATAAAGTGTAAAGCCTGGGGTGCCT

AATGAGTGAGCTAACTCACATTAATTGCGTTGCGCTCACTGCCCGCTTTCCAGTCGGGAAACCT

GTCGTGCCAGCTGCATTAATGAATCGGCCAACGCGCGGGAGAGGCGGTTTGCGTATTGGGCGC

TCTTCCGGTTCCTCGCTCACTGACTCGCTGCGCTCGGTCGTTCGGCTGCGGGAGCGGTATCAG

CTCACTCAAAGGCGGTAATACGGTTATCCACAGAATCAGGGGATAACGCAGGAAAGAACATGTG

AGCAAAAGGCCAGCAAAAGGCCAGGAACCGTAAAAAGGCCGCGTTGCTGGCGTTTTTCCATAGG

CTCCGCCCCCCTGACGAGCATCACAAAAATCGACGCTCAAGTCAGAGGTGGCGAAACCCGACAG

GACTATAAAGATACCAGGCGTTTCCCCCTGGAAGCTCCCTCGTGCGCTCTCCTGTTCCGACCCT

GCCGCTTACCGGATACCTGTCCGCCTTTCTCCCTTCGGGAAGCGTGGCGCTTTCTCATAGCTCA

CGCTGTAGGTATCTCAGTTCGGTGTAGGTCGTTCGCTCCAAGCTGGGCTGTGTGCACGAACCCC

CCGTTCAGCCCGACCGCTGCGCCTTATCCGGTAACTATCGTCTTGAGTCCAACCCGGTAAGACA

CGACTTATCGCCACTGGCAGCAGCCACTGGTAACAGGATTAGCAGAGCGAGGTATGTAGGCGGT

GCTACAGAGTTCTTGAAGTGGTGGCCTAACTACGGCTACACTAGAAGAACAGTATTTGGTATCT
```

-continued

```
GCGCTCTGCTGAAGCCAGTTACCTTCGGAAAAAGAGTTGGTAGCTCTTGATCCGGCAAACAAAC

CACCGCTGGTAGCGGTTTTTTTGTTTGCAAGCAGCAGATTACGCGCAGAAAAAAAGGATCTCAA

GAAGATCCTTTGATCTTTTCTACGGGGTCTGACGCTCAGTGGAACGAAAACTCACGTTAAGGGA

TTTTGGTCATGAGATTATCAAAAAGGATCTTCACCTAGATCCTTTTAAATTAAAAATGAAGTTT

TAAATCAATCTAAAGTATATATGAGTAAACTTGGTCTGACAGTTACCAATGCTTAATCAGTGAG

GCACCTATCTCAGCGATCTGTCTATTTCGTTCATCCATAGTTGCCTGACTCCCCGTCGTGTAGA

TAACTACGATACGGGAGGGCTTACCATCTGGCCCCAGTGCTGCAATGATACCGCGAGACCCACG

CTCACCGGCTCCAGATTTATCAGCAATAAACCAGCCAGCCGGAAGGGCCGAGCGCAGAAGTGGT

CCTGCAACTTTATCCGCCTCGATCCAGTCTATTAATTGTTGCGGGGAAGCTAGAGTAAGTAGTT

CGCCAGTTAATAGTTTGCGCAACGTTGTTGCCATTGCTACAGGCATCGTGGTGTCACGCTCGTC

GTTTGGTATGGCTTCATTCAGCTCCGGTTCCGAACGATCAAGGCGAGTTACATGATCCCCCATG

TTGTGCAAAAAAGCGGTTAGCTCCTTCGGTCCTCCGATCGTTGTCAGAAGTAAGTTGGCCGCAG

TGTTATCACTCATGGTTATGGCAGCACTGCATAATTCTCTTAGTGTCATGCCATCCGTAAGATG

CTTTTCTGTGACTGGTGAGTACTCAACCAAGTCATTCTGAGAATAGTGTATGCGGCGACCGAGT

TGCTCTTGCCCGGCGTCAATACGGGATAATACCGCGCCACATAGCAGAACTTTAAAAGTGCTCA

TCATTGGAAAACGTTCTTCGGGGCGAAAACTCTCAAGGATCTTACCGCTGTTGAGATCCAGTTC

GATGTAACCCACTCGTGCACCCAACTGATGTTCAGCATCTTTTACTTTCACCAGCGTTTCTGGG

TGAGCAAAAACAGGAAGGCAAAATGCCGCAAAAAAGGGAATAAGGGCGACACGGAAATGTTGAA

TACTCATACTCTTCCTTTTTCAATATTATTGAAGCATTTATCAGGGTTATTGTCTCATGAGCGG

ATACATATTTGAATGTATTTAGAAABATAAACAAATAGGGGTTCCGCGCACATTTCCCCGAAAA

GTGCCACCTGACGTC
```

SEQ ID NO: 57. Intermolecular biosensor Nluc-YAP15 in pcDNA3.1/hygro(+) vector (6,693 nucleotides)

```
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGAGGTCTATATAAGCAGAGCTCTCTGGCTAACTAG

AGAACCCACTGCTTACTGGCTTATCGAAATTAATACGACTCACTATAGGGAGACCCAAGCTGGC

TAGCGTTTAAACTTAAGCTTGGTACCGAGCTCGGATCCATGGAAGACGCCAAAAACATAAAGAA

AGGCCCGGCGCCATTCTATCCGCTGGAAGATGGAACCGCTGGAGAGCAACTGCATAAGGCTATG

AAGAGATACGCCCTGGTTCCTGGAACAATTGCTTTTACAGATGCACATATCGAGGTGGACATCA

CTTACGCTGAGTACTTCGAAATGTCCGTTCGGTTGGCAGAAGCTATGAAACGATATGGGCTGAA

TACAAATCACAGAATCGTCGTATGCAGTGAAAACTCTCTTCAATTCTTTATGCCGGTGTTGGGC
```

-continued

GCGTTATTTATCGGAGTTGCAGTTGCGCCCGCGAACGACATTTATAATGAACGTGAATTGCTCA

ACAGTATGGGCATTTCGCAGCCTACCGTGGTGTTCGTTTCCAAAAAGGGGTTGCGAAAAATTTT

GAACGTGCAAAAAAAGCTCCCAATCATCCAAAAAATTATTATCATGGATTCTAAAACGGATTAC

CAGGGATTTCAGTCGATGTACACGTTCGTCACATCTCATCTACCTCCCGGTTTTAATGAATACG

ATTTTGTGCCAGAGTCCTTCGATAGGGACAAGACAATTGCACTGGTCATGAACTCCTCTGGATC

TACTGGTCTGCCTAAAGGTGTCGCTCTGCCTCATAGAACTGCCTGCGTGAGATTCTCGCATGCC

AGAGATCCTATTTTTGGCAATCAAATCATTCCGGATACTGCGATTTTAAGTGTTGTTCCATTCC

ATCACGGTTTTGGAATGTTTACTACACTCGGATATTTGATATGTGGATTTCGAGTCGTCTTAAT

GTATAGATTTGAAGAAGAGCTGTTTCTGAGGAGCCTTCAGGATTACAAGATTCAAAGTGCGCTG

CTGGTGCCAACCCTATTCTCCTTCTTCGCCAAAAGCACTCTGATTGACAAATACGATTTATCTA

ATTTACACGAAATTGCTTCTGGTGGCGCTCCCCTCTCTAAGGAAGTCGGGGAAGCGGTTGCCAA

GAGGTTCCATCTGCCAGGTATCAGGCAAGGATATGGGCTCACTGAGACTACATCAGCTATTCTG

ATTACACCCGAGGGGATGATAAACCGGGCGCGGTCGGTAAAGTTGTTCCATTTTTTGAAGCGA

AGGTTGTGGATCTGGATACCGGGAAAACGCTGGGCGTTAATCAAAGAGGCGAACTGTGTGTGAG

AGGTCCTATGATTATGTCCGGTTATGTAAACAATCCGGAAGCGACCAACGCCTTGATTGACAAG

GATGGAGGAGGAGCTGGAGGCCCACAGCATGTTCGAGCTCATTCCTCTCCAGCTTCTCTGCAGT

TGGCGGCCGCTCGAGTCTAGAGGGCCCGTTTAAACCCGCTGATCAGCCTCGACTGTGCCTTCTA

GTTGCCAGCCATCTGTTGTTTGCCCCTCCCCCGTGCCTTCCTTGACCCTGGAAGGTGCCACTCC

CACTGTCCTTTCCTAATAAAATGAGGAAATTGCATCGCATTGTCTGAGTAGGTGTCATTCTATT

CTGGGGGGTGGGGTGGGGCAGGACAGCAAGGGGGAGGATTGGGAAGACAATAGCAGGCATGCTG

GGGATGCGGTGGGCTCTATGGCTTCTGAGGCGGAAAGAACCAGCTGGGGCTCTAGGGGGTATCC

CCACGCGCCCTGTAGCGGCGCATTAAGCGCGGCGGGTGTGGTGGTTACGCGCAGCGTGACCGCT

ACACTTGCCAGCGCCCTAGCGCCCGCTCCTTTCGCTTTCTTCCCTTCCTTTCTCGCCACGTTCG

CCGGCTTTCCCCGTCAAGCTCTAAATCGGGGGCTCCCTTTAGGGTTCCGATTTAGTGCTTTACG

GCACCTCGACCCCAAAAAACTTGATTAGGGTGATGGTTCACGTAGTGGGCCATCGCCCTGATAG

ACGGTTTTTCGCCCTTTGACGTTGGAGTCCACGTTCTTTAATAGTGGACTCTTGTTCCAAACTG

GAACAACACTCAACCCTATCTCGGTCTATTCTTTTGATTTATAAGGGATTTTGCCGATTTCGGC

CTATTGGTTAAAAAATGAGCTGATTTAACAAAAATTTAACGCGAATTAATTCTGTGGAATGTGT

GTCAGTTAGGGTGTGGAAAGTCCCCAGGCTCCCCAGCAGGCAGAAGTATGCAAAGCATGCATCT

CAATTAGTCAGCAACCAGGTGTGGAAAGTCCCCAGGCTCCCCAGCAGGCAGAAGTATGCAAAGC

ATGCATCTCAATTAGTCAGCAACCATAGTCCCGCCCCTAACTCCGCCCATCCCGCCCCTAACTC

CGCCCAGTTCCGCCCATTCTCCGCCCCATGGCTGACTAATTTTTTTATTTATGCAGAGGCCGA

GGCCGCCTCTGCCTCTGAGCTATTCCAGAAGTAGTGAGGAGGCTTTTTTGGAGGCCTAGGCTTT

TGCAAAAAGCTCCCGGGAGCTTGTATATCCATTTTCGGATCTGATCAAGAGACAGGATGAGGAT

CGTTTCGCATGATTGAACAAGATGGATTGCACGCAGGTTCTCCGGCCGCTTGGGTGGAGAGGCT

ATTCGGCTATGACTGGGCACAACAGAGAATCGGCTGCTCTGATGCCGCCGTGTTCCGGCTGTCA

GCGCAGGGGCGCCCGGTTCTTTTTGTCAAGACCGACCTGTCCGGTGCCCTGAATGAACTGCAGG

ACGAGGCAGCGCGGCTATCGTGGCTGGCCACGACGGGCGTTCCTTGCGCAGCTGTGCTCGACGT

TGTCACTGAAGCGGGAAGGGACTGGCTGCTATTGGGCGAAGTGCCGGGGCAGGATCTCCTGTCA

TCTCACCTTGCTCCTGCCGAGAAAGTATCCATCATGGCTGATGCAATGCGGCGGCTGCATACGC

-continued

```
TTGATCCGGCTACCTGCCCATTCGACCACCAAGCGAAACATCGCATCGAGCGAGCACGTACTCG
GATGGAAGCCGGTCTTGTCGATCAGGATGATCTGGACGAAGAGCATCAGGGGCTCGCGCCAGCC
GAACTGTTCGCCAGGCTCAAGGCGCGCATGCCCGACGGCGAGGATCTCGTCGTGACCCATGGCG
ATGCCTGCTTGCCGAATATCATGGTGGAAAATGGCCGCTTTTCTGGATTCATCGACTGTGGCCG
GCTGGGTGTGGCGGACCGCTATCAGGACATAGCGTTGGCTACCCGTGATATTGCTGAAGAGCTT
GGCGGCGAATGGGCTGACCGCTTCCTCGTGCTTTACGGTATCGCCGCTCCCGATTCGCAGCGCA
TCGCCTTCTATCGCCTTCTTGACGAGTTCTTCTGAGCGGGACTCTGGGGTTCGAAATGACCGAC
CAAGGGACGCCCAACCTGCCATCACGAGATTTCGATTCCACCGCCGCCTTCTATGAAAGGTTGG
GCTTCGGAATCGTTTTCCGGGACGCCGGCTGGATGATCCTCCAGCGCGGGGATCTCATGCTGGA
GTTCTTCGCCCACCCCAACTTGTTTATTGCAGCTTATAATGGTTACAAATAAAGCAATAGCATC
ACAAATTTCACAAATAAAGCATTTTTTTCACTGCATTCTAGTTGTGGTTTGTCCAAACTCATCA
ATGTATCTTATCATGTCTGTATACCGTCGACCTCTAGCTAGAGCTTGGCGTAATCATGGTCATA
GCTGTTTCCTGTGTGAAATTGTTATCCGCTCACAATTCCACACAACATACGAGCCGGAAGCATA
AAGTGTAAAGCCTGGGGTGCCTAATGAGTGAGCTAACTCACATTAATTGCGTTGCGCTCACTGC
CCGCTTTCCAGTCGGGAAACCTGTCGTGCCAGCTGCATTAATGAATCGGCCAACGCGCGGGGAG
AGGCGGTTTGCGTATTGGGCGCTCTTCCGCTTCCTCGCTCACTGACTCGCTGCGCTCGGTCGTT
CGGCTGCGGCGAGCGGTATCAGCTCACTCAAAGGCGGTAATACGGTTATCCACAGAATCAGGGG
ATAACGCAGGAAAGAACATGTGAGCAAAAGGCCAGCAAAAGGCCAGGAACCGTAAAAAGGCCGC
GTTGCTGGCGTTTTTCCATAGGCTCCGCCCCCCTGACGAGCATCACAAAAATCGACGCTCAAGT
CAGAGGTGGCGAAACCCGACAGGACTATAAAGATACCAGGCGTTTCCCCCTGGAAGCTCCCTCG
TGCGCTCTCCTGTTCCGACCCTGCCGCTTACCGGATACCTGTCGGCCTTTCTCCCTTCGGGAAG
CGTGGCGCTTTCTCATAGCTCACGCTGTAGGTATCTCAGTTCGGTGTAGGTCGTTCGCTCCAAG
CTGGGCTGTGTGCACGAACCGCCCGTTCAGCCCGACCGCTGCGCCTTATCCGGTAACTATCGTC
TTGAGTCCAACCCGGTAAGACACGACTTATCGCCACTGGCAGCAGCCACTGGTAACAGGATTAG
CAGAGCGAGGTATGTAGGCGGTGCTACAGAGTTCTTGAAGTGGTGGCCTAACTACGGCTACACT
AGAAGAACAGTATTTGGTATCTGCGCTCTGCTGAAGCCAGTTACCTTCGGAAAAAGAGTTGGTA
GCTCTTGATCCGGCAAACAAACCACCGCTGGTAGCGGTTTTTTTGTTTGCAAGCAGCAGATTAC
GCGCAGAAAAAAAGGATCTCAAGAAGATCCTTTGATCTTTTCTACGGGGTGTGACGCTCAGTGG
AACGAAAACTCACGTTAAGGGATTTTGGTCATGAGATTATCAAAAAGGATCTTCACCTAGATCC
TTTTAAATTAAAAATGAAGTTTTAAATCAATCTAAAGTATATATGAGTAAACTTGGTCTGACAG
TTACCAATGCTTAATCAGTGAGGCACCTATCTCAGCGATCTGTCTATTTCGTTCATCCATAGTT
GCCTGACTCCCCGTCGTGTAGATAACTAGGATACGGGAGGGCTTACCATCTGGCCCCAGTGCTG
CAATGATACCGCGAGACCCACGCTCACCGGCTCCAGATTTATCAGCAATAAACCAGCCAGCCGG
AAGGGCCGAGCGCAGAAGTGGTCCTGCAACTTTATCCGCCTCCATCCAGTCTATTAATTGTTGC
CGGGAAGCTAGAGTAAGTAGTTCGCCAGTTAATAGTTTGCGCAACGTTGTTGCGATTGCTACAG
GCATCGTGGTGTCACGCTCGTCGTTTGGTATGGCTTCATTCAGCTCCGGTTCCCAACGATCAAG
GCGAGTTACATGATCCCCCATGTTGTGCAAAAAAGCGGTTAGCTCCTTCGGTCCTCCGATCGTT
GTCAGAAGTAAGTTGGCCGCAGTGTTATCACTCATGGTTATGGCAGCACTGCATAATTCTCTTA
CTGTCATGCCATCCGTAAGATGCTTTTCTGTGACTGGTGAGTACTCAACCAAGTCATTCTGAGA
ATAGTGTATGCGGCGACCGAGTTGCTCTTGCCCGGCGTCAATACGGGATAATACCGCGCGACAT
AGCAGAACTTTAAAAGTGCTCATCATTGGAAAACGTTCTTCGGGGCGAAAACTCTCAAGGATCT
```

-continued

TACCGCTGTTGAGATCCAGTTCGATGTAACCCACTCGTGCACCCAACTGATCTTCAGCATCTTT

TACTTTCACCAGCGTTTCTGGGTGAGCAAAAACAGGAAGGCAAAATGCCGCAAAAAGGGAATA

AGGGCGACACGGAAATGTTGAATACTCATACTCTTCGTTTTTCAATATTATTGAAGCATTTATC

AGGGTTATTGTCTCATGAGCGGATACATATTTGAATGTATTTAGAAAAATAAACAAATAGGGGT

TCCGCGCACATTTCCCCGAAAAGTGCCACCTGACGTC

SEQ ID NO: 58. Intermolecular biosensor 14-3-3-Cluc in pcDNA3.1/
hygro(+) vector (6,621 nucleotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGACTAGTGCGCGAGCAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGGCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGACTCACTATAGGGAGACCCAAGCTGGC

TAGCGTTTAAACTTAAGCTTGGTACCGAGCTCGGATCCATGGAAGACTGAGCTGATCCAGAA

GGCCAAGCTGGCCGAGCAGGCCGAGCGCTACGACGACATGGCCACCTGCATGAAGGCAGTGACC

GAGCAGGGGGCCGAGCTGTCCAACGAGGAGCGCAACCTGCTCTCCGTGGCCTACAAGAACGTGG

TCGGGGCCGCAGGTCCGCCTGGAGGGTCATCTCTAGCATCGAGCAGAAGACCGACACCTCCGA

CAAGAAGTTGCAGCTGATTAAGGACTATCGGGAGAAAGTGGAGTCCGAGCTGAGATCCATCTGC

ACCACGGTGCTGGAATTGTTGGATAAATATTTAATAGCCAATGCAACTAATCCAGAGAGTAAGG

TCTTCTATCTGAAAATGAAGGGTGATTACTTCCGGTACCTTGCTGAAGTTGCGTGTGGTGATGA

TCGAAAACAAACGATAGATAATTCCCAAGGAGCTTACCAAGAGGCATTTGATATAAGCAAGAAA

GAGATGCAACCCACACACCCAATCCGCCTGGGGCTTGCTCTTAACTTTTCTGTATTTTACTATG

AGATTCTTAATAACCCAGAGCTTGCCTGCACGCTGGCTAAAACGGCTTTTGATGAGGCCATTGC

TGAACTTGATACACTGAATGAAGACTCATACAAAGACAGCACCCTCATCATGCAGTTGCTTAGA

GACAACCTAACACTTTGGACATCAGACAGTGCAGGAGAAGAATGTGATGCGGCAGAAGGGCTG

AAAACGGAGGAGGAGGTAGTGGAGGAGGAGGTAGTCCTATGATTATGTCCGGTTATGTAAACAA

TCCGGAAGCGACCAACGCCTTGATTGACAAGGATGGATGGCTACATTCTGGAGACATAGCTTAC

TGGGACGAAGACGAACACTTCTTCATCGTTGACCGCCTGAAGTCTCTGATTAAGTACAAAGGCT

ATCAGGTGGCTCCCGCTGAATTGGAATCCATCTTGCTCCAACACCCCAACATCTTCGACGCAGG

TGTCGCAGGTCTTCCCGACGATGACGCCGGTGAACTTCCCGCCGCCGTTGTTGTTTGGAGCAC

GGAAAGACGATGACGGAAAGAGAGATCGTGGATTACGTCGCCAGTCAAGTAACAACCGCGGAAA

AGTTGCGCGGAGGAGTTGTGTTTGTGGACGAAGTACCGAAAGGTCTTACCGGAAAACTCGACGC

AAGAAAAAATCAGAGAGATCCTCATAAAGGCCAAGAAGGGCGGAAAGATCGCCGTGTAAGCGGCC

-continued

```
GCTCGAGTCTAGAGGGCCCGTTTAAACCCGCTGATCAGCCTCGACTGTGCCTTCTAGTTGCCAG

CCATCTGTTGTTTGCCCCTCCCCCGTGCCTTCCTTGACCCTGGAAGGTGCCACTCCCACTGTCC

TTTCCTAATAAAATGAGGAAATTGCATCGCATTGTCTGAGTAGGTGTCATTCTATTCTGGGGGG

TGGGGTGGGGCAGGACAGCAAGGGGGAGGATTGGGAAGACAATAGCAGGCATGCTGGGGATGGG

GTGGGCTCTATGGCTTCTGAGGCGGAAAGAACCAGCTGGGGCTCTAGGGGGTATCCCCACGCGC

CCTGTAGCGGCGCATTAAGCGCGGCGGGTGTGGTGGTTACGCGCAGCGTGACCGCTACACTTGC

CAGCGCCCTAGCGCCCGCTCCTTTCGCTTTCTTCCCTTCCTTTCTCGCCACGTTCGCCGGCTTT

CCCCGTCAAGCTCTAAATCGGGGGCTCCCTTTAGGGTTCCGATTTAGTGCTTTACGGCACCTCG

ACCCCAAAAAACTTGATTAGGGTGATGGTTCACGTAGTGGGCCATCGCCCTGATAGACGGTTTT

TCGCCCTTTGACGTTGGAGTCCACGTTCTTTAATAGTGGACTCTTGTTCCAAACTGGAACAACA

CTCAACCCTATCTCGGTCTATTCTTTTGATTTATAAGGGATTTTGCCGATTTCGGCCTATTGGT

TAAAAAATGAGCTGATTTAACAAAAATTTAACGCGAATTAATTCTGTGGAATGTGTGTCAGTTA

GGGTGTGGAAAGTCCCCAGGCTCCCCAGCAGGCAGAAGTATGCAAAGCATGCATCTCAATTAGT

CAGCAACCAGGTGTGGAAAGTCCCCAGGCTCCCCAGCAGGCAGAAGTATGCAAAGCATGCATCT

CAATTAGTCAGCAACCATAGTCCCGCCCCTAACTCCGCCCATCCCGCCCCTAACTCCGCCCAGT

TCCGCCCATTCTCCGCCCCATGGCTGACTAATTTTTTTTATTTATGCAGAGGCCGAGGCCGCCT

CTGCCTCTGAGCTATTCCAGAAGTAGTGAGGAGGCTTTTTTGGAGGCCTAGGCTTTTGCAAAAA

GCTCCCGGGAGCTTGTATATCCATTTTCGGATCTGATCAAGAGACAGGATGAGGATCGTTTCGC

ATGATTGAACAAGATGGATTGCACGCAGGTTCTCCGGCCGCTTGGGTGGAGAGGCTATTCGGCT

ATGACTGGGCACAACAGACAATCGGCTGCTCTGATGCCGCCGTGTTCCGGCTGTCAGCGCAGGG

GCGCCCGGTTCTTTTTGTCAAGACCGACCTGTCCGGTGCCCTGAATGAACTGCAGGACGAGGCA

GCGCGGCTATCGTGGCTGGCCACGACGGGCGTTCCTTGCGCAGCTGTGCTCGACGTTGTCACTG

AAGCGGGAAGGGACTGGCTGCTATTGGGCGAAGTGCCGGGGCAGGATCTCCTGTCATCTCACCT

TGCTCCTGCCGAGAAAGTATCCATCATGGCTGATGCAATGCGGCGGCTGCATACGCTTGATCCG

GCTACCTGCCCATTCGACCACCAAGCGAAACATCGCATCGAGCGAGCACGTACTCGGATGGAAG

CCGGTCTTGTCGATCAGGATGATCTGGACGAAGAGCATCAGGGGCTCGCGCCAGCCGAACTGTT

CGCCAGGCTCAAGGCGCGCATGCCCGACGGCGAGGATCTCGTCGTGACCCATGGCGATGCCTGC

TTGCCGAATATCATGGTGGAAAATGGCCGCTTTTCTGGATTCATCGACTGTGGCCGGCTGGGTG

TGGCGGACCGCTATCAGGACATAGCGTTGGCTACCCGTGATATTGCTGAAGAGCTTGGCGGCGA

ATGGGCTGACCGCTTCCTCGTGCTTTACGGTATCGCCGCTCCCGATTCGCAGCGCATCGCCTTC

TATCGCCTTCTTGACGAGTTCTTCTGAGCGGGACTCTGGGGTTCGAAATGACCGACCAAGCGAC

GCCCAACCTGCCATCACGAGATTTCGATTCCACCGCCGCCTTCTATGAAAGGTTGGGCTTCGGA

ATCGTTTTCCGGGACGCCGGCTGGATGATCCTCCAGCGCGGGGATCTCATGCTGGAGTTCTTCG

CCCACCCCAACTTGTTTATTGCAGCTTATAATGGTTACAAATAAAGCAATAGCATCACAAATTT

CACAAATAAAGCATTTTTTTCACTGCATTCTAGTTGTGGTTTGTCCAAACTCATCAATGTATCT

TATCATGTCTGTATACCGTCGACCTCTAGCTAGAGCTTGGGGTAATCATGGTCATAGCTGTTTC

CTGTGTGAAATTGTTATCCGCTCACAATTCCACACAACATACGAGCCGGAAGCATAAAGTGTAA

AGCCTGGGGTGCCTAATGAGTGAGCTAACTCACATTAATTGCGTTGCGCTCACTGCCCGCTTTC

CAGTCGGGAAACCTGTCGTGCCAGCTGCATTAATGAATCGGCCAACGCGCGGGGAGAGGCGGTT

TGCGTATTGGGCGCTCTTCCGCTTCCTCGCTCACTGACTCGCTGCGCTCGGTCGTTCGGCTGCG

GCGAGCGGTATCAGCTCACTCAAAGGCGGTAATACGGTTATCCACAGAATCAGGGGATAACGCA
```

-continued

```
GGAAAGAACATGTGAGCAAAAGGCCAGCAAAAGGCCAGGAACCGTAAAAAGGCCGCGTTGCTGG

CGTTTTTCCATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCGTGCGCTCT

CCTGTTCCGACCCTGCCGCTTACCGGATACCTGTCCGCCTTTCTCCCTTCGGGAAGCGTGGCGC

TTTCTCATAGCTCACGCTGTAGGTATCTCAGTTCGGTGTAGGTCGTTCGCTCCAAGCTGGGCTG

TGTGCACGAACCCCCCGTTCAGCCCGACCGCTGCGCCTTATCCGGTAACTATCGTCTTGAGTCC

AACCCGGTAAGACACGACTTATCGCCACTGGCAGCAGCCACTGGTAACAGGATTAGCAGAGCGA

GGTATGTAGGCGGTGCTACAGAGTTCTTGAAGTGGTGGCCTAACTACGGCTACACTAGAAGAAC

AGTATTTGGTATCTGCGCTCTGCTGAAGCCAGTTACCTTCGGAAAAAGAGTTGGTAGCTCTTGA

TCCGGCAAACAAACCACCGCTGGTAGCGGTTTTTTTGTTTGCAAGCAGCAGATTACGCGCAGAA

AAAAAGGATCTCAAGAAGATCCTTTGATCTTTTCTACGGGGTCTGACGCTCAGTGGAACGAAAA

CTCACGTTAAGGGATTTTGGTCATGAGATTATCAAAAAGGATCTTCACCTAGATCCTTTTAAAT

TAAAAATGAAGTTTTAAATCAATCTAAAGTATATATGAGTAAACTTGGTCTGACAGTTACCAAT

GCTTAATCAGTGAGGCACCTATCTCAGCGATCTGTCTATTTCGTTCATCCATAGTTGCCTGACT

CCCCGTCGTGTAGATAACTACGATACGGGAGGGCTTACCATCTGGCCCCAGTGCTGCAATGATA

CCGCGAGACCCACGCTCACCGGCTCCAGATTTATCAGCAATAAACCAGCCAGCCGGAAGGGCCG

AGCGCAGAAGTGGTCCTGCAACTTTATCCGCCTCCATCCAGTCTATTAATTGTTGCCGGGAAGC

TAGAGTAAGTAGTTCGCCAGTTAATAGTTTGCGCAACGTTGTTGCCATTGCTACAGGCATCGTG

GTGTCACGCTCGTCGTTTGGTATGGCTTCATTCAGCTCCGGTTCCCAACGATCAAGGCGAGTTA

CATGATCCCCCATGTTGTGCAAAAAAGCGGTTAGCTCCTTCGGTCCTCCGATCGTTGTCAGAAG

TAAGTTGGCCGCAGTGTTATCACTCATGGTTATGGCAGCACTGCATAATTCTCTTACTGTCATG

CCATCCGTAAGATGCTTTTCTGTGACTGGTGAGTACTCAACCAAGTCATTCTGAGAATAGTGTA

TGCGGCGACCGAGTTGCTCTTGCCCGGCGTCAATACGGGATAATACCGCGCCACATAGCAGAAC

TTTAAAAGTGCTCATCATTGGAAAACGTTCTTCGGGGCGAAAACTCTCAAGGATCTTACCGCTG

TTGAGATCCAGTTCGATGTAACCCACTCGTGCACCCAACTGATCTTCAGCATCTTTTACTTTCA

CCAGCGTTTCTGGGTGAGCAAAAACAGGAAGGCAAAATGCCGCAAAAAAGGGAATAAGGGCGAC

ACGGAAATGTTGAATACTCATACTCTTCCTTTTTCAATATTATTGAAGCATTTATCAGGGTTAT

TGTCTCATGAGCGGATACATATTTGAATGTATTTAGAAAAATAAACAAATAGGGGTTCCGCGCA

CATTTCCCCGAAAAGTGCCACCTGACGTC

SEQ ID NO: 59. NanoBiT Biosensor: LgBiT-YAP15 in pBiT 1.1 N
vector (3,890 nucleotides)
GGCCTAACTGGCCGGTACCTGAGTCTAAATGAGTCTTCGGACCTCGCGGGGCCGCTTAAGCGG

TGGTTAGGGTTTGTCTGACGCGGGGGGAGGGGGAAGGAACGAAACACTCTCATTCGGAGGCGGC

TCGGGGTTTGGTGTTGGTGGCCACGGGCACGCAGAAGAGCGCCGCGATCCTCTTAAGCACCCCC

CCGCCCTCCGTGGAGGCGGGGGTTTGGTCGGCGGGTGGTAACTGGCGGGCCGCTGACTCGGGCG

GGTCGCGCGCCCCAGAGTGTGACCTTTTCGGTCTGCTCGCAACCCCCGGGCGGCGCCGCCGCGG

CGGCGACGGGCTCGCTGGGTCCTAGGCTCCATGGGGACCGTATACGTGGACAGGCTCTGGAGCA

TCCGCACGACTGCGGTGATATTACCGGAGACCTTCTGCGGGACGAGCCGGGTCACGCGGCTGAC

CCGGAGCGTCCGTTGGGCGACAAACACCAGGACGGGGCACAGGTACACTATCTTGTCACCCGGA

GGCGCGAGGGACTGCAGGAGCTTGAGGGAGTGGCGCAGCTGCTTCATCCCCGTGGCCCGTTGCT

CGCGTTTGCTGGCGGTGTCCCCGGAAGAAATATATTTGCATGTCTTTAGTTCTATGATGACACA
```

-continued

AACCCCGCCCAGCGTCTTGTCATTGGCGAAGTCGAACACGCAGATGCAGTCGGGGCGGCGGGT

CCCAGGTCCACTTCGCATATTAAGGTGACGCGTGTGGCCTCGAACACCGAGCGACCCTGCAGCG

ACCCGCTTAAAAGCTTGGCAATCCGGTACTGTTGGTAAAGCCACCATGGTCTTCACACTCGAAG

ATTTCGTTGGGGACTGGGAACAGACAGCCGCCTACAACCTGGACCGAGTCCTTGAACAGGGAGG

TGTGTCCAGTTTGCTGCAGAATCTCGCCGTGTCCGTAACTCCGATCCAAAGGATTGTCCGGAGC

GGTGAAAATGCCCTGAAGATCGACATCCATGTCATCATCCCGTATGAAGGTCTGGGCGCCGACC

AAATGGCCCAGATCGAAGAGGTGTTTAAGGTGGTGTACCCTGTGGATGATCATCACTTTAAGGT

GATCCTGCCCTATGGCACACTGGTAATCGACGGGGTTACGCCGAACATGCTGAACTATTTCGGA

CGGCCGTATGAAGGCATCGCCGTGTTCGACGGCAAAAAGATCACTGTAACAGGGACCCTGTGGA

ACGGCAACAAAATTATCGACGAGCGCCTGATCACCCCCGACGGCTCCATGCTGTTCCGAGTAAC

CATCAACAGTGGGAGTTCCGGTGGTGGCGGGAGCGGAGGTGGAGGCTCGAGCGGTGGAGCTCAG

GGGAATTCCCCACAGCATGTTCGAGCTCATTCCTCTCCAGCTTCTCTGCAGTTGAGATCTTCTA

GAGTCGGGGCGGCCGGCCGCTTCGAGCAGACATGATAAGATACATTGATGAGTTTGGACAAACC

ACAACTAGAATGCAGTGAAAAAAATGCTTTATTTGTGAAATTTGTGATGCTATTGCTTTATTTG

TAACCATTATAAGCTGCAATAAACAAGTTAACAACAACAATTGCATTCATTTTATGTTTCAGGT

TCAGGGGGAGGTGTGGGAGGTTTTTTAAAGCAAGTAAAACCTCTACAAATCTGGTAAAATCGAT

AAGGATCCGTCGACCGATGCCCTTGAGAGCCTTCAACCCAGTCAGCTCCTTCCGGTGGGCGCGG

GGCATGACTATCGTCGCCGCACTTATGACTGTCTTCTTTATCATGCAACTCGTAGGACAGGTGC

CGGCAGCGCTCTTCCGCTTCCTCGCTCACTGACTCGCTGCGCTCGGTCGTTCGGCTGCGGCGAG

CGGTATCAGCTCACTCAAAGGCGGTAATACGGTTATCCACAGAATCAGGGGATAACGCAGGAAA

GAACATGTGAGCAAAAGGCCAGCAAAAGGCCAGGAACCGTAAAAAGGCCGCGTTGCTGGCGTTT

TTCCATAGGCTCCGCCCCCCTGACGAGCATCACAAAAATCGACGCTCAAGTCAGAGGTGGCGAA

ACCCGACAGGACTATAAAGATACCAGGCGTTTCCCCCTGGAAGCTCCCTCGTGCGCTCTCCTGT

TCCGACCCTGCCGCTTACCGGATACCTGTCCGCCTTTCTCCCTTCGGGAAGCGTGGCGCTTTCT

CATAGCTCACGCTGTAGGTATCTCAGTTCGGTGTAGGTGGTTCGCTCCAAGCTGGGCTGTGTGC

ACGAACCCCCCGTTCAGCCCGACCGCTGCGCCTTATCCGGTAACTATCGTCTTGAGTCCAACCC

GGTAAGACACGACTTATCGCCACTGGCAGCAGCCACTGGTAACAGGATTAGCAGAGCGAGGTAT

GTAGGCGGTGCTACAGAGTTCTTGAAGTGGTGGCCTAACTACGGCTACACTAGAAGAACAGTAT

TTGGTATCTGCGGTCTGCTGAAGCCAGTTACCTTCGGAAAAAGAGTTGGTAGCTCTTGATCCGG

CAAACAAACCACCGCTGGTAGCGGTGGTTTTTTTGTTTGCAAGCAGCAGATTACGCGCAGAAAA

AAAGGATCTCAAGAAGATCCTTTGATCTTTTCTACGGGGTCTGACGCTCAGTGGAACGAAAACT

CACGTTAAGGGATTTTGGTCATGAGATTATCAAAAAGGATCTTCACCTAGATCCTTTTAAATTA

AAAATGAAGTTTTAAATCAATCTAAAGTATATATGAGTAAACTTGGTCTGACAGCGGCCGCAAA

TGCTAAACCACTGCAGTGGTTACCAGTGCTTGATCAGTGAGGCACCGATCTCAGCGATCTGCCT

ATTTCGTTCGTCCATAGTGGCCTGACTCCCCGTCGTGTAGATCACTACGATTCGTGAGGGCTTA

CCATCAGGCCCCAGCGCAGCAATGATGCCGCGAGAGCCGCGTTCACCGGCCCCCGATTTGTCAG

CAATGAACCAGCCAGCAGGGAGGGCCGAGCGAAGAAGTGGTCCTGCTACTTTGTCCGCCTCCAT

CCAGTCTATGAGCTGCTGTCGTGATGCTAGAGTAAGAAGTTCGCCAGTGAGTAGTTTCCGAAGA

GTTGTGGCCATTGCTACTGGCATCGTGGTATCACGCTCGTCGTTCGGTATGGCTTCGTTCAACT

CTGGTTCCCAGCGGTCAAGCCGGGTCACATGATCACCCATATTATGAAGAAATGCAGTCAGCTC

CTTAGGGCCTCCGATCGTTGTCAGAAGTAAGTTGGCCGCGGTGTTGTCGCTCATGGTAATGGCA

GCACTACACAATTCTCTTACCGTCATGCCATCCGTAAGATGCTTTTCCGTGACCGGCGAGTACT

CAACCAAGTCGTTTTGTGAGTAGTGTATACGGCGACCAAGCTGCTCTTGCCCGGCGTCTATACG

GGACAACACCGCGCCACATAGCAGTACTTTGAAAGTGCTCATCATCGGGAATCGTTCTTCGGGG

CGGAAAGACTCAAGGATCTTGCCGCTATTGAGATCCAGTTCGATATAGCCCACTCTTGCACCCA

GTTGATCTTCAGCATCTTTTACTTTCACCAGCGTTTCGGGGTGTGCAAAAACAGGCAAGCAAAA

TGCCGCAAAGAAGGGAATGAGTGCGACACGAAAATGTTGGATGCTCATACTCGTCCTTTTTCAA

TATTATTGAAGCATTTATCAGGGTTACTAGTACGTCTCTCAAGGATAAGTAAGTAATATTAAGG

TACGGGAGGTATTGGACAGGCCGCAATAAAATATCTTTATTTTCATTACATCTGTGTGTTGGTT

TTTTGTGTGAATCGATAGTACTAACATACGCTCTCCATCAAAACAAAACGAAACAAAACAAACT

AGCAAAATAGGCTGTCCCCAGTGCAAGTGCAGGTGCCAGAACATTTCTCT

SEQ ID NO: 60. NanoBiT Biosensor: 14-3-3-LgBiT in pBiT2.1-C
vector (4,131 nucleotides)
GGCCTAACTGGCCGGTACCTGAGTCTAAATGAGTCTTCGGACCTCGCGGGGGCCGCTTAAGCGG

TGGTTAGGGTTTGTCTGACGCGGGGGGAGGGGAAGGAACGAAACACTCTCATTCGGAGGCGGC

TCGGGGTTTGGTCTTGGTGGCCACGGGCACGCAGAAGAGCGCCGCGATCCTCTTAAGCACCCCC

CCGCCCTCCGTGGAGGCGGGGGTTTGGTCGGCGGGTGGTAACTGGCGGGCCGCTGACTCGGGCG

GGTCGCGCGCCCCAGAGTGTGACCTTTTCGGTCTGCTCGCAGACCCCCGGGCGGCGCCGCCGCG

GCGGCGACGGGCTCGCTGGGTCCTAGGCTCCATGGGGACCGTATACGTGGACAGGCTCTGGAGC

ATCCGCACGACTGCGGTGATATTACCGGAGACCTTCTGCGGGACGAGCCGGGTCACGCGGCTGA

CGCGGAGCGTCCGTTGGGCGACAAACACCAGGACGGGGCACAGGTACACTATCTTGTCACCCGG

AGGCGCGAGGGACTGCAGGAGCTTCAGGGAGTGGCGCAGCTGCTTCATCCCCGTGGCCCGTTGC

TCGCGTTTGCTGGCGGTGTCCCCGGAAGAAATATATTTGCATGTCTTTAGTTCTATGATGACAC

AAACCCCGCCCAGCGTCTTGTCATTGGCGAAGTCGAACACGCAGATGCAGTCGGGGCGGCGCGG

TCCCAGGTCCACTTCGCATATTAAGGTGACGCGTGTGGCCTCGAACACCGAGCGACCCTGCAGC

GACCCGCTTAAAAGCTTGGCAATCCGGTACTGTGGTAAAGCCACCAGATCTAATGGAGAAGACT

GAGCTGATCCAGAAGGCCAAGCTGGCCGAGCAGGCCGAGCGCTACGACGACATGGCCACCTGCA

TGAAGGCAGTGACCGAGCAGGGCGCCGAGCTGTCCAACGAGGAGCGCAACCTGCTCTCCGTGGC

CTACAAGAACGTGGTCGGGGGCCGCAGGTCCGCCTGGAGGGTCATCTCTAGCATCGAGCAGAAG

ACCGACACCTCCGACAAGAAGTTGCAGCTGATTAAGGACTATCGGGAGAAAGTGGAGTCCGAGC

TGAGATCCATCTGCACCACGGTGCTGGAATTGTTGGATAAATATTTAATAGCCAATGCAACTAA

TCCAGAGAGTAAGGTCTTCTATCTGAAAATGAAGGGTGATTACTTCCGGTACCTTGCTGAAGTT

GCGTGTGGTGATGATCGAAAACAAACGATAGATAATTCCCAAGGAGCTTACCAAGAGGCATTTG

ATATAAGCAAGAAAGAGATGCAACCCACACACCCAATCCGCCTGGGGCTTGCTCTTAACTTTTC

TGTATTTTACTATGAGATTCTTAATAACCCAGAGCTTGCCTGCACGCTGGCTAAAACGGCTTTT

GATGAGGCCATTGCTGAACTTGATACACTGAATGAAGACTCATACAAAGACAGCACCCTCATCA

TGCAGTTGCTTAGAGACAACCTAACACTTTGGACATCAGACAGTGCAGGAGAAGAATGTGATGC

GGCAGAAGGGGCTGAAAACCCGAATTCTGGCTCGAGCGGTGGTGGCGGGAGCGGAGGTGGAGGG

TCGTCAGGTGTGACCGGCTACCGGCTGTTCGAGGAGATTCTGTAATCTAGAGTCGGGGCGGCCG

GCCGCTTCGAGCAGACATGATAAGATACATTGATGAGTTTGGACAAACCACAACTAGAATGCAG

TGAAAAAAATGCTTTATTTGTGAAATTTGTGATGCTATTGCTTTATTTGTAACCATTATAAGCT

GCAATAAACAAGTTAACAACAACAATTGCATTCATTTTATGTTTCAGGTTCAGGGGGAGGTGTG

```
GGAGGTTTTTTAAAGCAAGTAAAACCTCTACAAATGTGGTAAAATCGATAAGGATCCGTCGACC
GATGCCCTTGAGAGCCTTCAACCCAGTCAGCTCCTTCCGGTGGGCGCGGGGCATGACTATCGTC
GCCGCACTTATGACTGTCTTCTTTATCATGCAACTCGTAGGACAGGTGCCGGCAGCGCTCTTCC
GCTTCCTCGCTGACTGACTCGCTGCGCTCGGTCGTTCGGCTGCGGCGAGCGGTATCAGCTCACT
CAAAGGCGGTAATACGGTTATCCACAGAATCAGGGGATAACGCAGGAAAGAACATGTGAGCAAA
AGGCCAGCAAAAGGCCAGGAACCGTAAAAAGGCCGCGTTGCTGGCGTTTTTCCATAGGCTCCGC
CCCCCTGACGAGCATCACAAAAATCGACGCTCAAGTCAGAGGTGGCGAAACCCGACAGGACTAT
AAAGATACCAGGCGTTTCCCCCTGGAAGCTCCCTCGTGCGCTCTCCTGTTCCGACCCTGCCGCT
TACCGGATACCTGTCCGCCTTTCTCCCTTCGGGAAGCGTGGCGCTTTCTCATAGCTCACGCTGT
AGGTATCTCAGTTCGGTGTAGGTCGTTCGCTCCAAGCTGGGCTGTGTGCACGAACCCCCCGTTC
AGCCCGAGCGCTGCGCCTTATCCGGTAACTATCGTCTTGAGTCCAACCCGGTAAGACACGACTT
ATCGCCACTGGCAGCAGCCACTGGTAACAGGATTAGCAGAGCGAGGTATGTAGGCGGTGCTACA
GAGTTCTTGAAGTGGTGGCCTAACTACGGCTACACTAGAAGAACAGTATTTGGTATCTGCGCTC
TGCTGAAGCCAGTTACCTTCGGAAAAAGAGTTGGTAGCTCTTGATCCGGCAAACAAACCACCGC
TGGTAGCGGTGGTTTTTTTGTTTGCAAGCAGCAGATTACGCGCAGAAAAAAAGGATCTCAAGAA
GATCCTTTGATCTTTTCTACGGGGTCTGACGCTCAGTGGAACGAAAACTCACGTTAAGGGATTT
TGGTCATGAGATTATCAAAAAGGATCTTCACCTAGATCCTTTTAAATTAAAAATGAAGTTTTAA
ATCAATCTAAAGTATATATGAGTAAACTTGGTCTGACAGCGGCCGCAAATGCTAAACCACTGCA
GTGGTTACCAGTGCTTGATCAGTGAGGCACCGATCTCAGCGATCTGCCTATTTCGTTCGTCCAT
AGTGGCCTGACTCCCCGTCGTGTAGATCACTACGATTCGTGAGGGCTTACCATCAGGCCCCAGC
GCAGCAATGATGCCGCGAGAGCCGCGTTCACCGGCCCCCGATTTGTCAGCAATGAACCAGCCAG
CAGGGAGGGCCGAGCGAAGAAGTGGTCCTGCTACTTTGTCCGCCTCCATCCAGTCTATGAGCTG
CTGTCGTGATGCTAGAGTAAGAAGTTCGCCAGTGAGTAGTTTCCGAAGAGTTGTGGCCATTGCT
ACTGGCATCGTGGTATCACGCTCGTCGTTCGGTATGGCTTCGTTCAACTCTGGTTCCCAGCGGT
CAAGCCGGGTCACATGATCACCCATATTATGAAGAAATGCAGTCAGCTCCTTAGGGCCTCCGAT
CGTTGTCAGAAGTAAGTTGGCCGCGGTGTTGTCGCTCATGGTAATGGCAGCACTACACAATTCT
CTTACCGTCATGCCATCCGTAAGATGCTTTTCCGTGACCGGCGAGTACTCAACCAAGTCGTTTT
GTGAGTAGTGTATACGGCGACCAAGCTGCTCTTGCCCGGCGTCTATACGGGACAACACCGCGCC
ACATAGCAGTACTTTGAAAGTGCTCATCATCGGGAATCGTTCTTCGGGGCGGAAAGACTCAAGG
ATCTTGCCGCTATTGAGATCCAGTTCGATATAGCCCACTCTTGCACCCAGTTGATCTTCAGCAT
CTTTTACTTTCACCAGCGTTTCGGGGTGTGCAAAAACAGGCAAGCAAATGCCGCAAAGAAGGG
AATGAGTGCGACACGAAAATGTTGGATGCTCATACTCGTCCTTTTTCAATATTATTGAAGCATT
TATCAGGGTTACTAGTACGTCTCTCAAGGATAAGTAAGTAATATTAAGGTACGGGAGGTATTGG
ACAGGCCGCAATAAAATATCTTTATTTTCATTACATCTGTGTGTTGGTTTTTTGTGTGAATCGA
TAGTACTAACATACGCTCTCCATCAAAACAAAACGAAACAAAACAAACTAGCAAAATAGGCTGT
CCCCAGTGCAAGTGCAGGTGCCAGAACATTTCTCT
```

SEQ ID NO: 61. NanoBiT Biosensor: LgBiT-YAP15 in pET16b vector
(6,291 nucleotides)

```
TTCTTGAAGACGAAAGGGCCTCGTGATACGCCTATTTTTATAGGTTAATGTCATGATAATAATG
GTTTCTTAGACGTCAGGTGGCACTTTTCGGGGAAATGTGCGCGGAACCCCTATTTGTTTATTTT
TCTAAATACATTCAAATATGTATCCGCTCATGAGACAATAACCCTGATAAATGCTTCAATAATA
TTGAAAAAGGAAGAGTATGAGTATTCAACATTTCCGTGTCGCCCTTATTCCCTTTTTTGCGGCA
```

-continued

```
TTTTGCCTTCCTGTTTTTGCTCACCCAGAAACGCTGGTGAAAGTAAAAGATGCTGAAGATCAGT
TGGGTGCACGAGTGGGTTACATCGAACTGGATCTCAACAGCGGTAAGATCCTTGAGAGTTTTCG
CCCCGAAGAACGTTTTCCAATGATGAGCACTTTTAAAGTTCTGCTATGTGGCGCGGTATTATCC
CGTGTTGACGCCGGGCAAGAGCAACTCGGTCGCCGCATACACTATTCTCAGAATGACTTGGTTG
AGTACTCACCAGTCACAGAAAAGCATCTTACGGATGGCATGACAGTAAGAGAATTATGCAGTGC
TGCCATAACCATGAGTGATAACACTGCGGCCAACTTACTTCTGACAACGATCGGAGGACCGAAG
GAGCTAACCGCTTTTTTGCACAACATGGGGGATCATGTAACTCGCCTTGATCGTTGGGAACCGG
AGCTGAATGAAGCCATACCAAACGACGAGCGTGACACCACGATGCCTGCAGCAATGGCAACAAC
GTTGCGCAAACTATTAACTGGCGAACTACTTACTCTAGCTTCCCGGCAACAATTAATAGACTGG
ATGGAGGCGGATAAAGTTGCAGGACCACTTCTGCGCTCGGCCCTTCCGGCTGGCTGGTTTATTG
CTGATAAATCTGGAGCCGGTGAGCGTGGGTCTCGCGGTATCATTGCAGCACTGGGGCCAGATGG
TAAGCCCTCCCGTATCGTAGTTATCTACACGACGGGGAGTCAGGCAACTATGGATGAACGAAAT
AGACAGATCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAAGATCCT
TTTTGATAATCTCATGACCAAAATCCCTTAACGTGAGTTTTCGTTCCACTGAGCGTCAGACCCC
GTAGAAAAGATCAAAGGATCTTCTTGAGATCCTTTTTTTCTGCGCGTAATCTGCTGCTTGCAAA
CAAAAAAACCACCGCTACCAGCGGTGGTTTGTTTGCCGGATCAAGAGCTACCAACTCTTTTTCC
GAAGGTAACTGGCTTCAGCAGAGCGCAGATACCAAATACTGTCCTTCTAGTGTAGCCGTAGTTA
GGCCACCACTTCAAGAACTCTGTAGCACCGCCTACATACGTCGCTCTGCTAATCCTGTTACCAG
TGGCTGCTGCCAGTGGCGATAAGTCGTGTCTTACCGGGTTGGACTCAAGACGATAGTTACCGGA
TAAGGCGCAGCGGTCGGGCTGAACGGGGGGTTCGTGCACACAGCCCAGCTTGGAGCGAACGACC
TACACCGAACTGAGATACCTACAGCGTGAGCTATGAGAAAGCGCCACGCTTCCCGAAGGGAGAA
AGGCGGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGATTT
TTGTGATGCTCGTCAGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCCTGATTCTGTGGA
TAACCGTATTACCGCCTTTGAGTGAGCTGATACCGCTCGCCGCAGCCGAACGACCGAGCGCAGC
GAGTCAGTGAGCGAGGAAGCGGAAGAGCGCCTGATGCGGTATTTTCTCCTTACGCATCTGTGCG
GTATTTCACACCGCATATATGGTGCACTCTCAGTACAATCTGCTCTGATGCCGCATAGTTAAGC
CAGTATACACTCCGCTATCGCTACGTGACTGGGTCATGGCTGCGCCCCGACACCCGGCAACACC
CGCTGACGCGCCCTGACGGGCTTGTCTGCTCCCGGCATCCGCTTACAGACAAGCTGTGACCGTC
TCCGGGAGCTGCATGTGTCAGAGGTTTTCACCGTCATCACCGAAACGCGCGAGGCAGCTGCGGT
AAAGCTCATCAGCGTGGTCGTGAAGCGATTCACAGATGTCTGCCTGTTCATCCGCGTCCAGCTC
GTTGAGTTTCTCCAGAAGCGTTAATGTCTGGCTTCTGATAAAGCGGGCCATGTTAAGGGCGGTT
TTTTCCTGTTTGGTCACTGATGCCTCCGTGTAAGGGGGATTTCTGTTCATGGGGGTAATGATAC
CGATGAAACGAGAGAGGATGCTCACGATACGGGTTACTGATGATGAACATGCCCGGTTACTGGA
ACGTTGTGAGGGTAAACAACTGGCGGTATGGATGCGGCGGGACCAGAGAAAAATCACTCAGGGT
CAATGCCAGCGCTTCGTTAATACAGATGTAGGTGTTCCACAGGGTAGCCAGCAGCATCCTGCGA
TGCAGATCCGGAACATAATGGTGCAGGGCGCTGACTTCCGCGTTTCCAGACTTTACGAAACACG
GAAACCGAAGACCATTCATGTTGTTGCTCAGGTCGCAGACGTTTTGCAGCAGCAGTCGCTTCAC
```

-continued

```
GTTCGCTCGCGTATCGGTGATTCATTCTGCTAACCAGTAAGGCAACCCCGCCAGCCTAGCCGGG

TCCTCAACGACAGGAGCACGATCATGCGCACCCGTGGCCAGGACCCAACGCTGCCCGAGATGCG

CCGCGTGCGGCTGCTGGAGATGGCGGACGCGATGGATATGTTCTGCCAAGGGTTGGTTTGCGCA

TTCACAGTTCTCCGCAAGAATTGATTGGCTCCAATTCTTGGAGTGGTGAATCCGTTAGCGAGGT

GCCGCCGGCTTCCATTCAGGTCGAGGTGGCCCGGCTCCATGCACCGCGACGCAACGCGGGGAGG

CAGACAAGGTATAGGGCGGCGCCTACAATCCATGCCAACCCGTTCCATGTGCTCGCCGAGGCGG

CATAAATCGCCGTGACGATCAGCGGTCCAGTGATCGAAGTTAGGCTGGTAAGAGCCGCGAGCGA

TCCTTGAAGCTGTCCCTGATGGTCGTCATCTACCTGCCTGGACAGCATGGCCTGCAACGCGGGC

ATCCCGATGCCGCCGGAAGCGAGAAGAATCATAATGGGGAAGGCCATCCAGCCTCGCGTCGCGA

ACGCCAGCAAGACGTAGCCCAGCGCGTCGGCCGCCATGCCGGCGATAATGGCCTGCTTCTCGCC

GAAACGTTTGGTGGCGGGACCAGTGACGAAGGCTTGAGCGAGGGCGTGCAAGATTCCGAATACC

GCAAGCGACAGGCCGATCATCGTCGCGCTCCAGCGAAAGCGGTCCTCGCCGAAAATGACCCAGA

GCGCTGCCGGCACCTGTCCTACGAGTTGCATGATAAAGAAGACAGTCATAAGTGCGGCGACGAT

AGTCATGCCCCGCGCCCACCGGAAGGAGCTGACTGGGTTGAAGGCTCTCAAGGGCATCGGTCGA

GATCCCGGTGCCTAATGAGTGAGCTAACTTACATTAATTGCGTTGCGCTCACTGCCCGCTTTCC

AGTCGGGAAACCTGTCGTGCCAGCTGCATTAATGAATCGGCCAACGCGCGGGGAGAGGCGGTTT

GCGTATTGGGCGCCAGGGTGGTTTTTCTTTTCACCAGTGAGACGGGCAACAGCTGATTGCCCTT

CACCGCCTGGCCCTGAGAGAGTTGCAGCAAGCGGTCCACGCTGGTTTGCCCCAGCAGGCGAAAA

TCCTGTTTGATGGTGGTTAACGGCGGGATATAACATGAGCTGTCTTCGGTATCGTCGTATCCCA

CTACCGAGATATCCGCACCAACGCGCAGCCCGGACTCGGTAATGGCGCGCATTGCGCCCAGCGC

CATCTGATCGTTGGCAACCAGCATCGCAGTGGGAACGATGCCCTCATTCAGCATTTGCATGGTT

TGTTGAAAACCGGACATGGCACTCCAGTCGCCTTCCCGTTCCGCTATCGGCTGAATTTGATTGC

GAGTGAGATATTTATGCCAGCCAGCCAGACGCAGACGCGCCGAGACAGAACTTAATGGGCCCGC

TAACAGCGCGATTTGCTGGTGACCCAATGCGACCAGATGCTCCACGCCCAGTCGCGTACCGTCT

TCATGGGAGAAAATAATACTGTTGATGGGTGTCTGGTCAGAGACATCAAGAAATAACGCCGGAA

CATTAGTGCAGGCAGCTTCCACAGCAATGGCATCCTGGTCATCCAGCGGATAGTTAATGATCAG

CCCACTGACGCGTTGCGCGAGAAGATTGTGCACCGCCGCTTTACAGGCTTCGACGCCGCTTCGT

TCTACCATCGACACCACCACGCTGGCACCCACTTGATCGGCGCGAGATTTAATCGCCGCCACAA

TTTGCGACGGCGCGTGCAGGGCCAGACTGGAGGTGGCAACGCCAATCAGCAACGACTGTTTGCC

CGCCAGTTGTTGTGCCACGCGGTTGGGAATGTAATTCAGCTCCGCCATCGCCGCTTCCACTTTT

TCCCGCGTTTTCGCAGAAACGTGGCTGGCCTGGTTCACCACGCGGGAAACGGTCTGATAAGAGA

CACCGGCATACTCTGCGACATCGTATAACGTTACTGGTTTGACATTCACCACCCTGAATTGACT

CTCTTCCGGGCGCTATCATGCCATACCGCGAAAGGTTTTGCGCCATTCGATGGTGTCCGGGATC

TCGACGCTCTCCCTTATGCGACTCCTGCATTAGGAAGCAGCCCAGTAGTAGGTTGAGGCCGTTG

AGCACCGCCGCCGCAAGGAATGGTGCATGCAAGGAGATGGCGCCCAACAGTCCCCGGCCACGG

GGCCTGCCACCATACCCACGCCGAAACAAGCGCTCATGAGCCCGAAGTGGCGAGCCCGATCTTC

CCCATCGGTGATGTCGGCGATATAGGCGCCAGCAACCGCACCTGTGGCGCCGGTGATGCCGGCC

ACGATGCGTCCGGCGTAGAGGATCGAGATCTCGATCCCGCGAAATTAATACGACTCACTATAGG

GGAATTGTGAGCGGATAACAATTCCCCTCTAGAAATAATTTTGTTTAACTTTAAGAAGGAGATA

TACCATGGGCCATCATCATCATCATCATGATCATCACAGCAGCGGCCATATCGAAGGTCGT

CATATGATGGTCTTCACACTCGAAGATTTCGTTGGGGACTGGGAACAGACAGCCGCCTACAACC
```

-continued

<u>TGGACCAAGTCCTTGAACAGGGAGGTGTGTCCAGTTTGCTGCAGAATCTCGCCGTGTCCGTAAC</u>

<u>TCCGATCCAAAGGATTGTCCGGAGCGGTGAAAATGCCCTGAAGATCGACATCCATGTCATCATC</u>

<u>CCGTATGAAGGTCTGAGCGCCGACCAAATGGCCCAGATCGAAGAGGTGTTTAAGGTGGTGTACC</u>

<u>CTGTGGATGATCATCACTTTAAGGTGATCCTGCCCTATGGCACACTGGTAATCGACGGGGTTAC</u>

<u>GCCGAACATGCTGAACTATTTCGGACGGCCGTATGAAGGCATCGCCGTGTTCGACGGCAAAAAG</u>

<u>ATCACTGTAACAGGGACCCTGTGGAACGGCAACAAAATTATCGACGAGCGCCTGATCACCCCCG</u>

<u>ACGGCTCCATGCTGTTCCGAGTAACCATCAGCAGTGGGAGTTCCGGTGGTGGCGGGAGCGGAGG</u>

<u>TGGAGGCTCGAGCGGTGGAGCTCAGGGGAATTCCCCACAGCATGTTCGAGCTCATTCCTCTCCA</u>

<u>GCTTCTCTGCAGTTG</u>GGATCCGGCTGCTAACAAAGCCCGAAAGGAAGCTGAGTTGGCTCCTGCC

ACCGGTGAGCAATAACTAGCATAACCCCTTGGGGCCTCTAAACGGGTCTTGAGGGGTTTTTTGC

TGAAAGGAGGAACTATATCCGGATATCCCGCAAGAGGCCCGGCAGTACCGGCATAACCAAGCCT

ATGCCTACAGCATCCAGGGTGACGGTGCTGAGGATGACGATGAGCGCATTGTTAGATTTCATAC

ACGGTGCCTGACTGCGTTAGCAATTTAACTGTGATAAACTACCGCATTAAAGCTTATCGATGAT

AAGCTGTCAAACATGAGAA

SEQ ID NO: 62. NanoBiT Biosensor: SmBiT in pET16b vector
(6,531 nucleotides)
TTCTTGAAGACGAAAGGGCCTCGTGATACGCCTATTTTTATAGGTTAATGTCATGATAATAATG

GTTTCTTAGACGTCAGGTGGCACTTTTCGGGGAAATGTGCGCGGAACCCCTATTTGTTTATTTT

TCTAAATACATTCAAATATGTATCCGCTCATGAGACAATAACCCTGATAAATGCTTCAATAATA

TTGAAAAAGGAAGAGTATGAGTATTCAACATTTCCGTGTCGCCCTTATTCCCTTTTTTGCGGCA

TTTTGCCTTCCTGTTTTTGCTCACCCAGAAACGCTGGTGAAAGTAAAAGATGCTGAAGATCAGT

TGGGTGCACGAGTGGGTTACATCGAACTGGATCTCAACAGCGGTAAGATCCTTGAGAGTTTTCG

CCCCGAAGAACGTTTTCCAATGATGAGCACTTTTAAAGTTCTGCTATGTGGCGCGGTATTATCC

CGTGTTGACGCCGGGCAAGAGCAACTCGGTCGCCGCATACACTATTCTCAGAATGACTTGGTTG

AGTACTCACCAGTCACAGAAAAGCATCTTACGGATGGCATGACAGTAAGAGAATTATGCAGTGC

TGCCATAACCATGAGTGATAACACTGCGGCCAACTTACTTGTGACAACGATCGGAGGACCGAAG

GAGCTAACCGCTTTTTTGCACAACATGGGGGATCATGTAACTCGCCTTGATCGTTGGGAACCGG

AGCTGAATGAAGCCATACCAAACGACGAGCGTGACACCACGATGCCTGCAGCAATGGCAACAAC

GTTGCGCAAACTATTAACTGGCGAACTACTTACTCTAGCTTCCCGGCAACAATTAATAGACTGG

ATGGAGGCGGATAAAGTTGCAGGACCACTTCTGCGCTCGGCCCTTCCGGCTGGCTGGTTTATTG

CTGATAAATCTGGAGCCGGTGAGCGTGGGTCTCGCGGTATCATTGCAGCACTGGGGCCAGATGG

TAAGCCCTCCCGTATCGTAGTTATCTACACGACGGGGAGTCAGGCAACTATGGATGAACGAAAT

AGACAGATCGCTGAGATAGGTGCCTCACTGATTAAGCATTGGTAACTGTCAGACCAAGTTTACT

CATATATACTTTAGATTGATTTAAAACTTCATTTTTAATTTAAAAGGATCTAGGTGAAGATCCT

TTTTGATAATCTCATGACCAAAATCCCTTAACGTGAGTTTTCGTTCCACTGAGCGTCAGACCCC

GTAGAAAAGATCAAAGGATCTTCTTGAGATCCTTTTTTTCTGCGCGTAATCTGCTGCTTGCAAA

CAAAAAAACCACCGCTACCAGCGGTGGTTTGTTTGCCGGATCAAGAGCTACCAACTCTTTTTCC

GAAGGTAACTGGCTTCAGCAGAGCGCAGATACGAAATACTGTCCTaCTAGTGTAGCCGTAGTTA

GGCCACCACTTCAAGAACTCTGTAGCACCGCCTACATACCTCGCTCTGCTAATCCTGTTACCAG

TGGCTGCTGCCAGTGGCGATAAGTCGTGTCTTACCGGGTTGGACTCAAGACGATAGTTACCGGA

TAAGGCGCAGCGGTCGGGCTGAACGGGGGGTTCGTGCACACAGCCCAGCTTGGAGCGAACGACG

-continued

```
TACACCGAACTGAGATACCTACAGCGTGAGCTATGAGAAAGCGCCACGCTTCCCGAAGGGAGAA
AGGCGGACAGGTATCCGGTAAGCGGCAGGGTCGGAACAGGAGAGCGCACGAGGGAGCTTCCAGG
GGGAAACGCCTGGTATCTTTATAGTCCTGTCGGGTTTCGCCACCTCTGACTTGAGCGTCGATTT
TTGTGATGCTCGTCAGGGGGGCGGAGCCTATGGAAAAACGCCAGCAACGCGGCCTTTTTACGGT
TCCTGGCCTTTTGCTGGCCTTTTGCTCACATGTTCTTTCCTGCGTTATCCCCTGATTCTGTGGA
TAACCGTATTACCGGCTTTGAGTGAGCTGATACCGCTCGCCGCAGCCGAACGACCGAGCGCAGC
GAGTCAGTGAGCGAGGAAGCGGAAGAGCGCCTGATGCGGTATTTTCTCCTTACGCATCTGTGCG
GTATTTCACACCGCATATATGGTGCACTCTCAGTACAATGTGCTCTGATGCCGCATAGTTAAGC
CAGTATACACTCCGCTATCGCTACGTGACTGGGTCATGGCTGCGCCCCGACACCCGCCAAGACC
CGCTGACGCGCCCTGACGGGCTTGTGTGCTCCCGGCATCCGCTTACAGACAAGCTGTGACCGTC
TCCGGGAGCTGCATGTGTGAGAGGTTTTCACGGTGATCACCGAAACGCGCGAGGCAGCTGCGGT
AAAGCTCATCAGCGTGGTCGTGAAGCGATTCACAGATGTCTGCCTGTTCATCCGCGTCCAGCTC
GTTGAGTTTCTCCAGAAGCGTTAATGTCTGGCTTCTGATAAAGCGGGCCATGTTAAGGGCGGTT
TTTTCCTGTTTGGTCACTGATGCCTCCGTGTAAGGGGGATTTCTGTTGATGGGGGTAATGATAC
CGATGAAACGAGAGAGGATGCTCACGATACGGGTTACTGATGATGAACATGCCCGGTTACTGGA
ACGTTGTGAGGGTAAACAACTGGCGGTATGGATGCGGCGGGACCAGAGAAAAATCACTCAGGGT
CAATGCCAGCGCTTCGTTAATACAGATGTAGGTGTTCCACAGGGTAGCCAGCAGCATCCTGCGA
TGCAGATCCGGAACATAATGGTGCAGGGCGCTGACTTCCGCGTTTCCAGACTTTACGAAACACG
GAAACCGAAGACCATTCATGTTGTTGCTCAGGTCGCAGACGTTTTGCAGCAGCAGTCGCTTCAC
GTTCGCTCGCGTATCGGTGATTCATTCTGCTAACCAGTAAGGCAACCCCGCCAGCCTAGCCGGG
TCCTCAACGACAGGAGCACGATCATGCGCACCCGTGGCCAGGACCCAACGCTGCCCGAGATGCG
CCGCGTGCGGCTGCTGGAGATGGCGGACGCGATGGATATGTTCTGCCAAGGGTTGGTTTGCGCA
TTCACAGTTCTCCGCAAGAATTGATTGGCTCCAATTCTTGGAGTGGTGAATCCGTTAGCGAGGT
GCCGCCGGCTTCCATTCAGGTCGAGGTGGCCCGGCTCCATGCACCGCGACGCAACGCGGGGAGG
CAGACAAGGTATAGGGCGGCGCCTACAATCCATGCCAACCCGTTCCATGTGCTCGCCGAGGCGG
CATAAATCGCCGTGACGATCAGCGGTCCAGTGATCGAAGTTAGGCTGGTAAGAGCCGCGAGCGA
TCCTTGAAGCTGTCCCTGATGGTCGTCATCTACCTGCCTGGACAGCATGGCCTGCAACGCGGGC
ATCCCGATGCCGCCGGAAGCGAGAAGAATCATAATGGGGAAGGCCATCCAGCCTCGCGTCGCGA
ACGCCAGCAAGACGTAGCCCAGCGCGTCGGCCGCCATGCCGGCGATAATGGCCTGCTTCTCGCC
GAAACGTTTGGTGGCGGGACCAGTGACGAAGGCTTGAGCGAGGGCGTGCAAGATTCCGAATACC
GCAAGCGACAGGCCGATCATCGTCGCGCTCCAGCGAAAGCGGTCCTCGCCGAAAATGACCCAGA
GCGCTGCCGGCACCTGTCCTACGAGTTGCATGATAAAGAAGACAGTCATAAGTGCGGCGACGAT
AGTCATGCCCCGCGCCCACCGGAAGGAGCTGACTGGGTTGAAGGCTCTCAAGGGCATCGGTCGA
GATCCCGGTGCCTAATGAGTGAGCTAACTTACATTAATTGCGTTGCGCTCACTGCCCGCTTTCC
AGTCGGGAAACCTGTCGTGCCAGCTGCATTAATGAATCGGCCAACGCGCGGGGAGAGGCGGTTT
GCGTATTGGGCGCCAGGGTGGTTTTTCTTTTCACCAGTGAGACGGGCAAGAGCTGATTGCGCTT
CACCGCCTGGCCCTGAGAGAGTTGCAGCAAGCGGTCCACGCTGGTTTGCCCCAGCAGGCGAAAA
TCGTGTTTGATGGTGGTTAACGGCGGGATATAACATGAGCTGTCTTCGGTATCGTCGTATCCCA
CTACCGAGATATCCGCACCAACGCGCAGGCCGGACTCGGTAATGGCGCGCATTGCGCCCAGCGC
CATCTGATCGTTGGCAACCAGCATCGCAGTGGGAACGATGCCCTCATTCAGCATTTGCATGGTT
TGTTGAAAACCGGACATGGCACTCCAGTCGCCTTCCCGTTCCGCTATCGGCTGAATTTGATTGC
```

-continued

```
GAGTGAGATATTTATGCCAGCCAGCCAGACGCAGACGCGCCGAGACAGAACTTAATGGGCCCGC

TAACAGCGCGATTTGCTGGTGACCCAATGCGACCAGATGCTCCACGCCCAGTCGCGTACCGTCT

TCATGGGAGAAAATAATACTGTTGATGGGTGTCTGGTCAGAGACATCAAGAAATAACGCCGGAA

CATTAGTGCAGGCAGCTTCCACAGCAATGGCATCCTGGTCATCCAGCGGATAGTTAATGATCAG

CCCACTGACGCGTTGCGCGAGAAGATTGTGCACCGCCGCTTTACAGGCTTCGACGCCGCTTCGT

TCTACCATCGACACCACCACGCTGGCACCCAGTTGATCGGCGCGAGATTTAATCGCCGCGACAA

TTTGCGACGGCGCGTGCAGGGCCAGACTGGAGGTGGCAACGCCAATCAGCAACGACTGTTTGCC

CGCCAGTTGTTGTGCCACGCGGTTGGGAATGTAATTCAGCTCCGCCATCGCCGCTTCCACTTTT

TCCCGCGTTTTCGCAGAAACGTGGCTGGCCTGGTTCACCACGCGGGAAACGGTCTGATAAGAGA

CACCGGCATACTCTGCGACATCGTATAACGTTACTGGTTTCACATTCACCACCCTGAATTGACT

CTCTTCCGGGCGCTATCATGCCATACCGCGAAAGGTTTTGCGCCATTCGATGGTGTCCGGGATC

TCGACGCTCTCCCTTATGCGACTCCTGCATTAGGAAGCAGCCCAGTAGTAGGTTGAGGCCGTTG

AGCACCGCCGCCGCAAGGAATGGTGCATGCAAGGAGATGGCGCCCAACAGTCCCCCGGCCACGG

GGCCTGCCACCATACCCACGCCGAAACAAGCGCTCATGAGCCCGAAGTGGCGAGCCCGATCTTC

CCCATCGGTGATGTCGGCGATATAGGCGCCAGCAACCGCACCTGTGGCGCCGGTGATGCCGGCC

ACGATGCGTCCGGCGTAGACGATCGAGATCTCGATCCCGCGAAATTAATACGACTCACTATAGG

GGAATTGTGAGCGGATAACAATTCCCCTCTAGAAATAATTTTGTTTAACTTTAAGAAGGAGATA

TACCATGGGCCATCATCATCATCATCATCATCATCACAGCAGCGGCCATATCGAAGGTCGT

CATATGATGGAGGAGACTGAGCTGATCCAGAGGGCCAAGCTGGCCGAGCAGGCCGGGCGCTACG

ACGACATGGCCACCTGCATGAAGGCAGTGACCGAGCAGGGCGCCGAGCTGTCCAACGAGGAGCG

CAACCTGCTCTCCGTGGCCTACAAGAACGTGGTCGGGGCCGCAGGTCCGCCTGGAGGGTCATC

TCTAGCATCGAGCAGAAGACCGACACCTCCGACAAGAAGTTGCGGCTGATTAAGGACTATCGGG

AGAAAGTGGAGTCCGAGCTGAGATCCATCTGCACCACGGTGCTGGAATTGTTGGATAAATATTT

AATAGCCAATGCAACTAATCCAGAGAGTAAGGTCTTCTATCTGAAAATGAAGGGTGATTACTTC

CGGTACCTTGCTGAAGTTGCGTGTGGTGATGATCGAAAACAAACGATAGATAATTCCCAAGGAG

CTTACCAAGAGGCATTTGATATAAGCAAGAAAGAGATGCAACCCACACACCCAATCCGCCTGGG

GCTTGCTCTTAACTTTTCTGTATTTTACTATGAGATTCTTAATAACCCAGAGCTTGCCTGCACG

CTGGCTAAAACGGCTTTTGATGAGGCCATTGCTGAACTTGATACACTGAATGAAGACTCATACA

AAGACAGCACCCTCATCATGCAGTTGCTTAGAGACAACCTAACACTTTGGACATCAGACAGTGC

AGGAGAAGAATGTGATGCGGCAGAAGGGGCTGAAAACCCGAATTCTGGCTCGAGCGGTGGTGGC

GGGAGCGGAGGTGGAGGGTCGTCAGGTGTGACCGGCTGCCGGCTGTTCGAGGAGATTCTGTAAG

GATCCGGCTGCTAACAAAGCCCGAAAGGAAGCTGAGTTGGCTGCTGCCACCGCTGAGCAATAAC

TAGCATAACCCCTTGGGGCCTCTAAACGGGTCTTGAGGGGTTTTTTGCTGAAAGGAGGAACTAT

ATCCGGATATCCCGCAAGAGGCCCGGCAGTACCGGCATAACCAAGCCTATGCCTACAGCATCCA

GGGTGACGGTGCCGAGGATGACGATGAGCGCATTGTTAGATTTCATACACGGTGCCTGACTGCG

TTAGCAATTTAACTGTGATAAACTACCGCATTAAAGCTTATCGATGATAAGCTGTCAAACATGA

GAA
```

SEQ ID NO: 63. YAP-TEAD NanoBiT biosensor construct 1: LgBiT-YAP50-171-Flag in pcDNA3.1-hygro vector (6,297 nucleotides)

```
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA
```

-continued

```
ATTTAAGCTACAACAAGGCAAGGCTTGACCGACAATTGCATGAAGAATCTGCTTAGGGTTAGGC
GTTTTGCGCTGCTTCGCGATGTACGGGCCAGATATACGCGTTGACATTGATTATTGACTAGTTA
TTAATAGTAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGTATTTACG
GTAAACTGCCCACTTGGCAGTACATCAAGTGTATCATATGCCAAGTACGCCCCCTATTGACGTC
AATGACGGTAAATGGCCCGCGTGGCATTATGCCCAGTACATGACCTTATGGGACTTTCCTACTT
GGCAGTACATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAATGGG
AGTTTGTTTTGGCACCAAAATCAACGGGACTTTCCAAAATGTCGTAACAACTCCGCCCCATTGA
CGCAAATGGGCGGTAGGCGTGTACGGTGGGAGGTCTATATAAGCAGAGCTCTCTGGCTAACTAG
AGAACCCACTGCTTACTGGCTTATCGAAATTAATACGACTCACTATAGGGAGACCCAAGCTGGC
TAGCGTTTAAACTTAAGCTTGGTACCGAGCTCGGATCCATGGTCTTCACACTCGAAGATTTCGT
TGGGGACTGGGAACAGACAGCCGCCTACAACCTGGACCAAGTCCTTGAACAGGGAGGTGTGTCC
AGTTTGCTGCAGAATCTCGCCGTGTCCGTAACTCCGATCCAAAGGATTGTCCGGAGCGGTGAAA
ATGCCCTGAAGATCGACATCCATGTCATCATCCCGTATGAAGGTCTGAGCGCCGACCAAATGGC
CCAGATCGAAGAGGTGTTTAAGGTGGTGTACCCTGTGGATGATCATCACTTTAAGGTGATCCTG
CCCTATGGCACACTGGTAATCGACGGGGTTACGCCGAACATGCTGAACTATTTCGGACGGCCGT
ATGAAGGCATCGCCGTGTTCGACGGCAAAAAGATCACTGTAACAGGGACCCTGTGGAACGGCAA
CAAAATTATCGACGAGCGCCTGATCACCCCCGACGGCTCCATGCTGTTCCGAGTAACCATCAAC
AGTGGGAGTTCCGGTGGTGGCGGGAGCGGAGGTGGGGGGTCGAGCGGTGCCGGGCATCAGATCG
TGCACGTCCGCGGGGACTCGGAGACCGACCTGGAGGCGCTCTTCAACGCCGTCATGAACCCCAA
GACGGCCAACGTGCCCCAGACCGTGCCCATGAGGCTCCGGAAGCTGCCCGACTCCTTCTTCAAG
CCGCCGGAGCCCAAATCCCACTCCCGACAGGCCAGTACTGATGCAGGCACTGCAGGAGCCCTGA
CTCCACAGCATGTTCGAGCTCATTCCTCTCCAGCTTCTCTGCAGTTGGGAGCTGTTTCTCCTGG
GACACTGACCCCCACTGGAGTAGTCTCTGGCCCAGCAGCTACACCCACAGCTCAGCATCTTCGA
CAGTCTTCTTTTGAGATACCTGATGATGTACTTGTCGTCATCGTCTTTGTAGTCGCGGCCGCTC
GAGTCTAGAGGGCCCGTTTAAACCCGCTGATCAGCCTCGACTGTGCCTTCTAGTTGCCAGCCAT
CTGTTGTTTGCCCCTCCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGCTGGGGATGCGGTGG
GCTCTATGGCTTCTGAGGCGGAAAGAACCAGCTGGGGCTCTAGGGGGTATCCCCACGCGCCCTG
TAGCGGCGCATTAAGCGCGGCGGGTGTGGTGGTTACGCGCAGCGTGACCGCTACACTTGCCAGC
GCCCTAGCGCCCGCTCCTTTCGCTTTCTTCCCTTCCTTTCTCGCCACGTTCGCCGGCTTTCCCC
GTCAAGCTCTAAATCGGGGGCTCCCTTTAGGGTTCCGATTTAGTGCTTTACGGCACCTCGACCC
CAAAAAAGTTGATTAGGGTGATGGTTGACGTAGTGGGCCATCGCCCTGATAGACGGTTTTTGGC
CCTTTGACGTTGGAGTCCACGTTCTTTAATAGTGGACTCTTGTTCCAAACTGGAACAACACTCA
ACCCTATCTCGGTCTATTCTTTTGATTTATAAGGGATTTTGCCGATTTCGGCCTATTGGTTAAA
AAATGAGCTGATTTAACAAAAATTTAACGCGAATTAATTCTGTGGAATGTGTGTCAGTTAGGGT
GTGGAAAGTCCCCAGGCTCCCCAGCAGGCAGAAGTATGCAAAGCATGCATCTCAATTAGTCAGC
AACCAGGTGTGGAAAGTCCCCAGGCTCCCCAGCAGGCAGAAGTATGCAAAGCATGCATCTCAAT
```

-continued

```
TAGTCAGCAACCATAGTCCCGCCCCTAACTCCGCCCATCCCGCCCCTAACTCCGCCCAGTTCCG

CCCATTCTCCGCCCCATGGCTGACTAATTTTTTTATTTATGCAGAGGCCGAGGCCGCCTCTGC

CTGTGAGCTATTCGAGAAGTAGTGAGGAGGCTTTTTTGGAGGCGTAGGCTTTTGCAAAAAGCTC

GCGGGAGCTTGTATATCCATTTTCGGATCTGATCAAGAGACAGGATGAGGATCGTTTCGCATGA

TTGAACAAGATGGATTGCACGCAGGTTCTCCGGCCGCTTGGGTGGAGAGGCTATTCGGCTATGA

CTGGGCACAACAGACAATCGGCTGGTCTGATGCCGCCGTGTTCCGGCTGTCAGCGCAGGGGCGC

CCGGTTCTTTTTGTCAAGACCGACCTGTCCGGTGGCCTGAATGAACTGCAGGACGAGGCAGCGC

GGCTATCGTGGCTGGCCACGACGGGCGTTCCTTGCGCAGCTGTGCTCGACGTTGTCACTGAAGC

GGGAAGGGACTGGCTGCTATTGGGCGAAGTGCCGGGGCAGGATCTCCTGTCATCTCACCTTGCT

CCTGCCGAGAAAGTATCCATCATGGCTGATGCAATGCGGCGGCTGCATACGCTTGATCCGGCTA

CCTGCCCATTCGACCACCAAGCGAAACATCGCATCGAGCGAGCACGTACTCGGATGGAAGCCGG

TCTTGTCGATCAGGATGATCTGGACGAAGAGCATCAGGGGCTCGCGCCAGCCGAACTGTTCGCC

AGGCTCAAGGCGCGCATGCCCGACGGCGAGGATCTCGTCGTGACCGATGGCGATGCCTGCTTGC

CGAATATCATGGTGGAAAATGGCCGCTTTTCTGGATTCATCGACTGTGGCCGGCTGGGTGTGGC

GGACCGCTATCAGGACATAGCGTTGGCTACCCGTGATATTGCTGAAGAGCTTGGCGGCGAATGG

GCTGACCGCTTCCTCGTGCTTTACGGTATCGCCGCTCCCGATTCGCAGCGCATCGCCTTCTATC

GCCTTCTTGACGAGTTCTTCTGAGGGGGACTCTGGGGTTGGAAATGACCGACCAAGCGACGCCC

AACCTGCCATCACGAGATTTCGATTCCACCGCCGCCTTCTATGAaAGGTTGGGCTTCGGAATCG

TTTTCCGGGACGCCGGCTGGATGATCCTCCAGCGCGGGGATCTCATGCTGGAGTTCTTCGCCCA

CCCCAACTTGTTTATTGCAGCTTATAATGGTTACAAATAAAGCAATAGCATCACAAATTTCACA

AATAAAGCATTTTTTTCACTGCATTCTAGTTGTGGTTTGTCGAAACTCATCAATGTATCTTATC

ATGTCTGTATACCGTCGACCTCTAGCTAGAGCTTGGCGTAATCATGGTCATAGCTGTTTCCTGT

GTGAAATTGTTATCCGCTCACAATTCCACACAACATACGAGCCGGAAGCATAAAGTGTAAAGCC

TGGGGTGCCTAATGAGTGAGCTAACTCACATTAATTGCGTTGCGCTCACTGCCCGCTTTCCAGT

CGGGAAACCTGTCGTGCCAGCTGCATTAATGAATCGGCCAACGCGCGGGGAGAGGCGGTTTGCG

TATTGGGCGCTCTTCCGCTTCCTCGCTCACTGACTCGCTGCGCTCGGTCGTTCGGCTGCGGCGA

GCGGTATCAGCTCACTCAAAGGCGGTAATACGGTTATCCACAGAATCAGGGGATAACGCAGGAA

AGAACATGTGAGCAAAAGGCCAGCAAAAGGCCAGGAACCGTAAAAAGGCCGCGTTGCTGGCGTT

TTTCCATAGGCTCCGCCCCCCTGACGAGCATCACAAAAATCGACGCTCAAGTCAGAGGTGGCGA

AACCCGACAGGACTATAAAGATACCAGGCGTTTCCCCCTGGAAGCTCCCTCGTGCGCTCTCCTG

TTCCGACCCTGCCGCTTACCGGATACCTGTCCGCCTTTCTCCCTTCGGGAAGCGTGGCGCTTTC

TCATAGCTCACGCTGTAGGTATCTCAGTTCGGTGTAGGTCGTTCGCTCCAAGCTGGGCTGTGTG

CACGAACCCCCCGTTCAGCCGGACCGGTGCGCCTTATCCGGTAACTATCGTCTTGAGTCCAACC

CGGTAAGACACGACTTATCGCCACTGGCAGCAGCCACTGGTAACAGGATTAGCAGAGCGAGGTA

TGTAGGCGGTGCTACAGAGTTCTTGAAGTGGTGGCCTAACTACGGCTACACTAGAAGAACAGTA

TTTGGTATCTGCGCTCTGCTGAAGCCAGTTACCTTCGGAAAAAGAGTTGGTAGCTCTTGATCCG

GCAAACAAACCACCGCTGGTAGCGGTTTTTTTGTTTGCAAGCAGCAGATTACGCGCAGAAAAAA

AGGATCTCAAGAAGATCCTTTGATCTTTTCTACGGGGTCTGACGCTCAGTGGAACGAAAACTCA

CGTTAAGGGATTTTGGTCATGAGATTATCAAAAAGGATCTTCACCTAGATCCTTTTAAATTAAA

AATGAAGTTTTAAATCAATCTAAAGTATATATGAGTAAACTTGGTCTGACAGTTACCAATGCTT
```

AATCAGTGAGGCACCTATCTCAGCGATCTGTCTATTTCGTTCATCCATAGTTGCCTGACTCCCC

GTCGTGTAGATAACTACGATACGGGAGGGCTTACCATCTGGCCCCAGTGCTGCAATGATACCGC

GAGACCCACGCTCACCGGCTCCAGATTTATCAGCAATAAACCAGCCAGCCGGAAGGGCCGAGCG

CAGAAGTGGTCCTGCAACTTTATCCGCCTCCATCCAGTCTATTAATTGTTGCCGGGAAGCTAGA

GTAAGTAGTTCGCCAGTTAATAGTTTGCGCAACGTTGTTGCCATTGCTACAGGCATCGTGGTGT

CACGCTCGTCGTTTGGTATGGCTTCATTCAGCTCCGGTTCCCAACGATCAAGGCGAGTTACATG

ATCCCCATGTTGTGCAAAAAAGCGGTTAGCTCCTTCGGTCCTCCGATCGTTGTCAGAAGTAAG

TTGGCGGCAGTGTTATCACTGATGGTTATGGGAGCACTGCATAATTCTCTTACTGTCATGCGAT

CCGTAAGATGCTTTTCTGTGACTGGTGAGTACTCAACCAAGTCATTCTGAGAATAGTGTATGCG

GCGACCGAGTTGCTCTTGGCCGGCGTCAATACGGGATAATACCGCGCCACATAGCAGAACTTTA

AAAGTGCTCATCATTGGAAAACGTTCTTCGGGGCGAAAACTCTCAAGGATCTTACCGCTGTTGA

GATCCAGTTCGATGTAACCCACTCGTGCACCCAACTGATCTTCAGCATCTTTTACTTTCACCAG

CGTTTCTGGGTGAGCAAAAACAGGAAGGCAAAATGCCGCAAAAAAGGGAATAAGGGCGACACGG

AAATGTTGAATACTCATACTCTTCCTTTTTCAATATTATTGAAGCATTTATCAGGGTTATTGTC

TCATGAGCGGATACATATTTGAATGTATTTAGAAAAATAAACAAATAGGGGTTCCGCGCACATT

TCCCCGAAAAGTGCCACCTGACGTC

SEQ ID NO: 64. YAP-TEAD NanoBiT biosensor construct 2: Flag-
YAP50-171-LgBiT in pcDNA3.1-hygro vector (6,270 nucieotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGGTAACTAG

AGAACCCACTGCTTACTGGCTTATCGAAATTAATACGACTCACTATAGGGAGACCCAAGCTGGC

TAGCGTTTAAACTTAAGCTTGGTACCGAGCTCGGATCCGCCGGGCATCGGATCGTGCACGTCCG

CGGGGACTCGGAGACCGACCTGGAGGCGCTCTTCAACGCCGTCATGAACCCAAGACGGCCAAC

GTGCCCCAGACCGTGCCCATGAGGCTCCGGAAGCTGCCCGACTCCTTCTTCAAGCCGCCGGAGC

CCAAATCCCACTCCCGACAGGCCAGTACTGATGCAGGCACTGCAGGAGCCCTGACTCCACAGCA

TGTTCGAGCTCATTCCTCTCCAGCTTCTCTGCAGTTGGGAGCTGTTTCTCCTGGGACACTGACC

CCCACTGGAGTAGTCTCTGGCCCAGCAGCTACACCCACAGCTCAGCATCTTCGACAGTCTTCTT

TTGAGATACCTGATGATGTAGGCTCGAGCGGTGGTGGCGGGAGCGGAGGTGGAGGGTCGTCAGG

TGTCTTCACACTCGAAGATTTCGTTGGGGACTGGGAACAGACAGCCGCCTACAACCTGGACCAA

GTCCTTGAACAGGGAGGTGTGTCCAGTTTGCTGCAGAGTCTCGCCGTGTCCGTAGCTCCGATCC

AAAGGATTGTCCGGAGCGGTGAAAATGCCCTGAAGATCGACATCCATGTCATCATCCCGTATGA

-continued

AGGTCTGAGCGCCGACCAAATGGCCCAGATCGAAGAGGTGTTTAAGGTGGTGTACCCTGTGGAT

GATCATCACTTTAAGGTGATCCTGCCCTATGGCACACTGGTAATCGACGGGGTTACGCCGAACA

TGCTGAACTATTTCGGACGGCCGTATGAAGGCATCGCCGTGTTCGACGGCAAAAAGATCACTGT

AACAGGGACCCTGTGGAACGGCAACAAAATTATCGACGAGCGCCTGATCACCCCCGACGGCTCC

ATGCTGTTCCGAGTAACCATCAACAGCGCGGCCGCTCGAGTCTAGAGGGCCCGTTTAAACCCGC

TGATCAGCCTCGACTGTGCCTTCTAGTTGCCAGCCATCTGTTGTTTGCCCCTCCCCCGTGCCTT

CCTTGACCCTGGAAGGTGCCACTCCCACTGTCCTTTCCTAATAAAATGAGGAAATTGCATCGCA

TTGTCTGAGTAGGTGTCATTCTATTCTGGGGGGTGGGGTGGGGCAGGACAGCAAGGGGGAGGAT

TGGGAAGACAATAGCAGGCATGCTGGGGATGCGGTGGGCTCTATGGCTTCTGAGGCGGAAAGAA

CCAGCTGGGGCTCTAGGGGGTATCCCCACGCGCCCTGTAGCGGCGCATTAAGCGCGGCGGGTGT

GGTGGTTACGCGCAGCGTGACCGCTACACTTGCCAGCGCCCTAGCGCCCGCTCCTTTCGCTTTC

TTCCCTTCCTTTCTCGCCACGTTCGCCGGCTTTCCCCGTCAAGCTCTAAATCGGGGCTCCCTT

TAGGGTTCCGATTTAGTGCTTTACGGCACCTCGACCCCAAAAAACTTGATTAGGGTGATGGTTC

ACGTAGTGGGCCATCGCCCTGATAGACGGTTTTTCGCCCTTTGACGTTGGAGTCCACGTTCTTT

AATAGTGGACTCTTGTTCCAAACTGGAACAACACTCAACCCTATCTCGGTCTATTCTTTTGATT

TATAAGGGATTTTGCCGATTTCGGCCTATTGGTTAAAAAATGAGCTGATTTAACAAAAATTTAA

CGCGAATTAATTCTGTGGAATGTGTGTCAGTTAGGGTGTGGAAAGTCCCCAGGCTCCCCAGCAG

GCAGAAGTATGCAAAGCATGCATCTCAATTAGTCAGCAACCAGGTGTGGAAAGTCCCCAGGCTC

CCCAGCAGGCAGAAGTATGCAAAGCATGCATCTCAATTAGTCAGCAACCATAGTCCCGCCCCTA

ACTCCGCCCATCCCGCCCCTAACTCCGCCCAGTTCCGCCCATTCTCCGCCCCATGGCTGACTAA

TTTTTTTTATTTATGCAGAGGCCGAGGCCGCCTCTGCCTCTGAGCTATTCCAGAAGTAGTGAGG

AGGCTTTTTTGGAGGCCTAGGCTTTTGCAAAAAGCTCCCGGGAGCTTGTATATCCATTTTCGGA

TCTGATCAAGAGACAGGATGAGGATCGTTTCGCATGATTGAACAAGATGGATTGCACGCAGGTT

CTCCGGCCGCTTGGGTGGAGAGGCTATTCGGCTATGACTGGGCACAACAGACAATCGGCTGCTC

TGATGCCGCCGTGTTCCGGCTGTCAGCGCAGGGGCGCCCGGTTCTTTTTGTCAAGACCGACCTG

TCCGGTGCCCTGAATGAACTGCAGGACGAGGCAGCGCGGCTATCGTGGCTGGCCACGACGGGCG

TTCCTTGCGCAGCTGTGCTCGACGTTGTCACTGAAGCGGGAAGGGACTGGCTGCTATTGGGCGA

AGTGCCGGGGCAGGATCTCCTGTCATCTCACCTTGCTCCTGCCGGAGAAAGTATCCATCATGGCT

GATGCAATGCGGCGGCTGCATACGCTTGATCCGGCTACCTGCCCATTGGACCACCAAGCGAAAC

ATCGCATCGAGCGAGCACGTACTCGGATGGAAGCCGGTCTTGTCGATCAGGATGATCTGGACGA

AGAGCATCAGGGGCTCGCGCCAGCCGAACTGTTCGCCAGGCTCAAGGCGCGCATGCCCGACGGC

GAGGATCTCGTCGTGACCGATGGCGATGCCTGCTTGCCGAATATCATGGTGGAAAATGGCCGCT

TTTCTGGATTCATCGACTGTGGCCGGCTGGGTGTGGCGGACCGCTATCAGGACATAGCGTTGGC

TACCCGTGATATTGCTGAAGAGCTTGGCGGCGAATGGGCTGACCGCTTCCTCGTGCTTTACGGT

ATCGCCGCTCCCGATTCGCAGCGCATCGCCTTCTATCGCCTTCTTGACGAGTTCTTCTGAGCGG

GACTCTGGGGTTCGAAATGACCGACCAAGCGACGCCCAACCTGCCATCACGAGATTTCGATTCC

ACCGCCGCCTTCTATGAAAGGTTGGGCTTCGGAATCGTTTTCCGGGACGCCGGCTGGATGATCC

TCCAGCGCGGGGATCTCATGCTGGAGTTCTTCGCCCACCCCAACTTGTTTATTGCAGCTTATAA

TGGTTACAAATAAAGCAATAGCATCACAAATTTCACAAATAAAGCATTTTTTTCACTGCATTCT

AGTTGTGGTTTGTCCAAACTCATCAATGTATCTTATGATGTCTGTATACCGTCGACCTCTAGCT

```
AGAGCTTGGCGTAATCATGGTCATAGCTGTTTCCTGTGTGAAATTGTTATCCGCTCACAATTCC
ACACAACATACGAGCCGGAAGCATAAAGTGTAAAGCCTGGGGTGCCTAATGAGTGAGCTAACTC
ACATTAATTGCGTTGCGCTCACTGCCCGCTTTCCAGTCGGGAAACCTGTCGTGCCAGGTGCATT
AATGAATCGGCCAACGCGCGGGGAGAGGCGGTTTGCGTATTGGGCGCTCTTCCGCTTCCTCGCT
CACTGACTCGCTGCGCTCGGTCGTTCGGCTGCGGCGAGCGGTATCAGCTCACTCAAAGGCGGTA
ATACGGTTATCCACAGAATCAGGGGATAACGCAGGAAAGAACATGTGAGCAAAAGGCCAGCAAA
AGGCCAGGAACCGTAAAAAGGCCGCGTTGCTGGCGTTTTTCCATAGGCTCCGCCCCCCTGACGA
GCATCACAAAAATCGACGCTCAAGTCAGAGGTGGCGAAACCCGACAGGACTATAAAGATACCAG
GCGTTTCCCCCTGGAAGCTCCCTCGTGCGCTCTCCTGTTCCGACCCTGCCGCTTACCGGATACC
TGTCCGCCTTTCTCCCTTCGGGAAGCGTGGCGGTTTGTGATAGCTCACGCTGTAGGTATCTCAG
TTCGGTGTAGGTCGTTCGCTCCAAGCTGGGCTGTGTGCACGAACCCCCCGTTCAGCCCGACCGC
TGCGCCTTATCCGGTAACTATCGTCTTGAGTCCAACCCGGTAAGACACGACTTATCGCCACTGG
CAGCAGCCACTGGTAACAGGATTAGCAGAGCGAGGTATGTAGGCGGTGCTACAGAGTTCTTGAA
GTGGTGGCCTAACTACGGCTACACTAGAAGAACAGTATTTGGTATCTGCGCTCTGCTGAAGCCA
GTTACCTTCGGAAAAAGAGTTGGTAGCTCTTGATCCGGCAAACAAACCACCGCTGGTAGCGGTT
TTTTTGTTTGCAAGCAGCAGATTACGCGCAGAAAAAAAGGATCTCAAGAAGATCCTTTGATCTT
TTCTACGGGGTCTGACGCTCAGTGGAACGAAAACTCACGTTAAGGGATTTTGGTCATGAGATTA
TCAAAAAGGATCTTCACCTAGATCCTTTTAAATTAAAAATGAAGTTTTAAATCAATCTAAAGTA
TATATGAGTAAACTTGGTCTGACAGTTACCAATGCTTAATCAGTGAGGCACCTATCTCAGCGAT
CTGTCTATTTCGTTCATCCATAGTTGCCTGACTCCCCGTCGTGTAGATAACTACGATACGGGAG
GGCTTACCATCTGGCCCCAGTGCTGCAATGATACCGCGAGACCCACGCTCACCGGCTCCAGATT
TATCAGCAATAAACCAGCCAGCCGGAAGGGCCGAGCGCAGAAGTGGTCCTGCAACTTTATCCGC
CTCCATCCAGTCTATTAATTGTTGCCGGGAAGCTAGAGTAAGTAGTTCGCCAGTTAATAGTTTG
CGCAACGTTGTTGCCATTGCTACAGGCATCGTGGTGTCACGCTCGTCGTTTGGTATGGCTTCAT
TCAGCTCCGGTTCCCAACGATCAAGGCGAGTTACATGATCCCCCATGTTGTGCAAAAAAGCGGT
TAGCTCCTTCGGTCCTCCGATCGTTGTCAGAAGTAAGTTGGCCGCAGTGTTATCACTCATGGTT
ATGGCAGCACTGCATAATTCTCTTACTGTCATGCCATCCGTAAGATGCTTTTCTGTGACTGGTG
AGTACTCAACCAAGTCATTCTGAGAATAGTGTATGCGGCGACCGAGTTGCTCTTGCCCGGCGTC
AATACGGGATAATACCGCGCCACATAGCAGAACTTTAAAAGTGCTCATCATTGGAAAACGTTCT
TCGGGGCGAAAACTCTCAAGGATCTTACCGCTGTTGAGATCCAGTTCGATGTAACCCACTCGTG
CACCCAACTGATCTTCAGCATCTTTTACTTTCACCAGCGTTTCTGGGTGAGCAAAAACAGGAAG
GCAAAATGCCGCAAAAAAGGGAATAAGGGCGACACGGAAATGTTGAATACTCATACTCTTCCTT
TTTCAATATTATTGAAGCATTTATCAGGGTTATTGTCTCATGAGCGGATACATATTTGAATGTA
TTTAGAAAAATAAACAAATAGGGGTTCCGCGCACATTTCCCCGAAAAGTGCCACCTGACGTC
SEQ ID NO: 65. YAP-TEAD NanoBiT biosensor construct 3: SmBiT-
YAP50-171-Flag in pcDNA3.1-hygro vector (5,856 nucleotides)
GACGGATCGGGAGATCTCCCGATCCCCTATGGTGCACTCTCAGTACAATCTGCTCTGATGCCGC
ATAGTTAAGCCAGTATCTGCTCCCTGCTTGTGTGTTGGAGGTCGCTGAGTAGTGCGCGAGCAAA
ATTTAAGCTACAACAAGGCAAGGCTTGACCGACAATTGCATGAAGAATCTGCTTAGGGTTAGGC
GTTTTGCGCTGCTTCGCGATGTACGGGCCAGATATACGCGTTGACATTGATTATTGACTAGTTA
TTAATAGTAATCAATTACGGGGTCATTAGTTCATAGCCCATATATGGAGTTCCGCGTTACATAA
CTTACGGTAAATGGCCCGGCCTGGCTGACCGCCCAACGACCCCCGCCCATTGACGTCAATAATGA
```

-continued

```
CGTATGTTCCCATAGTAACGCCAATAGGCACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATGGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGACTCAGTATAGGGAGACCCAAGCTGGC

TAGCGTTTAAACTTAAGCTTGGTACCGAGCTCGGATCCATGGTGACCGGCTACCGGCTGTTCGA

GGAGATTCTCGGGAGTTCCGGTGGTGGCGGGAGCGGAGGTGGAGGCTCGAGCGGTGCCGGGCAT

CAGATCGTGCACGTCCGCGGGACTCGGAGACCGACCTGGAGGCGCTCTTCAACGCCGTCATGA

ACCCCAAGACGGCCAACGTGCCCCAGACCGTGCCCATGAGGCTCCGGAAGCTGCCCGACTCCTT

CTTCAAGCCGCCGGAGCCCAAATCCCACTCCCGACAGGCCAGTACTGATGCGGGCGCTGCGGA

GCCCTGACTCCACAGCATGTTCGAGCTCATTCCTCTCCAGCTTCTCTGCAGTTGGGAGCTGTTT

CTCCTGGGACACTGACCCCCACTGGAGTAGTCTCTGGCCCAGCAGCTACACCCACAGCTCAGCA

TCTTCGACAGTCTTCTTTTGAGATACCTGATGATGTACTTGTCGTCATCGTCTTTGTAGTCGCG

GCCGCTCGAGTCTAGAGGGCCCGTTTAAACCCGCTGATCAGCCTCGACTGTGCCTTCTAGTTGC

CAGCCATCTGTTGTTTGCCCCTCCCCCGTGCCTTCGTTGACCCTGGAAGGTGCCACTCCCACTG

TCCTTTCCTAATAAAATGAGGAAATTGCATCGCATTGTCTGAGTAGGTGTCATTCTATTCTGGG

GGGTGGGGTGGGCAGGACAGCAAGGGGGAGGATTGGGAAGACAATAGCAGGCATGCTGGGGAT

GCGGTGGGCTCTATGGCTTCTGAGGCGGAAAGAACCAGCTGGGGCTCTAGGGGGTATCCCCACG

CGCCCTGTAGCGGCGCATTAAGCGCGGCGGGTGTGGTGGTTACGCGCAGCGTGACCGCTACACT

TGCCAGCGCCCTAGCGCCCGCTCCTTTCGCTTTCTTCCCTTCCTTTCTCGCCACGTTCGCCGGC

TTTCCCCGTCAAGCTCTAAATCGGGGGCTCCCTTTAGGGTTCCGATTTAGTGCTTTACGGCACC

TCGACCCCAAAAAACTTGATTAGGGTGATGGTTCACGTAGTGGGCCATCGCCCTGATAGACGGT

TTTTCGCCCTTTGACGTTGGAGTCCACGTTCTTTAATAGTGGACTCTTGTTCCAAACTGGAACA

ACACTCAACCCTATCTCGGTCTATTCTTTTGATTTATAAGGGATTTTGCCGATTTCGGCCTATT

GGTTAAAAAATGAGCTGATTTAACAAAAATTTAACGCGAATTAATTCTGTGGAATGTGTGTCAG

TTAGGGTGTGGAAAGTCCCCAGGCTCCCCAGCAGGGAGAAGTATGCAAAGCATGCATCTCAATT

AGTCAGCAACCAGGTGTGGAAAGTCCCCAGGCTCCCCAGCAGGCAGAAGTATGCAAAGCATGCA

TCTCAATTAGTCAGCAACCATAGTCCCGCCCCTAACTCCGCCCATCCCGCCCCTAACTCCGCCC

AGTTCCGCCCATTCTCCGCCCCATGGCTGACTAATTTTTTTATTTATGCAGAGGCCGAGGCCG

CCTCTGCCTCTGAGCTATTCCAGAAGTAGTGAGGAGGCTTTTTTGGAGGCCTAGGCTTTTGCAA

AAAGCTCCCGGGAGCTTGTATATCCATTTTCGGATCTGATCAAGAGACAGGATGAGGATCGTTT

CGCATGATTGAACAAGATGGATTGCACGCAGGTTCTCCGGCCGCTTGGGTGGAGAGGCTATTCG

GCTATGACTGGGCACAACAGACAATCGGCTGCTCTGATGCCGCCGTGTTCCGGCTGTCAGCGCA

GGGGCGCCCGGTTCTTTTTGTCAAGACCGACCTGTCCGGTGCCCTGAATGAACTGCAGGACGAG

GCAGCGCGGCTATCGTGGCTGGCCACGACGGGCGTTCCTTGCGCAGCTGTGCTCGACGTTGTCA

CTGAAGCGGGAAGGGACTGGCTGCTATTGGGCGAAGTGCCGGGGCAGGATCTCCTGTCATCTCA

CCTTGCTCCTGCCGAGAAAGTATCCATCATGGCTGATGCAATGCGGCGGCTGCATACGCTTGAT
```

-continued

```
CCGGCTACCTGCCCATTCGACCACCAAGCGAAACATCGCATCGAGCGAGCACGTACTCGGATGG

AAGCCGGTCTTGTCGATCAGGATGATCTGGACCAAGAGCATCAGGGGCTCGCGCCAGCCGAACT

GTTCGCCAGGCTCAAGGCGCGCATGCCCGACGGCGAGGATCTCGTCGTGACCCATGGCGATGCC

TGCTTGCCGAATATCATGGTGGAAAATGGCCGCTTTTCTGGATTCATCGACTGTGGCCGGCTGG

GTGTGGCGGACCGCTATCAGGACATAGCGTTGGCTACCCGTGATATTGCTGAAGAGCTTGGCGG

CGAATGGGCTGACCGCTTCCTCGTGCTTTACGGTATCGCCGCTCCCGATTCGCAGCGCATCGCC

TTCTATCGCCTTCTTGACGAGTTCTTCTGAGCGGGACTCTGGGGTTCGAAATGACCGACCAAGC

GACGCCCAACCTGCCATCACGAGATTTCGATTCCACCGCCGCCTTCTATGAAAGGTTGGGCTTC

GGAATCGTTTTCGGGGACGCGGGCTGGATGATCCTCCAGCGCGGGATCTCATGCTGGAGTTCT

TCGCCCACCCCAACTTGTTTATTGCAGCTTATAATGGTTACAAATAAAGCAATAGCATCACAAA

TTTCACAAATAAAGCATTTTTTTCACTGCATTCTAGTTGTGGTTTGTCCAAACTCATCAATGTA

TCTTATCATGTCTGTATACCGTCGACCTCTAGCTAGAGCTTGGCGTAATCATGGTCATAGCTGT

TTCCTGTGTGAAATTGTTATCCGCTCACAATTCCACACAACATACGAGCCGGAAGCATAAAGTG

TAAAGCCTGGGGTGCCTAATGAGTGAGCTAACTCACATTAATTGCGTTGCGCTCACTGCCCGCT

TTCCAGTCGGGAAACCTGTCGTGCCAGCTGCATTAATGAATCGGCCAACGCGCGGGAGAGGCG

GTTTGCGTATTGGGCGCTCTTCCGCTTCCTCGCTCACTGACTCGCTGCGCTCGGTCGTTCGGCT

GCGGCGAGCGGTATCAGCTCACTCAAAGGCGGTAATACGGTTATCCACAGAATCAGGGGATAAC

GCAGGAAAGAACATGTGAGCAAAAGGCCAGCAAAAGGCCAGGAACCGTAAAAAGGCCGCGTTGC

TGGCGTTTTTCCATAGGCTCCGCCCCCCTGACGAGCATCACAAAAATCGACGCTCAAGTCAGAG

GTGGCGAAACCCGACAGGACTATAAAGATACCAGGCGTTTCCCCCTGGAAGCTCCCTCGTGCGC

TCTCCTGTTCCGACCCTGCCGCTTACCGGATACCTGTCCGCCTTTCTCCCTTCGGGAAGCGTGG

CGCTTTCTCATAGCTCACGCTGTAGGTATCTCAGTTCGGTGTAGGTCGTTCGCTCCAAGCTGGG

CTGTGTGCACGAACCCCCCGTTCAGCCCGACCGCTGCGCCTTATCCGGTAACTATCGTCTTGAG

TCCAACCCGGTAAGACACGACTTATCGCCACTGGCAGCAGCCACTGGTAACAGGATTAGCAGAG

CGAGGTATGTAGGCGGTGCTACAGAGTTCTTGAAGTGGTGGCCTAACTACGGCTACACTAGAAG

AACAGTATTTGGTATCTGCGCTCTGCTGAAGCCAGTTACCTTCGGAAAAAGAGTTGGTAGCTCT

TGATCCGGCAAAGAAACCACCGCTGGTAGCGGTTTTTTTGTTTGCAAGCAGCAGATTACGCGCA

GAAAAAAAGGATCTCAAGAAGATCCTTTGATCTTTTCTACGGGGTCTGACGCTCAGTGGAACGA

AAACTCACGTTAAGGGATTTTGGTCATGAGATTATCAAAAAGGATCTTCACCTAGATCCTTTTA

AATTAAAAATGAAGTTTTAAATCAATCTAAAGTATATATGAGTAAACTTGGTCTGACAGTTACC

AATGCTTAATCACTGAGGCACCTATCTCAGCGATCTGTCTATTTCGTTCATCCATAGTTGCCTG

ACTCCCCGTCGTGTAGATAACTACGATACGGGAGGGCTTACCATCTGGCCCCAGTGCTGCAATG

ATACCGCGAGACCCACGCTCACCGGCTCCAGATTTATCAGCAATAAACCAGCCAGCCGGAAGGG

CCGAGCGCAGAAGTGGTCCTGCAACTTTATCCGCCTCCATCCAGTCTATTAATTGTTGCCGGGA

AGCTAGAGTAAGTAGTTCGCCAGTTAATAGTTTGCGCAACGTTGTTGCCATTGCTACAGGCATC

GTGGTGTCACGCTCGTCGTTTGGTATGGCTTCATTCAGCTCCGGTTCCCAACGATCAAGGCGAG

TTACATGATCCCCCATGTTGTGCAAAAAAGCGGTTAGCTCCTTCGGTCCTCCGATCGTTGTCAG

AAGTAAGTTGGCCGCAGTGTTATCACTCATGGTTATGGCAGCACTGCATAATTCTCTTACTGTC

ATGCCATCCGTAAGATGCTTTTCTGTGACTGGTGAGTACTCAACCAAGTCATTCTGAGAATAGT

GTATGCGGCGACCGAGTTGCTCTTGCCCGGCGTCAATACGGGATAATACCGCGCCACATAGCAG

AACTTTAAAAGTGCTCATCATTGGAAAACGTTCTTCGGGGCGAAAACTCTCAAGGATCTTACCG
```

-continued

CTGTTGAGATCCAGTTCGATGTAACCCACTCGTGCACCCAACTGATCTTCAGCATCTTTTACTT

TCACCAGCGTTTCTGGGTGAGCAAAAACAGGAAGGCAAAATGCCGCAAAAAAGGGAATAAGGGC

GACACGGAAATGTTGAATACTGATACTCTTCCTTTTTCAATATTATTGAAGCATTTATCAGGGT

TATTGTCTCATGAGCGGATACATATTTGAATGTATTTAGAAAAATAAACAAATAGGGGTTCCGC

GCACATTTCCCCGAAAAGTGCCACCTGACGTC

SEQ ID NO: 66. YAP-TEAD NanoBiT biosensor construct 4: Flag-YAP50-171-SmBiT in pcDNA3.1-hygro vector (5,829 nucleotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTGATTAGTTCATAGCCCATATATGGAGTTCCGCGTTACATAA

CTTACGGTAAATGGCCCGCCTGGCTGACCGGCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGACTCACTATAGGGAGACCGAAGCTGGC

TAGCGTTTAAACTTAAGCTTGGTACCGAGCTCGGATCCGCCGGGCATCAGATCGTGCACGTCCG

CGGGGACTCGGAGACCGACCTGGAGGCGCTCTTCAACGCCGTCATGAACCCAAGACGGCCAAC

GTGCCCCAGACCGTGCCCATGAGGCTCCGGAAGCTGCCCGACTCCTTCTTCAAGCCGCCGGAGC

CCAAATCCCACTCCCGACAGGCCAGTACTGATGCAGGCACTGCAGGAGCCCTGACTCCACAGCA

TGTTCGAGCTCATTCCTCTCCAGCTTCTCTGCAGTTGGGAGCTGTTTCTCCTGGGACACTGACC

CCCACTGGAGTAGTCTCTGGCCCAGCAGCTACACCCACAGCTCAGCGTCTTCGACAGTCTTCTT

TTGAGGTACCTGATGATGTAGGCTCGAGCGGTGGTGGCGGGAGCGGAGGTGGAGGGTCGTCAGG

TGTGACCGGCTACCGGCTGTTCGAGGAGATTCTGGCGGCCGCTCGAGTCTAGAGGGCCCGTTTA

AACCCGCTGATCAGCCTCGACTGTGCCTTCTAGTTGCCAGCCATCTGTTGTTTGCCCCTCCCCC

GTGCCTTCCTTGACCCTGGAAGGTGCCACTCCCACTGTCCTTTCCTAATAAAATGAGGAAATTG

CATCGCATTGTCTGAGTAGGTGTCATTCTATTCTGGGGGGTGGGGTGGGCAGGACAGCAAGGG

GGAGGATTGGGAAGAGAATAGCAGGCATGCTGGGGATGCGGTGGGCTCTATGGCTTCTGAGGGG

GAAAGAACCAGCTGGGGCTCTAGGGGGTATCCCCACGCGCCCTGTAGCGGCGCATTAAGCGCGG

CGGGTGTGGTGGTTACGCGCAGCGTGACCGCTACACTTGCCAGCGCCCTAGCGCCCGCTCGTTT

CGCTTTCTTCCCTTCCTTTCTCGCCACGTTGGCCGGCTTTCCCCGTCAAGCTCTAAATCGGGGG

GTCCCTTTAGGGTTCCGATTTAGTGCTTTACGGCACCTCGACCCCAAAAAACTTGATTAGGGTG

ATGGTTCACGTAGTGGGCCATCGCCCTGATAGACGGTTTTTCGCCCTTTGACGTTGGAGTCCAC

GTTCTTTAATAGTGGAGTCTTGTTCCAAACTGGAACAACACTCAACCCTATCTCGGTCTATTCT

TTTGATTTATAAGGGATTTTGCCGATTTCGGCCTATTGGTTAAAAAATGAGCTGATTTAACAAA

AATTTAACGGGAATTAATTCTGTGGAATGTGTGTCAGTTAGGGTGTGGAAAGTCCCCAGGCTCC

```
CCAGCAGGCAGAAGTATGCAAAGCATGCATCTCAATTAGTCAGCAACCAGGTGTGGAAAGTCCC

CAGGCTCCCCAGCAGGCAGAAGTATGCAAAGCATGCATCTCAATTAGTCAGCAACCATAGTCCC

GCCCCTAACTCCGCCCATCCCGCCCCTAACTCCGCCCAGTTCCGCCCATTCTCCGCCCCATGGC

TGACTAATTTTTTTATTTATGCAGAGGCCGAGGCCGCCTCTGCCTCTGAGCTATTCCAGAAGT

AGTGAGGAGGCTTTTTTGGAGGCCTAGGCTTTTGCAAAAAGCTCCCGGGAGCTTGTATATCCAT

TTTCGGATCTGATCAAGAGACAGGATGAGGATCGTTTCGCATGATTGAACAAGATGGATTGGAC

GCAGGTTCTCCGGCCGCTTGGGTGGAGAGGCTATTCGGCTATGACTGGGCACAACAGACAATCG

GCTGCTCTGATGCCGCCGTGTTCCGGCTGTCAGCGCAGGGGCGCCCGGTTCTTTTTGTCAAGAC

CGACCTGTCCGGTGCCCTGAATGAACTGCAGGACGAGGCAGCGCGGCTATCGTGGCTGGCCACG

ACGGGCGTTCCTTGCGCAGCTGTGCTCGACGTTGTCACTGAAGCGGGAAGGGACTGGCTGCTAT

TGGGCGAAGTGCCGGGGCAGGATCTCCTGTCATCTCACCTTGCTCCTGCCGAGAAAGTATCCAT

CATGGCTGATGCAATGGGGGGCTGCATACGCTTGATCCGGCTACCTGCCCATTCGACCAGCAA

GCGAAACATCGCATCGAGCGAGCACGTACTCGGATGGAAGCCGGTCTTGTCGATCAGGATGATC

TGGACGAAGAGCATCAGGGGCTCGCGCCAGCCGAACTGTTCGCCAGGCTCAAGGCGCGCATGCC

CGACGGCGAGGATCTCGTCGTGACCCATGGCGATGCCTGCTTGCCGAATATCATGGTGGAAAAT

GGCCGCTTTTCTGGATTCATCGACTGTGGCCGGCTGGGTGTGGCGGACCGCTATCAGGACATAG

CGTTGGCTACCCGTGATATTGCTGAAGAGCTTGGCGGCGAATGGGCTGACCGCTTCCTCGTGCT

TTACGGTATCGCCGCTCCCGATTCGCAGCGCATCGCCTTCTATCGCCTTCTTGACGAGTTCTTC

TGAGCGGGACTCTGGGGTTCGAAATGACCGACCAAGCGACGCCCAACCTGCCATCACGAGATTT

CGATTCCACCGCCGCCTTCTATGAAAGGTTGGGCTTCGGAATCGTTTTCCGGGACGCCGGCTGG

ATGATCCTCCAGCGCGGGGATCTCATGCTGGAGTTCTTCGCCCACCCCAACTTGTTTATTGCAG

CTTATAATGGTTACAAATAAAGCAATAGCATCACAAATTTCACAAATAAAGCATTTTTTTCACT

GCATTCAGTTGTGGTTTGTCCAAACTCATCAATGTATCTTATCATGTCTGTATACCGTCGACC

TCTAGCTAGAGCTTGGCGTAATCATGGTCATAGCTGTTTCCTGTGTGAAATTGTTATCCGCTCA

CAATTCCACACAACATACGAGCCGGAAGCATAAAGTGTAAAGCCTGGGGTGCCTAATGAGTGAG

CTAACTCACATTAATTGCGTTGCGCTCACTGCCCGCTTTCCAGTCGGGAAACCTGTCGTGCCAG

CTGCATTAATGAATCGGCCAACGCGCGGGGAGAGGCGGTTTGCGTATTGGGCGCTCTTCCGCTT

CCTCGCTCACTGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGTGAGCAAAAGGC

CAGCAAAAGGCCAGGAACCGTAAAAAGGCCGCGTTGCTGGCGTTTTTCCATAGGCTCCGCCCCC

CTGACGAGCATCACAAAAATCGACGCTCAAGTCAGAGGTGGCGAAACCCGACAGGACTATAAAG

ATACCAGGCGTTTCCCCCTGGAAGCTCCCTCGTGCGCTCTCCTGTTCCGACCCTGCCGCTTACC

GGATACCTGTCCGCCTTTCTCCCTTCGGGAAGCGTGGCGCTTTCTCATAGCTCACGCTGTAGGT

ATCTCAGTTCGGTGTAGGTCGTTCGCTCCAAGCTGGGCTGTGTGCACGAACCCCCCGTTCAGCC

CGACCGCTGCGCCTTATCCGGTAACTATCGTCTTGAGTCCAACCCGGTAAGACACGACTTATCG

CCACTGGCAGCAGCCACTGGTAACAGGATTAGCAGAGCGAGGTATGTAGGCGGTGCTACAGAGT

TCTTGAAGTGGTGGCCTAACTACGGCTACACTAGAAGAACAGTATTTGGTATCTGCGCTCTGCT

GAAGCCAGTTACCTTCGGAAAAAGAGTTGGTAGCTCTTGATCCGGCAAACAAACCACCGCTGGT

AGCGGTTTTTTTGTTTGCAAGCAGCAGATTACGCGCAGAAAAAAAGGATCTCAAGAAGATCCTT

TGATCTTTTCTACGGGGTGTGAGGCTCAGTGGAAGGAAAACTCACGTTAAGGGATTTTGGTCAT

GAGATTATCAAAAAGGATCTTCACCTAGATCCTTTTAAATTAAAAATGAAGTTTTAAATCAATC
```

```
TAAAGTATATATGAGTAAACTTGGTCTGACAGTTACCAATGCTTAATCAGTGAGGCACCTATCT
CAGCGATCTGTCTATTTCGTTCATCCATAGTTGCCTGACTCCCCGTCGTGTAGATAACTACGAT
ACGGGAGGGCTTACCATCTGGCCCCAGTGCTGCAATGATACCGCGAGACCCACGCTCACCGGCT
CCAGATTTATCAGCAATAAACCAGCCAGCCGGAAGGGCCGAGCGCAGAAGTGGTCCTGCAACTT
TATCCGCCTCCATCCAGTCTATTAATTGTTGCCGGGAAGCTAGAGTAAGTAGTTCGCCAGTTAA
TAGTTTGCGCAACGTTGTTGCCATTGCTACAGGCATCGTGGTGTCACGCTCGTCGTTTGGTATG
GCTTCATTCAGCTCCGGTTCCCAACGATCAAGGCGAGTTACATGATCCCCCATGTTGTGCAAAA
AAGCGGTTAGCTCCTTCGGTCCTCCGATCGTTGTCAGAAGTAAGTTGGCCGCAGTGTTATCAGT
CATGGTTATGGCAGCACTGCATAATTCTCTTACTGTCATGCCATCCGTAAGATGCTTTTCTGTG
ACTGGTGAGTACTCAACCAAGTCATTCTGAGAATAGTGTATGCGGCGACCGAGTTGCTCTTGCC
CGGCGTCAATACGGGATAATACCGCGCCACATAGCAGAACTTTAAAAGTGCTCATCATTGGAAA
ACGTTCTTCGGGGCGAAAACTCTCAAGGATCTTACCGCTGTTGAGATCCAGTTCGATGTAACCC
ACTCGTGCACCCAACTGATCTTCAGCATCTTTTACTTTCACCAGCGTTTCTGGGTGAGCAAAA
CAGGAAGGCAAAATGCCGCAAAAAAGGGAATAAGGGCGACACGGAAATGTTGAATACTCATACT
CTTCCTTTTTCAATATTATTGAAGCATTTATCAGGGTTATTGTCTCATGAGCGGATAGATATTT
GAATGTATTTAGAAAAATAAACAATAGGGGTTCCGCGCACATTTCCCCGAAAAGTGCCACCTG
ACGTC

SEQ ID NO: 67. YAP-TEAD NanoBiT biosensor construct 5: LgBiT-
TEAD1-194-411-Myc in pcDNA3.1-hygro vector (6,592 nucleotides)
GACGGATCGGGAGATCTCCCGATCCCCTATGGTGCACTCTCAGTACAATCTGCTCTGATGCCGC
ATAGTTAAGCCAGTATCTGCTCCCTGCTTGTGTGTTGGAGGTCGCTGAGTAGTGCGCGAGCAAA
ATTTAAGCTACAACAAGGCAAGGCTTGACCGAGAATTGCATGAAGAATCTGCTTAGGGTTAGGC
GTTTTGCGCTGCTTCGCGATGTACGGGCCAGATATACGCGTTGACATTGATTATTGACTAGTTA
TTAATAGTAATCAATTACGGGGTCATTAGTTCATAGCCCATATATGGAGTTCCGCGTTACATAA
CTTACGGTAAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGTATTTACG
GTAAACTGGCCAGTTGGCAGTACATCAAGTGTATCATATGCCAAGTACGCCCCCTATTGACGTC
AATGACGGTAAATGGCCCGCCTGGCATTATGCCCAGTACATGACCTTATGGGACTTTCCTACTT
GGCAGTACATCTACGTATTAGTCATCGCTATTACCATGGTGATGCGGTTTTGGCAGTACATCAA
TGGGCGTGGATAGCGGTTTGACTCACGGGGATTTCCAAGTCTCCACCCCATTGACGTCAATGGG
AGTTTGTTTTGGCACCAAAATCAACGGGACTTTCCAAAATGTCGTAACAACTCCGCCCCATTGA
CGCAAATGGGCGGTAGGCGTGTACGGTGGGAGGTCTATATAAGCAGAGCTCTCTGGCTAACTAG
AGAACCCACTGCTTACTGGCTTATCGAAATTAATACGACTCACTATAGGGAGACCCAAGCTGGC
TAGCGTTTAAACTTAAGCTTGGTACCGAGCTCGGATCCATGGTCTTCACACTCGAAGGTTTCGT
TCGGGACTGGGAACAGACAGCCGCCTACAACCTGGACCAAGTCCTTGAACAGGGAGGTGTGTCC
AGTTTGCTGCAGAATCTCGCCGTGTCCGTAACTCCGATCCAAAGGATTGTCCGGAGCGGTGAAA
ATGCCCTGAAGATCGACATCCATGTCATCATCCCGTATGAAGGTCTGAGCGCCGACCAAATGGC
CCAGATCGAAGAGGTGTTTAAGGTGGTGTACCCTGTGGATGATCATCACTTTAAGGTGATCCTG
CCCTATGGCACACTGGTAATCGACGGGGTTACGCCGAACATGCTGAACTATTTCGGACGGCCGT
ATGAAGGCATCGCCGTGTTCGACGGCAAAAAGATCACTGTAACAGGGACCCTGTGGAACGGCAA
CAAAATTATCGACGAGCGCCTGATCACCCCCGACGGCTCCATGCTGTTCCGAGTAACCATCAAC
```

-continued

AGTGGGAGTTCCGGTGGTGGCGGGAGCGGAGGTGGAGGCTCGAGCGGTTGAGCCTGCATCGGCC

CCAGCTCCCTCAGTCCCTGCCTGGCAAGGTCGCTCCATTGGCACGACCGAGCTTCGCCTGGTGG

AATTTTCAGCTTTTCTCGAGCAGCAGCGAGACCCAGACTCGTACAACAAACACCTCTTCGTGCA

CATTGGGCATGCCGACCGTTCTTACAGTGACCCATTGCTTGAATCAGTGGGCATTCGTCAGATT

TATGACAAATTTCCTGAAAAGAAGGGTGGCTTAAAGGAACTGTTTGGAAAGGGCCCTCAAGATG

CCTTCTTCCTCGTAAAATTCTGGGCTGATTTAAACTGCAATATTCAAGATGATGCTGGGGCTTT

TTATGGTGTAACCAGTCAGTACGAGAGTTCTGAAAATATGACAGTCACCTGTTCCACCAAAGTT

TGCTCCTTTGGGGAGCAAGTGGTAGAGAAAGTAGAGACGGAGTATGCAAGGTTTGAGGATGGCC

GATTTGTATACCGAATAAACCGCTCCCCAATGTGTGAATATATGATCAACTTCATCCACAAGCT

CAAACACTTACCAGAGAAATATATGATGAACAGTGTTTTGGAAAACTTCACAATTTTATTGGTG

GTAACAAACAGGGATACACAAGAAACTCTACTCTGCATGGCCTGTGTGTTTGAAGTTTCAAATC

AGATCCTCTTCTGAGATGAGTTTTTGTTCGCGGCCGCTCGAGTCTAGAGGGCCCGTTTAAACCC

GCTGATCAGCCTCGACTGTGCCTTCTAGTTGCCAGCCATCTGTTGTTTGCCCCTCCGCCGTGCC

TTCCTTGACCCTGGAAGGTGCCACTCCCACTGTCCTTTCCTAATAAAATGAGGAAATTGCATCG

CATTGTCTGAGTAGGTGTCATTCTATTCTGGGGGGTGGGGTGGGCAGGACAGCAAGGGGGAGG

ATTGGGAAGACAATAGCAGGGATGCTGGGGATGCGGTGGGCTCTATGGCTTCTGAGGCGGAAAG

AACCAGCTGGGGCTCTAGGGGGTATCCCGACGCGCCCTGTAGCGGCGCATTAAGCGCGGCGGGT

GTGGTGGTTACGCGCAGCGTGACCGCTACACTTGCCAGCGCCCTAGCGCCCGCTCCTTTCGCTT

TCTTCCCTTCCTTTCTCGCCACGTTCGCCGGCTTTCCCCGTCAAGCTCTAAATCGGGGGCTCCC

TTTAGGGTTCCGATTTAGTGCTTTACGGCACCTCGACCCCAAAAAACTTGATTAGGGTGATGGT

TCACGTAGTGGGCCATCGGCCTGATAGAGGGTTTTTCGCCCTTTGAGGTTGGAGTCCACGTTGT

TTAATAGTGGACTCTTGTTCCAAACTGGAACAACACTCAACCCTATCTGGGTGTATTCTTTTGA

TTTATAAGGGATTTTGCCGATTTCGGCCTATTGGTTAAAAAATGAGCTGATTTAAGAAAAATTT

AACGCGAATTAATTCTGTGGAATGTGTGTCAGTTAGGGTGTGGAAAGTCCCCAGGCTCCCCAGC

AGGCAGAAGTATGCAAAGCATGCATCTGAATTAGTCAGCAACCAGGTGTGGAAAGTCCCCAGGC

TCCCGAGCAGGCAGAAGTATGCAAAGCATGCATGTCAATTAGTCAGCAACGATAGTCCCGCCCC

TAACTCCGCCCATCCCGCCCCTAACTCCGCCCAGTTCCGCCCATTCTCCGCCCCATGGCTGACT

AATTTTTTTTATTTATGCAGAGGCCGAGGCCGCCTCTGCCTCTGAGCTATTCCAGAAGTAGTGA

GGAGGCTTTTTTGGAGGCCTAGGCTTTTGCAAAAAGCTCCCGGGAGCTTGTATATCCATTTTCG

GATCTGATCAAGAGACAGGATGAGGATCGTTTCGCATGATTGAACAAGATGGATTGCACGCAGG

TTCTCCGGCCGCTTGGGTGGAGAGGCTATTCGGCTATGACTGGGCACAACAGACAATCGGCTGC

TCTGATGCCGCCGTGTTCCGGCTGTCAGCGCAGGGGCGCCCGGTTCTTTTTGTCAAGACCGACC

TGTCCGGTGCCCTGAATGAACTGCAGGACGAGGCAGCGCGGCTATCGTGGCTGGCCACGACGGG

CGTTCCTTGCGCAGCTGTGCTCGACGTTGTCACTGAAGCGGGAAGGGACTGGCTGCTATTGGGC

GAAGTGCCGGGGCAGGATCTCCTGTCATCTCACCTTGCTCCTGCCGAGAAAGTATCCATCATGG

CTGATGCAATGCGGCGGCTGCATACGCTTGATCCGGCTACCTGCCCATTCGACCACCAAGCGAA

ACATCGCATCGAGCGAGCACGTACTCGGATGGAAGCCGGTCTTGTCGATCAGGATGATCTGGAC

GAAGAGCATCAGGGGCTCGCGCCAGCCGAACTGTTCGCCAGGCTCAAGGCGCGCATGCCCGACG

GCGAGGATCTCGTCGTGACCCATGGCGATGCCTGCTTGCCGAATATCATGGTGGAAAATGGCCG

CTTTTCTGGATTCATCGACTGTGGCCGGCTGGGTGTGGCGGACCGCTATCAGGACATAGCGTTG

GCTACCCGTGATATTGCTGAAGAGCTTGGCCGCGAATGGGCTGACCGCTTCCTCGTGCTTTACG

```
GTATCGCCGCTCCCGATTCGCAGCGCATCGCCTTCTATCGCCTTCTTGACGAGTTCTTCTGAGC

GGGACTCTGGGGTTCGAAATGACCGACCAAGCGACGCCGAACCTGCCATCACGAGATTTCGATT

CCACCGCCGCCTTCTATGAAAGGTTGGGCTTCGGAATCGTTTTCCGGGACGCCGGCTGGATGAT

CCTCCAGCGCGGGGATCTCATGCTGGAGTTCTTCGCCCACCCCAACTTGTTTATTGCAGCTTAT

AATGGTTACAAATAAAGCAATAGCATCACAAATTTCACAAATAAAGCATTTTTTTCACTGCATT

CTAGTTGTGGTTTGTCCAAACTCATCAATGTATCTTATCATGTCTGTATACCGTCGACCTCTAG

CTAGAGCTTGGCGTAATCATGGTCATAGCTGTTTCCTGTGTGAAATTGTTATCCGCTCACAATT

CCACACAACATACGAGCCGGAAGCATAAAGTGTAAAGCCTGGGGTGCCTAATGAGTGAGCTAAC

TCACATTAATTGCGTTGCGCTCACTGCCCGCTTTCCAGTCGGGAAACCTGTCGTGCCAGCTGCA

TTAATGAATCGGCCAACGCGCGGGGAGAGGCGGTTTGCGTATTGGGCGCTCTTCCGCTTCCTCG

CTCACTGACTCGCTGCGCTCGGTCGTTCGGCTGCGGCGAGCGGTATCAGCTCACTCAAAGGCGG

TAATACGGTTATCCACAGAATCAGGGGATAACGCAGGAAAGAACATGTGAGCAAAAGGCCAGCA

AAAGGCCAGGAACCGTAAAAAGGCCGCGTTGCTGGCGTTTTTCCATAGGCTCCGCCCCCCTGAC

GAGCATCACAAAAATCGACGCTCAAGTCAGAGGTGGCGAAACCCGACAGGACTATAAAGATACC

AGGCGTTTCCCCCTGGAAGCTCCCTCGTGCGCTCTCCTGTTCCGACCCTGCCGCTTACCGGATA

CCTGTCCGCCTTTCTCCCTTCGGGAAGCGTGGCGCTTTCTCATAGCTCACGCTGTAGGTATCTC

AGTTCGGTGTAGGTCGTTCGCTCCAAGCTGGGCTGTGTGCACGAACCCCCCGTTCAGCCCGACC

GCTGCGCCTTATCCGGTAACTATCGTCTTGAGTCCAACCCGGTAAGACACGACTTATCGCCACT

GGCAGCAGCCACTGGTAACAGGATTAGCAGAGCGAGGTATGTAGGGGGTGCTACAGAGTTCTTG

AAGTGGTGGCCTAACTACGGCTACACTAGAAGAACAGTATTTGGTATCTGCGCTCTGCTGAAGC

CAGTTACCTTCGGAAAAAGAGTTGGTAGCTCTTGATCCGGCAAACAAACCACCGCTGGTAGCGG

TTTTTTTGTTTGCAAGCAGCAGATTACGCGCAGAAAAAAAGGATCTCAAGAAGATCCTTTGATC

TTTTCTACGGGGTCTGACGCTCAGTGGAACGAAAACTCACGTTAAGGGATTTTGGTCATGAGAT

TATCAAAAAGGATCTTCACCTAGATCCTTTTAAATTAAAAATGAAGTTTTAAATCAATCTAAAG

TATATATGAGTAAACTTGGTCTGACAGTTACCAATGCTTAATCAGTGAGGCACCTATGTCAGCG

ATCTGTCTATTTCGTTCATCCATAGTTGCCTGACTCCCCGTCGTGTAGATAACTACGATACGGG

AGGGCTTACCATCTGGCCCCAGTGCTGCAATGATACCGCGAGACCCACGCTCACCGGCTCCAGA

TTTATCAGCAATAAACCAGCCAGCCGGAAGGGCGGAGCGCAGAAGTGGTCCTGCAACTTTATCC

GCCTCCATCCAGTCTATTAATTGTTGCCGGGAAGCTAGAGTAAGTAGTTCGCCAGTTAATAGTT

TGCGCAACGTTGTTGCCATTGCTACAGGCATCGTGGTGTCACGCTCGTCGTTTGGTATGGCTTC

ATTCAGCTCCGGTTCCCAACGATCAAGGCGAGTTACATGATCCCCCATGTTGTGCAAAAAAGCG

GTTAGCTCCTTCGGTCCTCCGATCGTTGTCAGAAGTAAGTTGGCCGCAGTGTTATCACTCATGG

TTATGGCAGCACTGCATAATTCTCTTACTGTCATGCCATCCGTAAGATGCTTTTCTGTGACTGG

TGAGTACTCAACCAAGTCATTCTGAGAATAGTGTATGCGGCGACCGAGTTGCTCTTGCCCGGCG

TCAATACGGGATAATACCGCGCCACATAGCAGAACTTTAAAAGTGCTCATCATTGGAAAACGTT

CTTCGGGGCGAAAACTCTCAAGGATCTTACCGCTGTTGAGATCCAGTTCGATGTAACCCACTCG

TGCACCCAACTGATCTTCAGCATCTTTTACTTTCACCAGCGTTTCTGGGTGAGCAAAAACAGGA

AGGCAAAATGCCGCAAAAAAGGGAATAAGGGCGACACGGAAATGTTGAATACTCATACTCTTCC

TTTTTCAATATTATTGAAGCATTTATCAGGGTTATTGTCTCATGAGCGGATACATATTTGAATG

TATTTAGAAAAATAAACAAATAGGGGTTCCGCGCACATTTCCCCGAAAAGTGCCACCTGACGTC
```

SEQ ID NO: 68. YAP-TEAD NanoBiT biosensor construct 6: Myc-
TEAD1-194-411-LgBiT in pcDNA3.1-hygro vector (6,559 nucleotides)
GACGGATCGGGAGATCTCCCGATCCCCTATGGTGCACTCTCACTACAATCTGCTCTGATCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGACTCACTATAGGGAGACCCAAGCTGGC

TAGCGTTTAAACTTAAGCTTGGTACCGAGCTCGGATCCTGAGCCTGCATCGGCGCCAGCTCCCT

CAGTCCCTGCCTGGCAAGGTCGCTCCATTGGCACAACCAAGCTTCGCCTGGTGGAATTTTCGGC

TTTTCTCGAGCAGCAGCGAGACCCAGACTCGTACAACAAACACCTCTTCGTGCACGTTGGGCAT

GCCAACCATTCTTACAGTGACCCATTGCTTGAATCAGTGGACATTCGTCAGATTTATGACAAAT

TTCCTGAAAAGAAAGGTGGCTTAAAGGAACTGTTTGGAAAGGGCCCTCAAAATGCCTTCTTCCT

CGTAAAATTCTGGGCTGATTTAAACTGCAATATTCAAGATGATGCTGGGGCTTTTTATGGTGTA

ACCAGTCAGTACGAGAGTTCTGAAAATATGACAGTCACCTGTTCCACCAAAGTTTGCTCCTTTG

GGAAGCAAGTAGTAGAAAAAGTAGAGACGGAGTATGCAAGGTTTGAGAGTGGCCGATTTGTATA

CCGAATAAACCGCTCCCCAATGTGTGAATATATGATCAACTTCATCCACAAGCTCAAACACTTA

CCAGAGAAATATATGATGAACAGTGTTTTGGAAAACTTCACAATTTTATTGGTGGTAACAAACA

GGGATACACAAGAAACTCTACTCTGCATGGCCTGTGTGTTTGAAGTTTCAAATGGCTCGAGCGG

TGGTGGCGGGAGCGGAGGTGGAGGGTCGTCAGGTGTCTTCACACTCGAAGATTTCGTTGGGGAC

TGGGAACAGACAGCCGCCTACAACCTGGACCAAGTCCTTGAACAGGGAGGTGTGTCCAGTTTGC

TGCAGAATCTCGCCGTGTCCGTAACTCCGATCCAAAGGATTGTCCGGAGCGGTGAAAATGCCCT

GAAGATCGACATCCATGTCATCATCCCGTATGAAGGTCTGAGCGCCGACCAAATGGCCCAGATC

GAAGAGGTGTTTAAGGTGGTGTACCCTGTGGATGATCATCACTTTAAGGTGATCCTGCCCTATG

GCACACTGGTAATCGACGGGGTTACGCCGAACATGCTGAACTATTTCGGACGGCCGTATGAAGG

CATCGCCGTGTTCGACGGCAAAAAGATCACTGTAACAGGGACCCTGTGGAACGGCAACAAAATT

ATCGACGAGCGCCTGATCACCCCCGACGGCTCCATGCTGTTCCGAGTAACCATCAACAGCGCGG

CCGCTCGAGTCTAGAGGGCCCGTTTAAACCCGCTGATCAGCCTCGACTGTGCCTTCTAGTTGCC

AGCCATCTGTTGTTTGCCCCTCCCCCGTGCCTTCCTTGACCCTGGAAGGTGCCACTCCCACTGT

CCTTTCCTAATAAAATGAGGAAATTGCATCGCATTGTCTGAGTAGGTGTCATTCTATTCTGGGG

GGTGGGGTGGGGCAGGACAGCAAGGGGGAGGATTGGGAAGACAATAGCAGGCATGCTGGGGATG

CGGTGGGCTCTATGGCTTCTGAGGCGGAAAGAACCAGCTGGGGCTCTAGGGGGTATCCCCACGC

GCGCTGTAGCGGCGCATTAAGCGCGGCGGGTGTGGTGGTTACGCGCAGCGTGACCGGTACACTT

GCCAGCGCCCTAGCGCCCGCTCCTTTCGCTTTCTTCGCTTCCTTTCTCGCCACGTTCGCCGGCT

TTCCCCGTCAAGCTCTAAATCGGGGGCTCCCTTTAGGGTTCCGATTTAGTGCTTTACGGCACCT

-continued

```
CGACCCCAAAAAACTTGATTAGGGTGATGGTTCACGTAGTGGGCCATCGCCCTGATAGACGGTT
TTTCGCCCTTTGACGTTGGAGTCCACGTTCTTTAATAGTGGACTCTTGTTCCAAACTGGAACAA
CACTCAACCCTATCTCGGTCTATTCTTTTGATTTATAAGGGATTTTGCCGATTTCGGCCTATTG
GTTAAAAAATGAGCTGATTTAACAAAAATTTAACGCGAATTAATTCTGTGGAATGTGTGTCAGT
TAGGGTGTGGAAAGTCCCCAGGCTCCCCAGCAGGCAGAAGTATGCAAAGCATCCATCTCAATTA
GTCAGCAACCAGGTGTGGAAAGTCCCCAGGCTCCCCAGCAGGCAGAAGTATGCAAAGCATGCAT
CTCAATTAGTCAGCAACCATAGTCCCGCCCCTAACTCCGCCCATCCCGCCCCTAACTCCGCCCA
GTTCCGCCCATTCTCCGCCCCATGGCTGACTAATTTTTTTATTTATGCAGAGGCCGAGGCCGC
CTCTGCCTCTGAGCTATTCCAGAAGTAGTGAGGAGGCTTTTTGGAGGCCTAGGCTTTTGCAAA
AAGCTCCCGGGAGCTTGTATATCCATTTTCGGATCTGATCAAGAGACAGGATGAGGATCGTTTC
GCATGATTGAACAAGATGGATTGCACGCAGGTTCTCCGGCCGCTTGGGTGGAGAGGCTATTCGG
CTATGACTGGGCACAACAGACAATCGGCTGCTCTGATGCCGCCGTGTTCCGGCTGTCAGCGCAG
GGGCGCCCGGTTCTTTTTGTCAAGACCGACCTGTCCGGTGCCCTGAATGAACTGCAGGACGAGG
CAGCGCGGCTATCGTGGCTGGCCACGACGGGCGTTCCTTGCGCAGCTGTGCTCGACGTTGTCAC
TGAAGCGGGAAGGGACTGGCTGCTATTGGGCGAAGTGCCGGGGCAGGATCTCCTGTCATCTCAC
CTTGCTCCTGCCGAGAAAGTATCCATCATGGCTGATGCAATGCGGCGGCTGCATACGCTTGATC
CGGCTACCTGCCCATTCGACCACCAAGCGAAACATCGCATCGAGCGAGCACGTACTCGGATGGA
AGCCGGTCTTGTCGATCAGGATGATCTGGACGAAGAGCATCAGGGGCTCGCGCCAGCCGAACTG
TTCGCCAGGCTCAAGGCGCGCATGCCCGACGGCGAGGATCTCGTCGTGACCCATGGCGATGCCT
GCTTGCCGAATATCATGGTGGAAAATGGCCGCTTTTCTGGATTCATCGACTGTGGCCGGCTGGG
TGTGGCGGACCGCTATCAGGACATAGCGTTGGCTACCCGTGATATTGCTGAAGAGCTTGGCGGC
GAATGGGCTGACCGCTTCCTCGTGCTTTACGGTATCGCCGCTCCCGATTCGCAGCGCATCGCCT
TCTATCGCCTTCTTGACGAGTTCTTCTGAGCGGGACTCTGGGGTTCGAAATGACCGACCAAGCG
ACGCCCAACCTGCCATCACGAGATTTCGATTCCACCGCCGCCTTCTATGAAAGGTTGGGCTTCG
GAATCGTTTTCCGGGACGCCGGCTGGATGATCCTCCAGCGCGGGGATCTCATGCTGGAGTTCTT
CGCCCACCCCAACTTGTTTATTGCAGCTTATAATGGTTACAAATAAAGCAATAGCATCACAAAT
TTCACAAATAAAGCATTTTTTTCACTGCATTCTAGTTGTGGTTTGTCCAAACTCATCAATGTAT
CTTATCATGTCTGTATACCGTCGACCTCTAGCTAGAGCTTGGCGTAATCATGGTCATAGCTGTT
TCCTGTGTGAAATTGTTATCCGCTCACAATTCCACACAACATACGAGCCGGAAGCATAAAGTGT
AAAGCCTGGGGTGCCTAATGAGTGAGCTAACTCACATTAATTGCGTTGCGCTCACTGCCCGCTT
TCCAGTCGGGAAACCTGTCGTGCCAGCTGCATTAATGAATCGGCCAACGCGCGGGGAGAGGCGG
TTTGCGTATTGGGCGCTCTTCCGCTTCCTCGCTCACTGACTCGCTGCGCTCGGTCGTTCGGCTG
CGGCGAGCGGTATCAGCTCACTCAAAGGCGGTAATACGGTTATCCACAGAATCAGGGGATAACG
CAGGAAAGAACATGTGAGCAAAAGGCCAGCAAAAGGCCAGGAACCGTAAAAAGGCCGCGTTGCT
GGCGTTTTTCCATAGGCTCCGCCCCCCTGACGAGCATCACAAAAATCGACGCTCAAGTCAGAGG
TGGCGAAACCCGACAGGACTATAAAGATACCAGGCGTTTCCCCCTGGAAGCTCCCTCGTGCGCT
CTCCTGTTCCGACCCTGCCGCTTACCGGATACCTGTCCGCCTTTCTCCCTTCGGGAAGCGTGGC
GCTTTCTCATAGCTCACGCTGTAGGTATCTCAGTTCGGTGTAGGTCGTTCGCTCCAAGCTGGGC
TGTGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGAGC
```

```
GAGGTATGTAGGCGGTGCTACAGAGTTCTTGAAGTGGTGGCCTAACTACGGCTACACTAGAAGA

ACAGTATTTGGTATCTGCGCTCTGCTGAAGCCAGTTAGCTTCGGAAAAAGAGTTGGTAGCTCTT

GATCCGGCAAACAAACCACCGCTGGTAGCGGTTTTTTTGTTTGCAAGCAGCAGATTACGCGCAG

AAAAAAAGGATCTCAAGAAGATCCTTTGATCTTTTCTACGGGGTCTGACGCTCAGTGGAACGAA

AACTCACGTTAAGGGATTTTGGTCATGAGATTATCAAAAAGGATCTTCACCTAGATCCTTTTAA

ATTAAAAATGAAGTTTTAAATCAATCTAAAGTATATATGAGTAAACTTGGTCTGACAGTTACCA

ATGCTTAATCAGTGAGGCACCTATCTCAGCGATCTGTCTATTTCGTTCATCCATAGTTGCCTGA

CTCCCCGTCGTGTAGATAACTACGATACGGGAGGGCTTACCATCTGGCCCCAGTGCTGCAATGA

TACCGCGAGACCCACGCTCACCGGCTCCAGATTTATCAGCAATAAACCAGCCAGCCGGAAGGGC

CGAGCGCAGAAGTGGTCCTGCAACTTTATCCGCCTCCATCCAGTCTATTAATTGTTGCCGGGAA

GCTAGAGTAAGTAGTTCGCCAGTTAATAGTTTGCGCAACGTTGTTGCCATTGCTACAGGCATCG

TGGTGTCACGCTCGTCGTTTGGTATGGCTTCATTCAGCTCCGGTTCCCAACGATCAAGGCGAGT

TACATGATCCCCCATGTTGTGCAAAAAAGCGGTTAGCTCCTTCGGTCCTCCGATCGTTGTCAGA

AGTAAGTTGGCCGCAGTGTTATCACTCATGGTTATGGCAGCACTGCATAATTCTCTTACTGTCA

TGCCATCCGTAAGATGCTTTTCTGTGACTGGTGAGTACTCAACCAAGTCATTCTGAGAATAGTG

TATGCGGCGACCGAGTTGCTCTTGCCCGGCGTCAATACGGGATAATACCGCGCCACATAGCAGA

ACTTTAAAAGTGCTCATCATTGGAAAACGTTCTTCGGGGCGAAAACTCTCAAGGATCTTACCGC

TGTTGAGATCCAGTTCGATGTAACCCACTCGTGCACCCAACTGATCTTCAGCATCTTTTACTTT

CACCAGCGTTTCTGGGTGAGCAAAAACAGGAAGGCAAAATGCCGCAAAAAAGGGAATAAGGGCG

ACACGGAAATGTTGAATACTCATACTCTTCCTTTTTCAATATTATTGAAGCATTTATCAGGGTT

ATTGTCTCATGAGCGGATACATATTTGAATGTATTTAGAAAAATAAACAAATAGGGGTTCCGCG

CACATTTCCCCGAAAAGTGCCACCTGACGTC

SEQ ID NO: 69. YAP-TEAD NanoBiT biosensor construct 7: SmBiT-
TEAD1-194-411-Myc in pcDNA3.1-hygro vector (6,151 nucleotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCGATGTACGGGCCAGATATACGCGTTGACATTGATTATTGACTAGTTA

TTAATAGTAATCAATTACGGGGTGATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTCAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGAGTCACTATAGGGAGACCCAAGCTGGC

TAGCGTTTAAACTTAAGCTTGGTACCGAGCTCGGATCCATGGTGACCGGCTACCGGGTGTTCGA

GGAGATTCTCGGGAGTTCCGGTGGTGGCGGGAGCGGAGGTGGAGGCTCGAGCGGTTGAGCCTGC

ATCGGCCCCAGCTCCCTCAGTCCCTGCCTGGCAAGGTCGCTCCATTGGCACAACCAAGCTTCGC

CTGGTGGAATTTTCAGCTTTTCTCGAGCAGCAGCGAGACCCAGACTCGTACAACAAACACCTCT
```

-continued

TCGTGCACATTGGGCATGCCAACCATTCTTACAGTGACCCATTGCTTGAATCAGTGGACATTCG

TCAGATTTATGACAAATTTCCTGAAAAGAAAGGTGGCTTAAAGGAACTGTTTGGAAAGGGCCCT

CAAAATGCCTTCTTCCTCGTAAAATTCTGGGCTGATTTAAACTGCAATATTCAAGATGATGCTG

GGGCTTTTTATGGTGTAACCAGTCAGTACGAGAGTTCTGAAAATATGACAGTCACCTGTTCCAC

CAAAGTTTGCTCCTTTGGGAAGCAAGTAGTAGAAAAAGTAGAGACGGAGTATGCAAGGTTTGAG

AGTGGCCGATTTGTATACCGAATAAACCGCTCCCCAATGTGTGAATATATGATCAACTTCATCC

ACAAGCTCAAACACTTACCAGAGAAGTATATGATGAACAGTGTTTTGGAAAACTTCACAATTTT

ATTGGTGGTAACAAACAGGGATACACAAGAAACTCTACTCTGCATGGCCTGTGTGTTTGAAGTT

TCAAATCAGATCCTCTTCTGAGATGAGTTTTTGTTCGCGGCCGCTCGAGTCTAGAGGGCCCGTT

TAAACCCGCTGATCAGCCTCGACTGTGCCTTCTAGTTGCGAGCCATCTGTTGTTTGCCCCTCCC

CCGTGCCTTCCTTGACCCTGGAAGGTGCGACTCCCACTGTCCTTTCCTAATAAAATGAGGAAAT

TGCATCGCATTGTCTGAGTAGGTGTCATTCTATTCTGGGGGGTGGGGTGGGGCAGGACAGCAAG

GGGGAGGATTGGGAAGACAATAGCAGGCATGCTGGGGATGCGGTGGGCTCTATGGCTTCTGAGG

CGGAAAGAACCAGCTGGGGCTCTAGGGGGTATCCCCACGCGCCCTGTAGCGGCGCATTAAGCGC

GGCGGGTGTGGTGGTTACGCGCAGCGTGACCGCTACACTTGCCAGCGCCCTAGCGCCCGCTCCT

TTCGCTTTCTTCCCTTCCTTTCTCGCCACGTTCGCCGGCTTTCCCCGTCAAGCTCTAAATCGGG

GGCTCCCTTTAGGGTTCCGATTTAGTGCTTTACGGCACCTCGACCCCAAAAAACTTGATTAGGG

TGATGGTTCACGTAGTGGGCCATCGCCCTGATAGACGGTTTTTCGCCCTTTGACGTTGGAGTCC

ACGTTCTTTAATAGTGGACTCTTGTTCCAAACTGGAACAACACTCAACCCTATCTCGGTCTATT

CTTTTGATTTATAAGGGATTTTGCCGATTTCGGCCTATTGGTTAAAAAATGAGCTGATTTAACA

AAAATTTAACGCGAATTAATTCTGTGGAATGTGTGTCAGTTAGGGTGTGGAAAGTCCCCAGGCT

CCCCAGCAGGCAGAAGTATGCAAAGCATGCATCTCAATTAGTCAGCAACCAGGTGTGGAAAGTC

CCCAGGCTCCCCAGCAGGCAGAAGTATGCAAAGCATGCATCTCAATTAGTCAGCAACCATAGTC

CCGCCCCTAACTCCGCCCATCCCGCCCCTAACTCCGCCCAGTTCCGCCCATTCTCCGCCCCATG

GCTGACTAATTTTTTTTATTTATGCAGAGGCCGAGGCCGCCTCTGCCTCTGAGCTATTCCAGAA

GTAGTGAGGAGGCTTTTTTGGAGGCCTAGGCTTTTGCAAAAAGCTCCCGGGAGCTTGTATATCC

ATTTTCGGATCTGATCAAGAGACAGGATGAGGATCGTTTCGCATGATTGAACAAGATGGATTGC

ACGCAGGTTCTCCGGCCGCTTGGGTGGAGAGGCTATTCGGCTATGACTGGGCACAACAGACAAT

CGGCTGCTCTGATGCCGCCGTGTTCCGGCTGTCAGCGGAGGGGCGCCCGGTTCTTTTTGTCAAG

ACCGACCTGTCCGGTGCCCTGAATGAACTGGAGGACGAGGCAGCGCGGCTATCGTGGCTGGCGA

CGACGGGCGTTCCTTGCGCAGCTGTGCTCGACGTTGTCACTGAAGCGGGAAGGGACTGGCTGCT

ATTGGGCGAAGTGCCGGGGCAGGATCTCCTGTCATCTCACCTTGCTCCTGCCGAGAAAGTATCC

ATCATGGCTGATGCAATGCGGCGGCTGCATACGCTTGATCCGGCTACCTGCCCATTCGACCACC

AAGCGAAACATCGCATCGAGCGAGCACGTACTCGGATGGAAGCCGGTCTTGTCGATCAGGATGA

TCTGGACGAAGAGCATCAGGGGCTCGCGCCAGCCGAACTGTTCGCCAGGCTCAAGGCGCGCATG

CCCGACGGCGAGGATCTCGTCGTGACCCATGGCGATGCCTGCTTGCCGAATATCATGGTGGAAA

ATGGCCGCTTTTCTGGATTCATCGACTGTGGCCGGCTGGGTGTGGCGGACCGCTATCAGGACAT

AGCGTTGGCTACCCGTGATATTGCTGAAGAGCTTGGCGGCGAATGGGCTGACCGCTTCCTCGTG

CTTTACGGTATCGCCGCTCCCGATTCGCAGCGCATCGCCTTCTATCGCCTTCTTGACGAGTTCT

TCTGAGCGGGACTCTGGGGTTCGAAATGACCGACCAAGCGACGCCCAACCTGCCATCACGAGAT

```
TTCGATTCCACCGCCGCCTTCTATGAAAGGTTGGGCTTCGGAATCGTTTTCCGGGACGCCGGCT

GGATGATCCTCCAGCGCGGGGATCTCATGCTGGAGTTCTTCGCCCACCCCAACTTGTTTATTGC

AGCTTATAATGGTTACAAATAAAGCAATAGCATCACAAATTTCACAAATAAAGCATTTTTTTCA

CTGCATTCTAGTTGTGGTTTGTCCAAACTCATCAATGTATCTTATCATGTCTGTATACCGTCGA

CCTCTAGCTAGAGCTTGGCGTAATCATGGTCATAGCTGTTTCCTGTGTGAAATTGTTATCCGCT

CACAATTCCAGACAACATAGGAGCCGGAAGCATAAAGTGTAAAGCCTGGGGTGCCTAATGAGTG

AGCTAACTCACATTAATTGCGTTGCGCTCACTGCCCGGTTTCCAGTCGGGAAACCTGTCGTGCC

AGCTGCATTAATGAATCGGCCAACGCGCGGGGAGAGGCGGTTTGCGTATTGGGCGCTCTTCCGC

TTCCTCGCTCACTGACTCGCTGCGCTCGGTCGTTCGGCTGCGGCGAGCGGTATCAGCTCACTCA

AAGGCGGTAATAGGGTTATCCACAGAATCAGGGGATAACGCAGGAAAGAACATGTGAGCAAAAG

GCCAGCAAAAGGCCAGGAACCGTAAAAAGGCCGCGTTGCTGGCGTTTTTCCATAGGCTCCGCCC

CCCTGACGAGCATCACAAAAATCGACGCTCAAGTCAGAGGTGGCGAAACCCGACAGGACTATAA

AGATACCAGGCGTTTCCCCCTGGAAGCTCCCTCGTGCGCTCTCCTGTTCCGACCCTGCCGCTTA

CCGGATACCTGTCCGCCTTTCTCCCTTCGGGAAGCGTGGCGCTTTCTCATAGCTCACGCTGTAG

GTATCTCAGTTCGGTGTAGGTCGTTCGCTCCAAGCTGGGCTGTGTGCACGAACCCCCCGTTCAG

CCCGACCGCTGCGCGTTATCCGGTAACTATCGTCTTGAGTCCAACCCGGTAAGACACGACTTAT

CGCCACTGGCAGCAGCCACTGGTAACAGGATTAGCAGAGCGAGGTATGTAGGCGGTGCTACAGA

GTTCTTGAAGTGGTGGCCTAACTACGGCTACACTAGAAGAACAGTATTTGGTATCTGCGCTCTG

CTGAAGCCAGTTACCTTCGGAAAAAGAGTTGGTAGCTCTTGATCCGGCAAACAAACCAGCGCTG

GTAGCGGTTTTTTTGTTTGCAAGCAGCAGATTACGCGCAGAAAAAAAGGATCTCAAGAAGATCC

TTTGATCTTTTCTACGGGGTCTGACGCTCAGTGGAACGAAAACTGACGTTAAGGGATTTTGGTC

ATGAGATTATCAAAAAGGATCTTCACCTAGATCCTTTTAAATTAAAAATGAAGTTTTAAATCAA

TGTAAAGTATATATGAGTAAACTTGGTCTGACAGTTACCAATGCTTAATCAGTGAGGCACGTAT

CTCAGCGATCTGTGTATTTCGTTCATCCATAGTTGCCTGACTCCCCGTCGTGTAGATAACTACG

ATACGGGAGGGCTTACCATCTGGCCCCAGTGCTGCAATGATACCGCGAGACCCACGCTCACCGG

CTCCAGATTTATCAGCAATAAACCAGCCAGCCGGAAGGGCCGAGCGCAGAAGTGGTCCTGCAAC

TTTATCCGCCTCCATCCAGTCTATTAATTGTTGCCGGGAAGCTAGAGTAAGTAGTTCGGCAGTT

AATAGTTTGCGCAACGTTGTTGCCATTGGTACAGGCATCGTGGTGTCACGCTCGTCGTTTGGTA

TGGCTTCATTCAGCTCCGGTTCCCAACGATCAAGGCGAGTTACATGATCCCCCATGTTGTGCAA

AAAAGCGGTTAGCTCCTTCGGTCCTCCGATCGTTGTCAGAAGTAAGTTGGCCGCAGTGTTATGA

CTCATGGTTATGGCAGCACTGCATAATTGTCTTACTGTCATGCCATCCGTAAGATGCTTTTCTG

TGACTGGTGAGTACTCAACGAAGTCATTCTGAGAATAGTGTATGCGGCGAGCGAGTTGGTCTTG

CCCGGGGTCAATAGGGGATAATACCGCGCCACATAGCAGAACTTTAAAAGTGCTCATCATTGGA

AAACGTTCTTCGGGGCGAAAACTCTCAAGGATCTTACCGCTGTTGAGATCCAGTTCGATGTAAC

CCACTCGTGCACCCAACTGATCTTCAGCATCTTTTACTTTCACCAGCGTTTCTGGGTGAGCAAA

AACAGGAAGGCAAAATGCCGCAAAAAAGGGAATAAGGGCGACACGGAAATGTTGAATACTCATA

CTCTTCCTTTTTCAATATTATTGAAGCATTTATCAGGGTTATTGTCTCATGAGCGGATACATAT

TTGAATGTATTTAGAAAAATAAACAAATAGGGGTTCCGCGCACATTTCCCCGAAAAGTGCCACC

TGACGTC
```

SEQ ID NO: 70. YAP-TEAD NanoBiT biosensor construct 8: Myc-
TEAD1-194-411-SmBiT in pcDNA3.1-hygro vector (6,118 nucleotides)
GACGGATCGGGAGATCTCCCGATCCCCTATGGTGCACTCTCAGTACAATCTGCTCTGATGCCGC

ATAGTTAAGCCAGTATCTGCTCCCTGCTTGTGTGTTGGAGGTCGCTGAGTAGTGCGCGAGCAAA

ATTTAAGCTACAACAAGGCAAGGCTTGACCGACAATTGCATGAAGAATCTGCTTAGGGTTAGGC

GTTTTGCGCTGCTTCGCGATGTAGGGGCCAGATATACGCGTTGACATTGATTATTGACTAGTTA

TTAATAGTAATCAATTACGGGGTCATTAGTTCATAGCCCATATATGGAGTTCCGCGTTACATAA

CTTACGGTAAATGGCCCGCCTGGCTGACCGCCCAACGACCCCCGCCCATTGACGTCAATAATGA

CGTATGTTCCCATAGTAACGCCAATAGGGACTTTCCATTGACGTCAATGGGTGGAGTATTTACG

GTAAACTGCCCACTTGGCAGTACATCAAGTGTATCATATGCCAAGTACGCCCCCTATTGACGTC

AATGACGGTAAATGGCCCGCCTGGCATTATGCCCAGTACATGACCTTATGGGACTTTCCTACTT

GGCAGTACATCTACGTATTAGTCATCGCTATTACCATGGTGATGCGGTTTTGGCAGTACATCAA

TGGGCGTGGATAGCGGTTTGACTCACGGGGATTTCCAAGTCTCCACCCCATTGACGTGAATGGG

AGTTTGTTTTGGCACCAAAATCAACGGGACTTTCCAAAATGTCGTAACAACTCCGCCCCATTGA

CGCAAATGGGCGGTAGGCGTGTACGGTGGGAGGTCTATATAAGCAGAGCTCTCTGGCTAACTAG

AGAACCCACTGCTTACTGGCTTATCGAAATTAATACGACTCACTATAGGGAGACCCAAGCTGGC

TAGCGTTTAAACTTAAGCTTGGTACCGAGCTCGGATCCTGAGCCTGCATCGGCCCCAGCTCCCT

CAGTCCCTGCCTGGCAAGGTCGCTCCATTGGCACAACCAAGCTTCGCCTGGTGGAATTTTCAGC

TTTTCTCGAGCGGCAGCGAGACCCAGACTCGTACAACAAACACCTCTTCGTGCACATTGGGCAT

GCCAACCATTCTTACAGTGACCCATTGCTTGAATCAGTGGACATTCGTCAGATTTATGACAAAT

TTCCTGAAAAGAAAGGTGGCTTAAAGGAACTGTTTGGAAAGGGCCCTCAAAATGCCTTCTTCCT

CGTAAAATTCTGGGCTGATTTAAGCTGCAATATTCAAGATGATGCTGGGGCTTTTTGTGGTGTA

ACCAGTCAGTACGAGAGTTCTGAAAATATGACAGTCACCTGTTCCACCAAAGTTTGCTCCTTTG

GGAAGCAGGTAGTAGAAGAAGTAGAGACGGAGTATGCAAGGTTTGAGAATGGCCGATTTGTATA

CCGAATAAACCGCTCCCCAATGTGTGAATATATGATCAACTTCATCCACAAGCTCAAACACTTA

CCAGAGAAATATATGATGAACAGTGTTTTGGAAAACTTCACAATTTTATTGGTGGTAACAAACA

GGGATACACAAGAAACTCTACTCTGCATGGCCTGTGTGTTTGAAGTTTCAAATGGCTCGAGCGG

TGGTGGCGGGAGCGGAGGTGGAGGGTCGTCAGGTGTGACCGGCTACCGGCTGTTCGAGGAGATT

CTGGCGGCCGCTCGAGTCTAGAGGGCCCGTTTAAACCCGCTGATCAGCCTGGACTGTGCCTTCT

AGTTGCCAGCCATCTGTTGTTTGCCCCTCCCCCGTGCCTTCCTTGACCCTGGAAGGTGCCACTC

CCACTGTCCTTTCCTAATAAAATGAGGAAATTGCATGGCATTGTCTGAGTAGGTGTCATTCTAT

TCTGGGGGGTGGGGTGGGGCAGGACAGCAAGGGGGAGGATTGGGAAGACAATAGCAGGCATGCT

GGGGATGCGGTGGGCTCTATGGCTTCTGAGGCGGAAAGAACCAGCTGGGGCTCTAGGGGGTATC

CCCACGCGCCGTGTAGCGGGGCATTAAGCGCGGCGGGTGTGGTGGTTACGCGCAGCGTGACCGC

TACACTTGCCAGCGCCCTAGCGCCCGCTCCTTTCGCTTTCTTCCCTTCCTTTCTCGCCACGTTC

GCCGGCTTTCCCCGTCAAGCTCTAAATCGGGGGCTCCCTTTAGGGTTCCGATTTAGTGCTTTAC

GGCACCTCGACCCCAAAAAACTTGATTAGGGTGATGGTTCACGTAGTGGGCCATCGCCCTGATA

GACGGTTTTTCGCCCTTTGACGTTGGAGTCCACGTTCTTTAATAGTGGACTCTTGTTCCAAACT

GGAAGAACACTCAACCCTATCTCGGTCTATTCTTTTGATTTATAAGGGATTTTGCCGATTTCGG

CCTATTGGTTAAAAAATGAGCTGATTTAACAAAAATTTAACGCGAATTAATTCTGTGGAATGTG

TGTCAGTTAGGGTGTGGAAAGTCCCCAGGCTCCCCAGCAGGCAGAAGTATGCAAAGCATGCATC

```
TCAATTAGTCAGCAACCAGGTGTGGAAAGTCCCCAGGCTCCCCAGCAGGCAGAAGTATGCAAAG

CATGCATGTCAATTAGTCAGCAACCATAGTCCCGCCCCTAACTCCGCCCATCCCGCCCCTAACT

CCGCCCAGTTCCGCCGATTCTCCGGCCCATGGCTGACTAATTTTTTTATTTATGCAGAGGCCG

AGGCCGCCTCTGCCTCTGAGCTATTCCAGAAGTAGTGAGGAGGCTTTTTTGGAGGCCTAGGCTT

TTGCAAAAGCTCCCGGGAGCTTGTATATCCATTTTCGGATCTGATCAAGAGACAGGATGAGGA

TCGTTTCGCATGATTGAACAAGATGGATTGCACGCAGGTTCTCCGGCCGCTTGGGTGGAGAGGC

TATTCGGCTATGAGTGGGCACAACAGACAATCGGCTGCTCTGATGCCGCCGTGTTCCGGGTGTC

AGCGCAGGGGCGCCCGGTTCTTTTTGTCAAGACCGACCTGTCCGGTGCCCTGAATGAACTGCAG

GACGAGGCAGCGCGGGTATCGTGGCTGGCCACGACGGGCGTTCCTTGGGCAGCTGTGCTCGACG

TTGTCACTGAAGCGGGAAGGGACTGGCTGCTATTGGGCGAAGTGCCGGGGCAGGATCTCCTGTC

ATCTCACCTTGCTCCTGCCGAGAAAGTATCCATCATGGCTGATGCAATGCGGGGGGTGCATACG

CTTGATCCGGCTACCTGCCCATTCGACCACCAAGCGAAACATCGCATCGAGCGAGCACGTACTC

GGATGGAAGCCGGTCTTGTCGATCAGGATGATCTGGACGAAGAGCATCAGGGGCTCGCGCCAGC

CGAACTGTTCGCCAGGCTCAAGGCGCGCATGCCCGACGGCGAGGATCTCGTCGTGACCCATGGC

GATGCCTGCTTGCCGAATATCATGGTGGAAAATGGCCGCTTTTCTGGATTCATCGACTGTGGCC

GGCTGGGTGTGGCGGACCGCTATCAGGACATAGCGTTGGCTACCCGTGATATTGCTGAAGAGCT

TGGCGGCGAATGGGCTGACCGCTTCCTCGTGCTTTACGGTATCGCCGCTCCCGATTCGCAGCGC

ATCGCCTTCTATCGCCTTCTTGACGAGTTCTTCTGAGCGGGACTCTGGGGTTCGAAATGACCGA

CCAAGCGACGCCCAACCTGCCATCACGAGATTTCGATTCCACCGCCGCCTTCTATGAAAGGTTG

GGCTTCGGAATCGTTTTCCGGGACGCGGGCTGGATGATCCTCCAGCGCGGGGATCTCATGCTGG

AGTTCTTCGCCCACCCCAACTTGTTTATTGCAGCTTATAATGGTTACAAATAAAGCAATAGCAT

CACAAATTTCACAAATAAAGCATTTTTTTCACTGCATTCTAGTTGTGGTTTGTCCAAACTCATC

AATGTATCTTATCATGTCTGTATACCGTCGACCTCTAGCTAGAGCTTGGCGTAATCATGGTCAT

AGCTGTTTCCTGTGTGAAATTGTTATCCGCTCACAATTCCACACAACATACGAGCCGGAAGCAT

AAAGTGTAAAGCCTGGGGTGCCTAATGAGTGAGCTAACTCACATTAATTGCGTTGCGCTCACTG

CCCGCTTTCCAGTCGGGAAACCTGTCGTGCCAGCTGCATTAATGAATCGGCCAACGCGCGGGGA

GAGGCGGTTTGCGTATTGGGCGCTCTTCCGCTTCCTCGCTCACTGACTCGCTGCGCTCGGTCGT

TCGGCTGCGCCGAGCGGTATCAGCTCACTCAAAGGCGGTAATACGGTTATCCACAGAATCAGGG

GATAACGCAGGAAAGAACATGTGAGCAAAAGGCCAGCAAAAGGCCAGGAACCGTAAAAAGGCCG

CGTTGCTGGCGTTTTTCCATAGGCTCCGCCCCCCTGACGAGCATCACAAAAATCGACGCTCAAG

TCAGAGGTGGCGAAACCCGACAGGACTATAAAGATACCAGGCGTTTCCCCCTGGAAGCTCCCTC

GTGCGCTCTCCTGTTCCGACCCTGCCGCTTACCGGATACCTGTCCGCCTTTCTCCCTTCGGGAA

GCGTGGCGCTTTCTCATAGCTCACGCTGTAGGTATCTCAGTTCGGTGTAGGTCGTTCGCTCCAA

GCTGGGCTGTGTGCACGAACCCCCCGTTCAGCCCGACCGCTGCGCCTTATCCGGTAACTATCGT

CTTGAGTCCAACCCGGTAAGACACGACTTATCGCCACTGGCAGCAGCCACTGGTAACAGGATTA

GCAGAGCGAGGTATGTAGGCGGTGCTACAGAGTTCTTGAAGTGGTGGCCTAACTACGGCTACAC

TAGAAGAACAGTATTTGGTATCTGCGCTCTGCTGAAGCCAGTTACCTTCGGAAAAAGAGTTGGT

AGCTCTTGATCCGGCAAACAAACCACCGCTGGTAGCGGTTTTTTTGTTTGCAAGCAGCAGATTA

CGCGCAGAAAAAAAGGATCTCAAGAAGATCCTTTGATCTTTTCTACGGGGTCTGACGCTCAGTG

GAACGGGCCGAGCGCAGAAGTGGTCCTGCAACTTTATCCGCCTCCATCCAGTCTATTAATTGTTG

CTTTTAAATTAAAAATGAAGTTTTAAATCAATCTAAAGTATATATGAGTAAACTTGGTCTGACA
```

-continued

```
GTTAGCAATGCTTAATCAGTGAGGCACCTATCTCAGCGATCTGTCTATTTCGTTCATCCATAGT

TGCCTGACTCCCCGTCGTGTAGATAAGTACGATACGGGAGGGCTTACCATCTGGCCCCAGTGCT

GCAATGATACCGCGAGACCCACGCTCACCGGCTCCAGATTTATCAGCAATAAACCAGCCAGCCG

GAAGGGCCGAGCGCAGAAGTGGTCCTGCAACTTTATCCGCCTCCATCCAGTCTATTAATTGTTG

CCGGGAAGCTAGAGTAAGTAGTTCGCCAGTTAATAGTTTGCGCAACGTTGTTGCCATTGCTACA

GGCATCGTGGTGTCACGCTCGTCGTTTGGTATGGCTTCATTCAGCTCCGGTTCCCAACGATCAA

GGCGAGTTACATGATCCCCATGTTGTGCAAAAAAGCGGTTAGCTCCTTCGGTCCTCCGATCGT

TGTCAGAAGTAAGTTGGCCGCAGTGTTATCACTCATGGTTATGGCAGCACTGCATAATTCTCTT

ACTGTCATGCCATCCGTAAGATGCTTTTCTGTGACTGGTGAGTACTCAACCAAGTCATTCTGAG

AATAGTGTATGCGGCGACCGAGTTGCTCTTGCCCGGCGTCAATACGGGATAATACCGCGCCACA

TAGCAGAACTTTAAAAGTGCTCATCATTGGAAAACGTTCTTCGGGGCGAAAACTCTCAAGGATC

TTACCGCTGTTGAGATCCAGTTCGATGTAACCCACTCGTGCACCCAACTGATCTTCAGCATCTT

TTACTTTCACCAGCGTTTCTGGGTGAGCAAAAACAGGAAGGCAAAATGCCGCAAAAAGGGAAT

AAGGGCGACACGGAAATGTTGAATACTCATACTCTTCCTTTTTCAATATTATTGAAGCATTTAT

CAGGGTTATTGTCTCATGAGCGGATACATATTTGAATGTATTTAGAAAAATAAACAAATAGGGG

TTCCGCGCACATTTCCCCGAAAAGTGCCACCTGACGTC
```

EQUIVALENTS

While the invention has been described with respect to illustrative embodiments thereof, it will be understood that various changes may be made to the embodiments without departing from the scope of the invention. Accordingly, the described embodiments are to be considered merely exemplary and the invention is not to be limited thereby.

REFERENCES

1. Leach, J. P. et al. Hippo pathway deficiency reverses systolic heart failure after infarction. *Nature* 550, 260-264 (2017).
2. Pfleger, C. M. The Hippo Pathway: A Master Regulatory Network Important in Development and Dysregulated in Disease. *Curr. Top. Dev. Biol.* 123, 181-228 (2017).
3. Mo, J. S. The role of extracellular biophysical cues in modulating the Hippo-YAP pathway. *BMB Rep.* 50, 71-78 (2017).
4. Zhang, Y. & Del Re, D. P. A growing role for the Hippo signaling pathway in the heart. *J. Mol. Med. (Berl)* 95, 465-472 (2017).
5. Janse van Rensburg, H. J. & Yang, X. The roles of the Hippo pathway in cancer metastasis. *Cell. Signal.* 28, 1761-1772 (2016).
6. Meng, Z., Moroishi, T. & Guan, K. L. Mechanisms of Hippo pathway regulation. *Genes Dev.* 30, 1-17 (2016).
7. Maugeri-Sacca, M. & De Maria, R. Hippo pathway and breast cancer stem cells. *Crit. Rev. Oncol. Hematol.* 99, 115-122 (2016).
8. Yu, F. X., Zhao, B. & Guan, K. L. Hippo Pathway in Organ Size Control, Tissue Homeostasis, and Cancer. *Cell* 163, 811-828 (2015).
9. Zhao, Y. & Yang, X. The Hippo pathway in chemotherapeutic drug resistance. *Int. J. Cancer* 137, 2767-2773 (2015).
10. Hao, Y., Chun, A., Cheung, K., Rashidi, B. & Yang, X. Tumor suppressor LATS1 is a negative regulator of oncogene YAP. *J. Biol. Chem.* 283, 5496-5509 (2008).
11. Zhao, B. et al. TEAD mediates YAP-dependent gene induction and growth control. *Genes Dev.* 22, 1962-1971 (2008).
12. Zhao, B. et al. Inactivation of YAP oncoprotein by the Hippo pathway is involved in cell contact inhibition and tissue growth control. *Genes Dev.* 21, 2747-2761 (2007).
13. Lei, Q. Y. et al. TAZ promotes cell proliferation and epithelial-mesenchymal transition and is inhibited by the hippo pathway. *Mol. Cell. Biol.* 28, 2426-2436 (2008).
14. Chan, E. H. et al. The Ste20-like kinase Mst2 activates the human large tumor suppressor kinase Lats1. *Oncogene* 24, 2076-2086 (2005).

The invention claimed is:

1. A DNA construct comprising a nucleic acid sequence encoding a fusion protein comprising a fragment of firefly luciferase fused to at least one fragment of YAP.

2. The DNA construct of claim 1, wherein the fragment of firefly luciferase comprises amino acids 1-416 of SEQ ID NO:6 and is N-terminal to the at least one fragment of YAP comprising amino acids 120-134 of SEQ ID NO:2.

3. The DNA construct of claim 1, wherein the fragment of firefly luciferase comprises amino acids 1-544 of SEQ ID NO:6 and is N-terminal to the at least one fragment of YAP comprising amino acids 120-134 of SEQ ID NO:2.

4. A DNA construct comprising a nucleic acid sequence encoding a fusion protein comprising a fragment of firefly luciferase fused to at least one fragment of 14-3-3 protein, wherein the at least one fragment of 14-3-3 protein is capable of binding to YAP.

5. The DNA construct of claim 4, wherein the at least one fragment of 14-3-3 protein comprises SEQ ID NO:4 and is N-terminal to the fragment of firefly luciferase comprising amino acids 394-550 of SEQ ID NO:6.

6. A DNA construct comprising a nucleic acid sequence encoding a fusion protein comprising a fragment of NanoBiT luciferase fused to at least one fragment of YAP.

7. The DNA construct of claim 6, wherein the fragment of NanoBit luciferase is LgBiT comprising amino acid sequence SEQ ID NO:52 and is N-terminal to the at least one fragment of YAP comprising amino acids 120-134 of SEQ ID NO:2.

8. A DNA construct comprising a nucleic acid sequence encoding a fusion protein comprising a fragment of NanoBiT luciferase fused to at least one fragment of 14-3-3 protein, wherein the at least one fragment of 14-3-3 protein is capable of binding to YAP.

9. The DNA construct of claim 8, wherein the at least one fragment of 14-3-3 protein comprises SEQ ID NO:4 and is N-terminal to the fragment of NanoBit luciferase that is SmBiT comprising amino acid sequence SEQ ID NO:54.

10. A DNA construct comprising a nucleic acid sequence encoding a fusion protein comprising a fragment of NanoBit luciferase that is LgBiT comprising amino acid sequence SEQ ID NO:52 and a fragment of YAP comprising amino acids 50-171 of SEQ ID NO:2.

11. A DNA construct comprising a nucleic acid sequence encoding a fusion protein comprising a fragment of NanoBit luciferase that is SmBiT comprising amino acid sequence SEQ ID NO:54 and a fragment of YAP comprising amino acids 50-171 of SEQ ID NO:2.

12. A DNA construct comprising a nucleic acid sequence encoding a fusion protein comprising a fragment of NanoBiT luciferase fused to at least one fragment of TEAD protein, wherein the at least one fragment of TEAD protein is capable of binding to YAP.

13. The DNA construct of claim 12, wherein the fragment of NanoBit luciferase is LgBiT comprising amino acid sequence SEQ ID NO:52 and the at least one fragment of TEAD protein comprises amino acids 194-411 of SEQ ID NO:50.

14. The DNA construct of claim 12, wherein the fragment of NanoBit luciferase is SmBiT comprising amino acid sequence SEQ ID NO:54 and the at least one fragment of TEAD protein comprises amino acids 194-411 of SEQ ID NO:50.

* * * * *

SEQUENCE LISTING

<160> NUMBER OF SEQ ID NOS: 74

<210> SEQ ID NO 1
<211> LENGTH: 1401
<212> TYPE: DNA
<213> ORGANISM: Homo sapiens

<400> SEQUENCE: 1

```
atggatcccg ggcagcagcc gccgcctcaa ccggcccccc agggccaagg gcagccgcct    60
tcgcagcccc cgcaggggca gggcccgccg tccggacccg gcaaccggc acccgcggcg   120
acccaggcgg cgccgcaggc acccccgcc gggcatcaga tcgtgcacgt ccgcggggac   180
tcggagaccg acctggaggc gctcttcaac gccgtcatga ccccaagac ggccaacgtg   240
ccccagaccg tgcccatgag gctccggaag ctgcccgact ccttcttcaa gccgccggag   300
cccaaatccc actcccgaca ggccagtact gatgcaggca ctgcaggagc cctgactcca   360
cagcatgttc gagctcattc ctctccagct tctctgcagt tgggagctgt ttctcctggg   420
acactgaccc ccactggagt agtctctggc ccagcagcta cacccacagc tcagcatctt   480
cgacagtctt cttttgagat acctgatgat gtacctctgc cagcaggttg ggagatggca   540
aagacatctt ctggtcagag atacttctta aatcacatcg atcagacaac aacatggcag   600
gaccccagga aggccatgct gtcccagatg aacgtcacag ccccaccag tccaccagtg   660
cagcagaata tgatgaactc ggcttcagcc atgaaccaga gaatcagtca gagtgctcca   720
gtgaaacagc caccacccct ggctccccag agcccacagg gaggcgtcat gggtggcagc   780
aactccaacc agcagcaaca gatgcgactg cagcaactgc agatggagaa ggagaggctg   840
cggctgaaaac agcaagaact gcttcggcag gcaatgcgga atatcaatcc agcacagca   900
aattctccaa atgtcagga gttagccctg cgtagccagt accaacact ggagcaggat   960
ggtgggactc aaaatccagt gtcttctccc gggatgtctc aggaattgag aacaatgacg  1020
accaatagct cagatccttt ccttaacagt ggcacctatc actctcgaga tgagagtaca  1080
gacagtggac taagcatgag cagctacagt gtccctcgaa ccccagatga cttcctgaac  1140
agtgtggatg agatggatac aggtgatact atcaaccaaa gcaccctgcc ctcacagcag  1200
aaccgtttcc cagactacct tgaagccatt cctgggacaa atgtggacct tggaacactg  1260
gaaggagatg gaatgaacat agaaggagag gagctgatgc aagtctgca ggaagctttg  1320
agttctgaca tccttaatga catggagtct gtttggctg ccaccaagct agataaagaa  1380
agctttctta catggttata g                                             1401
```

<210> SEQ ID NO 2
<211> LENGTH: 504
<212> TYPE: PRT
<213> ORGANISM: Homo sapiens

<400> SEQUENCE: 2

```
Met Asp Pro Gly Gln Gln Pro Pro Gln Pro Ala Pro Gln Gly Gln
 1               5                  10                  15

Gly Gln Pro Pro Ser Gln Pro Pro Gln Gly Gly Pro Pro Ser Gly
                20                  25                  30

Pro Gly Gln Pro Ala Pro Ala Ala Thr Gln Ala Ala Pro Gln Ala Pro
                35                  40                  45

Pro Ala Gly His Gln Ile Val His Val Arg Gly Asp Ser Glu Thr Asp
                50                  55                  60

Leu Glu Ala Leu Phe Asn Ala Val Met Asn Pro Lys Thr Ala Asn Val
65                  70                  75                  80

Pro Gln Thr Val Pro Met Arg Leu Arg Lys Leu Pro Asp Ser Phe Phe
                85                  90                  95

Lys Pro Pro Glu Pro Lys Ser His Ser Arg Gln Ala Ser Thr Asp Ala
                100                 105                 110
```

-continued

Gly Thr Ala Gly Ala Leu Thr Pro Gln His Val Arg Ala His Ser Ser
            115                 120                 125

Pro Ala Ser Leu Gln Leu Gly Ala Val Ser Pro Gly Thr Leu Thr Pro
        130                 135                 140

Thr Gly Val Val Ser Gly Pro Ala Ala Thr Pro Thr Ala Gln His Leu
145                 150                 155                 160

Arg Gln Ser Ser Phe Glu Ile Pro Asp Asp Val Pro Leu Pro Ala Gly
                165                 170                 175

Trp Glu Met Ala Lys Thr Ser Ser Gly Gln Arg Tyr Phe Leu Asn His
                180                 185                 190

Ile Asp Gln Thr Thr Thr Trp Gln Asp Pro Arg Lys Ala Met Leu Ser
            195                 200                 205

Gln Met Asn Val Thr Ala Pro Thr Ser Pro Pro Val Gln Gln Asn Met
        210                 215                 220

Met Asn Ser Ala Ser Gly Pro Leu Pro Asp Gly Trp Glu Gln Ala Met
225                 230                 235                 240

Thr Gln Asp Gly Glu Ile Tyr Tyr Ile Asn His Lys Asn Lys Thr Thr
                245                 250                 255

Ser Trp Leu Asp Pro Arg Leu Asp Pro Arg Phe Ala Met Asn Gln Arg
                260                 265                 270

Ile Ser Gln Ser Ala Pro Val Lys Gln Pro Pro Leu Ala Pro Gln
            275                 280                 285

Ser Pro Gln Gly Gly Val Met Gly Gly Ser Asn Ser Asn Gln Gln Gln
        290                 295                 300

Gln Met Arg Leu Gln Leu Gln Met Glu Lys Glu Arg Leu Arg Leu
305                 310                 315                 320

Lys Gln Gln Glu Leu Leu Arg Gln Ala Met Arg Asn Ile Asn Pro Ser
                325                 330                 335

Thr Ala Asn Ser Pro Lys Cys Gln Glu Leu Ala Leu Arg Ser Gln Leu
            340                 345                 350

Pro Thr Leu Glu Gln Asp Gly Gly Thr Gln Asn Pro Val Ser Ser Pro
        355                 360                 365

Gly Met Ser Gln Glu Leu Arg Thr Met Thr Thr Asn Ser Ser Asp Pro
370                 375                 380

Phe Leu Asn Ser Gly Thr Tyr His Ser Arg Asp Glu Ser Thr Asp Ser
385                 390                 395                 400

Gly Leu Ser Met Ser Ser Tyr Ser Val Pro Arg Thr Pro Asp Asp Phe
                405                 410                 415

Leu Asn Ser Val Asp Glu Met Asp Thr Gly Asp Thr Ile Asn Gln Ser
                420                 425                 430

Thr Leu Pro Ser Gln Gln Asn Arg Phe Pro Asp Tyr Leu Glu Ala Ile
        435                 440                 445

Pro Gly Thr Asn Val Asp Leu Gly Thr Leu Glu Gly Asp Gly Met Asn
450                 455                 460

Ile Glu Gly Glu Glu Leu Met Pro Ser Leu Gln Glu Ala Leu Ser Ser
465                 470                 475                 480

Asp Ile Leu Asn Asp Met Glu Ser Val Leu Ala Ala Thr Lys Leu Asp
                485                 490                 495

Lys Glu Ser Phe Leu Thr Trp Leu
                500

<210> SEQ ID NO 3
<211> LENGTH: 738

-continued

```
<212> TYPE: DNA
<213> ORGANISM: Homo sapiens

<400> SEQUENCE: 3
atggagaaga ctgagctgat ccagaaggcc aagctggccg agcaggccga gcgctacgac      60
gacatggcca cctgcatgaa ggcagtgacc gagcagggcg ccgagctgtc caacgaggag     120
cgcaacctgc tctccgtggc ctacaagaac gtggtcgggg ccgcaggtc cgcctggagg      180 gtcatctcta gcatcgagca aagaccgac acctccgaca agaagttgca gctgattaag      240
gactatcggg agaaagtgga gtccgagctg agatccatct gcaccacggt gctggaattg     300
ttggataaat atttaatagc caatgcaact aatccagaga gtaaggtctt ctatctgaaa     360
atgaagggtg attacttccg gtaccttgct gaagttgcgt gtggtgatga tcgaaaacaa     420
acgatagata attcccaagg agcttaccaa gaggcatttg atataagcaa aaagagatg     480 caacccacac acccaatccg cctggggctt gctcttaact tttctgtatt ttactatgag     540
attcttaata acccagagct tgcctgcacg ctggctaaaa cggcttttga tgaggccatt     600
gctgaacttg atacactgaa tgaagactca tacaaagaca gcaccctcat catgcagttg     660
cttagagaca acctaacact ttggacatca gacagtgcag gagaagaatg tgatgcggca     720 gaagggggctg aaaactaa                                                  738

<210> SEQ ID NO 4
<211> LENGTH: 245
<212> TYPE: PRT
<213> ORGANISM: Homo sapiens

<400> SEQUENCE: 4

Met Glu Lys Thr Glu Leu Ile Gln Lys Ala Lys Leu Ala Glu Gln Ala
1               5                   10                  15

Glu Arg Tyr Asp Asp Met Ala Thr Cys Met Lys Ala Val Thr Glu Gln
            20                  25                  30

Gly Ala Glu Leu Ser Asn Glu Glu Arg Asn Leu Leu Ser Val Ala Tyr
        35                  40                  45

Lys Asn Val Val Gly Arg Arg Ser Ala Trp Arg Val Ile Ser Ser
    50                  55                  60

Ile Glu Gln Lys Thr Asp Thr Ser Asp Lys Lys Leu Gln Leu Ile Lys
65                  70                  75                  80

Asp Tyr Arg Glu Lys Val Glu Ser Glu Leu Arg Ser Ile Cys Thr Thr
                85                  90                  95

Val Leu Glu Leu Leu Asp Lys Tyr Leu Ile Ala Asn Ala Thr Asn Pro
            100                 105                 110

Glu Ser Lys Val Phe Tyr Leu Lys Met Lys Gly Asp Tyr Phe Arg Tyr
        115                 120                 125

Leu Ala Glu Val Ala Cys Gly Asp Asp Arg Lys Gln Thr Ile Asp Asn
    130                 135                 140

Ser Gln Gly Ala Tyr Gln Glu Ala Phe Asp Ile Ser Lys Lys Glu Met
145                 150                 155                 160

Gln Pro Thr His Pro Ile Arg Leu Gly Leu Ala Leu Asn Phe Ser Val
                165                 170                 175

Phe Tyr Tyr Glu Ile Leu Asn Asn Pro Glu Leu Ala Cys Thr Leu Ala
            180                 185                 190

Lys Thr Ala Phe Asp Glu Ala Ile Ala Glu Leu Asp Thr Leu Asn Glu
        195                 200                 205
```

Asp Ser Tyr Lys Asp Ser Thr Leu Ile Met Gln Leu Leu Arg Asp Asn
        210                 215                 220

Leu Thr Leu Trp Thr Ser Asp Ser Ala Gly Glu Glu Cys Asp Ala Ala
225                 230                 235                 240

Glu Gly Ala Glu Asn
            245

<210> SEQ ID NO 5
<211> LENGTH: 1653
<212> TYPE: DNA
<213> ORGANISM: Photinus pyralis

<400> SEQUENCE: 5

```
atggaagacg ccaaaaacat aaagaaaggc ccggcgccat tctatccgct ggaagatgga      60
accgctggag agcaactgca taaggctatg aagagatacg ccctggttcc tggaacaatt     120
gcttttacag atgcacatat cgaggtggac atcacttacg ctgagtactt cgaaatgtcc     180
gttcggttgg cagaagctat gaaacgatat gggctgaata caaatcacag aatcgtcgta     240
tgcagtgaaa actctcttca attctttatg ccggtgttgg gcgcgttatt tatcggagtt     300
gcagttgcgc ccgcgaacga catttataat gaacgtgaat tgctcaacag tatgggcatt     360
tcgcagccta ccgtggtgtt cgtttccaaa aaggggttgc aaaaaatttt gaacgtgcaa     420
aaaaagctcc caatcatcca aaaaattatt atcatggatt ctaaaacgga ttaccaggga     480
tttcagtcga tgtacacgtt cgtcacatct catctacctc ccggttttaa tgaatacgat     540
tttgtgccag agtccttcga tagggacaag acaattgcac tgatcatgaa ctcctctgga     600
tctactggtc tgcctaaagg tgtcgctctg cctcatagaa ctgcctgcgt gagattctcg     660
catgccagag atcctatttt tggcaatcaa atcattccgg atactgcgat tttaagtgtt     720
gttccattcc atcacggttt tggaatgttt actacactcg gatatttgat atgtggattt     780
cgagtcgtct taatgtatag atttgaagaa gagctgtttc tgaggagcct tcaggattac     840
aagattcaaa gtgcgctgct ggtgccaacc ctattctcct tcttcgccaa agcactctg      900
attgacaaat acgatttatc taatttacac gaaattgctt ctggtggcgc tcccctctct     960
aaggaagtcg gggaagcggt tgccaagagg ttccatctgc caggtatcag gcaaggatat    1020
gggctcactg agactacatc agctattctg attacacccg agggggatga taaaccgggc    1080
gcggtcggta aagttgttcc attttttgaa gcgaaggttg tggatctgga taccgggaaa    1140
acgctgggcg ttaatcaaag aggcgaactg tgtgtgagag gtcctatgat tatgtccggt    1200
tatgtaaaca atccggaagc gaccaacgcc ttgattgaca aggatggatg gctacattct    1260
ggagacatag cttactggga cgaagacgaa cacttcttca tcgttgaccg cctgaagtct    1320
ctgattaagt acaaaggcta tcaggtggct cccgctgaat tggaatccat cttgctccaa    1380
cacccccaaca tcttcgacgc aggtgtcgca ggtcttcccg acgatgacgc cggtgaactt    1440
cccgccgccg ttgttgtttt ggagcacgga aagacgatga cggaaaaaga gatcgtggat    1500
tacgtcgcca gtcaagtaac aaccgcgaaa aagttgcgcg gaggagttgt gtttgtggac    1560
gaagtaccga aaggtcttac cggaaaactc gacgcaagaa aaatcagaga gatcctcata    1620
aaggccaaga agggcggaaa gatcgccgtg taa                                 1653
```

<210> SEQ ID NO 6
<211> LENGTH: 550
<212> TYPE: PRT
<213> ORGANISM: Photinus pyralis

<400> SEQUENCE: 6

```
Met Glu Asp Ala Lys Asn Ile Lys Lys Gly Pro Ala Pro Phe Tyr Pro
1               5                   10                  15
Leu Glu Asp Gly Thr Ala Gly Glu Gln Leu His Lys Ala Met Lys Arg
            20                  25                  30
Tyr Ala Leu Val Pro Gly Thr Ile Ala Phe Thr Asp Ala His Ile Glu
        35                  40                  45
Val Asp Ile Thr Tyr Ala Glu Tyr Phe Glu Met Ser Val Arg Leu Ala
50                  55                  60
Glu Ala Met Lys Arg Tyr Gly Leu Asn Thr Asn His Arg Ile Val Val
65                  70                  75                  80
Cys Ser Glu Asn Ser Leu Gln Phe Phe Met Pro Val Leu Gly Ala Leu
                85                  90                  95
Phe Ile Gly Val Ala Val Ala Pro Ala Asn Asp Ile Tyr Asn Glu Arg
            100                 105                 110
Glu Leu Leu Asn Ser Met Gly Ile Ser Gln Pro Thr Val Val Phe Val
        115                 120                 125
Ser Lys Lys Gly Leu Gln Lys Ile Leu Asn Val Gln Lys Lys Leu Pro
130                 135                 140
Ile Ile Gln Lys Ile Ile Ile Met Asp Ser Lys Thr Asp Tyr Gln Gly
145                 150                 155                 160
Phe Gln Ser Met Tyr Thr Phe Val Thr Ser His Leu Pro Pro Gly Phe
                165                 170                 175
Asn Glu Tyr Asp Phe Val Pro Glu Ser Phe Asp Arg Asp Lys Thr Ile
            180                 185                 190
Ala Leu Ile Met Asn Ser Ser Gly Ser Thr Gly Leu Pro Lys Gly Val
        195                 200                 205
Ala Leu Pro His Arg Thr Ala Cys Val Arg Phe Ser His Ala Arg Asp
210                 215                 220
Pro Ile Phe Gly Asn Gln Ile Ile Pro Asp Thr Ala Ile Leu Ser Val
225                 230                 235                 240
Val Pro Phe His His Gly Phe Gly Met Phe Thr Thr Leu Gly Tyr Leu
                245                 250                 255
Ile Cys Gly Phe Arg Val Val Leu Met Tyr Arg Phe Glu Glu Glu Leu
            260                 265                 270
Phe Leu Arg Ser Leu Gln Asp Tyr Lys Ile Gln Ser Ala Leu Leu Val
        275                 280                 285
Pro Thr Leu Phe Ser Phe Phe Ala Lys Ser Thr Leu Ile Asp Lys Tyr
290                 295                 300
Asp Leu Ser Asn Leu His Glu Ile Ala Ser Gly Gly Ala Pro Leu Ser
305                 310                 315                 320
Lys Glu Val Gly Glu Ala Val Ala Lys Arg Phe His Leu Pro Gly Ile
                325                 330                 335
Arg Gln Gly Tyr Gly Leu Thr Glu Thr Thr Ser Ala Ile Leu Ile Thr
            340                 345                 350
Pro Glu Gly Asp Asp Lys Pro Gly Ala Val Gly Lys Val Val Pro Phe
        355                 360                 365
Phe Glu Ala Lys Val Val Asp Leu Asp Thr Gly Lys Thr Leu Gly Val
370                 375                 380
Asn Gln Arg Gly Glu Leu Cys Val Arg Gly Pro Met Ile Met Ser Gly
385                 390                 395                 400
```

-continued

Tyr Val Asn Asn Pro Glu Ala Thr Asn Ala Leu Ile Asp Lys Asp Gly
                405                 410                 415

Trp Leu His Ser Gly Asp Ile Ala Tyr Trp Asp Glu Asp Glu His Phe
            420                 425                 430

Phe Ile Val Asp Arg Leu Lys Ser Leu Ile Lys Tyr Lys Gly Tyr Gln
        435                 440                 445

Val Ala Pro Ala Glu Leu Glu Ser Ile Leu Leu Gln His Pro Asn Ile
    450                 455                 460

Phe Asp Ala Gly Val Ala Gly Leu Pro Asp Asp Asp Ala Gly Glu Leu
465                 470                 475                 480

Pro Ala Ala Val Val Leu Glu His Gly Lys Thr Met Thr Glu Lys
                485                 490                 495

Glu Ile Val Asp Tyr Val Ala Ser Gln Val Thr Thr Ala Lys Lys Leu
                500                 505                 510

Arg Gly Gly Val Val Phe Val Asp Glu Val Pro Lys Gly Leu Thr Gly
            515                 520                 525

Lys Leu Asp Ala Arg Lys Ile Arg Glu Ile Leu Ile Lys Ala Lys Lys
    530                 535                 540

Gly Gly Lys Ile Ala Val
545                 550

<210> SEQ ID NO 7
<211> LENGTH: 15
<212> TYPE: PRT
<213> ORGANISM: Homo sapiens

<400> SEQUENCE: 7

Pro Gln His Val Arg His Ala Ser Ser Pro Ala Ser Leu Gln Leu
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthesized

<400> SEQUENCE: 8

Pro Gln His Val Arg His Ala Ala Ser Pro Ala Ser Leu Gln Leu
1               5                   10                  15

<210> SEQ ID NO 9
<211> LENGTH: 5597
<212> TYPE: DNA
<213> ORGANISM: Artificial Sequence
<220> FEATURE:
<223> OTHER INFORMATION: Vector

<400> SEQUENCE: 9
gacggatcgg gagatctccc gatccctat ggtgcactct cagtacaatc tgctctgatg    60
ccgcatagtt aagccagtat ctgctccctg cttgtgtgtt ggaggtcgct gagtagtgcg   120
cgagcaaaat ttaagctaca acaaggcaag gcttgaccga caattgcatg aagaatctgc   180
ttagggttag gcgttttgcg ctgcttcgcg atgtacgggc cagatatacg cgttgacatt   240
gattattgac tagttattaa tagtaatcaa ttacggggtc attagttcat agcccatata   300
tggagttccg cgttacataa cttacggtaa atggcccgcc tggctgaccg cccaacgacc   360
cccgcccatt gacgtcaata atgacgtatg ttcccatagt aacgccaata gggactttcc   420

-continued

```
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg ggggtgggg tggggcagga cagcaagggg    1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata gacggttttt   1560
cgccctttga cgttggagtc acgttctttt aatagtggac tcttgttcca aactggaaca   1620
acactcaacc ctatctcggt ctattctttt gatttataag ggattttgcc gatttcggcc   1680
tattggttaa aaaatgagct gatttaacaa aaatttaacg cgaattaatt ctgtggaatg   1740
tgtgtcagtt agggtgtgga agtccccag gctccccagc aggcagaagt atgcaaagca    1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccatttcg    2100
gatctgatca gcacgtgatg aaaaagcctg aactcaccgc gacgtctgtc gagaagtttc   2160
tgatcgaaaa gttcgacagc gtctccgacc tgatgcagct ctcggagggc gaagaatctc   2220
gtgctttcag cttcgatgta ggagggcgtg gatatgtcct gcgggtaaat agctgcgccg   2280
atggtttcta caaagatcgt tatgtttatc ggcactttgc atcggccgcg ctcccgattc   2340
cggaagtgct tgacattggg gaattcagcg agagcctgac ctattgcatc tcccgccgtg   2400
cacagggtgt cacgttgcaa gacctgcctg aaaccgaact gcccgctgtt ctgcagccgg   2460
tcgcggaggc catggatgcg atcgctgcgg ccgatcttag ccagacgagc gggttcggcc   2520
cattcggacc gcaaggaatc ggtcaataca ctacatggcg tgatttcata tgcgcgattg   2580
ctgatcccca tgtgtatcac tggcaaactg tgatggacga ccgtcagt gcgtccgtcg    2640
cgcaggctct cgatgagctg atgctttggg ccgaggactg ccccgaagtc cggcacctcg   2700
tgcacgcgga tttcggctcc aacaatgtcc tgacggacaa tggccgcata acagcggtca   2760
ttgactggag cgaggcgatg ttcggggatt cccaatacga ggtcgccaac atcttcttct   2820
```

```
ggaggccgtg gttggcttgt atggagcagc agacgcgcta cttcgagcgg aggcatccgg   2880
agcttgcagg atcgccgcgg ctccgggcgt atatgctccg cattggtctt gaccaactct   2940
atcagagctt ggttgacggc aatttcgatg atgcagcttg gcgcagggt cgatgcgacg    3000 caatcgtccg atccggagcc gggactgtcg gcgtacaca aatcgcccgc agaagcgcgg    3060
ccgtctggac cgatggctgt gtagaagtac tcgccgatag tggaaaccga cgccccagca   3120
ctcgtccgag ggcaaaggaa tagcacgtgc tacgagattt cgattccacc gccgccttct   3180
atgaaaggtt gggcttcgga atcgttttcc gggacgccgg ctggatgatc tccagcgcg    3240 gggatctcat gctggagttc ttcgcccacc ccaacttgtt tattgcagct tataatggtt   3300
acaaataaag caatagcatc acaaatttca caaataaagc attttttca ctgcattcta    3360 gttgtggttt gtccaaactc atcaatgtat cttatcatgt ctgtataccg tcgacctcta   3420
gctagagctt ggcgtaatca tggtcatagc tgtttcctgt gtgaaattgt tatccgctca   3480
caattccaca caacatacga gccgaagca taaagtgtaa agcctggggt gcctaatgag    3540
tgagctaact cacattaatt gcgttgcgct cactgcccgc tttccagtcg ggaaacctgt   3600
cgtgccagct gcattaatga atcggccaac gcgcggggag aggcggtttg cgtattgggc   3660
gctcttccgc ttcctcgctc actgactcgc tgcgctcggt cgttcggctg cggcgagcgg   3720
tatcagctca ctcaaaggcg gtaatacggt tatccacaga atcaggggat aacgcaggaa   3780
agaacatgtg agcaaaaggc cagcaaaagg ccaggaaccg taaaaaggcc gcgttgctgg   3840 cgttttttcca taggctccgc cccctgacg agcatcacaa aaatcgacgc tcaagtcaga    3900
ggtggcgaaa cccgacagga ctataaagat accaggcgtt tcccctgga agctccctcg    3960 tgcgctctcc tgttccgacc ctgccgctta ccggatacct gtccgccttt ctcccttcgg   4020
gaagcgtggc gctttctcat agctcacgct gtaggtatct cagttcggtg taggtcgttc   4080
gctccaagct gggctgtgtg cacgaaccc ccgttcagcc cgaccgctgc gccttatccg    4140
gtaactatcg tcttgagtcc aacccggtaa gacacgactt atcgccactg gcagcagcca   4200
ctggtaacag gattagcaga gcgaggtatg taggcggtgc tacagagttc ttgaagtggt   4260
ggcctaacta cggctacact agaagaacag tatttggtat ctgcgctctg ctgaagccag   4320
ttaccttcgg aaaaagagtt ggtagctctt gatccggcaa acaaaccacc gctggtagcg   4380
gtttttttgt ttgcaagcag cagattacgc gcagaaaaaa aggatctcaa gaagatcctt   4440
tgatcttttc tacggggtct gacgctcagt ggaacgaaaa ctcacgttaa gggattttgg   4500
tcatgagatt atcaaaaagg atcttcacct agatcctttt aaattaaaaa tgaagtttta   4560
aatcaatcta agtatatat gagtaaactt ggtctgacag ttaccaatgc ttaatcagtg   4620
aggcacctat ctcagcgatc tgtctatttc gttcatccat agttgcctga ctccccgtcg   4680
tgtagataac tacgatacgg gagggcttac catctggccc cagtgctgca atgataccgc   4740
gagacccacg ctcaccggct ccagatttat cagcaataaa ccagccagcc ggaagggccg   4800
agcgcagaag tggtcctgca actttatccg cctccatcca gtctattaat tgttgccggg   4860
aagctagagt aagtagttcg ccagttaata gtttgcgcaa cgttgttgcc attgctacag   4920
gcatcgtggt gtcacgctcg tcgtttggta tggcttcatt cagctccggt tcccaacgat   4980
caaggcgagt tacatgatcc cccatgttgt gcaaaaaagc ggttagctcc ttcggtcctc   5040
cgatcgttgt cagaagtaag ttggccgcag tgttatcact catggttatg gcagcactgc   5100
ataattctct tactgtcatg ccatccgtaa gatgcttttc tgtgactggt gagtactcaa   5160
```

```
ccaagtcatt ctgagaatag tgtatgcggc gaccgagttg ctcttgcccg gcgtcaatac    5220
gggataatac cgcgccacat agcagaactt taaaagtgct catcattgga aaacgttctt    5280
cggggcgaaa actctcaagg atcttaccgc tgttgagatc cagttcgatg taacccactc    5340
gtgcacccaa ctgatcttca gcatcttta ctttcaccag cgtttctggg tgagcaaaaa     5400
caggaaggca aaatgccgca aaaaagggaa taagggcgac acggaaatgt tgaatactca    5460
tactcttcct ttttcaatat tattgaagca tttatcaggg ttattgtctc atgagcggat    5520
acatatttga atgtatttag aaaaataaac aatagggggt tccgcgcaca tttccccgaa    5580
aagtgccacc tgacgtc                                                  5597

<210> SEQ ID NO 10
<211> LENGTH: 41
<212> TYPE: DNA
<213> ORGANISM: Artificial Sequence
<220> FEATURE:
<223> OTHER INFORMATION: Primer

<400> SEQUENCE: 10
ctggatccgc cgccaccatg gaagacgcca aaaacataaa g                        41

<210> SEQ ID NO 11
<211> LENGTH: 84
<212> TYPE: DNA
<213> ORGANISM: Artificial Sequence
<220> FEATURE:
<223> OTHER INFORMATION: Primer

<400> SEQUENCE: 11
ttacaactgc agagaagctg gagaggaatg agctcgaaca tgctgtgggc ctccagctcc    60
tcctccatcc ttgtcaatca aggc                                          84

<210> SEQ ID NO 12
<211> LENGTH: 36
<212> TYPE: DNA
<213> ORGANISM: Artificial Sequence
<220> FEATURE:
<223> OTHER INFORMATION: Primer

<400> SEQUENCE: 12
atgaaactgc ggccgcttac aactgcagag aagctg                             36

<210> SEQ ID NO 13
<211> LENGTH: 38
<212> TYPE: DNA
<213> ORGANISM: Artificial Sequence
<220> FEATURE:
<223> OTHER INFORMATION: Primer

<400> SEQUENCE: 13
ctggatccgc cgccaccatg gagaagactg agctgatc                           38

<210> SEQ ID NO 14
<211> LENGTH: 51
<212> TYPE: DNA
<213> ORGANISM: Artificial Sequence
<220> FEATURE:
<223> OTHER INFORMATION: Primer

<400> SEQUENCE: 14
actacctcct cctccactac ctcctcctcc gttttcagcc ccttctgccg c             51
```

```
<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
ggtagtggag gaggaggtag tggtcctatg attatgtcc                              39

<210> SEQ ID NO 16
<211> LENGTH: 34
<212> TYPE: DNA
<213> ORGANISM: Artificial Sequence
<220> FEATURE:
<223> OTHER INFORMATION: Primer

<400> SEQUENCE: 16
atgaaactgc ggccgcttac acggcgatct ttcc                                   34

<210> SEQ ID NO 17
<211> LENGTH: 81
<212> TYPE: DNA
<213> ORGANISM: Artificial Sequence
<220> FEATURE:
<223> OTHER INFORMATION: Primer

<400> SEQUENCE: 17
caactgcaga gaagctggag aggaatgagc tcgaacatgc tgtgggcctc cagctcctcc       60
cataatcata ggacctctca c                                                 81

<210> SEQ ID NO 18
<211> LENGTH: 42
<212> TYPE: DNA
<213> ORGANISM: Artificial Sequence
<220> FEATURE:
<223> OTHER INFORMATION: Primer

<400> SEQUENCE: 18
tctccagctt ctctgcagtt gggtcctatg attatgtccg gt                          42

<210> SEQ ID NO 19
<211> LENGTH: 86
<212> TYPE: DNA
<213> ORGANISM: Artificial Sequence
<220> FEATURE:
<223> OTHER INFORMATION: Primer

<400> SEQUENCE: 19
atgaaactgc ggccgcttac aactgcagag aagctggaga ggaatgagct cgaacatgct       60
gtggcttctt ggcctttatg aggatc                                            86

<210> SEQ ID NO 20
<211> LENGTH: 55
<212> TYPE: DNA
<213> ORGANISM: Artificial Sequence
<220> FEATURE:
<223> OTHER INFORMATION: Primer

<400> SEQUENCE: 20
aattcaccac agcatgttcg agctcattcc tctccagctt ctctgcagtt gtgaa            55

<210> SEQ ID NO 21
<211> LENGTH: 55
<212> TYPE: DNA
```

```
<213> ORGANISM: Artificial Sequence
<220> FEATURE:
<223> OTHER INFORMATION: Primer

<400> SEQUENCE: 21
gatcttcaca actgcagaga agctggagag gaatgagctc gaacatgctg tggtg        55

<210> SEQ ID NO 22
<211> LENGTH: 55
<212> TYPE: DNA
<213> ORGANISM: Artificial Sequence
<220> FEATURE:
<223> OTHER INFORMATION: Primer

<400> SEQUENCE: 22
aattcaccac agcatgttcg agctcatgcg tctccagctt ctctgcagtt gtgaa        55

<210> SEQ ID NO 23
<211> LENGTH: 55
<212> TYPE: DNA
<213> ORGANISM: Artificial Sequence
<220> FEATURE:
<223> OTHER INFORMATION: Primer

<400> SEQUENCE: 23
gatcttcaca actgcagaga agctggagac gcatgagctc gaacatgctg tggtg        55

<210> SEQ ID NO 24
<211> LENGTH: 31
<212> TYPE: DNA
<213> ORGANISM: Artificial Sequence
<220> FEATURE:
<223> OTHER INFORMATION: Primer

<400> SEQUENCE: 24
ggaagatcta atggagaaga ctgagctgat c                                  31

<210> SEQ ID NO 25
<211> LENGTH: 34
<212> TYPE: DNA
<213> ORGANISM: Artificial Sequence
<220> FEATURE:
<223> OTHER INFORMATION: Primer

<400> SEQUENCE: 25
cgccggaatt cccgttttca gccccttctg ccgc                               34

<210> SEQ ID NO 26
<211> LENGTH: 3858
<212> TYPE: DNA
<213> ORGANISM: Artificial Sequence
<220> FEATURE:
<223> OTHER INFORMATION: Vector

<400> SEQUENCE: 26
ggcctaactg gccggtacct gagtctaaat gagtcttcgg acctcgcggg ggccgcttaa   60
gcggtggtta gggtttgtct gacgcggggg gaggggaag gaacgaaaca ctctcattcg   120
gaggcggctc ggggtttggt cttggtggcc acgggcacgc agaagagcgc cgcgatcctc   180
ttaagcaccc ccccgccctc cgtggaggcg ggggtttggt cggcgggtgg taactggcgg   240
gccgctgact cgggcgggtc gcgcgcccca gagtgtgacc ttttcggtct gctcgcagac   300
ccccgggcgg cgccgccgcg gcggcgacgg gctcgctggg tcctaggctc catgggacc   360 gtatacgtgg acaggctctg gagcatccgc acgactgcgg tgatattacc ggagaccttc   420
```

```
tgcgggacga gccgggtcac gcggctgacg cggagcgtcc gttgggcgac aaacaccagg      480
acggggcaca ggtacactat cttgtcaccc ggaggcgcga gggactgcag gagcttcagg      540
gagtggcgca gctgcttcat ccccgtggcc cgttgctcgc gtttgctggc ggtgtccccg      600
gaagaaatat atttgcatgt ctttagttct atgatgacac aaaccccgcc cagcgtcttg      660
tcattggcga agtcgaacac gcagatgcag tcggggcggc gcggtcccag gtccacttcg      720
catattaagg tgacgcgtgt ggcctcgaac accgagcgac cctgcagcga cccgcttaaa      780
agcttggcaa tccggtactg ttggtaaagc caccatggtc ttcacactcg aagatttcgt      840
tggggactgg gaacagacag ccgcctacaa cctggaccaa gtccttgaac agggaggtgt      900
gtccagtttg ctgcagaatc tcgccgtgtc cgtaactccg atccaaagga ttgtccggag      960
cggtgaaaat gccctgaaga tcgacatcca tgtcatcatc ccgtatgaag gtctgagcgc     1020
cgaccaaatg gcccagatcg aagaggtgtt taaggtggtg taccctgtgg atgatcatca     1080
ctttaaggtg atcctgccct atggcacact ggtaatcgac ggggttacgc cgaacatgct     1140
gaactatttc ggacggccgt atgaaggcat cgccgtgttc gacggcaaaa agatcactgt     1200
aacagggacc ctgtggaacg gcaacaaaat tatcgacgag cgcctgatca cccccgacgg     1260
ctccatgctg ttccgagtaa ccatcaacag tgggagttcc ggtggtggcg ggagcggagg     1320
tggaggctcg agcggtggag ctcaggggaa ttcagtctaa gctagcagat cttctagagt     1380
cggggcggcc ggccgcttcg agcagacatg ataagataca ttgatgagtt tggacaaacc     1440
acaactagaa tgcagtgaaa aaaatgcttt atttgtgaaa tttgtgatgc tattgcttta     1500
tttgtaacca ttataagctg caataaacaa gttaacaaca caattgcat tcattttatg     1560 tttcaggttc aggggggagt gtgggaggtt ttttaaagca agtaaaacct ctacaaatgt     1620
ggtaaaatcg ataaggatcc gtcgaccgat gcccttgaga gccttcaacc cagtcagctc     1680
cttccggtgg gcgcggggca tgactatcgt cgccgcactt atgactgtct tctttatcat     1740
gcaactcgta ggacaggtgc cggcagcgct cttccgcttc ctcgctcact gactcgctgc     1800
gctcggtcgt tcggctgcgg cgagcggtat cagctcactc aaaggcggta atacggttat     1860
ccacagaatc agggggataac gcaggaaaga acatgtgagc aaaaggccag caaaaggcca     1920
ggaaccgtaa aaaggccgcg ttgctggcgt ttttccatag gctccgcccc cctgacgagc     1980
atcacaaaaa tcgacgctca agtcagaggt ggcgaaaccc gacaggacta taaagatacc     2040
aggcgtttcc ccctggaagc tccctcgtgc gctctcctgt tccgaccctg ccgcttaccg     2100
gatacctgtc cgcctttctc ccttcgggaa gcgtggcgct ttctcatagc tcacgctgta     2160
ggtatctcag ttcggtgtag tcgttcgct ccaagctggg ctgtgtgcac gaaccccccg     2220
ttcagcccga ccgctgcgcc ttatccgta actatcgtct tgagtccaac ccggtaagac     2280
acgacttatc gccactggca gcagccactg gtaacaggat tagcagagcg aggtatgtag     2340
gcggtgctac agagttcttg aagtggtggc ctaactacgg ctacactaga agaacagtat     2400
ttggtatctg cgctctgctg aagccagtta ccttcggaaa aagagttggt agctcttgat     2460
ccggcaaaca aaccaccgct ggtagcggtg gtttttttgt ttgcaagcag cagattacgc     2520
gcagaaaaaa aggatctcaa gaagatcctt tgatctttc tacggggtct gacgctcagt     2580
ggaacgaaaa ctcacgttaa gggattttgg tcatgagatt atcaaaaagg atcttcacct     2640
agatcctttt aaattaaaaa tgaagtttta aatcaatcta agtatatat gagtaaactt     2700 ggtctgacag cggccgcaaa tgctaaacca ctgcagtggt taccagtgct tgatcagtga     2760
```

| | |
|---|---|
| ggcaccgatc tcagcgatct gcctatttcg ttcgtccata gtggcctgac tccccgtcgt | 2820 |
| gtagatcact acgattcgtg agggcttacc atcaggcccc agcgcagcaa tgatgccgcg | 2880 |
| agagccgcgt tcaccggccc ccgatttgtc agcaatgaac cagccagcag ggagggccga | 2940 |
| gcgaagaagt ggtcctgcta ctttgtccgc ctccatccag tctatgagct gctgtcgtga | 3000 |
| tgctagagta agaagttcgc cagtgagtag tttccgaaga gttgtggcca ttgctactgg | 3060 |
| catcgtggta tcacgctcgt cgttcggtat ggcttcgttc aactctggtt cccagcggtc | 3120 |
| aagccgggtc acatgatcac ccatattatg aagaaatgca gtcagctcct tagggcctcc | 3180 |
| gatcgttgtc agaagtaagt tggccgcggt gttgtcgctc atggtaatgg cagcactaca | 3240 |
| caattctctt accgtcatgc catccgtaag atgcttttcc gtgaccggcg agtactcaac | 3300 |
| caagtcgttt tgtgagtagt gtatacggcg accaagctgc tcttgcccgg cgtctatacg | 3360 |
| ggacaacacc gcgccacata gcagtacttt gaaagtgctc atcatcggga atcgttcttc | 3420 |
| ggggcggaaa gactcaagga tcttgccgct attgagatcc agttcgatat agcccactct | 3480 |
| tgcacccagt tgatcttcag catcttttac tttcaccagc gtttcggggt gtgcaaaaac | 3540 |
| aggcaagcaa aatgccgcaa agaagggaat gagtgcgaca cgaaaatgtt ggatgctcat | 3600 |
| actcgtcctt tttcaatatt attgaagcat ttatcagggt tactagtacg tctctcaagg | 3660 |
| ataagtaagt aatattaagg tacgggaggt attggacagg ccgcaataaa atatctttat | 3720 |
| tttcattaca tctgtgtgtt ggttttttgt gtgaatcgat agtactaaca tacgctctcc | 3780 |
| atcaaaacaa aacgaaacaa aacaaactag caaaataggc tgtccccagt gcaagtgcag | 3840 |
| gtgccagaac atttctct | 3858 |

<210> SEQ ID NO 27
<211> LENGTH: 3423
<212> TYPE: DNA
<213> ORGANISM: Artificial Sequence
<220> FEATURE:
<223> OTHER INFORMATION: Vector

<400> SEQUENCE: 27

| | |
|---|---|
| ggcctaactg gccggtacct gagtctaaat gagtcttcgg acctcgcggg ggccgcttaa | 60 |
| gcggtggtta gggtttgtct gacgcggggg gaggggaag gaacgaaaca ctctcattcg | 120 |
| gaggcggctc gggg gtttggt cttggtggcc acggcacgc agaagagcgc cgcgatcctc | 180 |
| ttaagcaccc ccccgccctc cgtggaggcg ggggtttggt cggcgggtgg taactggcgg | 240 |
| gccgctgact cgggcgggtc gcgcgcccca gagtgtgacc ttttcggtct gctcgcagac | 300 |
| ccccgggcgg cgccgccgcg gcggcgacgg gctcgctggg tcctaggctc catggggacc | 360 |
| gtatacgtgg acaggctctg gagcatccgc acgactgcgg tgatattacc ggagaccttc | 420 |
| tgcgggacga gccgggtcac gcggctgacg cggagcgtcc gttggcgac aaacaccagg | 480 |
| acggggcaca ggtacactat cttgtcaccc ggaggcgcga gggactgcag gagcttcagg | 540 |
| gagtggcgca gctgcttcat ccccgtggcc cgttgctcgc gtttgctggc ggtgtccccg | 600 |
| gaagaaatat atttgcatgt ctttagttct atgatgacac aaaccccgcc cagcgtcttg | 660 |
| tcattggcga agtcgaacac gcagatgcag tcgggcggc gcggtcccag gtccacttcg | 720 |
| catattaagg tgacgcgtgt ggcctcgaac accgagcgac cctgcagcga cccgcttaaa | 780 |
| agcttggcaa tccggtactg tggtaaagcc accagatctg ctagcgatcg cctaagtggg | 840 |
| agctcagggg aattctggct cgagcggtgg tggcgggagc ggaggtggag ggtcgtcagg | 900 |
| tgtgaccggc taccggctgt tcgaggagat tctgtaatct agagtcgggg cggccggccg | 960 |

-continued

| | |
|---|---|
| cttcgagcag acatgataag atacattgat gagtttggac aaaccacaac tagaatgcag | 1020 |
| tgaaaaaaat gctttatttg tgaaatttgt gatgctattg ctttatttgt aaccattata | 1080 |
| agctgcaata aacaagttaa caacaacaat tgcattcatt ttatgtttca ggttcagggg | 1140 |
| gaggtgtggg aggtttttta aagcaagtaa aacctctaca aatgtggtaa aatcgataag | 1200 |
| gatccgtcga ccgatgccct tgagagcctt caacccagtc agctccttcc ggtgggcgcg | 1260 |
| gggcatgact atcgtcgccg cacttatgac tgtcttcttt atcatgcaac tcgtaggaca | 1320 |
| ggtgccggca gcgctcttcc gcttcctcgc tcactgactc gctgcgctcg gtcgttcggc | 1380 |
| tgcggcgagc ggtatcagct cactcaaagg cggtaatacg gttatccaca gaatcagggg | 1440 |
| ataacgcagg aaagaacatg tgagcaaaag gccagcaaaa ggccaggaac cgtaaaaagg | 1500 |
| ccgcgttgct ggcgttttc cataggctcc gcccccctga cgagcatcac aaaaatcgac | 1560 |
| gctcaagtca gaggtggcga aacccgacag gactataaag ataccaggcg tttccccctg | 1620 |
| gaagctccct cgtgcgctct cctgttccga ccctgccgct taccggatac ctgtccgcct | 1680 |
| ttctcccttc gggaagcgtg gcgctttctc atagctcacg ctgtaggtat ctcagttcgg | 1740 |
| tgtaggtcgt tcgctccaag ctgggctgtg tgcacgaacc ccccgttcag cccgaccgct | 1800 |
| gcgccttatc cggtaactat cgtcttgagt ccaacccggt aagacacgac ttatcgccac | 1860 |
| tggcagcagc cactggtaac aggattagca gagcgaggta tgtaggcggt gctacagagt | 1920 |
| tcttgaagtg gtggcctaac tacggctaca ctagaagaac agtatttggt atctgcgctc | 1980 |
| tgctgaagcc agttaccttc ggaaaaagag ttggtagctc ttgatccggc aaacaaacca | 2040 |
| ccgctggtag cggtggtttt tttgtttgca agcagcagat tacgcgcaga aaaaaggat | 2100 |
| ctcaagaaga tcctttgatc ttttctacgg ggtctgacgc tcagtggaac gaaaactcac | 2160 |
| gttaagggat tttggtcatg agattatcaa aaaggatctt cacctagatc cttttaaatt | 2220 |
| aaaaatgaag ttttaaatca atctaaagta tatatgagta aacttggtct gacagcggcc | 2280 |
| gcaaatgcta aaccactgca gtggttacca gtgcttgatc agtgaggcac cgatctcagc | 2340 |
| gatctgccta tttcgttcgt ccatagtggc ctgactcccc gtcgtgtaga tcactacgat | 2400 |
| tcgtgagggc ttaccatcag gccccagcgc agcaatgatg ccgcgagagc cgcgttcacc | 2460 |
| ggcccccgat tgtcagcaa tgaaccagcc agcgggagg gccgagcgaa gaagtggtcc | 2520 |
| tgctactttg tccgcctcca tccagtctat gagctgctgt cgtgatgcta gagtaagaag | 2580 |
| ttcgccagtg agtagtttcc gaagagttgt ggccattgct actggcatcg tggtatcacg | 2640 |
| ctcgtcgttc ggtatggctt cgttcaactc tggttcccag cggtcaagcc gggtcacatg | 2700 |
| atcacccata ttatgaagaa atgcagtcag ctccttaggg cctccgatcg ttgtcagaag | 2760 |
| taagttggcc gcggtgttgt cgctcatggt aatggcagca ctacacaatt ctcttaccgt | 2820 |
| catgccatcc gtaagatgct tttccgtgac cggcgagtac tcaaccaagt cgttttgtga | 2880 |
| gtagtgtata cggcgaccaa gctgctcttg cccggcgtct atacgggaca caccgcgcc | 2940 |
| acatagcagt actttgaaag tgctcatcat cgggaatcgt tcttcggggc ggaaagactc | 3000 |
| aaggatcttg ccgctattga gatccagttc gatatagccc actcttgcac ccagttgatc | 3060 |
| ttcagcatct tttactttca ccagcgtttc ggggtgtgca aaaacaggca agcaaaatgc | 3120 |
| cgcaaagaag ggaatgagtg cgacacgaaa atgttggatg ctcatactcg tccttttca | 3180 |
| atattattga agcatttatc agggttacta gtacgtctct caaggataag taagtaatat | 3240 |
| taaggtacgg gaggtattgg acaggccgca ataaatatc tttattttca ttacatctgt | 3300 |

```
gtgttggttt tttgtgtgaa tcgatagtac taacatacgc tctccatcaa aacaaaacga    3360
aacaaaacaa actagcaaaa taggctgtcc ccagtgcaag tgcaggtgcc agaacatttc    3420
tct                                                                  3423
```

<210> SEQ ID NO 28
<211> LENGTH: 38
<212> TYPE: DNA
<213> ORGANISM: Artificial Sequence
<220> FEATURE:
<223> OTHER INFORMATION: Primer

<400> SEQUENCE: 28

```
ggaattcata tgatggtctt cacactcgaa gatttcgt                              38
```

<210> SEQ ID NO 29
<211> LENGTH: 40
<212> TYPE: DNA
<213> ORGANISM: Artificial Sequence
<220> FEATURE:
<223> OTHER INFORMATION: Primer

<400> SEQUENCE: 29

```
cgcgggatcc ttacaactgc agagaagctg gagaggaatg                            40
```

<210> SEQ ID NO 30
<211> LENGTH: 43
<212> TYPE: DNA
<213> ORGANISM: Artificial Sequence
<220> FEATURE:
<223> OTHER INFORMATION: Primer

<400> SEQUENCE: 30

```
cgcgggatcc ttacaactgc agagaagctg gagacgcatg agc                        43
```

<210> SEQ ID NO 31
<211> LENGTH: 38
<212> TYPE: DNA
<213> ORGANISM: Artificial Sequence
<220> FEATURE:
<223> OTHER INFORMATION: Primer

<400> SEQUENCE: 31

```
ggaattcata tgatggagaa gactgagctg atccagaa                              38
```

<210> SEQ ID NO 32
<211> LENGTH: 40
<212> TYPE: DNA
<213> ORGANISM: Artificial Sequence
<220> FEATURE:
<223> OTHER INFORMATION: Primer

<400> SEQUENCE: 32

```
cgcgggatcc ttacagaatc tcctcgaaca gccggtagcc                            40
```

<210> SEQ ID NO 33
<211> LENGTH: 5711
<212> TYPE: DNA
<213> ORGANISM: Artificial Sequence
<220> FEATURE:
<223> OTHER INFORMATION: Vector

<400> SEQUENCE: 33

```
ttctcatgtt tgacagctta tcatcgataa gctttaatgc ggtagtttat cacagttaaa    60
ttgctaacgc agtcaggcac cgtgtatgaa atctaacaat gcgctcatcg tcatcctcgg   120
```

```
caccgtcacc ctggatgctg taggcatagg cttggttatg ccggtactgc cgggcctctt    180
gcgggatatc cggatatagt tcctcctttc agcaaaaaac ccctcaagac ccgtttagag    240
gccccaaggg gttatgctag ttattgctca gcggtggcag cagccaactc agcttccttt    300
cgggctttgt tagcagccgg atcctcgagc atatgacgac cttcgatatg ccgctgctg    360
tgatgatgat gatgatgatg atgatgatgg cccatggtat atctccttct taaagttaaa    420
caaaattatt tctagagggg aattgttatc cgctcacaat tccctatag tgagtcgtat     480
taatttcgcg ggatcgagat ctcgatcctc tacgccggac gcatcgtggc cggcatcacc    540
ggcgccacag gtgcggttgc tggcgcctat atcgccgaca tcaccgatgg gaagatcgg     600
gctcgccact tcgggctcat gagcgcttgt ttcggcgtgg gtatggtggc aggccccgtg    660
gccgggggac tgttgggcgc catctccttg catgcaccat tccttgcggc ggcggtgctc    720
aacggcctca acctactact gggctgcttc ctaatgcagg agtcgcataa gggagagcgt    780
cgagatcccg gacaccatcg aatggcgcaa aacctttcgc ggtatggcat gatagcgccc    840
ggaagagagt caattcaggg tggtgaatgt gaaaccagta acgttatacg atgtcgcaga    900
gtatgccggt gtctcttatc agaccgtttc ccgcgtggtg aaccaggcca gccacgtttc    960
tgcgaaaacg cgggaaaaag tggaagcggc gatggcggag ctgaattaca ttcccaaccg   1020
cgtggcacaa caactggcgg gcaaacagtc gttgctgatt ggcgttgcca cctccagtct   1080
ggccctgcac gcgccgtcgc aaattgtcgc ggcgattaaa tctcgcgccg atcaactggg   1140
tgccagcgtg gtggtgtcga tggtagaacg aagcggcgtc gaagcctgta aagcggcggt   1200
gcacaatctt ctcgcgcaac gcgtcagtgg gctgatcatt aactatccgc tggatgacca   1260
ggatgccatt gctgtggaag ctgcctgcac taatgttccg gcgttatttc ttgatgtctc   1320
tgaccagaca cccatcaaca gtattatttt ctcccatgaa gacggtacgc gactgggcgt   1380
ggagcatctg gtcgcattgg gtcaccagca aatcgcgctg ttagcgggcc cattaagttc   1440
tgtctcggcg cgtctgcgtc tggctggctg gcataaatat ctcactcgca atcaaattca   1500
gccgatagcg gaacgggaag gcgactggag tgccatgtcc ggttttcaac aaaccatgca   1560
aatgctgaat gagggcatcg ttcccactgc gatgctggtt gccaacgatc agatggcgct   1620
gggcgcaatg cgcgccatta ccgagtccgg gctgcgcgtt ggtgcggata tctcggtagt   1680
gggatacgac gataccgaag acagctcatg ttatatcccg ccgttaacca ccatcaaaca   1740
ggattttcgc ctgctggggc aaaccagcgt ggaccgcttg ctgcaactct ctcagggcca   1800
ggcggtgaag gcaatcagc tgttgcccgt ctcactggtg aaaagaaaaa ccaccctggc   1860
gcccaatacg caaaccgcct ctccccgcgc gttggccgat tcattaatgc agctggcacg   1920
acaggtttcc cgactggaaa gcgggcagtg agcgcaacgc aattaatgta agttagctca   1980
ctcattaggc accgggatct cgaccgatgc ccttgagagc cttcaaccca gtcagctcct   2040
tccggtgggc gcgggcatg actatcgtcg ccgcacttat gactgtcttc tttatcatgc   2100
aactcgtagg acaggtgccg gcagcgctct gggtcatttt cggcgaggac cgctttcgct   2160
ggagcgcgac gatgatcggc ctgtcgcttg cggtattcgg aatcttgcac gccctcgctc   2220
aagccttcgt cactggtccc gccaccaaac gtttcggcga agcaggcc attatcgccg    2280
gcatggcggc cgacgcgctg ggctacgtct tgctggcgtt cgcgacgcga ggctggatgg   2340
ccttcccat tatgattctt ctcgcttccg gcggcatcgg gatgcccgcg ttgcaggcca    2400
tgctgtccag gcaggtagat gacgaccatc agggacagct tcaaggatcg ctcgcggctc   2460
```

```
ttaccagcct aacttcgatc actggaccgc tgatcgtcac ggcgatttat gccgcctcgg    2520
cgagcacatg gaacgggttg gcatggattg taggcgccgc cctataccct tgtctgcctcc   2580
ccgcgttgcg tcgcggtgca tggagccggg ccacctcgac ctgaatggaa gccggcggca    2640
cctcgctaac ggattcacca ctccaagaat tggagccaat caattcttgc ggagaactgt    2700
gaatgcgcaa accaacccct tggcagaacat atccatcgcg tccgccatct ccagcagccg    2760
cacgcggcgc atctcgggca gcgttgggtc ctggccacgg gtgcgcatga tcgtgctcct    2820
gtcgttgagg acccggctag gctggcgggg ttgccttact ggttagcaga atgaatcacc    2880
gatacgcgag cgaacgtgaa gcgactgctg ctgcaaaacg tctgcgacct gagcaacaac    2940
atgaatggtc ttcggtttcc gtgtttcgta aagtctggaa acgcggaagt cagcgccctg    3000
caccattatg ttccggatct gcatcgcagg atgctgctgg ctaccctgtg gaacacctac    3060
atctgtatta acgaagcgct ggcattgacc ctgagtgatt tttctctggt cccgccgcat    3120
ccataccgcc agttgtttac cctcacaacg ttccagtaac cgggcatgtt catcatcagt    3180
aacccgtatc gtgagcatcc tctctcgttt catcggtatc attaccccca tgaacagaaa    3240
tcccccttac acggaggcat cagtgaccaa acaggaaaaa accgccctta acatggcccg    3300
ctttatcaga agccagacat taacgcttct ggagaaactc aacgagctgg acgcggatga    3360
acaggcagac atctgtgaat cgcttcacga ccacgctgat gagctttacc gcagctgcct    3420
cgcgcgtttc ggtgatgacg gtgaaaacct ctgacacatg cagctcccgg agacggtcac    3480
agcttgtctg taagcggatg ccgggagcag acaagcccgt cagggcgcgt cagcgggtgt    3540
tggcgggtgt cggggcgcag ccatgaccca gtcacgtagc gatagcggag tgtatactgg    3600
cttaactatg cggcatcaga gcagattgta ctgagagtgc accatatatg cggtgtgaaa    3660
taccgcacag atgcgtaagg agaaaatacc gcatcaggcg ctcttccgct tcctcgctca    3720
ctgactcgct gcgctcggtc gttcggctgc ggcgagcggt atcagctcac tcaaaggcgg    3780
taatacggtt atccacagaa tcaggggata acgcaggaaa gaacatgtga gcaaaaggcc    3840
agcaaaaggc caggaaccgt aaaaaggccg cgttgctggc gtttttccat aggctccgcc    3900
cccctgacga gcatcacaaa aatcgacgct caagtcagag gtggcgaaac ccgacaggac    3960
tataaagata ccaggcgttt ccccctggaa gctccctcgt gcgctctcct gttccgaccc    4020
tgccgcttac cggatacctg tccgcctttc tcccttcggg aagcgtggcg ctttctcata    4080
gctcacgctg taggtatctc agttcggtgt aggtcgttcg ctccaagctg ggctgtgtgc    4140
acgaaccccc cgttcagccc gaccgctgcg ccttatccgg taactatcgt cttgagtcca    4200
acccggtaag acacgactta tcgccactgg cagcagccac tggtaacagg attagcagag    4260
cgaggtatgt aggcggtgct acagagttct tgaagtggtg gcctaactac ggctacacta    4320
gaaggacagt atttggtatc tgcgctctgc tgaagccagt taccttcgga aaaagagttg    4380
gtagctcttg atccggcaaa caaaccaccg ctggtagcgg tggtttttt gtttgcaagc    4440
agcagattac gcgcagaaaa aaaggatctc aagaagatcc tttgatcttt tctacggggt    4500
ctgacgctca gtggaacgaa aactcacgtt aagggatttt ggtcatgaga ttatcaaaaa    4560
ggatcttcac ctagatcctt ttaaattaaa aatgaagttt taaatcaatc taaagtatat    4620
atgagtaaac ttggtctgac agttaccaat gcttaatcag tgaggcacct atctcagcga    4680
tctgtctatt tcgttcatcc atagttgcct gactccccgt cgtgtagata actacgatac    4740
gggagggctt accatctggc cccagtgctg caatgatacc gcgagaccca cgctcaccgg    4800
ctccagattt atcagcaata aaccagccag ccggaagggc cgagcgcaga agtggtcctg    4860
```

```
caactttatc cgcctccatc cagtctatta attgttgccg ggaagctaga gtaagtagtt    4920
cgccagttaa tagtttgcgc aacgttgttg ccattgctgc aggcatcgtg gtgtcacgct    4980
cgtcgtttgg tatggcttca ttcagctccg gttcccaacg atcaaggcga gttacatgat    5040
cccccatgtt gtgcaaaaaa gcggttagct ccttcggtcc tccgatcgtt gtcagaagta    5100
agttggccgc agtgttatca ctcatggtta tggcagcact gcataattct cttactgtca    5160
tgccatccgt aagatgcttt tctgtgactg gtgagtactc aaccaagtca ttctgagaat    5220
agtgtatgcg gcgaccgagt tgctcttgcc cggcgtcaac acgggataat accgcgccac    5280
atagcagaac tttaaaagtg ctcatcattg gaaaacgttc ttcggggcga aaactctcaa    5340
ggatcttacc gctgttgaga tccagttcga tgtaacccac tcgtgcaccc aactgatctt    5400
cagcatcttt tactttcacc agcgtttctg gtgagcaaa acaggaagg caaaatgccg     5460 caaaaaggg aataagggcg acacggaaat gttgaatact catactcttc cttttcaat    5520 attattgaag catttatcag ggttattgtc tcatgagcgg atacatattt gaatgtattt    5580
agaaaaataa acaaataggg gttccgcgca catttcccg aaaagtgcca cctgacgtct    5640
aagaaaccat tattatcatg acattaacct ataaaaatag gcgtatcacg aggccctttc    5700
gtcttcaaga a                                                         5711

<210> SEQ ID NO 34
<211> LENGTH: 41
<212> TYPE: DNA
<213> ORGANISM: Artificial Sequence
<220> FEATURE:
<223> OTHER INFORMATION: Primer

<400> SEQUENCE: 34
ctggatccgc cgccaccatg gtcttcacac tcgaagattt c                        41

<210> SEQ ID NO 35
<211> LENGTH: 54
<212> TYPE: DNA
<213> ORGANISM: Artificial Sequence
<220> FEATURE:
<223> OTHER INFORMATION: Primer

<400> SEQUENCE: 35
accgctcgag cctccaccctc cgctcccgcc accaccggaa ctcccactgt tgat          54

<210> SEQ ID NO 36
<211> LENGTH: 69
<212> TYPE: DNA
<213> ORGANISM: Artificial Sequence
<220> FEATURE:
<223> OTHER INFORMATION: Primer

<400> SEQUENCE: 36
gggagttccg gtggtggcgg gagcggaggt ggaggctcga gcggtgccgg gcatcagatc    60
gtgcacgtc                                                            69

<210> SEQ ID NO 37
<211> LENGTH: 63
<212> TYPE: DNA
<213> ORGANISM: Artificial Sequence
<220> FEATURE:
<223> OTHER INFORMATION: Primer
```

<400> SEQUENCE: 37
atgaaactgc ggccgccttg tcgtcatcgt ctttgtagtc tacatcatca ggtatctcaa    60
aag                                                                  63

<210> SEQ ID NO 38
<211> LENGTH: 32
<212> TYPE: DNA
<213> ORGANISM: Artificial Sequence
<220> FEATURE:
<223> OTHER INFORMATION: Primer

<400> SEQUENCE: 38
ctggatccgc cgggcatcag atcgtgcacg tc                                  32

<210> SEQ ID NO 39
<211> LENGTH: 68
<212> TYPE: DNA
<213> ORGANISM: Artificial Sequence
<220> FEATURE:
<223> OTHER INFORMATION: Primer

<400> SEQUENCE: 39
acctgacgac cctccacctc cgctcccgcc accaccgctc gagcctacat catcaggtat    60
ctcaaaag                                                             68

<210> SEQ ID NO 40
<211> LENGTH: 66
<212> TYPE: DNA
<213> ORGANISM: Artificial Sequence
<220> FEATURE:
<223> OTHER INFORMATION: Primer

<400> SEQUENCE: 40
ggctcgagcg gtggtggcgg gagcggaggt ggagggtcgt caggtgtctt cacactcgaa    60
gatttc                                                               66

<210> SEQ ID NO 41
<211> LENGTH: 43
<212> TYPE: DNA
<213> ORGANISM: Artificial Sequence
<220> FEATURE:
<223> OTHER INFORMATION: Primer

<400> SEQUENCE: 41
atgaaactgc ggccgcttaa ctgttgatgg ttactcggaa cag                      43

<210> SEQ ID NO 42
<211> LENGTH: 98
<212> TYPE: DNA
<213> ORGANISM: Artificial Sequence
<220> FEATURE:
<223> OTHER INFORMATION: Primer

<400> SEQUENCE: 42
ctggatccgc cgccaccatg gtgaccggct accggctgtt cgaggagatt ctcgggagtt    60
ccggtggtgg cgggagcgga ggtggaggct cgagcggt                            98

<210> SEQ ID NO 43
<211> LENGTH: 97
<212> TYPE: DNA
<213> ORGANISM: Artificial Sequence
<220> FEATURE:

<223> OTHER INFORMATION: Primer

<400> SEQUENCE: 43
atgaaactgc ggccgcttag agaatctcct cgaacagccg gtagccggtc acacctgacg    60
accctccacc tccgctcccg ccaccaccgc tcgagcc    97

<210> SEQ ID NO 44
<211> LENGTH: 73
<212> TYPE: DNA
<213> ORGANISM: Artificial Sequence
<220> FEATURE:
<223> OTHER INFORMATION: Primer

<400> SEQUENCE: 44
gggagttccg gtggtggcgg gagcggaggt ggaggctcga gcggtgagcc tgcatcggcc    60
ccagctccct cag    73

<210> SEQ ID NO 45
<211> LENGTH: 73
<212> TYPE: DNA
<213> ORGANISM: Artificial Sequence
<220> FEATURE:
<223> OTHER INFORMATION: Primer

<400> SEQUENCE: 45
atgaaactgc ggccgcttac agatcctctt ctgagatgag tttttgttca tttgaaactt    60
caaacacaca ggc    73

<210> SEQ ID NO 46
<211> LENGTH: 36
<212> TYPE: DNA
<213> ORGANISM: Artificial Sequence
<220> FEATURE:
<223> OTHER INFORMATION: Primer

<400> SEQUENCE: 46
ctggatccga gcctgcatcg gccccagctc cctcag    36

<210> SEQ ID NO 47
<211> LENGTH: 69
<212> TYPE: DNA
<213> ORGANISM: Artificial Sequence
<220> FEATURE:
<223> OTHER INFORMATION: Primer

<400> SEQUENCE: 47
acctgacgac cctccacctc cgctcccgcc accaccgctc gagccatttg aaacttcaaa    60
cacacaggc    69

<210> SEQ ID NO 48
<211> LENGTH: 73
<212> TYPE: DNA
<213> ORGANISM: Artificial Sequence
<220> FEATURE:
<223> OTHER INFORMATION: Primer

<400> SEQUENCE: 48
gggagttccg gtggtggcgg gagcggaggt ggaggctcga gcggtgagcc tgcatcggcc    60
ccagctccct cag    73

<210> SEQ ID NO 49
<211> LENGTH: 1281

<212> TYPE: DNA
<213> ORGANISM: Homo sapiens

<400> SEQUENCE: 49

```
attgagccca gcagctggag cggcagtgag agccctgccg aaaacatgga aaggatgagt      60
gactctgcag ataagccaat tgacaatgat gcagaagggg tctggagccc cgacatcgag     120
caaagctttc aggaggccct ggctatctat ccaccatgtg ggaggaggaa aatcatctta     180
tcagacgaag gcaaaatgta tggtaggaat gaattgatag ccagatacat caaactcagg     240
acaggcaaga cgaggaccag aaaacaggtg tctagtcaca ttcaggttct tgccagaagg     300
aaatctcgtg attttcattc caagctaaag gatcagactg caaaggataa ggccctgcag     360
cacatggcgg ccatgtcctc agcccagatc gtctcggcca ctgccattca taacaagctg     420
gggctgcctg ggattccacg cccgaccttc ccaggggcgc cggggttctg ccgggaatg      480
attcaaacag ggcagccagg atcctcacaa gacgtcaagc cttttgtgca gcaggcctac     540
cccatccagc cagcggtcac agcccccatt ccagggtttg agcctgcatc ggccccagct     600
ccctcagtcc ctgcctggca aggtcgctcc attggcacaa ccaagcttcg cctggtggaa     660
ttttcagctt ttctcgagca gcagcgagac ccagactcgt acaacaaaca cctcttcgtg     720
cacattgggc atgccaacca ttcttacagt gacccattgc ttgaatcagt ggacattcgt     780
cagatttatg acaaatttcc tgaaaagaaa ggtggcttaa aggaactgtt tggaaagggc     840
cctcaaaatg ccttcttcct cgtaaaattc tgggctgatt taaactgcaa tattcaagat     900
gatgctgggg cttttatgg tgtaaccagt cagtacgaga gttctgaaaa tatgacagtc     960
acctgttcca ccaaagtttg ctcctttggg aagcaagtag tagaaaaagt agagacggag    1020
tatgcaaggt ttgagaatgg ccgatttgta taccgaataa accgctcccc aatgtgtgaa    1080
tatatgatca acttcatcca caagctcaaa cacttaccag agaaatatat gatgaacagt    1140
gttttggaaa acttcacaat tttattggtg gtaacaaaca gggatacaca agaaactcta    1200
ctctgcatgg cctgtgtgtt tgaagtttca aatagtgaac acggagcaca acatcatatt    1260
tacaggcttg taaaggactg a                                              1281
```

<210> SEQ ID NO 50
<211> LENGTH: 426
<212> TYPE: PRT
<213> ORGANISM: Homo sapiens

<400> SEQUENCE: 50

```
Met Glu Pro Ser Ser Trp Ser Gly Ser Glu Ser Pro Ala Glu Asn Met
1               5                   10                  15

Glu Arg Met Ser Asp Ser Ala Asp Lys Pro Ile Asp Asn Asp Ala Glu
            20                  25                  30

Gly Val Trp Ser Pro Asp Ile Glu Gln Ser Phe Gln Glu Ala Leu Ala
        35                  40                  45

Ile Tyr Pro Pro Cys Gly Arg Arg Lys Ile Ile Leu Ser Asp Glu Gly
    50                  55                  60

Lys Met Tyr Gly Arg Asn Glu Leu Ile Ala Arg Tyr Ile Lys Leu Arg
65                  70                  75                  80

Thr Gly Lys Thr Arg Thr Arg Lys Gln Val Ser Ser His Ile Gln Val
                85                  90                  95

Leu Ala Arg Arg Lys Ser Arg Asp Phe His Ser Lys Leu Lys Asp Gln
            100                 105                 110
```

Thr Ala Lys Asp Lys Ala Leu Gln His Met Ala Ala Met Ser Ser Ala
            115                 120                 125

Gln Ile Val Ser Ala Thr Ala Ile His Asn Lys Leu Gly Leu Pro Gly
        130                 135                 140

Ile Pro Arg Pro Thr Phe Pro Gly Ala Pro Gly Phe Trp Pro Gly Met
145                 150                 155                 160

Ile Gln Thr Gly Gln Pro Gly Ser Ser Gln Asp Val Lys Pro Phe Val
                165                 170                 175

Gln Gln Ala Tyr Pro Ile Gln Pro Ala Val Thr Ala Pro Ile Pro Gly
            180                 185                 190

Phe Glu Pro Ala Ser Ala Pro Ala Pro Ser Val Pro Ala Trp Gln Gly
        195                 200                 205

Arg Ser Ile Gly Thr Thr Lys Leu Arg Leu Val Glu Phe Ser Ala Phe
    210                 215                 220

Leu Glu Gln Gln Arg Asp Pro Asp Ser Tyr Asn Lys His Leu Phe Val
225                 230                 235                 240

His Ile Gly His Ala Asn His Ser Tyr Ser Asp Pro Leu Leu Glu Ser
                245                 250                 255

Val Asp Ile Arg Gln Ile Tyr Asp Lys Phe Pro Glu Lys Lys Gly Gly
            260                 265                 270

Leu Lys Glu Leu Phe Gly Lys Gly Pro Gln Asn Ala Phe Phe Leu Val
        275                 280                 285

Lys Phe Trp Ala Asp Leu Asn Cys Asn Ile Gln Asp Asp Ala Gly Ala
    290                 295                 300

Phe Tyr Gly Val Thr Ser Gln Tyr Glu Ser Ser Glu Asn Met Thr Val
305                 310                 315                 320

Thr Cys Ser Thr Lys Val Cys Ser Phe Gly Lys Gln Val Val Glu Lys
                325                 330                 335

Val Glu Thr Glu Tyr Ala Arg Phe Glu Asn Gly Arg Phe Val Tyr Arg
            340                 345                 350

Ile Asn Arg Ser Pro Met Cys Glu Tyr Met Ile Asn Phe Ile His Lys
        355                 360                 365

Leu Lys His Leu Pro Glu Lys Tyr Met Met Asn Ser Val Leu Glu Asn
    370                 375                 380

Phe Thr Ile Leu Leu Val Val Thr Asn Arg Asp Thr Gln Glu Thr Leu
385                 390                 395                 400

Leu Cys Met Ala Cys Val Phe Glu Val Ser Asn Ser Glu His Gly Ala
                405                 410                 415

Gln His His Ile Tyr Arg Leu Val Lys Asp
            420                 425

<210> SEQ ID NO 51
<211> LENGTH: 477
<212> TYPE: DNA
<213> ORGANISM: Artificial Sequence
<220> FEATURE:
<223> OTHER INFORMATION: Synthesized

<400> SEQUENCE: 51
atggtcttca cactcgaaga tttcgttggg gactgggaac agacagccgc ctacaacctg    60
gaccaagtcc ttgaacaggg aggtgtgtcc agtttgctgc agaatctcgc cgtgtccgta   120
actccgatcc aaaggattgt ccggagcggt gaaaatgccc tgaagatcga catccatgtc   180
atcatcccgt atgaaggtct gagcgccgac caaatggccc agatcgaaga ggtgtttaag   240

```
gtggtgtacc ctgtggatga tcatcacttt aaggtgatcc tgccctatgg cacactggta    300
atcgacgggg ttacgccgaa catgctgaac tatttcggac ggccgtatga aggcatcgcc    360
gtgttcgacg gcaaaaagat cactgtaaca gggaccctgt ggaacggcaa caaaattatc    420
gacgagcgcc tgatcacccc cgacggctcc atgctgttcc gagtaaccat caacagt       477
```

```
<210> SEQ ID NO 52
<211> LENGTH: 159
<212> TYPE: PRT
<213> ORGANISM: Artificial Sequence
<220> FEATURE:
<223> OTHER INFORMATION: Synthesized

<400> SEQUENCE: 52

Met Val Phe Thr Leu Glu Asp Phe Val Gly Asp Trp Glu Gln Thr Ala
1               5                   10                  15

Ala Tyr Asn Leu Asp Gln Val Leu Glu Gln Gly Gly Val Ser Ser Leu
            20                  25                  30

Leu Gln Asn Leu Ala Val Ser Val Thr Pro Ile Gln Arg Ile Val Arg
        35                  40                  45

Ser Gly Glu Asn Ala Leu Lys Ile Asp Ile His Val Ile Ile Pro Tyr
    50                  55                  60

Glu Gly Leu Ser Ala Asp Gln Met Ala Gln Ile Glu Glu Val Phe Lys
65                  70                  75                  80

Val Val Tyr Pro Val Asp Asp His His Phe Lys Val Ile Leu Pro Tyr
                85                  90                  95

Gly Thr Leu Val Ile Asp Gly Val Thr Pro Asn Met Leu Asn Tyr Phe
            100                 105                 110

Gly Arg Pro Tyr Glu Gly Ile Ala Val Phe Asp Gly Lys Lys Ile Thr
        115                 120                 125

Val Thr Gly Thr Leu Trp Asn Gly Asn Lys Ile Ile Asp Glu Arg Leu
    130                 135                 140

Ile Thr Pro Asp Gly Ser Met Leu Phe Arg Val Thr Ile Asn Ser
145                 150                 155
```

```
<210> SEQ ID NO 53
<211> LENGTH: 36
<212> TYPE: DNA
<213> ORGANISM: Artificial Sequence
<220> FEATURE:
<223> OTHER INFORMATION: Synthesized

<400> SEQUENCE: 53
atggtgaccg gctaccggct gttcgaggag attctc                               36
```

```
<210> SEQ ID NO 54
<211> LENGTH: 11
<212> TYPE: PRT
<213> ORGANISM: Artificial Sequence
<220> FEATURE:
<223> OTHER INFORMATION: Synthesized

<400> SEQUENCE: 54

Met Val Thr Gly Tyr Arg Leu Phe Glu Ile Leu
1               5                   10
```

```
<210> SEQ ID NO 55
<211> LENGTH: 5490
<212> TYPE: DNA
<213> ORGANISM: Artificial Sequence
<220> FEATURE:
```

<223> OTHER INFORMATION: Vector

<400> SEQUENCE: 55

```
gacggatcgg gagatctccc gatccsctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca caaggcaagg cttgaccgac aattgcatga agaatctgct     180
tagggttagg cgttttgcgc tgcttcgcga tgtacgggcc agatatacgc gttgacattg     240
attattgact agttattaat agtaatcaat tacggggtca ttagttcata gcccatatat     300
ggagttccgc gttacataac ttacggtaaa tggcccgcct ggctgaccgc ccaacgaccc     360
ccgcccattg acgtcaataa tgacgtatgt tcccatagta acgccaatag ggactttcca     420
ttgacgtcaa tgggtggagt atttacggta aactgcccac ttggcagtac atcaagtgta     480
tcatatgcca agtacgcccc ctattgacgt caatgacggt aaatggcccg cctggcatta     540
tgcccagtac atgaccttat gggactttcc tacttggcag tacatctacg tattagtcat     600
cgctattacc atggtgatgc ggttttggca gtacatcaat gggcgtggat agcggtttga     660
ctcacgggga tttccaagtc tccaccccat tgacgtcaat gggagtttgt tttggcacca     720
aaatcaacgg gactttccaa aatgtcgtaa caactccgcc ccattgacgc aaatgggcgg     780
taggcgtgta cggtgggagg tctatataag cagagctctc tggctaacta gagaacccac     840
tgcttactgg cttatcgaaa ttaatacgac tcactatagg gagacccaag ctggctagcg     900
tttaaactta agcttggtac catggactac aaagacgatg acggtgatta taaagatcat     960
gacatctacc tgatgtttct ggtactgcca ggatccacta gtccagtgtg gtggaattct    1020
gcagatatcc agcacagtgg cggccgctcg agtctagagg gcccgtttaa acccgctgat    1080
cagcctcgac tgtgccttct agttgccagc catctgttgt ttgcccctcc cccgtgcctt    1140
ccttgaccct ggaaggtgcc actcccactg tcctttccta ataaaatgag gaaattgcat    1200
cgcattgtct gagtaggtgt cattctattc tggggggtgg ggtggggcag gacagcaagg    1260
gggaggattg ggaagacaat agcaggcatg ctggggatgc ggtgggctct atggcttctg    1320
aggcggaaag aaccagctgg ggctctaggg ggtatcccca cgcgccctgt agcggcgcat    1380
taagcgcggc gggtgtggtg gttacgcgca gcgtgaccgc tacacttgcc agcgccctag    1440
cgcccgctcc tttcgctttc ttcccttcct ttctcgccac gttcgccggc tttccccgtc    1500
aagctctaaa tcgggggctc cctttagggt tccgatttag tgctttacgg cacctcgacc    1560
ccaaaaaact tgattagggt gatggttcac gtagtgggcc atcgccctga tagacggttt    1620
ttcgcccttt gacgttggag tccacgttct ttaatagtgg actcttgttc caaactggaa    1680
caacactcaa ccctatctcg gtctattctt ttgatttata agggattttg ccgatttcgg    1740
cctattggtt aaaaaatgag ctgatttaac aaaaatttaa cgcgaattaa ttctgtggaa    1800
tgtgtgtcag ttagggtgtg gaaagtcccc aggctcccca gcaggcagaa gtatgcaaag    1860
catgcatctc aattagtcag caaccaggtg tggaaagtcc caggctccc cagcaggcag    1920
aagtatgcaa agcatgcatc tcaattagtc agcaaccata gtcccgcccc taactccgcc    1980
catcccgccc ctaactccgc ccagttccgc ccattctccg ccccatggct gactaatttt    2040
ttttatttat gcagaggccg aggccgcctc tgcctctgag ctattccaga agtagtgagg    2100
aggcttttt ggaggcctag gcttttgcaa aaagctcccg ggagcttgta tatccatttt    2160
cggatctgat caagagacag gatgaggatc gtttcgcatg attgaacaag atggattgca    2220
cgcaggttct ccggccgctt gggtggagag gctattcggc tatgactggg cacaacagac    2280
```

```
aatcggctgc tctgatgccg ccgtgttccg gctgtcagcg caggggcgcc cggttcttttt    2340 tgtcaagacc gacctgtccg gtgccctgaa tgaactgcag gacgaggcag cgcggctatc    2400
gtggctggcc acgacgggcg ttccttgcgc agctgtgctc gacgttgtca ctgaagcggg    2460
aagggactgg ctgctattgg gcgaagtgcc ggggcaggat ctcctgtcat ctcaccttgc    2520
tcctgccgag aaagtatcca tcatggctga tgcaatgcgg cggctgcata cgcttgatcc    2580
ggctacctgc ccattcgacc accaagcgaa acatcgcatc gagcgagcac gtactcggat    2640
ggaagccggt cttgtcgatc aggatgatct ggacgaagag catcaggggc tcgcgccagc    2700
cgaactgttc gccaggctca aggcgcgcat gcccgacggc gaggatctcg tcgtgacccA    2760
tggcgatgcc tgcttgccga atatcatggt ggaaaatggc cgcttttctg gattcatcga    2820
ctgtggccgg ctgggtgtgg cggaccgcta tcaggacata gcgttggcta cccgtgatat    2880
tgctgaagag cttggcggcg aatgggctga ccgcttcctc gtgctttacg gtatcgccgc    2940
tcccgattcg cagcgcatcg ccttctatcg ccttcttgac gagttcttct gagcgggact    3000
ctggggttcg aaatgaccga ccaagcgacg cccaacctgc catcacgaga tttcgattcc    3060
accgccgcct tctatgaaag gttgggcttc ggaatcgttt tccgggacgc cggctggatg    3120
atcctccagc gcggggatct catgctggag ttcttcgccc accccaactt gtttattgca    3180
gcttataatg gttacaaata aagcaatagc atcacaaatt tcacaaataa agcatttttt    3240
tcactgcatt ctagttgtgg tttgtccaaa ctcatcaatg tatcttatca tgtctgtata    3300
ccgtcgacct ctagctagag cttggcgtaa tcatggtcat agctgtttcc tgtgtgaaat    3360
tgttatccgc tcacaattcc acacaacata cgagccggaa gcataaagtg taaagcctgg    3420
ggtgcctaat gagtgagcta actcacatta attgcgttgc gctcactgcc cgctttccag    3480
tcgggaaacc tgtcgtgcca gctgcattaa tgaatcggcc aacgcgcggg gagaggcggt    3540
ttgcgtattg ggcgctcttc cgcttcctcg ctcactgact cgctgcgctc ggtcgttcgg    3600
ctgcggcgag cggtatcagc tcactcaaag gcggtaatac ggttatccac agaatcaggg    3660
gataacgcag gaaagaacat gtgagcaaaa ggccagcaaa aggccaggaa ccgtaaaaag    3720
gccgcgttgc tggcgttttt ccataggctc cgcccccctg acgagcatca caaaaatcga    3780
cgctcaagtc agaggtggcg aaacccgaca ggactataaa gataccaggc gtttccccct    3840
ggaagctccc tcgtgcgctc tcctgttccg accctgccgc ttaccggata cctgtccgcc    3900
tttctccctt cgggaagcgt ggcgctttct catagctcac gctgtaggta tctcagttcg    3960
gtgtaggtcg ttcgctccaa gctgggctgt gtgcacgaac cccccgttca gcccgaccgc    4020
tgcgccttat ccggtaacta tcgtcttgag tccaacccgg taagacacga cttatcgcca    4080
ctggcagcag ccactggtaa caggattagc agagcgaggt atgtaggcgg tgctacagag    4140
ttcttgaagt ggtggcctaa ctacggctac actagaagaa cagtatttgg tatctgcgct    4200
ctgctgaagc cagttacctt cggaaaaaga gttggtagct cttgatccgg caaacaaacc    4260
accgctggta gcggtttttt tgtttgcaag cagcagatta cgcgcagaaa aaaggatct    4320 caagaagatc ctttgatctt ttctacgggg tctgacgctc agtggaacga aaactcacgt    4380
taagggattt tggtcatgag attatcaaaa aggatcttca cctagatcct tttaaattaa    4440
aaatgaagtt ttaaatcaat ctaaagtata tatgagtaaa cttggtctga cagttaccaa    4500
tgcttaatca gtgaggcacc tatctcagcg atctgtctat ttcgttcatc catagttgcc    4560
tgactccccg tcgtgtagat aactacgata cgggagggct taccatctgg ccccagtgct    4620
```

```
gcaatgatac cgcgagaccc acgctcaccg gctccagatt tatcagcaat aaaccagcca    4680
gccggaaggg ccgagcgcag aagtggtcct gcaactttat ccgcctccat ccagtctatt    4740
aattgttgcc gggaagctag agtaagtagt tcgccagtta atagtttgcg caacgttgtt    4800
gccattgcta caggcatcgt ggtgtcacgc tcgtcgtttg gtatggcttc attcagctcc    4860
ggttcccaac gatcaaggcg agttacatga tcccccatgt tgtgcaaaaa agcggttagc    4920
tccttcggtc ctccgatcgt tgtcagaagt aagttggccg cagtgttatc actcatggtt    4980
atggcagcac tgcataattc tcttactgtc atgccatccg taagatgctt ttctgtgact    5040
ggtgagtact caaccaagtc attctgagaa tagtgtatgc ggcgaccgag ttgctcttgc    5100
ccggcgtcaa tacgggataa taccgcgcca catagcagaa ctttaaaagt gctcatcatt    5160
ggaaaacgtt cttcggggcg aaaactctca aggatcttac cgctgttgag atccagttcg    5220
atgtaaccca ctcgtgcacc caactgatct tcagcatctt ttactttcac cagcgtttct    5280
gggtgagcaa aaacaggaag gcaaaatgcc gcaaaaaagg gaataagggc gacacggaaa    5340
tgttgaatac tcatactctt ccttttcaa tattattgaa gcatttatca gggttattgt     5400
ctcatgagcg gatacatatt tgaatgtatt tagaaaaata acaaataggg gttccgcgc     5460
acatttcccc gaaaagtgcc acctgacgtc                                      5490

<210> SEQ ID NO 56
<211> LENGTH: 5455
<212> TYPE: DNA
<213> ORGANISM: Artificial Sequence
<220> FEATURE:
<223> OTHER INFORMATION: Vector

<400> SEQUENCE: 56
gacggatcgg gagatctccc gatccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag cttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccatggaaca aaaactcatc tcagaagagg atctgggatc    960
cactagtcca gtgtggtgga attctgcaga tatccagcac agtggcggcc gctcgagtct   1020
agagggcccg tttaaacccg ctgatcagcc tcgactgtgc cttctagttg ccagccatct   1080
gttgtttgcc cctcccccgt gccttccttg accctggaag gtgccactcc cactgtcctt   1140
tcctaataaa atgaggaaat tgcatcgcat tgtctgagta ggtgtcattc tattctgggg   1200
```

```
ggtggggtgg ggcaggacag caaggggag gattgggaag acaatagcag gcatgctggg      1260
gatgcggtgg gctctatggc ttctgaggcg gaaagaacca gctggggctc tagggggtat      1320
ccccacgcgc cctgtagcgg cgcattaagc gcggcgggtg tggtggttac gcgcagcgtg      1380
accgctacac ttgccagcgc cctagcgccc gctccttttcg ctttcttccc ttcctttctc      1440
gccacgttcg ccggctttcc ccgtcaagct ctaaatcggg ggctcccttt agggttccga      1500
tttagtgctt tacggcacct cgaccccaaa aaacttgatt agggtgatgg ttcacgtagt      1560
gggccatcgc cctgatagac ggttttttcgc cctttgacgt tggagtccac gttctttaat      1620
agtggactct tgttccaaac tggaacaaca ctcaaccta tctcggtcta ttcttttgat       1680
ttataaggga ttttgccgat ttcggcctat tggttaaaaa atgagctgat ttaacaaaaa      1740
tttaacgcga attaattctg tggaatgtgt gtcagttagg gtgtggaaag tccccaggct      1800
ccccagcagg cagaagtatg caaagcatgc atctcaatta gtcagcaacc aggtgtggaa      1860
agtccccagg ctccccagca ggcagaagta tgcaaagcat gcatctcaat tagtcagcaa      1920
ccatagtccc gccctaact ccgcccatcc cgcccctaac tccgcccagt tccgcccatt      1980
ctccgcccca tggctgacta atttttttta tttatgcaga ggccgaggcc gcctctgcct      2040
ctgagctatt ccagaagtag tgaggaggct ttttggagg cctaggcttt tgcaaaaagc      2100
tcccgggagc ttgtatatcc attttcggat ctgatcaaga gacaggatga ggatcgtttc      2160
gcatgattga acaagatgga ttgcacgcag gttctccggc cgcttgggtg gagaggctat      2220
tcggctatga ctgggcacaa cagacaatcg gctgctctga tgccgccgtg ttccggctgt      2280
cagcgcaggg gcgcccggtt cttttgtca agaccgacct gtccggtgcc ctgaatgaac      2340
tgcaggacga ggcagcgcgg ctatcgtggc tggccacgac gggcgttcct tgcgcagctg      2400
tgctcgacgt tgtcactgaa gcgggaaggg actggctgct attgggcgaa gtgccggggc      2460
aggatctcct gtcatctcac cttgctcctg ccgagaaagt atccatcatg gctgatgcaa      2520
tgcggcggct gcatacgctt gatccggcta cctgcccatt cgaccaccaa gcgaaacatc      2580
gcatcgagcg agcacgtact cggatggaag ccggtcttgt cgatcaggat gatctggacg      2640
aagagcatca ggggctcgcg ccagccgaac tgttcgccag gctcaaggcg cgcatgcccg      2700
acggcgagga tctcgtcgtg acccatggcg atgcctgctt gccgaatatc atggtggaaa      2760
atggccgctt ttctggattc atcgactgtg gccggctggg tgtggcggac cgctatcagg      2820
acatagcgtt ggctacccgt gatattgctg aagagcttgg cggcgaatgg gctgaccgct      2880
tcctcgtgct ttacggtatc gccgctcccg attcgcagcg catcgccttc tatcgccttc      2940
ttgacgagtt cttctgagcg ggactctggg gttcgaaatg accgaccaag cgacgcccaa      3000
cctgccatca cgagatttcg attccaccgc cgccttctat gaaaggttgg gcttcggaat      3060
cgttttccgg gacgccggct ggatgatcct ccagcgcggg gatctcatgc tggagttctt      3120
cgcccacccc aacttgttta ttgcagctta taatggttac aaataaagca atagcatcac      3180
aaatttcaca aataaagcat ttttttcact gcattctagt tgtggtttgt ccaaactcat      3240
caatgtatct tatcatgtct gtataccgtc gacctctagc tagagcttgg cgtaatcatg      3300
gtcatagctg tttcctgtgt gaaattgtta tccgctcaca attccacaca acatacgagc      3360
cggaagcata aagtgtaaag cctggggtgc ctaatgagtg agctaactca cattaattgc      3420
gttgcgctca ctgcccgctt tccagtcggg aaacctgtcg tgccagctgc attaatgaat      3480
cggccaacgc gcggggagag gcggtttgcg tattgggcgc tcttccgctt cctcgctcac      3540
```

```
tgactcgctg cgctcggtcg ttcggctgcg gcgagcggta tcagctcact caaaggcggt    3600
aatacggtta tccacagaat caggggataa cgcaggaaag aacatgtgag caaaaggcca    3660
gcaaaaggcc aggaaccgta aaaaggccgc gttgctggcg ttttttccata ggctccgccc    3720
ccctgacgag catcacaaaa atcgacgctc aagtcagagg tggcgaaacc cgacaggact    3780
ataaagatac caggcgtttc ccctggaag ctccctcgtg cgctctcctg ttccgaccct    3840
gccgcttacc ggatacctgt ccgcctttct cccttcggga agcgtggcgc tttctcatag    3900
ctcacgctgt aggtatctca gttcggtgta ggtcgttcgc tccaagctgg gctgtgtgca    3960
cgaacccccc gttcagcccg accgctgcgc cttatccggt aactatcgtc ttgagtccaa    4020
cccggtaaga cacgacttat cgccactggc agcagccact ggtaacagga ttagcagagc    4080
gaggtatgta ggcggtgcta cagagttctt gaagtggtgg cctaactacg gctacactag    4140
aagaacagta tttggtatct gcgctctgct gaagccagtt accttcggaa aaagagttgg    4200
tagctcttga tccggcaaac aaaccaccgc tggtagcggt ttttttgttt gcaagcagca    4260
gattacgcgc agaaaaaaag gatctcaaga agatcctttg atcttttcta cggggtctga    4320
cgctcagtgg aacgaaaact cacgttaagg gattttggtc atgagattat caaaaaggat    4380
cttcacctag atccttttaa attaaaaatg aagttttaaa tcaatctaaa gtatatatga    4440
gtaaacttgg tctgacagtt accaatgctt aatcagtgag gcacctatct cagcgatctg    4500
tctatttcgt tcatccatag ttgcctgact ccccgtcgtg tagataacta cgatacggga    4560
gggcttacca tctggcccca gtgctgcaat gataccgcga acccacgct caccggctcc    4620
agatttatca gcaataaacc agccagccgg aagggccgag cgcagaagtg gtcctgcaac    4680
tttatccgcc tccatccagt ctattaattg ttgccgggaa gctagagtaa gtagttcgcc    4740
agttaatagt ttgcgcaacg ttgttgccat tgctacaggc atcgtggtgt cacgctcgtc    4800
gtttggtatg gcttcattca gctccggttc ccaacgatca aggcgagtta catgatcccc    4860
catgttgtgc aaaaaagcgg ttagctcctt cggtcctccg atcgttgtca gaagtaagtt    4920
ggccgcagtg ttatcactca tggttatggc agcactgcat aattctctta ctgtcatgcc    4980
atccgtaaga tgcttttctg tgactggtga gtactcaacc aagtcattct gagaatagtg    5040
tatgcggcga ccgagttgct cttgcccggc gtcaatacgg gataataccg cgccacatag    5100
cagaacttta aaagtgctca tcattggaaa acgttcttcg gggcgaaaac tctcaaggat    5160
cttaccgctg ttgagatcca gttcgatgta acccactcgt gcacccaact gatcttcagc    5220
atcttttact ttcaccagcg tttctgggtg agcaaaaaca ggaaggcaaa atgccgcaaa    5280
aaagggaata agggcgacac ggaaatgttg aatactcata ctcttccttt ttcaatatta    5340
ttgaagcatt tatcagggtt attgtctcat gagcggatac atatttgaat gtatttagaa    5400
aaataaacaa ataggggttc cgcgcacatt tccccgaaaa gtgccacctg acgtc    5455

<210> SEQ ID NO 57
<211> LENGTH: 6693
<212> TYPE: DNA
<213> ORGANISM: Artificial Sequence
<220> FEATURE:
<223> OTHER INFORMATION: Construct

<400> SEQUENCE: 57
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
```

-continued

| | |
|---|---|
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaactt aagcttggta ccgagctcgg atccatggaa gacgccaaaa acataaagaa | 960 |
| aggcccggcg ccattctatc cgctggaaga tggaaccgct ggagagcaac tgcataaggc | 1020 |
| tatgaagaga tacgccctgg ttcctggaac aattgctttt acagatgcac atatcgaggt | 1080 |
| ggacatcact tacgctgagt acttcgaaat gtccgttcgg ttggcagaag ctatgaaacg | 1140 |
| atatgggctg aatacaaatc acagaatcgt cgtatgcagt gaaaactctc ttcaattctt | 1200 |
| tatgccggtt ttgggcgcgt tatttatcgg agttgcagtt gcgcccgcga acgacattta | 1260 |
| taatgaacgt gaattgctca acagtatggg catttcgcag cctaccgtgg tgttcgtttc | 1320 |
| caaaaagggg ttgcaaaaaa ttttgaacgt gcaaaaaaag ctcccaatca tccaaaaaat | 1380 |
| tattatcatg gattctaaaa cggattacca gggatttcag tcgatgtaca cgttcgtcac | 1440 |
| atctcatcta cctcccggtt ttaatgaata cgattttgtg ccagagtcct tcgatagggg | 1500 |
| caagacaatt gcactgatca tgaactcctc tggatctact ggtctgccta aaggtgtcgc | 1560 |
| tctgcctcat agaactgcct gcgtgagatt ctcgcatgcc agagatccta ttttggcaa | 1620 |
| tcaaatcatt ccggatactg cgattttaag tgttgttcca ttccatcacg gttttggaat | 1680 |
| gtttactaca ctcggatatt tgatatgtgg atttcgagtc gtcttaatgt atagatttga | 1740 |
| agaagagctg tttctgagga gccttcagga ttacaagatt caaagtgcgc tgctggtgcc | 1800 |
| aaccctattc tccttcttcg ccaaaagcac tctgattgac aaatacgatt tatctaattt | 1860 |
| acacgaaatt gcttctggtg gcgctcccct ctctaaggaa gtcggggaag cggttgccaa | 1920 |
| gaggttccat ctgccaggta tcaggcaagg atatgggctc actgagacta catcagctat | 1980 |
| tctgattaca cccgagggg atgataaacc gggcgcggtc ggtaaagttg ttccattttt | 2040 |
| tgaagcgaag gttgtggatc tggataccgg gaaaacgctg ggcgttaatc aaagaggcga | 2100 |
| actgtgtgtg agaggtccta tgattatgtc cggttatgta aacaatccgg aagcgaccaa | 2160 |
| cgccttgatt gacaaggatg gatggctaca ctgagggcca cagcatgttc gagctcattc | 2220 |
| ctctccagct tctctgcagt tggcggccgc tcgagtctag agggcccgtt taaacccgct | 2280 |
| gatcagcctc gactgtgcct tctagttgcc agccatctgt tgtttgcccc tcccccgtgc | 2340 |
| cttccttgac cctggaaggt gccactccca ctgtcctttc ctaataaaat gaggaaattg | 2400 |
| catcgcattg tctgagtagg tgtcattcta ttctgggggg tggggtgggg caggacagca | 2460 |
| agggggagga ttgggaagac aatagcaggc atgctgggga tgcggtgggc tctatggctt | 2520 |

```
ctgaggcgga aagaaccagc tggggctcta gggggtatcc ccacgcgccc tgtagcggcg      2580
cattaagcgc ggcgggtgtg gtggttacgc gcagcgtgac cgctacactt gccagcgccc      2640
tagcgcccgc tcctttcgct ttcttccctt cctttctcgc cacgttcgcc ggctttcccc      2700
gtcaagctct aaatcggggg ctcccttag ggttccgatt tagtgcttta cggcacctcg      2760
accccaaaaa acttgattag ggtgatggtt cacgtagtgg gccatcgccc tgatagacgg      2820 ttttcgccc tttgacgttg gagtccacgt tctttaatag tggactcttg ttccaaactg      2880
gaacaacact caaccctatc tcggtctatt cttttgattt ataagggatt ttgccgattt      2940
cggcctattg gttaaaaaat gagctgattt aacaaaaatt taacgcgaat taattctgtg      3000
gaatgtgtgt cagttagggt gtggaaagtc cccaggctcc ccagcaggca gaagtatgca      3060
aagcatgcat ctcaattagt cagcaaccag gtgtggaaag tccccaggct ccccagcagg      3120
cagaagtatg caaagcatgc atctcaatta gtcagcaacc atagtcccgc ccctaactcc      3180
gcccatcccg cccctaactc cgcccagttc cgcccattct ccgccccatg gctgactaat      3240 ttttttatt tatgcagagg ccgaggccgc ctctgcctct gagctattcc agaagtagtg      3300
aggaggcttt tttggaggcc taggcttttg caaaaagctc ccgggagctt gtatatccat      3360
tttcggatct gatcaagaga caggatgagg atcgtttcgc atgattgaac aagatggatt      3420
gcacgcaggt tctccggccg cttgggtgga ggctattc ggctatgact gggcacaaca      3480
gacaatcggc tgctctgatg ccgccgtgtt ccggctgtca gcgcagggc gcccggttct      3540 ttttgtcaag accgacctgt ccggtgccct gaatgaactg caggacgagg cagcgcggct      3600
atcgtggctg gccacgacgg gcgttccttg cgcagctgtg ctcgacgttg tcactgaagc      3660
gggaagggac tggctgctat tgggcgaagt gccggggcag atctcctgt catctcacct      3720 tgctcctgcc gagaaagtat ccatcatggc tgatgcaatg cggcggctgc atacgcttga      3780
tccggctacc tgcccattcg accaccaagc gaaacatcgc atcgagcgag cacgtactcg      3840 gatgaagcc ggtcttgtcg atcaggatga tctggacgaa gagcatcagg gctcgcgcc      3900 agccgaactg ttcgccaggc tcaaggcgcg catgcccgac ggcgaggatc tcgtcgtgac      3960
ccatggcgat gcctgcttgc cgaatatcat ggtggaaaat ggccgctttt ctggattcat      4020
cgactgtggc cggctgggtg tggcggaccg ctatcaggac atagcgttgg ctacccgtga      4080
tattgctgaa gagcttggcg gcgaatgggc tgaccgcttc ctcgtgcttt acggtatcgc      4140
cgctcccgat tcgcagcgca tcgccttcta tcgccttctt gacgagttct tctgagcggg      4200
actctggggt tcgaaatgac cgaccaagcg acgcccaacc tgccatcacg agatttcgat      4260
tccaccgccg ccttctatga aggttgggc ttcggaatcg ttttccggga cgccggctgg      4320
atgatcctcc agcgcgggga tctcatgctg gagttcttcg cccacccaa cttgtttatt      4380 gcagcttata atggttacaa ataaagcaat agcatcacaa atttcacaaa taaagcattt      4440
ttttcactgc attctagttg tggtttgtcc aaactcatca atgtatctta tcatgtctgt      4500
ataccgtcga cctctagcta gagcttggcg taatcatggt catagctgtt tcctgtgtga      4560
aattgttatc cgctcacaat tccacacaac atacgagccg aagcataaa gtgtaaagcc      4620 tggggtgcct aatgagtgag ctaactcaca ttaattgcgt tgcgctcact gcccgctttc      4680
cagtcgggaa acctgtcgtg ccagctgcat taatgaatcg gccaacgcgc ggggagaggc      4740
ggtttgcgta ttgggcgctc ttccgcttcc tcgctcactg actcgctgcg ctcggtcgtt      4800
cggctgcggc gagcggtatc agctcactca aaggcggtaa tacggttatc cacagaatca      4860
ggggataacg caggaaagaa catgtgagca aaaggccagc aaaaggccag gaaccgtaaa      4920
```

```
aaggccgcgt tgctggcgtt tttccatagg ctccgccccc ctgacgagca tcacaaaaat    4980
cgacgctcaa gtcagaggtg gcgaaacccg acaggactat aaagatacca ggcgtttccc    5040
cctggaagct ccctcgtgcg ctctcctgtt ccgaccctgc cgcttaccgg atacctgtcc    5100
gcctttctcc cttcgggaag cgtggcgctt tctcatagct cacgctgtag gtatctcagt    5160
tcggtgtagg tcgttcgctc caagctgggc tgtgtgcacg aaccccccgt tcagcccgac    5220
cgctgcgcct tatccggtaa ctatcgtctt gagtccaacc cggtaagaca cgacttatcg    5280
ccactggcag cagccactgg taacaggatt agcagagcga ggtatgtagg cggtgctaca    5340
gagttcttga agtggtggcc taactacggc tacactagaa gaacagtatt tggtatctgc    5400
gctctgctga agccagttac cttcggaaaa agagttggta gctcttgatc cggcaaacaa    5460
accaccgctg gtagcggttt ttttgtttgc aagcagcaga ttacgcgcag aaaaaaagga    5520
tctcaagaag atcctttgat cttttctacg gggtctgacg ctcagtggaa cgaaaactca    5580
cgttaaggga ttttggtcat gagattatca aaaaggatct tcacctagat ccttttaaat    5640
taaaaatgaa gttttaaatc aatctaaagt atatatgagt aaacttggtc tgacagttac    5700
caatgcttaa tcagtgaggc acctatctca gcgatctgtc tatttcgttc atccatagtt    5760
gcctgactcc ccgtcgtgta gataactacg atacgggagg gcttaccatc tggccccagt    5820
gctgcaatga taccgcgaga cccacgctca ccggctccag atttatcagc aataaaccag    5880
ccagccggaa gggccgagcg cagaagtggt cctgcaactt tatccgcctc catccagtct    5940
attaattgtt gccgggaagc tagagtaagt agttcgccag ttaatagttt gcgcaacgtt    6000
gttgccattg ctacaggcat cgtggtgtca cgctcgtcgt ttggtatggc ttcattcagc    6060
tccggttccc aacgatcaag gcgagttaca tgatccccca tgttgtgcaa aaaagcggtt    6120
agctccttcg gtcctccgat cgttgtcaga agtaagttgg ccgcagtgtt atcactcatg    6180
gttatggcag cactgcataa ttctcttact gtcatgccat ccgtaagatg cttttctgtg    6240
actggtgagt actcaaccaa gtcattctga gaatagtgta tgcggcgacc gagttgctct    6300
tgcccggcgt caatacggga taataccgcg ccacatagca gaactttaaa agtgctcatc    6360
attggaaaac gttcttcggg gcgaaaactc tcaaggatct taccgctgtt gagatccagt    6420
tcgatgtaac ccactcgtgc acccaactga tcttcagcat cttttacttt caccagcgtt    6480
tctgggtgag caaaaacagg aaggcaaaat gccgcaaaaa agggaataag ggcgacacgg    6540
aaatgttgaa tactcatact cttcctttttt caatattatt gaagcattta tcagggttat    6600
tgtctcatga gcggatacat atttgaatgt atttagaaaa ataaacaaat aggggttccg    6660
cgcacatttc cccgaaaagt gccacctgac gtc                                 6693
```

<210> SEQ ID NO 58
<211> LENGTH: 6621
<212> TYPE: DNA
<213> ORGANISM: Artificial Sequence
<220> FEATURE:
<223> OTHER INFORMATION: Construct

<400> SEQUENCE: 58

```
gacggatcgg gagatctccc gatcccctat ggtgcactct cagtacaatc tgctctgatg     60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
```

```
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccatggag aagactgagc tgatccagaa    960
ggccaagctg gccgagcagg ccgagcgcta cgacgacatg gccacctgca tgaaggcagt   1020
gaccgagcag ggcgccgagc tgtccaacga ggagcgcaac ctgctctccg tggcctacaa   1080
gaacgtggtc gggggccgca ggtccgcctg gagggtcatc tctagcatcg agcagaagac   1140
cgacacctcc gacaagaagt tgcagctgat taaggactat cgggagaaag tggagtccga   1200
gctgagatcc atctgcacca cggtgctgga attgttggat aaatatttaa tagccaatgc   1260
aactaatcca gagagtaagg tcttctatct gaaaatgaag ggtgattact tccggtacct   1320
tgctgaagtt gcgtgtggtg atgatcgaaa acaaacgata gataattccc aaggagctta   1380
ccaagaggca tttgatataa gcaagaaaga gatgcaaccc acacacccaa tccgcctggg   1440
gcttgctctt aacttttctg tattttacta tgagattctt aataacccag agcttgcctg   1500
cacgctggct aaaacggctt tgatgaggc cattgctgaa cttgatacac tgaatgaaga   1560
ctcatacaaa gacagcaccc tcatcatgca gttgcttaga gacaacctaa cactttggac   1620
atcagacagt gcaggagaag aatgtgatgc ggcagaaggg gctgaaaacg gaggaggagg   1680
tagtggagga ggaggtagtc ctatgattat gtccggttat gtaaacaatc cggaagcgac   1740
caacgccttg attgacaagg atggatggct acattctgga gacatagctt actgggacga   1800
agacgaacac ttcttcatcg ttgaccgcct gaagtctctg attaagtaca aaggctatca   1860
ggtggctccc gctgaattgg aatccatctt gctccaacac cccaacatct cgacgcagg   1920 tgtcgcaggt cttcccgacg atgacgccgg tgaacttccc gccgccgttg ttgtttggga   1980
gcacggaaag acgatgacgg aaaaagagat cgtggattac gtcgccagtc aagtaacaac   2040
cgcgaaaaaa ttgcgcggag gagttgtgtt tgtggacgaa gtaccgaaag gtcttaccgg   2100
aaaactcgac gcaagaaaaa tcagagagat cctcataaag gccaagaagg gcggaaagat   2160
cgccgtgtaa agcggccgct cgagtctaga gggcccgttta acccgctga tcagcctcga   2220 ctgtgccttc tagttgccag ccatctgttg tttgcccctc cccgtgcct tccttgaccc   2280 tggaaggtgc cactcccact gtcctttcct aataaaatga ggaaattgca tcgcattgtc   2340
tgagtaggtg tcattctatt ctgggggggt gggtggggca ggacagcaag ggggaggatt   2400
gggaagacaa tagcaggcat gctggggatg cggtgggctc tatggcttct gaggcggaaa   2460
gaaccagctg gggctctagg gggtatcccc acgcgccctg tagcggcgca ttaagcgcgg   2520
cgggtgtggt ggttacgcgc agcgtgaccg ctacacttgc cagcgcccta gcgcccgctc   2580
ctttcgcttt cttcccttcc tttctcgcca cgttcgccgg ctttccccgt caagctctaa   2640
```

```
atcggggct  cccttttaggg  ttccgattta  gtgctttacg  gcacctcgac  cccaaaaaac   2700
ttgattaggg  tgatggttca  cgtagtgggc  catcgccctg  atagacggtt  tttcgccctt   2760
tgacgttgga  gtccacgttc  tttaatagtg  gactcttgtt  ccaaactgga  acaacactca   2820
accctatctc  ggtctattct  tttgatttat  aagggatttt  gccgatttcg  gcctattggt   2880
taaaaaatga  gctgatttaa  caaaaattta  acgcgaatta  attctgtgga  atgtgtgtca   2940
gttagggtgt  ggaaagtccc  caggctcccc  agcaggcaga  agtatgcaaa  gcatgcatct   3000
caattagtca  gcaaccaggt  gtggaaagtc  cccaggctcc  ccagcaggca  gaagtatgca   3060
aagcatgcat  ctcaattagt  cagcaaccat  agtcccgccc  ctaactccgc  ccatcccgcc   3120
cctaactccg  cccagttccg  cccattctcc  gccccatggc  tgactaattt  ttttattta   3180
tgcagaggcc  gaggccgcct  ctgcctctga  gctattccag  aagtagtgag  gaggctttt   3240
tggaggccta  ggcttttgca  aaaagctccc  gggagcttgt  atatccattt  tcggatctga   3300
tcaagagaca  ggatgaggat  cgtttcgcat  gattgaacaa  gatggattgc  acgcaggttc   3360
tccggccgct  tgggtggaga  ggctattcgg  ctatgactgg  gcacaacaga  caatcggctg   3420
ctctgatgcc  gccgtgttcc  ggctgtcagc  gcaggggcgc  ccggttcttt  ttgtcaagac   3480
cgacctgtcc  ggtgccctga  atgaactgca  ggacgaggca  gcgcggctat  cgtggctggc   3540
cacgacgggc  gttccttgcg  cagctgtgct  cgacgttgtc  actgaagcgg  gaagggactg   3600
gctgctattg  ggcgaagtgc  cggggcagga  tctcctgtca  tctcaccttg  ctcctgccga   3660
gaaagtatcc  atcatggctg  atgcaatgcg  gcggctgcat  acgcttgatc  cggctacctg   3720
cccattcgac  caccaagcga  aacatcgcat  cgagcgagca  cgtactcgga  tggaagccgg   3780
tcttgtcgat  caggatgatc  tggacgaaga  gcatcagggg  ctcgcgccag  ccgaactgtt   3840
cgccaggctc  aaggcgcgca  tgcccgacgg  cgaggatctc  gtcgtgaccc  atggcgatgc   3900
ctgcttgccg  aatatcatgg  tggaaaatgg  ccgcttttct  ggattcatcg  actgtggccg   3960
gctgggtgtg  gcggaccgct  atcaggacat  agcgttggct  acccgtgata  ttgctgaaga   4020
gcttggcggc  gaatgggctg  accgcttcct  cgtgctttac  ggtatcgccg  ctcccgattc   4080
gcagcgcatc  gccttctatc  gccttcttga  cgagttcttc  tgagcgggac  tctggggttc   4140
gaaatgaccg  accaagcgac  gcccaacctg  ccatcacgag  atttcgattc  caccgccgcc   4200
ttctatgaaa  ggttgggctt  cggaatcgtt  ttccgggacg  ccggctggat  gatcctccag   4260
cgcggggatc  tcatgctgga  gttcttcgcc  caccccaact  tgtttattgc  agcttataat   4320
ggttacaaat  aaagcaatag  catcacaaat  ttcacaaata  aagcattttt  ttcactgcat   4380
tctagttgtg  gtttgtccaa  actcatcaat  gtatcttatc  atgtctgtat  accgtcgacc   4440
tctagctaga  gcttggcgta  atcatggtca  tagctgtttc  ctgtgtgaaa  ttgttatccg   4500
ctcacaattc  cacacaacat  acgagccgga  agcataaagt  gtaaagcctg  gggtgcctaa   4560
tgagtgagct  aactcacatt  aattgcgttg  cgctcactgc  ccgctttcca  gtcgggaaac   4620
ctgtcgtgcc  agctgcatta  atgaatcggc  caacgcgcgg  ggagaggcgg  tttgcgtatt   4680
gggcgctctt  ccgcttcctc  gctcactgac  tcgctgcgct  cggtcgttcg  gctgcggcga   4740
gcggtatcag  ctcactcaaa  ggcggtaata  cggttatcca  cagaatcagg  ggataacgca   4800
ggaaagaaca  tgtgagcaaa  aggccagcaa  aaggccagga  accgtaaaaa  ggccgcgttg   4860
ctggcgtttt  tccataggct  ccgcccccct  gacgagcatc  acaaaaatcg  acgctcaagt   4920
cagaggtggc  gaaacccgac  aggactataa  agataccagg  cgtttccccc  tggaagctcc   4980
```

| | |
|---|---:|
| ctcgtgcgct ctcctgttcc gaccctgccg cttaccggat acctgtccgc ctttctccct | 5040 |
| tcgggaagcg tggcgctttc tcatagctca cgctgtaggt atctcagttc ggtgtaggtc | 5100 |
| gttcgctcca agctgggctg tgtgcacgaa ccccccgttc agcccgaccg ctgcgcctta | 5160 |
| tccggtaact atcgtcttga gtccaacccg gtaagacacg acttatcgcc actggcagca | 5220 |
| gccactggta acaggattag cagagcgagg tatgtaggcg gtgctacaga gttcttgaag | 5280 |
| tggtggccta actacggcta cactagaaga acagtatttg gtatctgcgc tctgctgaag | 5340 |
| ccagttacct tcggaaaaag agttggtagc tcttgatccg gcaaacaaac caccgctggt | 5400 |
| agcggttttt ttgtttgcaa gcagcagatt acgcgcagaa aaaaggatc tcaagaagat | 5460 |
| cctttgatct tttctacggg gtctgacgct cagtggaacg aaaactcacg ttaagggatt | 5520 |
| ttggtcatga gattatcaaa aaggatcttc acctagatcc ttttaaatta aaaatgaagt | 5580 |
| tttaaatcaa tctaaagtat atatgagtaa acttggtctg acagttacca atgcttaatc | 5640 |
| agtgaggcac ctatctcagc gatctgtcta tttcgttcat ccatagttgc ctgactcccc | 5700 |
| gtcgtgtaga taactacgat acgggagggc ttaccatctg gccccagtgc tgcaatgata | 5760 |
| ccgcgagacc cacgctcacc ggctccagat ttatcagcaa taaaccagcc agccggaagg | 5820 |
| gccgagcgca gaagtggtcc tgcaacttta tccgcctcca tccagtctat taattgttgc | 5880 |
| cgggaagcta gagtaagtag ttcgccagtt aatagtttgc gcaacgttgt tgccattgct | 5940 |
| acaggcatcg tggtgtcacg ctcgtcgttt ggtatggctt cattcagctc cggttcccaa | 6000 |
| cgatcaaggc gagttacatg atcccccatg ttgtgcaaaa aagcggttag ctccttcggt | 6060 |
| cctccgatcg ttgtcagaag taagttggcc gcagtgttat cactcatggt tatggcagca | 6120 |
| ctgcataatt ctcttactgt catgccatcc gtaagatgct tttctgtgac tggtgagtac | 6180 |
| tcaaccaagt cattctgaga atagtgtatg cggcgaccga gttgctcttg cccggcgtca | 6240 |
| atacgggata ataccgcgcc acatagcaga actttaaaag tgctcatcat tggaaaacgt | 6300 |
| tcttcggggc gaaaactctc aaggatctta ccgctgttga tccagttc gatgtaaccc | 6360 |
| actcgtgcac ccaactgatc ttcagcatct tttactttca ccagcgtttc tgggtgagca | 6420 |
| aaaacaggaa ggcaaaatgc cgcaaaaaag gaataagggc gacacggaa atgttgaata | 6480 |
| ctcatactct tccttttca atattattga agcatttatc agggttattg tctcatgagc | 6540 |
| ggatacatat ttgaatgtat ttagaaaaat aaacaaatag gggttccgcg cacatttccc | 6600 |
| cgaaaagtgc cacctgacgt c | 6621 |

<210> SEQ ID NO 59
<211> LENGTH: 3890
<212> TYPE: DNA
<213> ORGANISM: Artificial Sequence
<220> FEATURE:
<223> OTHER INFORMATION: Construct

<400> SEQUENCE: 59

| | |
|---|---:|
| ggcctaactg gccggtacct gagtctaaat gagtcttcgg acctcgcggg ggccgcttaa | 60 |
| gcggtggtta gggtttgtct gacgcggggg gaggggaag gaacgaaaca ctctcattcg | 120 |
| gaggcggctc ggggtttggt cttggtggcc acggcacgc agaagagcgc cgcgatcctc | 180 |
| ttaagcaccc ccccgccctc cgtggaggcg ggggtttggt cggcgggtgg taactggcgg | 240 |
| gccgctgact cgggcgggtc gcgcgcccca gagtgtgacc ttttcggtct gctcgcaacc | 300 |
| cccgggcggc gccgccgcgg cggcgacggg ctcgctgggg cctaggctcc atggggaccg | 360 |
| tatacgtgga caggctctgg agcatccgca cgactgcggt gatattaccg gagaccttct | 420 |

```
gcgggacgag ccgggtcacg cggctgacgc ggagcgtccg ttgggcgaca aacaccagga      480
cggggcacag gtacactatc ttgtcacccg gaggcgcgag ggactgcagg agcttcaggg      540
agtggcgcag ctgcttcatc cccgtggccc gttgctcgcg tttgctggcg gtgtccccgg      600
aagaaatata tttgcatgtc tttagttcta tgatgacaca aaccccgccc agcgtcttgt      660
cattggcgaa gtcgaacacg cagatgcagt cggggcggcg cggtcccagg tccacttcgc      720
atattaaggt gacgcgtgtg gcctcgaaca ccgagcgacc ctgcagcgac ccgcttaaaa      780
gcttggcaat ccggtactgt tggtaaagcc accatggtct tcacactcga agatttcgtt      840
ggggactggg aacagacagc cgcctacaac ctggaccaag tccttgaaca gggaggtgtg      900
tccagtttgc tgcagaatct cgccgtgtcc gtaactccga tccaaaggat tgtccggagc      960
ggtgaaaatg ccctgaagat cgacatccat gtcatcatcc cgtatgaagg tctgagcgcc     1020
gaccaaatgg cccagatcga agaggtgttt aaggtggtgt accctgtgga tgatcatcac     1080
tttaaggtga tcctgcccta tggcacactg gtaatcgacg gggttacgcc gaacatgctg     1140
aactatttcg gacggccgta tgaaggcatc gccgtgttcg acggcaaaaa gatcactgta     1200
acagggaccc tgtggaacgg caacaaaatt atcgacgagc gcctgatcac ccccgacggc     1260
tccatgctgt tccgagtaac catcaacagt gggagttccg gtggtggcgg gagcggaggt     1320
ggaggctcga gcggtggagc tcaggggaat tccccacagc atgttcgagc tcattcctct     1380
ccagcttctc tgcagttgag atcttctaga gtcggggcgg ccggccgctt cgagcagaca     1440
tgataagata cattgatgag tttgacaaa ccacaactag aatgcagtga aaaaaatgct     1500
ttatttgtga aatttgtgat gctattgctt tatttgtaac cattataagc tgcaataaac     1560
aagttaacaa caacaattgc attcatttta tgtttcaggt tcaggggag gtgtgggagg     1620 ttttttaaag caagtaaaac ctctacaaat gtggtaaaat cgataaggat ccgtcgaccg     1680
atgcccttga gagccttcaa cccagtcagc tccttccggt gggcgcgggg catgactatc     1740
gtcgccgcac ttatgactgt cttctttatc atgcaactcg taggacaggt gccggcagcg     1800
ctcttccgct tcctcgctca ctgactcgct gcgctcggtc gttcggctgc ggcgagcggt     1860
atcagctcac tcaaaggcgg taatacggtt atccacagaa tcaggggata acgcaggaaa     1920
gaacatgtga gcaaaaggcc agcaaaaggc caggaaccgt aaaaaggccg cgttgctggc     1980
gtttttccat aggctccgcc ccctgacga gcatcacaaa aatcgacgct caagtcagag     2040
gtggcgaaac ccgacaggac tataaagata ccaggcgttt ccccctggaa gctccctcgt     2100
gcgctctcct gttccgaccc tgccgcttac cggatacctg tccgcctttc tcccttcggg     2160
aagcgtggcg ctttctcata gctcacgctg taggtatctc agttcggtgt aggtcgttcg     2220
ctccaagctg ggctgtgtgc acgaaccccc cgttcagccc gaccgctgcg ccttatccgg     2280
taactatcgt cttgagtcca acccggtaag acacgactta tcgccactgg cagcagccac     2340
tggtaacagg attagcagag cgaggtatgt aggcggtgct acagagttct tgaagtggtg     2400
gcctaactac ggctacacta gaagaacagt atttggtatc tgcgctctgc tgaagccagt     2460
taccttcgga aaaagagttg gtagctcttg atccggcaaa caaaccaccg ctggtagcgg     2520 tggtttttt gtttgcaagc agcagattac gcgcagaaaa aaaggatctc aagaagatcc     2580
tttgatcttt tctacggggt ctgacgctca gtggaacgaa aactcacgtt aagggatttt     2640
ggtcatgaga ttatcaaaaa ggatcttcac ctagatcctt ttaaattaaa aatgaagttt     2700
taaatcaatc taaagtatat atgagtaaac ttggtctgac agcggccgca aatgctaaac     2760
```

```
cactgcagtg gttaccagtg cttgatcagt gaggcaccga tctcagcgat ctgcctattt   2820
cgttcgtcca tagtggcctg actccccgtc gtgtagatca ctacgattcg tgagggctta   2880
ccatcaggcc ccagcgcagc aatgatgccg cgagagccgc gttcaccggc ccccgatttg   2940
tcagcaatga accagccagc agggagggcc gagcgaagaa gtggtcctgc tactttgtcc   3000
gcctccatcc agtctatgag ctgctgtcgt gatgctagag taagaagttc gccagtgagt   3060
agtttccgaa gagttgtggc cattgctact ggcatcgtgg tatcacgctc gtcgttcggt   3120
atggcttcgt tcaactctgg ttcccagcgg tcaagccggg tcacatgatc acccatatta   3180
tgaagaaatg cagtcagctc cttagggcct ccgatcgttg tcagaagtaa gttggccgcg   3240
gtgttgtcgc tcatggtaat ggcagcacta cacaattctc ttaccgtcat gccatccgta   3300
agatgctttt ccgtgaccgg cgagtactca accaagtcgt tttgtgagta gtgtatacgg   3360
cgaccaagct gctcttgccc ggcgtctata cgggacaaca ccgcgccaca tagcagtact   3420
ttgaaagtgc tcatcatcgg gaatcgttct tcggggcgga aagactcaag gatcttgccg   3480
ctattgagat ccagttcgat atagcccact cttgcaccca gttgatcttc agcatctttt   3540
actttcacca gcgtttcggg gtgtgcaaaa acaggcaagc aaaatgccgc aaagaaggga   3600
atgagtgcga cacgaaaatg ttggatgctc atactcgtcc tttttcaata ttattgaagc   3660
atttatcagg gttactagta cgtctctcaa ggataagtaa gtaatattaa ggtacgggag   3720
gtattggaca ggccgcaata aaatatcttt attttcatta catctgtgtg ttggttttt   3780 gtgtgaatcg atagtactaa catacgctct ccatcaaaac aaaacgaaac aaaacaaact   3840
agcaaaatag gctgtcccca gtgcaagtgc aggtgccaga acatttctct   3890

<210> SEQ ID NO 60
<211> LENGTH: 4131
<212> TYPE: DNA
<213> ORGANISM: Artificial Sequence
<220> FEATURE:
<223> OTHER INFORMATION: Construct

<400> SEQUENCE: 60
ggcctaactg gccggtacct gagtctaaat gagtcttcgg acctcgcggg ggccgcttaa     60
gcggtggtta gggtttgtct gacgcggggg gagggggaag gaacgaaaca ctctcattcg    120
gaggcggctc ggggttttggt cttggtggcc acgggcacgc agaagagcgc cgcgatcctc    180
ttaagcaccc cccgcccctc cgtggaggcg ggggtttggt cggcgggtgg taactggcgg    240
gccgctgact cgggcgggtc gcgcgcccca gagtgtgacc ttttcggtct gctcgcagac    300
ccccgggcgg cgccgccgcg gcggcgacgg gctcgctggg tcctaggctc catggggacc    360
gtatacgtgg acaggctctg gagcatccgc acgactgcgg tgatattacc ggagaccttc    420
tgcgggacga gccgggtcac gcggctgacg cggagcgtcc gttgggcgac aaacaccagg    480
acggggcaca ggtacactat cttgtcaccc ggaggcgcga gggactgcag gagcttcagg    540
gagtggcgca gctgcttcat ccccgtggcc cgttgctcgc gtttgctggc ggtgtccccg    600
gaagaaatat atttgcatgt ctttagttct atgatgacac aaaccccgcc cagcgtcttg    660
tcattggcga agtcgaacac gcagatgcag tcggggcggc gcggtcccag gtccacttcg    720
catattaagg tgacgcgtgt ggcctcgaac accgagcgac cctgcagcga cccgcttaaa    780
agcttggcaa tccggtactg tggtaaagcc accagatcta atggagaaga ctgagctgat    840
ccagaaggcc aagctggccg agcaggccga gcgctacgac gacatggcca cctgcatgaa    900
ggcagtgacc gagcagggcg ccgagctgtc caacgaggag cgcaacctgc tctccgtggc    960
```

```
ctacaagaac gtggtcgggg gccgcaggtc cgcctggagg gtcatctcta gcatcgagca    1020
gaagaccgac acctccgaca agaagttgca gctgattaag gactatcggg agaaagtgga    1080
gtccgagctg agatccatct gcaccacggt gctggaattg ttggataaat atttaatagc    1140
caatgcaact aatccagaga gtaaggtctt ctatctgaaa atgaagggtg attacttccg    1200
gtaccttgct gaagttgcgt gtggtgatga tcgaaaacaa acgatagata attcccaagg    1260
agcttaccaa gaggcatttg atataagcaa gaaagagatg caacccacac acccaatccg    1320
cctggggctt gctcttaact tttctgtatt ttactatgag attcttaata acccagagct    1380
tgcctgcacg ctggctaaaa cggcttttga tgaggccatt gctgaacttg atacactgaa    1440
tgaagactca tacaaagaca gcaccctcat catgcagttg cttagagaca acctaacact    1500
ttggacatca gacagtgcag gagaagaatg tgatgcggca aaggggctg aaaacccgaa     1560 ttctggctcg agcggtggtg gcgggagcgg aggtggaggg tcgtcaggtg tgaccggcta    1620
ccggctgttc gaggagattc tgtaatctag agtcggggcg gccggccgct tcgagcagac    1680
atgataagat acattgatga gtttggacaa accacaacta gaatgcagtg aaaaaaatgc    1740
tttatttgtg aaatttgtga tgctattgct ttatttgtaa ccattataag ctgcaataaa    1800
caagttaaca acaacaattg cattcatttt atgtttcagg ttcaggggga ggtgtgggag    1860
gttttttaaa gcaagtaaaa cctctacaaa tgtggtaaaa tcgataagga tccgtcgacc    1920
gatgcccttg agagccttca acccagtcag ctccttccgg tgggcgcggg gcatgactat    1980
cgtcgccgca cttatgactg tcttctttat catgcaactc gtaggacagg tgccggcagc    2040
gctcttccgc ttcctcgctc actgactcgc tgcgctcggt cgttcggctg cggcgagcgg    2100
tatcagctca ctcaaaggcg gtaatacggt tatccacaga atcaggggat aacgcaggaa    2160
agaacatgtg agcaaaaggc cagcaaaagg ccaggaaccg taaaaaggcc gcgttgctgg    2220
cgttttccca taggctccgc ccccctgacg agcatcacaa aaatcgacgc tcaagtcaga    2280
ggtggcgaaa cccgacagga ctataaagat accaggcgtt tccccctgga agctccctcg    2340
tgcgctctcc tgttccgacc ctgccgctta ccggatacct gtccgccttt ctcccttcgg    2400
gaagcgtggc gctttctcat agctcacgct gtaggtatct cagttcggtg taggtcgttc    2460
gctccaagct gggctgtgtg cacgaacccc ccgttcagcc cgaccgctgc gccttatccg    2520
gtaactatcg tcttgagtcc aacccggtaa gacacgactt atcgccactg gcagcagcca    2580
ctggtaacag gattagcaga gcgaggtatg taggcggtgc tacagagttc ttgaagtggt    2640
ggcctaacta cggctacact agaagaacag tatttggtat ctgcgctctg ctgaagccag    2700
ttaccttcgg aaaaagagtt ggtagctctt gatccggcaa acaaaccacc gctggtagcg    2760
gtggtttttt tgtttgcaag cagcagatta cgcgcagaaa aaaaggatct caagaagatc    2820
ctttgatctt ttctacgggg tctgacgctc agtggaacga aaactcacgt taagggattt    2880
tggtcatgag attatcaaaa aggatcttca cctagatcct tttaaattaa aaatgaagtt    2940
ttaaatcaat ctaaagtata tatgagtaaa cttggtctga cagcggccgc aaatgctaaa    3000
ccactgcagt ggttaccagt gcttgatcag tgaggcaccg atctcagcga tctgcctatt    3060
tcgttcgtcc atagtggcct gactcccgt cgtgtagatc actacgattc gtgagggctt     3120
accatcaggc cccagcgcag caatgatgcc gcgagagccg cgttcaccgg ccccgatttt    3180
gtcagcaatg aaccagccag cagggagggc cgagcgaaga agtggtcctg ctactttgtc    3240
cgcctccatc cagtctatga gctgctgtcg tgatgctaga gtaagaagtt cgccagtgag    3300
```

```
tagtttccga agagttgtgg ccattgctac tggcatcgtg gtatcacgct cgtcgttcgg    3360
tatggcttcg ttcaactctg gttcccagcg gtcaagccgg gtcacatgat cacccatatt    3420
atgaagaaat gcagtcagct ccttagggcc tccgatcgtt gtcagaagta agttggccgc    3480
ggtgttgtcg ctcatggtaa tggcagcact acacaattct cttaccgtca tgccatccgt    3540
aagatgcttt tccgtgaccg gcgagtactc aaccaagtcg ttttgtgagt agtgtatacg    3600
gcgaccaagc tgctcttgcc cggcgtctat acgggacaac accgcgccac atagcagtac    3660
tttgaaagtg ctcatcatcg ggaatcgttc ttcggggcgg aaagactcaa ggatcttgcc    3720
gctattgaga tccagttcga tatagcccac tcttgcaccc agttgatctt cagcatcttt    3780
tactttcacc agcgtttcgg ggtgtgcaaa acaggcaag caaaatgccg caagaaggg     3840 aatgagtgcg acacgaaaat gttggatgct catactcgtc cttttcaat attattgaag     3900 catttatcag ggttactagt acgtctctca aggataagta agtaatatta aggtacggga    3960
ggtattggac aggccgcaat aaaatatctt tattttcatt acatctgtgt gttggttttt    4020
tgtgtgaatc gatagtacta acatacgctc tccatcaaaa caaaacgaaa caaaacaaac    4080
tagcaaaata ggctgtcccc agtgcaagtg caggtgccag aacatttctc t             4131
```

<210> SEQ ID NO 61
<211> LENGTH: 6291
<212> TYPE: DNA
<213> ORGANISM: Artificial Sequence
<220> FEATURE:
<223> OTHER INFORMATION: Construct

<400> SEQUENCE: 61

```
ttcttgaaga cgaaagggcc tcgtgatacg cctattttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtat gagtattcaa catttccgtg tcgcccttat     240
tccctttttt gcggcatttt gccttcctgt ttttgctcac ccagaaacgc tggtgaaagt     300
aaaagatgct gaagatcagt tgggtgcacg agtgggttac atcgaactgg atctcaacag     360
cggtaagatc cttgagagtt ttcgccccga agaacgtttt ccaatgatga gcacttttaa     420
agttctgcta tgtggcgcgg tattatcccg tgttgacgcc gggcaagagc aactcggtcg     480
ccgcatacac tattctcaga atgacttggt tgagtactca ccagtcacag aaaagcatct     540
tacggatggc atgacagtaa gagaattatg cagtgctgcc ataaccatga gtgataacac     600
tgcggccaac ttacttctga caacgatcgg aggaccgaag gagctaaccg cttttttgca     660
caacatgggg gatcatgtaa ctcgccttga tcgttgggaa ccggagctga atgaagccat     720
accaaacgac gagcgtgaca ccacgatgcc tgcagcaatg gcaacaacgt tgcgcaaact     780
attaactggc gaactactta ctctagcttc ccggcaacaa ttaatagact ggatggaggc     840
ggataaagtt gcaggaccac ttctgcgctc ggcccttccg gctggctggt ttattgctga     900
taaatctgga gccggtgagc gtgggtctcg cggtatcatt gcagcactgg ggccagatgg     960
taagccctcc cgtatcgtag ttatctacac gacggggagt caggcaacta tggatgaacg    1020
aaatagacag atcgctgaga taggtgcctc actgattaag cattggtaac tgtcagacca    1080
agtttactca tatatacttt agattgattt aaaacttcat ttttaattta aaaggatcta    1140
ggtgaagatc ctttttgata atctcatgac caaaatccct taacgtgagt ttcgttcca     1200 ctgagcgtca gaccccgtag aaaagatcaa aggatcttct tgagatcctt ttttctgcg    1260
```

-continued

```
cgtaatctgc tgcttgcaaa caaaaaaacc accgctacca gcggtggttt gtttgccgga    1320
tcaagagcta ccaactcttt ttccgaaggt aactggcttc agcagagcgc agataccaaa    1380
tactgtcctt ctagtgtagc cgtagttagg ccaccacttc aagaactctg tagcaccgcc    1440
tacatacctc gctctgctaa tcctgttacc agtggctgct gccagtggcg ataagtcgtg    1500
tcttaccggg ttggactcaa gacgatagtt accggataag gcgcagcggt cgggctgaac    1560
ggggggttcg tgcacacagc ccagcttgga gcgaacgacc tacaccgaac tgagatacct    1620
acagcgtgag ctatgagaaa gcgccacgct tcccgaaggg agaaaggcgg acaggtatcc    1680
ggtaagcggc agggtcggaa caggagagcg cacgagggag cttccagggg gaaacgcctg    1740
gtatctttat agtcctgtcg ggtttcgcca cctctgactt gagcgtcgat ttttgtgatg    1800
ctcgtcaggg gggcggagcc tatggaaaaa cgccagcaac gcggcctttt tacgttcct     1860 ggccttttgc tggccttttg ctcacatgtt ctttcctgcg ttatcccctg attctgtgga    1920
taaccgtatt accgcctttg agtgagctga taccgctcgc cgcagccgaa cgaccgagcg    1980
cagcgagtca gtgagcgagg aagcggaaga gcgcctgatg cggtattttc tccttacgca    2040
tctgtgcggt atttcacacc gcatatatgg tgcactctca gtacaatctg ctctgatgcc    2100
gcatagttaa gccagtatac actccgctat cgctacgtga ctgggtcatg gctgcgcccc    2160
gacacccgcc aacacccgct gacgcgccct gacgggcttg tctgctcccg gcatccgctt    2220
acagacaagc tgtgaccgtc tccgggagct gcatgtgtca gaggttttca ccgtcatcac    2280
cgaaacgcgc gaggcagctg cggtaaagct catcagcgtg gtcgtgaagc gattcacaga    2340
tgtctgcctg ttcatccgcg tccagctcgt tgagtttctc cagaagcgtt aatgtctggc    2400
ttctgataaa gcgggccatg ttaagggcgg ttttttcctg tttggtcact gatgcctccg    2460 tgtaagggg atttctgttc atgggggtaa tgataccgat gaaacgagag aggatgctca    2520
cgatacgggt tactgatgat gaacatgccc ggttactgga acgttgtgag ggtaaacaac    2580
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggaccaacg ctgcccgaga    2940 tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag gcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga agaatcat     3360 aatgggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
```

```
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcgttggga atgtaattca gctccgccat cgccgcttcc acttttttccc   4740
gcgttttcgc agaaacgtgg ctggcctggt tcaccacgcg ggaaacggtc tgataagaga    4800
caccggcata ctctgcgaca tcgtataacg ttactggttt cacattcacc ccctgaatt     4860
gactctcttc cgggcgctat catgccatac cgcgaaaggt tttgcgccat cgatggtgt     4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg     5100
aagtggcgag cccgatcttc cccatcggtg atgtcggcga taggcgcc agcaaccgca      5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gccatcatca tcatcatcat    5340
catcatcatc acagcagcgg ccatatcgaa ggtcgtcata tgatggtctt cacactcgaa    5400
gatttcgttg gggactggga acagacagcc gcctacaacc tggaccaagt ccttgaacag    5460
ggaggtgtgt ccagtttgct gcagaatctc gccgtgtccg taactccgat ccaaaggatt    5520
gtccggagcg gtgaaaatgc cctgaagatc gacatccatg tcatcatccc gtatgaaggt    5580
ctgagcgccg accaaatggc ccagatcgaa gaggtgttta aggtggtgta ccctgtggat    5640
gatcatcact ttaaggtgat cctgcccat ggcacactgg taatcgacgg ggttacgccg    5700
aacatgctga actatttcgg acggccgtat gaaggcatcg ccgtgttcga cggcaaaaag    5760
atcactgtaa cagggaccct gtggaacggc aacaaaatta tcgacgagcg cctgatcacc    5820
cccgacggct ccatgctgtt ccgagtaacc atcaacagtg ggagttccgg tggtggcggg    5880
agcggaggtg gaggctcgag cggtggagct cagggggaatt ccccacagca tgttcgagct   5940
cattcctctc cagcttctct gcagttggga tccggctgct aacaaagccc gaaaggaagc    6000
```

```
tgagttggct gctgccaccg ctgagcaata actagcataa ccccttgggg cctctaaacg    6060
ggtcttgagg ggttttttgc tgaaaggagg aactatatcc ggatatcccg caagaggccc    6120
ggcagtaccg gcataaccaa gcctatgcct acagcatcca gggtgacggt gccgaggatg    6180
acgatgagcg cattgttaga tttcatacac ggtgcctgac tgcgttagca atttaactgt    6240
gataaactac cgcattaaag cttatcgatg ataagctgtc aaacatgaga a             6291
```

<210> SEQ ID NO 62
<211> LENGTH: 6531
<212> TYPE: DNA
<213> ORGANISM: Artificial Sequence
<220> FEATURE:
<223> OTHER INFORMATION: Construct

<400> SEQUENCE: 62

```
ttcttgaaga cgaaagggcc tcgtgatacg cctatttta taggttaatg tcatgataat      60
aatggtttct tagacgtcag gtggcacttt tcggggaaat gtgcgcggaa ccccctatttg   120 tttattttc taaatacatt caaatatgta tccgctcatg agacaataac cctgataaat    180
gcttcaataa tattgaaaaa ggaagagtat gagtattcaa catttccgtg tcgcccttat   240
tccctttttt gcggcatttt gccttcctgt ttttgctcac ccagaaacgc tggtgaaagt   300
aaaagatgct gaagatcagt tgggtgcacg agtgggttac atcgaactgg atctcaacag   360
cggtaagatc cttgagagtt ttcgccccga agaacgtttt ccaatgatga gcacttttaa   420
agttctgcta tgtggcgcgg tattatcccg tgttgacgcc gggcaagagc aactcggtcg   480
ccgcatacac tattctcaga atgacttggt tgagtactca ccagtcacag aaaagcatct   540
tacggatggc atgacagtaa gagaattatg cagtgctgcc ataaccatga gtgataacac   600
tgcggccaac ttacttctga caacgatcgg aggaccgaag gagctaaccg cttttttgca   660
caacatgggg gatcatgtaa ctcgccttga tcgttgggaa ccggagctga atgaagccat   720
accaaacgac gagcgtgaca ccacgatgcc tgcagcaatg gcaacaacgt tgcgcaaact   780
attaactggc gaactactta ctctagcttc ccggcaacaa ttaatagact ggatggaggc   840
ggataaagtt gcaggaccac ttctgcgctc ggcccttccg gctggctggt ttattgctga   900
taaatctgga gccggtgagc gtgggtctcg cggtatcatt gcagcactgg ggccagatgg   960
taagccctcc cgtatcgtag ttatctacac gacggggagt caggcaacta tggatgaacg   1020
aaatagacag atcgctgaga taggtgcctc actgattaag cattggtaac tgtcagacca   1080
agtttactca tatatacttt agattgattt aaaacttcat ttttaattta aaaggatcta   1140
ggtgaagatc cttttgata atctcatgac caaaatccct taacgtgagt tttcgttcca   1200
ctgagcgtca gaccccgtag aaaagatcaa aggatcttct tgagatcctt ttttctgcg   1260 cgtaatctgc tgcttgcaaa caaaaaaacc accgctacca gcggtggttt gtttgccgga   1320
tcaagagcta ccaactcttt ttccgaaggt aactggcttc agcagagcgc agataccaaa   1380
tactgtcctt ctagtgtagc cgtagttagg ccaccacttc aagaactctg tagcaccgcc   1440
tacatacctc gctctgctaa tcctgttacc agtggctgct gccagtggcg ataagtcgtg   1500
tcttaccggg ttggactcaa gacgatagtt accggataag gcgcagcggt cgggctgaac   1560
ggggggttcg tgcacacagc ccagcttgga gcgaacgacc tacaccgaac tgagatacct   1620
acagcgtgag ctatgagaaa gcgccacgct cccgaaggg agaaaggcgg acaggtatcc   1680
ggtaagcggc agggtcggaa caggagagcg cacgagggag cttccagggg gaaacgcctg   1740
```

```
gtatctttat agtcctgtcg ggtttcgcca cctctgactt gagcgtcgat ttttgtgatg   1800
ctcgtcaggg gggcggagcc tatggaaaaa cgccagcaac gcggccttttt tacggttcct   1860
ggccttttgc tggccttttg ctcacatgtt ctttcctgcg ttatcccctg attctgtgga   1920
taaccgtatt accgcctttg agtgagctga taccgctcgc cgcagccgaa cgaccgagcg   1980
cagcgagtca gtgagcgagg aagcggaaga gcgcctgatg cggtattttc tccttacgca   2040
tctgtgcggt atttcacacc gcatatatgg tgcactctca gtacaatctg ctctgatgcc   2100
gcatagttaa gccagtatac actccgctat cgctacgtga ctgggtcatg gctgcgcccc   2160
gacacccgcc aacacccgct gacgcgccct gacgggcttg tctgctcccg gcatccgctt   2220
acagacaagc tgtgaccgtc tccgggagct gcatgtgtca gaggttttca ccgtcatcac   2280
cgaaacgcgc gaggcagctg cggtaaagct catcagcgtg gtcgtgaagc gattcacaga   2340
tgtctgcctg ttcatccgcg tccagctcgt tgagtttctc cagaagcgtt aatgtctggc   2400
ttctgataaa gcgggccatg ttaagggcgg ttttttcctg tttggtcact gatgcctccg   2460
tgtaaggggg atttctgttc atgggggtaa tgataccgat gaaacgagag aggatgctca   2520
cgatacgggt tactgatgat gaacatgccc ggttactgga acgttgtgag ggtaaacaac   2580
tggcggtatg gatgcggcgg gaccagagaa aaatcactca gggtcaatgc cagcgcttcg   2640
ttaatacaga tgtaggtgtt ccacagggta gccagcagca tcctgcgatg cagatccgga   2700
acataatggt gcagggcgct gacttccgcg tttccagact ttacgaaaca cggaaaccga   2760
agaccattca tgttgttgct caggtcgcag acgttttgca gcagcagtcg cttcacgttc   2820
gctcgcgtat cggtgattca ttctgctaac cagtaaggca accccgccag cctagccggg   2880
tcctcaacga caggagcacg atcatgcgca cccgtggcca ggacccaacg ctgcccgaga   2940
tgcgccgcgt gcggctgctg gagatggcgg acgcgatgga tatgttctgc caagggttgg   3000
tttgcgcatt cacagttctc cgcaagaatt gattggctcc aattcttgga gtggtgaatc   3060
cgttagcgag gtgccgccgg cttccattca ggtcgaggtg gcccggctcc atgcaccgcg   3120
acgcaacgcg gggaggcaga caaggtatag gcggcgcct acaatccatg ccaacccgtt   3180
ccatgtgctc gccgaggcgg cataaatcgc cgtgacgatc agcggtccag tgatcgaagt   3240
taggctggta agagccgcga gcgatccttg aagctgtccc tgatggtcgt catctacctg   3300
cctggacagc atggcctgca acgcgggcat cccgatgccg ccggaagcga agaatcat    3360
aatgggaag gccatccagc ctcgcgtcgc gaacgccagc aagacgtagc ccagcgcgtc   3420
ggccgccatg ccggcgataa tggcctgctt ctcgccgaaa cgtttggtgg cgggaccagt   3480
gacgaaggct tgagcgaggg cgtgcaagat tccgaatacc gcaagcgaca ggccgatcat   3540
cgtcgcgctc cagcgaaagc ggtcctcgcc gaaaatgacc cagagcgctg ccggcacctg   3600
tcctacgagt tgcatgataa agaagacagt cataagtgcg gcgacgatag tcatgccccg   3660
cgcccaccgg aaggagctga ctgggttgaa ggctctcaag ggcatcggtc gagatcccgg   3720
tgcctaatga gtgagctaac ttacattaat tgcgttgcgc tcactgcccg ctttccagtc   3780
gggaaacctg tcgtgccagc tgcattaatg aatcggccaa cgcgcgggga gagcggtttt   3840
gcgtattggg cgccagggtg ttttctcttt tcaccagtga cgggcaac agctgattgc   3900
ccttcaccgc ctggccctga gagagttgca gcaagcggtc cacgctggtt tgccccagca   3960
ggcgaaaatc ctgtttgatg gtggttaacg gcgggatata acatgagctg tcttcggtat   4020
cgtcgtatcc cactaccgag atatccgcac caacgcgcag cccggactcg gtaatggcgc   4080
gcattgcgcc cagcgccatc tgatcgttgg caaccagcat cgcagtggga acgatgccct   4140
```

```
cattcagcat ttgcatggtt tgttgaaaac cggacatggc actccagtcg ccttcccgtt   4200
ccgctatcgg ctgaatttga ttgcgagtga gatatttatg ccagccagcc agacgcagac   4260
gcgccgagac agaacttaat gggcccgcta acagcgcgat ttgctggtga cccaatgcga   4320
ccagatgctc cacgcccagt cgcgtaccgt cttcatggga gaaaataata ctgttgatgg   4380
gtgtctggtc agagacatca agaaataacg ccggaacatt agtgcaggca gcttccacag   4440
caatggcatc ctggtcatcc agcggatagt taatgatcag cccactgacg cgttgcgcga   4500
gaagattgtg caccgccgct ttacaggctt cgacgccgct tcgttctacc atcgacacca   4560
ccacgctggc acccagttga tcggcgcgag atttaatcgc cgcgacaatt gcgacggcg   4620 cgtgcagggc cagactggag gtggcaacgc caatcagcaa cgactgtttg cccgccagtt   4680
gttgtgccac gcggttggga atgtaattca gctccgccat cgccgcttcc acttttcccc   4740
gcgttttcgc agaaacgtgg ctggcctggt tcaccacgcg ggaaacggtc tgataagaga   4800
caccggcata ctctgcgaca tcgtataacg ttactggttt cacattcacc accctgaatt   4860
gactctcttc cgggcgctat catgccatac cgcgaaaggt tttgcgccat tcgatggtgt   4920
ccgggatctc gacgctctcc cttatgcgac tcctgcatta ggaagcagcc cagtagtagg   4980
ttgaggccgt tgagcaccgc cgccgcaagg aatggtgcat gcaaggagat ggcgcccaac   5040
agtcccccgg ccacggggcc tgccaccata cccacgccga acaagcgct catgagcccg    5100 aagtggcgag cccgatcttc cccatcggtg atgtcggcga tataggcgcc agcaaccgca   5160
cctgtggcgc cggtgatgcc ggccacgatg cgtccggcgt agaggatcga gatctcgatc   5220
ccgcgaaatt aatacgactc actatagggg aattgtgagc ggataacaat tcccctctag   5280
aaataatttt gtttaacttt aagaaggaga tataccatgg ccatcatca tcatcatcat   5340 catcatcatc acagcagcgg ccatatcgaa ggtcgtcata tgatggagaa gactgagctg   5400
atccagaagg ccaagctggc cgagcaggcc gagcgctacg acgacatggc cacctgcatg   5460
aaggcagtga ccgagcaggg cgccgagctg tccaacgagg agcgcaacct gctctccgtg   5520
gcctacaaga acgtggtcgg gggccgcagg tccgcctgga gggtcatctc tagcatcgag   5580
cagaagaccg acacctccga caagaagttg cagctgatta aggactatcg ggagaaagtg   5640
gagtccgagc tgagatccat ctgccaccac gtgctggaat tgttggataa atatttaata   5700
gccaatgcaa ctaatccaga gagtaaggtc ttctatctga aaatgaaggg tgattacttc   5760
cggtaccttg ctgaagttgc gtgtggtgat gatcgaaaac aaacgataga taattcccaa   5820
ggagcttacc aagaggcatt tgatataagc aagaaagaga tgcaacccac acacccaatc   5880
cgcctggggc ttgctcttaa cttttctgta ttttactatg agattcttaa taacccagag   5940
cttgcctgca cgctggctaa aacggctttt gatgaggcca ttgctgaact tgatacactg   6000
aatgaagact catacaaaga cagcacactc atcatgcagt tgcttagaga caacctaaca   6060
ctttggacat cagacagtgc aggagaagaa tgtgatgcgg cagaagggc tgaaaacccg   6120 aattctggct cgagcggtgg tggcgggagc ggaggtggag ggtcgtcagg tgtgaccggc   6180
taccggctgt tcgaggagat tctgtaagga tccggctgct aacaaagccc gaaaggaagc   6240
tgagttggct gctgccaccg ctgagcaata actagcataa ccccttgggg cctctaaacg   6300
ggtcttgagg ggttttttgc tgaaaggagg aactatatcc ggatatcccg caagaggccc   6360
ggcagtaccg gcataaccaa gcctatgcct acagcatcca gggtgacggt gccgaggatg   6420
```

```
acgatgagcg cattgttaga tttcatacac ggtgcctgac tgcgttagca atttaactgt    6480
gataaactac cgcattaaag cttatcgatg ataagctgtc aaacatgaga a              6531
```

<210> SEQ ID NO 63
<211> LENGTH: 6297
<212> TYPE: DNA
<213> ORGANISM: Artificial Sequence
<220> FEATURE:
<223> OTHER INFORMATION: Construct

<400> SEQUENCE: 63

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta caactccgc cccattgacg caaatgggcg     780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccatggtc ttcacactcg aagatttcgt    960 tgggactgg gaacagacag ccgcctacaa cctggaccaa gtccttgaac agggaggtgt    1020
gtccagtttg ctgcagaatc tcgccgtgtc cgtaactccg atccaaagga ttgtccggag   1080
cggtgaaaat gccctgaaga tcgacatcca tgtcatcatc ccgtatgaag gtctgagcgc   1140
cgaccaaatg gcccagatcg aagaggtgtt taagtggtg taccctgtgg atgatcatca    1200
ctttaaggtg atcctgccct atggcacact ggtaatcgac ggggttacgc gaacatgct    1260 gaactatttc ggacggccgt atgaaggcat cgccgtgttc gacggcaaaa agatcactgt   1320
aacagggacc ctgtggaacg gcaacaaaat tatcgacgag cgcctgatca ccccgacgg    1380 ctccatgctg ttccgagtaa ccatcaacag tgggagttcc ggtggtggcg ggagcggagg   1440
tggaggctcg agcggtgccg ggcatcagat cgtgcacgtc gcgggggact cggagaccga   1500
cctggaggcg ctcttcaacg ccgtcatgaa cccaagacg ccaacgtgc cccagaccgt     1560 gcccatgagg ctccggaagc tgcccgactc cttcttcaag ccgccggagc caaatcca    1620 ctcccgacag gccagtactg atgcaggcac tgcaggagcc ctgactccac agcatgttcg   1680
agctcattcc tctccagctt ctctgcagtt gggagctgtt tctcctggga cactgacccc   1740
cactggagta gtctctggcc cagcagctac acccacagct cagcatcttc gacagtcttc   1800
ttttgagata cctgatgatg tacttgtcgt catcgtcttt gtagtcgcgg ccgctcgagt   1860
ctagagggcc cgtttaaacc cgctgatcag cctcgactgt gccttctagt tgccagccat   1920
```

```
ctgttgtttg cccctccccc gtgccttcct tgaccctgga aggtgccact cccactgtcc   1980
tttcctaata aaatgaggaa attgcatcgc attgtctgag taggtgtcat tctattctgg   2040
ggggtggggt ggggcaggac agcaagggg aggattggga agacaatagc aggcatgctg    2100
gggatgcggt gggctctatg gcttctgagg cggaaagaac cagctgggc tctagggggt    2160
atccccacgc gccctgtagc ggcgcattaa gcgcggcggg tgtggtggtt acgcgcagcg   2220
tgaccgctac acttgccagc gccctagcgc ccgctccttt cgctttcttc ccttcctttc   2280
tcgccacgtt cgccggcttt ccccgtcaag ctctaaatcg gggctccct ttagggttcc    2340
gatttagtgc tttacggcac ctcgacccca aaaaacttga ttagggtgat ggttcacgta   2400
gtgggccatc gccctgatag acggtttttc gccctttgac gttggagtcc acgttcttta   2460
atagtggact cttgttccaa actggaacaa cactcaaccc tatctcggtc tattcttttg   2520
atttataagg gattttgccg atttcggcct attggttaaa aaatgagctg atttaacaaa   2580
aatttaacgc gaattaattc tgtggaatgt gtgtcagtta gggtgtggaa agtccccagg   2640
ctccccagca ggcagaagta tgcaaagcat gcatctcaat tagtcagcaa ccaggtgtgg   2700
aaagtcccca ggctccccag caggcagaag tatgcaaagc atgcatctca attagtcagc   2760
aaccatagtc ccgcccctaa ctccgcccat cccgccccta actccgccca gttccgccca   2820
ttctccgccc catggctgac taattttttt tatttatgca gaggccgagg ccgcctctgc   2880
ctctgagcta ttccagaagt agtgaggagg cttttttgga ggcctaggct tttgcaaaaa   2940
gctcccggga gcttgtatat ccattttcgg atctgatcaa gagacaggat gaggatcgtt   3000
tcgcatgatt gaacaagatg gattgcacgc aggttctccg gccgcttggg tggagaggct   3060
attcggctat gactgggcac aacagacaat cggctgctct gatgccgccg tgttccggct   3120
gtcagcgcag gggcgcccgg ttcttttgt caagaccgac ctgtccggtg ccctgaatga    3180
actgcaggac gaggcagcgc ggctatcgtg gctggccacg acgggcgttc cttgcgcagc   3240
tgtgctcgac gttgtcactg aagcgggaag ggactggctg ctattgggcg aagtgccggg   3300
gcaggatctc ctgtcatctc accttgctcc tgccgagaaa gtatccatca tggctgatgc   3360
aatgcggcgg ctgcatacgc ttgatccggc tacctgccca ttcgaccacc aagcgaaaca   3420
tcgcatcgag cgagcacgta ctcggatgga agccggtctt gtcgatcagg atgatctgga   3480
cgaagagcat caggggctcg cgccagccga actgttcgcc aggctcaagg cgcgcatgcc   3540
cgacggcgag gatctcgtcg tgacccatgg cgatgcctgc ttgccgaata tcatggtgga   3600
aaatggccgc ttttctggat tcatcgactg tggccggctg ggtgtggcgg accgctatca   3660
ggacatagcg ttggctaccc gtgatattgc tgaagagctt ggcggcgaat gggctgaccg   3720
cttcctcgtg ctttacggta tcgccgctcc cgattcgcag cgcatcgcct tctatcgcct   3780
tcttgacgag ttcttctgag cgggactctg gggttcgaaa tgaccgacca agcgacgccc   3840
aacctgccat cacgagattt cgattccacc gccgccttct atgaaaggtt gggcttcgga   3900
atcgttttcc gggacgccgg ctggatgatc ctccagcgcg ggatctcat gctggagttc    3960
ttcgcccacc ccaacttgtt tattgcagct tataatggtt acaaataaag caatagcatc   4020
acaaatttca caaataaagc atttttttca ctgcattcta gttgtggttt gtccaaactc   4080
atcaatgtat cttatcatgt ctgtataccg tcgacctcta gctagagctt ggcgtaatca   4140
tggtcatagc tgtttcctgt gtgaaattgt tatccgctca caattccaca acatacga    4200
gccgaaagca taaagtgtaa agcctggggt gcctaatgag tgagctaact cacattaatt   4260
gcgttgcgct cactgcccgc tttccagtcg ggaaacctgt cgtgccagct gcattaatga   4320
```

```
atcggccaac gcgcggggag aggcggtttg cgtattgggc gctcttccgc ttcctcgctc    4380
actgactcgc tgcgctcggt cgttcggctg cggcgagcgg tatcagctca ctcaaaggcg    4440
gtaatacggt tatccacaga atcaggggat aacgcaggaa agaacatgtg agcaaaaggc    4500
cagcaaaagg ccaggaaccg taaaaaggcc gcgttgctgg cgtttttcca taggctccgc    4560 cccctgacg agcatcacaa aaatcgacgc tcaagtcaga ggtggcgaaa cccgacagga    4620
ctataaagat accaggcgtt tccccctgga agctccctcg tgcgctctcc tgttccgacc    4680
ctgccgctta ccggatacct gtccgccttt ctcccttcgg gaagcgtggc gctttctcat    4740
agctcacgct gtaggtatct cagttcggtg taggtcgttc gctccaagct gggctgtgtg    4800
cacgaacccc ccgttcagcc cgaccgctgc gccttatccg gtaactatcg tcttgagtcc    4860
aacccggtaa gacacgactt atcgccactg gcagcagcca ctggtaacag gattagcaga    4920
gcgaggtatg taggcggtgc tacagagttc ttgaagtggt ggcctaacta cggctacact    4980
agaagaacag tatttggtat ctgcgctctg ctgaagccag ttaccttcgg aaaaagagtt    5040
ggtagctctt gatccggcaa acaaaccacc gctggtagcg gtttttttgt ttgcaagcag    5100
cagattacgc gcagaaaaaa aggatctcaa gaagatcctt tgatcttttc tacggggtct    5160
gacgctcagt ggaacgaaaa ctcacgttaa gggattttgg tcatgagatt atcaaaaagg    5220
atcttcacct agatcctttt aaattaaaaa tgaagtttta aatcaatcta agtatatat    5280 gagtaaactt ggtctgacag ttaccaatgc ttaatcagtg aggcacctat ctcagcgatc    5340
tgtctatttc gttcatccat agttgcctga ctccccgtcg tgtagataac tacgatacgg    5400
gagggcttac catctggccc cagtgctgca atgataccgc gagacccacg ctcaccggct    5460
ccagatttat cagcaataaa ccagccagcc ggaagggccg agcgcagaag tggtcctgca    5520
actttatccg cctccatcca gtctattaat tgttgccggg aagctagagt aagtagttcg    5580
ccagttaata gtttgcgcaa cgttgttgcc attgctacag gcatcgtggt gtcacgctcg    5640
tcgtttggta tggcttcatt cagctccggt tcccaacgat caaggcgagt tacatgatcc    5700
cccatgttgt gcaaaaaagc ggttagctcc ttcggtcctc cgatcgttgt cagaagtaag    5760
ttggccgcag tgttatcact catggttatg gcagcactgc ataattctct tactgtcatg    5820
ccatccgtaa gatgcttttc tgtgactggt gagtactcaa ccaagtcatt ctgagaatag    5880
tgtatgcggc gaccgagttg ctcttgcccg gcgtcaatac gggataatac cgcgccacat    5940
agcagaactt taaaagtgct catcattgga aaacgttctt cggggcgaaa actctcaagg    6000
atcttaccgc tgttgagatc cagttcgatg taacccactc gtgcacccaa ctgatcttca    6060
gcatctttta ctttcaccag cgtttctggg tgagcaaaaa caggaaggca aaatgccgca    6120
aaaaagggaa taagggcgac acggaaatgt tgaatactca tactcttcct ttttcaatat    6180
tattgaagca tttatcaggg ttattgtctc atgagcggat acatatttga atgtatttag    6240
aaaaataaac aaatagggt tccgcgcaca tttccccgaa aagtgccacc tgacgtc       6297
```

<210> SEQ ID NO 64
<211> LENGTH: 6270
<212> TYPE: DNA
<213> ORGANISM: Artificial Sequence
<220> FEATURE:
<223> OTHER INFORMATION: Construct

<400> SEQUENCE: 64

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccgccggg catcagatcg tgcacgtccg     960
cggggactcg gagaccgacc tggaggcgct cttcaacgcc gtcatgaacc ccaagacggc    1020
caacgtgccc cagaccgtgc ccatgaggct ccggaagctg cccgactcct tcttcaagcc    1080
gccggagccc aaatcccact cccgacaggc cagtactgat gcaggcactg caggagccct    1140
gactccacag catgttcgag ctcattcctc tccagcttct ctgcagttgg gagctgtttc    1200
tcctgggaca ctgaccccca ctggagtagt ctctggccca gcagctacac ccacagctca    1260
gcatcttcga cagtcttctt ttgagatacc tgatgatgta ggctcgagcg gtggtggcgg    1320
gagcggaggt ggagggtcgt caggtgtctt cacactcgaa gatttcgttg gggactggga    1380
acagacagcc gcctacaacc tggaccaagt ccttgaacag ggaggtgtgt ccagtttgct    1440
gcagaatctc gccgtgtccg taactccgat ccaaaggatt gtccggagcg gtgaaaatgc    1500
cctgaagatc gacatccatg tcatcatccc gtatgaaggt ctgagcgccg accaaatggc    1560
ccagatcgaa gaggtgttta aggtggtgta ccctgtggat gatcatcact ttaaggtgat    1620
cctgccctat ggcacactgg taatcgacgg ggttacgccg aacatgctga actatttcgg    1680
acggccgtat gaaggcatcg ccgtgttcga cggcaaaaag atcactgtaa cagggaccct    1740
gtggaacggc aacaaaatta tcgacgagcg cctgatcacc cccgacggct ccatgctgtt    1800
ccgagtaacc atcaacagcg cggccgctcg agtctagagg gcccgtttaa acccgctgat    1860
cagcctcgac tgtgccttct agttgccagc catctgttgt ttgcccctcc cccgtgcctt    1920
ccttgaccct ggaaggtgcc actcccactg tcctttccta ataaaatgag gaaattgcat    1980
cgcattgtct gagtaggtgt cattctattc tggggggtgg ggtggggcag gacagcaagg    2040
gggaggattg ggaagacaat agcaggcatg ctggggatgc ggtgggctct atggcttctg    2100
aggcggaaag aaccagctgg ggctctaggg ggtatcccca cgcgccctgt agcggcgcat    2160
taagcgcggc gggtgtggtg gttacgcgca gcgtgaccgc tacacttgcc agcgccctag    2220
cgcccgctcc tttcgctttc ttcccttcct ttctcgccac gttcgccggc tttccccgtc    2280
```

```
aagctctaaa tcggggcctc cctttagggt tccgatttag tgctttacgg cacctcgacc    2340
ccaaaaaact tgattagggt gatggttcac gtagtgggcc atcgccctga tagacggttt    2400
ttcgcccttt gacgttggag tccacgttct ttaatagtgg actcttgttc caaactggaa    2460
caacactcaa ccctatctcg gtctattctt ttgatttata agggattttg ccgatttcgg    2520
cctattggtt aaaaaatgag ctgatttaac aaaaatttaa cgcgaattaa ttctgtggaa    2580
tgtgtgtcag ttagggtgtg gaaagtcccc aggctcccca gcaggcagaa gtatgcaaag    2640
catgcatctc aattagtcag caaccaggtg tggaaagtcc ccaggctccc cagcaggcag    2700
aagtatgcaa agcatgcatc tcaattagtc agcaaccata gtcccgcccc taactccgcc    2760
catcccgccc ctaactccgc ccagttccgc ccattctccg ccccatggct gactaatttt    2820
ttttatttat gcagaggccg aggccgcctc tgcctctgag ctattccaga agtagtgagg    2880 aggcttttt ggaggcctag gcttttgcaa aaagctcccg ggagcttgta tatccatttt    2940
cggatctgat caagacagc gatgaggatc gtttcgcatg attgaacaag atggattgca    3000
cgcaggttct ccggccgctt gggtggagag gctattcggc tatgactggg cacaacagac    3060
aatcggctgc tctgatgccg ccgtgttccg gctgtcagcg caggggcgcc cggttctttt    3120
tgtcaagacc gacctgtccg gtgccctgaa tgaactgcag gacgaggcag cgcggctatc    3180
gtggctggcc acgacgggcg ttccttgcgc agctgtgctc gacgttgtca ctgaagcggg    3240
aagggactgg ctgctattgg gcgaagtgcc ggggcaggat ctcctgtcat ctcaccttgc    3300
tcctgccgag aaagtatcca tcatggctga tgcaatgcgg cggctgcata cgcttgatcc    3360
ggctacctgc ccattcgacc accaagcgaa acatcgcatc gagcgagcac gtactcggat    3420
ggaagccggt cttgtcgatc aggatgatct ggacgaagag catcaggggc tcgcgccagc    3480
cgaactgttc gccaggctca aggcgcgcat gcccgacggc gaggatctcg tcgtgaccca    3540
tggcgatgcc tgcttgccga atatcatggt ggaaaatggc cgcttttctg gattcatcga    3600
ctgtggccgg ctgggtgtgg cggaccgcta tcaggacata gcgttggcta cccgtgatat    3660
tgctgaagag cttggcggcg aatgggctga ccgcttcctc gtgctttacg gtatcgccgc    3720
tcccgattcg cagcgcatcg ccttctatcg ccttcttgac gagttcttct gagcgggact    3780
ctggggttcg aaatgaccga ccaagcgacg cccaacctgc catcacgaga tttcgattcc    3840
accgccgcct tctatgaaag gttgggcttc ggaatcgttt tccggacgc ggctggatg    3900 atcctccagc gcggggatct catgctggag ttcttcgccc accccaactt gtttattgca    3960
gcttataatg gttacaaata aagcaatagc atcacaaatt tcacaaataa agcatttttt    4020
tcactgcatt ctagttgtgg tttgtccaaa ctcatcaatg tatcttatca tgtctgtata    4080
ccgtcgacct ctagctagag cttggcgtaa tcatggtcat agctgtttcc tgtgtgaaat    4140
tgttatccgc tcacaattcc acacaacata cgagccggaa gcataaagtg taaagcctgg    4200
ggtgcctaat gagtgagcta actcacatta attgcgttgc gctcactgcc cgctttccag    4260
tcgggaaacc tgtcgtgcca gctgcattaa tgaatcggcc aacgcgcggg gagaggcggt    4320
ttgcgtattg ggcgctcttc cgcttcctcg ctcactgact cgctgcgctc ggtcgttcgg    4380
ctgcggcgag cggtatcagc tcactcaaag gcggtaatac ggttatccac agaatcaggg    4440
gataacgcag gaaagaacat gtgagcaaaa ggccagcaaa aggccaggaa ccgtaaaaag    4500
gccgcgttgc tggcgttttt ccataggctc cgcccccctg acgagcatca caaaaatcga    4560
cgctcaagtc agaggtggcg aaacccgaca ggactataaa gataccaggc gtttccccct    4620
ggaagctccc tcgtgcgctc tcctgttccg accctgccgc ttaccggata cctgtccgcc    4680
```

```
tttctccctt cgggaagcgt ggcgctttct catagctcac gctgtaggta tctcagttcg    4740
gtgtaggtcg ttcgctccaa gctgggctgt gtgcacgaac ccccgttca gcccgaccgc    4800 tgcgccttat ccgtaacta tcgtcttgag tccaacccgg taagacacga cttatcgcca    4860
ctggcagcag ccactggtaa caggattagc agagcgaggt atgtaggcgg tgctacagag    4920
ttcttgaagt ggtggcctaa ctacggctac actagaagaa cagtatttgg tatctgcgct    4980
ctgctgaagc cagttacctt cggaaaaaga gttggtagct cttgatccgg caaacaaacc    5040
accgctggta gcggtttttt tgtttgcaag cagcagatta cgcgcagaaa aaaggatct    5100 caagaagatc ctttgatctt ttctacgggg tctgacgctc agtggaacga aaactcacgt    5160
taagggattt tggtcatgag attatcaaaa aggatcttca cctagatcct tttaaattaa    5220
aaatgaagtt ttaaatcaat ctaaagtata tatgagtaaa cttggtctga cagttaccaa    5280
tgcttaatca gtgaggcacc tatctcagcg atctgtctat ttcgttcatc catagttgcc    5340
tgactccccg tcgtgtagat aactacgata cgggagggct taccatctgg ccccagtgct    5400
gcaatgatac cgcgagaccc acgctcaccg gctccagatt tatcagcaat aaaccagcca    5460
gccggaaggg ccgagcgcag aagtggtcct gcaactttat ccgcctccat ccagtctatt    5520
aattgttgcc gggaagctag agtaagtagt tcgccagtta atagtttgcg caacgttgtt    5580
gccattgcta caggcatcgt ggtgtcacgc tcgtcgtttg gtatggcttc attcagctcc    5640
ggttcccaac gatcaaggcg agttacatga tcccccatgt tgtgcaaaaa agcggttagc    5700
tccttcggtc ctccgatcgt tgtcagaagt aagttggccg cagtgttatc actcatggtt    5760
atggcagcac tgcataattc tcttactgtc atgccatccg taagatgctt ttctgtgact    5820
ggtgagtact caaccaagtc attctgagaa tagtgtatgc ggcgaccgag ttgctcttgc    5880
ccggcgtcaa tacgggataa taccgcgcca catagcagaa ctttaaaagt gctcatcatt    5940
ggaaaacgtt cttcggggcg aaaactctca aggatcttac cgctgttgag atccagttcg    6000
atgtaaccca ctcgtgcacc caactgatct tcagcatctt ttactttcac cagcgtttct    6060
gggtgagcaa aaacaggaag gcaaaatgcc gcaaaaaagg gaataagggc gacacggaaa    6120
tgttgaatac tcatactctt cctttttcaa tattattgaa gcatttatca gggttattgt    6180
ctcatgagcg gatacatatt tgaatgtatt tagaaaaata acaaataggg gttccgcgc    6240 acatttcccc gaaaagtgcc acctgacgtc                                    6270
```

<210> SEQ ID NO 65
<211> LENGTH: 5856
<212> TYPE: DNA
<213> ORGANISM: Artificial Sequence
<220> FEATURE:
<223> OTHER INFORMATION: Construct

<400> SEQUENCE: 65

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180 ttaggggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
```

```
attgacgtca atgggtggag tatttacggt aaactgccca cttggcagta catcaagtgt    480
atcatatgcc aagtacgccc cctattgacg tcaatgacgg taaatggccc gcctggcatt   540
atgcccagta catgacctta tgggactttc ctacttggca gtacatctac gtattagtca   600
tcgctattac catggtgatg cggttttggc agtacatcaa tgggcgtgga tagcggtttg   660
actcacgggg atttccaagt ctccacccca ttgacgtcaa tgggagtttg ttttggcacc   720
aaaatcaacg ggactttcca aaatgtcgta acaactccgc cccattgacg caaatgggcg   780
gtaggcgtgt acggtgggag gtctatataa gcagagctct ctggctaact agagaaccca   840
ctgcttactg gcttatcgaa attaatacga ctcactatag ggagacccaa gctggctagc   900
gtttaaactt aagcttggta ccgagctcgg atccatggtg accggctacc ggctgttcga   960
ggagattctc gggagttccg gtggtggcgg gagcggaggt ggaggctcga gcggtgccgg  1020
gcatcagatc gtgcacgtcc gcggggactc ggagaccgac ctggaggcgc tcttcaacgc  1080
cgtcatgaac cccaagacgg ccaacgtgcc ccagaccgtg cccatgaggc tccggaagct  1140
gcccgactcc ttcttcaagc cgccggagcc caaatcccac tcccgacagg ccagtactga  1200
tgcaggcact gcaggagccc tgactccaca gcatgttcga gctcattcct ctccagcttc  1260
tctgcagttg ggagctgttt ctcctgggac actgaccccc actggagtag tctctggccc  1320
agcagctaca cccacagctc agcatcttcg acagtcttct tttgagatac ctgatgatgt  1380
acttgtcgtc atcgtctttg tagtcgcggc cgctcgagtc tagagggccc gtttaaaccc  1440
gctgatcagc ctcgactgtg ccttctagtt gccagccatc tgttgtttgc cctccccccg  1500
tgccttcctt gaccctggaa ggtgccactc ccactgtcct ttcctaataa aatgaggaaa  1560
ttgcatcgca ttgtctgagt aggtgtcatt ctattctggg gggtggggtg gggcaggaca  1620
gcaagggggga ggattgggaa gacaatagca ggcatgctgg ggatgcggtg ggctctatgg  1680
cttctgaggc ggaaagaacc agctggggct ctaggggggta tccccacgcg ccctgtagcg  1740
gcgcattaag cgcggcgggt gtggtggtta cgcgcagcgt gaccgctaca cttgccagcg  1800
ccctagcgcc cgctcctttc gctttcttcc cttcctttct cgccacgttc gccggctttc  1860
cccgtcaagc tctaaatcgg gggctccctt tagggttccg atttagtgct ttacggcacc  1920
tcgaccccaa aaaacttgat tagggtgatg gttcacgtag tgggccatcg ccctgataga  1980
cggtttttcg ccctttgacg ttggagtcca cgttctttaa tagtggactc ttgttccaaa  2040
ctggaacaac actcaaccct atctcggtct attcttttga tttataaggg attttgccga  2100
tttcggccta ttggttaaaa aatgagctga tttaacaaaa atttaacgcg aattaattct  2160
gtggaatgtg tgtcagttag ggtgtggaaa gtccccaggc tccccagcag gcagaagtat  2220
gcaaagcatg catctcaatt agtcagcaac caggtgtgga aagtcccag gctccccagc  2280
aggcagaagt atgcaaagca tgcatctcaa ttagtcagca accatagtcc cgcccctaac  2340
tccgcccatc ccgcccctaa ctccgcccag ttccgcccat tctccgcccc atggctgact  2400
aatttttttt atttatgcag aggccgaggc cgcctctgcc tctgagctat tccagaagta  2460
gtgaggaggc ttttttggag gcctaggctt ttgcaaaaag ctcccgggag cttgtatatc  2520
cattttcgga tctgatcaag agacaggatg aggatcgttt cgcatgattg aacaagatgg  2580
attgcacgca ggttctccgg ccgcttgggt ggagaggcta ttcggctatg actgggcaca  2640
acagacaatc ggctgctctg atgccgccgt gttccggctg tcagcgcagg ggcgcccggt  2700
tctttttgtc aagaccgacc tgtccggtgc cctgaatgaa ctgcaggacg aggcagcgcg  2760
gctatcgtgg ctggccacga cgggcgttcc ttgcgcagct gtgctcgacg ttgtcactga  2820
```

```
agcgggaagg gactggctgc tattgggcga agtgccgggg caggatctcc tgtcatctca    2880
ccttgctcct gccgagaaag tatccatcat ggctgatgca atgcggcggc tgcatacgct    2940
tgatccggct acctgcccat tcgaccacca agcgaaacat cgcatcgagc gagcacgtac    3000
tcggatggaa gccggtcttg tcgatcagga tgatctggac gaagagcatc aggggctcgc    3060
gccagccgaa ctgttcgcca ggctcaaggc gcgcatgccc gacggcgagg atctcgtcgt    3120
gacccatggc gatgcctgct tgccgaatat catggtggaa aatggccgct tttctggatt    3180
catcgactgt ggccggctgg gtgtggcgga ccgctatcag acatagcgt tggctacccg     3240
tgatattgct gaagagcttg gcggcgaatg ggctgaccgc ttcctcgtgc tttacggtat    3300
cgccgctccc gattcgcagc gcatcgcctt ctatcgcctt cttgacgagt tcttctgagc    3360
gggactctgg ggttcgaaat gaccgaccaa gcgacgccca acctgccatc acagagatttc   3420
gattccaccg ccgccttcta tgaaaggttg gcttcggaa tcgttttccg ggacgccggc     3480
tggatgatcc tccagcgcgg ggatctcatg ctggagttct tcgcccaccc caacttgttt    3540
attgcagctt ataatggtta caaataaagc aatagcatca caaatttcac aaataaagca    3600
ttttttttcac tgcattctag ttgtggtttg tccaaactca tcaatgtatc ttatcatgtc   3660
tgtataccgt cgacctctag ctagagcttg gcgtaatcat ggtcatagct gtttcctgtg    3720
tgaaattgtt atccgctcac aattccacac aacatacgag ccggaagcat aaagtgtaaa    3780
gcctggggtg cctaatgagt gagctaactc acattaattg cgttgcgctc actgcccgct    3840
ttccagtcgg gaaacctgtc gtgccagctg cattaatgaa tcggccaacg cgcgggagagg   3900
ggcggtttgc gtattgggcg ctcttccgct tcctcgctca ctgactcgct gcgctcggtc    3960
gttcggctgc ggcgagcggt atcagctcac tcaaaggcgg taatacggtt atccacagaa    4020
tcaggggata acgcaggaaa gaacatgtga gcaaaaggcc agcaaaaggc caggaaccgt    4080
aaaaaggccg cgttgctggc gttttttccat aggctccgcc cccctgacga gcatcacaaa   4140
aatcgacgct caagtcagag gtggcgaaac ccgacaggac tataaagata ccaggcgttt    4200
ccccctggaa gctccctcgt gcgctctcct gttccgaccc tgccgcttac cggatacctg    4260
tccgcctttc tcccttcggg aagcgtggcg ctttctcata gctcacgctg taggtatctc    4320
agttcggtgt aggtcgttcg ctccaagctg ggctgtgtgc acgaaccccc cgttcagccc    4380
gaccgctgcg ccttatccgg taactatcgt cttgagtcca acccggtaag acacgactta    4440
tcgccactgg cagcagccac tggtaacagg attagcagag cgaggtatgt aggcggtgct    4500
acagagttct tgaagtggtg gcctaactac ggctacacta agaacagt atttggtatc      4560
tgcgctctgc tgaagccagt taccttcgga aaaagagttg gtagctcttg atccggcaaa    4620
caaaccaccg ctggtagcgg tttttttgtt tgcaagcagc agattacgcg cagaaaaaaa    4680
ggatctcaag aagatccttt gatctttttct acggggtctg acgctcagtg aacgaaaac    4740
tcacgttaag ggattttggt catgagatta tcaaaaagga tcttcaccta gatccttta    4800
aattaaaaat gaagttttaa atcaatctaa agtatatatg agtaaacttg gtctgacagt    4860
taccaatgct taatcagtga ggcacctatc tcagcgatct gtctatttcg ttcatccata    4920
gttgcctgac tccccgtcgt gtagataact acgatacggg agggcttacc atctggcccc    4980
agtgctgcaa tgataccgcg agacccacgc tcaccggctc cagatttatc agcaataaac    5040
cagccagccg gaagggccga gcgcagaagt ggtcctgcaa ctttatccgc ctccatccag    5100
tctattaatt gttgccggga agctagagta agtagttcgc cagttaatag tttgcgcaac    5160
```

| | | |
|---|---|---|
| gttgttgcca ttgctacagg catcgtggtg tcacgctcgt cgtttggtat ggcttcattc | 5220 | |
| agctccggtt cccaacgatc aaggcgagtt acatgatccc ccatgttgtg caaaaaagcg | 5280 | |
| gttagctcct tcggtcctcc gatcgttgtc agaagtaagt tggccgcagt gttatcactc | 5340 | |
| atggttatgg cagcactgca taattctctt actgtcatgc catccgtaag atgcttttct | 5400 | |
| gtgactggtg agtactcaac caagtcattc tgagaatagt gtatgcggcg accgagttgc | 5460 | |
| tcttgcccgg cgtcaatacg ggataatacc gcgccacata gcagaacttt aaaagtgctc | 5520 | |
| atcattggaa aacgttcttc ggggcgaaaa ctctcaagga tcttaccgct gttgagatcc | 5580 | |
| agttcgatgt aacccactcg tgcacccaac tgatcttcag catcttttac tttcaccagc | 5640 | |
| gtttctgggt gagcaaaaac aggaaggcaa aatgccgcaa aaaagggaat aagggcgaca | 5700 | |
| cggaaatgtt gaatactcat actcttcctt tttcaatatt attgaagcat ttatcagggt | 5760 | |
| tattgtctca tgagcggata catatttgaa tgtatttaga aaaataaaca ataggggtt | 5820 | |
| ccgcgcacat ttccccgaaa agtgccacct gacgtc | 5856 | |

<210> SEQ ID NO 66
<211> LENGTH: 5829
<212> TYPE: DNA
<213> ORGANISM: Artificial Sequence
<220> FEATURE:
<223> OTHER INFORMATION: Construct

<400> SEQUENCE: 66

| | | |
|---|---|---|
| gacggatcgg gagatctccc gatccccctat ggtgcactct cagtacaatc tgctctgatg | 60 | |
| ccgcatagtt aagccagtat ctgctccctg cttgtgtgtt ggaggtcgct gagtagtgcg | 120 | |
| cgagcaaaat ttaagctaca acaaggcaag gcttgaccga caattgcatg aagaatctgc | 180 | |
| ttagggttag gcgttttgcg ctgcttcgcg atgtacgggc cagatatacg cgttgacatt | 240 | |
| gattattgac tagttattaa tagtaatcaa ttacggggtc attagttcat agcccatata | 300 | |
| tggagttccg cgttacataa cttacggtaa atggcccgcc tggctgaccg cccaacgacc | 360 | |
| cccgcccatt gacgtcaata atgacgtatg ttcccatagt aacgccaata gggactttcc | 420 | |
| attgacgtca atgggtggag tatttacggt aaactgccca cttggcagta catcaagtgt | 480 | |
| atcatatgcc aagtacgccc cctattgacg tcaatgacgg taaatggccc gcctggcatt | 540 | |
| atgcccagta catgacctta tgggactttc ctacttggca gtacatctac gtattagtca | 600 | |
| tcgctattac catggtgatg cggttttggc agtacatcaa tgggcgtgga tagcggtttg | 660 | |
| actcacgggg atttccaagt ctccacccca ttgacgtcaa tgggagtttg ttttggcacc | 720 | |
| aaaatcaacg ggactttcca aaatgtcgta acaactccgc cccattgacg caaatgggcg | 780 | |
| gtaggcgtgt acggtgggag gtctatataa gcagagctct ctggctaact agagaaccca | 840 | |
| ctgcttactg gcttatcgaa attaatacga ctcactatag ggagacccaa gctggctagc | 900 | |
| gtttaaactt aagcttggta ccgagctcgg atccgccggg catcagatcg tgcacgtccg | 960 | |
| cggggactcg gagaccgacc tggaggcgct cttcaacgcc gtcatgaacc ccaagacggc | 1020 | |
| caacgtgccc cagaccgtgc ccatgaggct ccggaagctg cccgactcct tcttcaagcc | 1080 | |
| gccggagccc aaatcccact cccgacaggc cagtactgat gcaggcactg caggagccct | 1140 | |
| gactccacag catgttcgag ctcattcctc tccagcttct ctgcagttgg gagctgtttc | 1200 | |
| tcctgggaca ctgaccccca ctggagtagt ctctggccca gcagctacac ccacagctca | 1260 | |
| gcatcttcga cagtcttctt ttgagatacc tgatgatgta ggctcgagcg gtggtggcgg | 1320 | |
| gagcggaggt ggagggtcgt caggtgtgac cggctaccgg ctgttcgagg agattctggc | 1380 | |

```
ggccgctcga gtctagaggg cccgtttaaa cccgctgatc agcctcgact gtgccttcta    1440
gttgccagcc atctgttgtt tgcccctccc ccgtgccttc cttgaccctg gaaggtgcca    1500
ctcccactgt cctttcctaa taaaatgagg aaattgcatc gcattgtctg agtaggtgtc    1560
attctattct gggggtggg gtggggcagg acagcaaggg ggaggattgg gaagacaata     1620
gcaggcatgc tggggatgcg gtgggctcta tggcttctga ggcggaaaga accagctggg    1680
gctctagggg gtatccccac gcgccctgta gcggcgcatt aagcgcggcg ggtgtggtgg    1740
ttacgcgcag cgtgaccgct acacttgcca gcgccctagc gcccgctcct ttcgctttct    1800
tcccttcctt tctcgccacg ttcgccggct ttccccgtca gctctaaat cgggggctcc     1860
ctttaggggtt ccgatttagt gctttacggc acctcgaccc caaaaaactt gattagggtg   1920
atggttcacg tagtgggcca tcgccctgat agacggtttt tcgccctttg acgttggagt    1980
ccacgttctt aatagtgga ctcttgttcc aaactggaac aacactcaac cctatctcgg     2040
tctattcttt tgatttataa gggattttgc cgatttcggc ctattggtta aaaaatgagc    2100
tgatttaaca aaaatttaac gcgaattaat tctgtggaat gtgtgtcagt tagggtgtgg   2160
aaagtcccca ggctcccag caggcagaag tatgcaaagc atgcatctca attagtcagc     2220
aaccaggtgt ggaaagtccc caggctcccc agcaggcaga agtatgcaaa gcatgcatct    2280
caattagtca gcaaccatag tcccgcccct aactccgccc atcccgcccc taactccgcc    2340
cagttccgcc cattctccgc cccatggctg actaatttt tttatttatg cagaggccga     2400
ggccgcctct gcctctgagc tattccagaa gtagtgagga ggcttttttg gaggcctagg    2460
cttttgcaaa aagctcccgg gagcttgtat atccattttc ggatctgatc aagagacagg    2520
atgaggatcg tttcgcatga ttgaacaaga tggattgcac gcaggttctc cggccgcttg    2580
ggtggagagg ctattcggct atgactgggc acaacagaca atcggctgct ctgatgccgc    2640
cgtgttccgg ctgtcagcgc aggggcgccc ggttcttttt gtcaagaccg acctgtccgg    2700
tgccctgaat gaactgcagg acgaggcagc gcggctatcg tggctggcca cgacgggcgt    2760
tccttgcgca gctgtgctcg acgttgtcac tgaagcggga agggactggc tgctattggg    2820
cgaagtgccg gggcaggatc tcctgtcatc tcaccttgct cctgccgaga aagtatccat    2880
catggctgat gcaatgcggc ggctgcatac gcttgatccg gctacctgcc cattcgacca    2940
ccaagcgaaa catcgcatcg agcgagcacg tactcggatg gaagccggtc ttgtcgatca    3000
ggatgatctg gacgaagagc atcaggggct cgcgccagcc gaactgttcg ccaggctcaa    3060
ggcgcgcatg cccgacggcg aggatctcgt cgtgacccat ggcgatgcct gcttgccgaa    3120
tatcatggtg gaaaatggcc gcttttctgg attcatcgac tgtggccggc tgggtgtggc    3180
ggaccgctat caggacatag cgttggctac ccgtgatatt gctgaagagc ttggcggcga    3240
atgggctgac cgcttcctcg tgctttacgg tatcgccgct cccgattcgc agcgcatcgc    3300
cttctatcgc cttcttgacg agttcttctg agcgggactc tggggttcga atgaccgac    3360
caagcgacgc ccaacctgcc atcacgagat ttcgattcca ccgccgcctt ctatgaaagg    3420
ttgggcttcg gaatcgtttt ccgggacgcc ggctggatga tcctccagcg cggggatctc    3480
atgctggagt tcttcgccca ccccaacttg tttattgcag cttataatgg ttacaaataa    3540
agcaatagca tcacaaattt cacaaataaa gcatttttttt cactgcattc tagttgtggt    3600
ttgtccaaac tcatcaatgt atcttatcat gtctgtatac cgtcgacctc tagctagagc    3660
ttggcgtaat catggtcata gctgtttcct gtgtgaaatt gttatccgct cacaattcca    3720
```

| | |
|---|---|
| cacaacatac gagccggaag cataaagtgt aaagcctggg gtgcctaatg agtgagctaa | 3780 |
| ctcacattaa ttgcgttgcg ctcactgccc gctttccagt cgggaaacct gtcgtgccag | 3840 |
| ctgcattaat gaatcggcca acgcgcgggg agaggcggtt tgcgtattgg gcgctcttcc | 3900 |
| gcttcctcgc tcactgactc gctgcgctcg gtcgttcggc tgcggcgagc ggtatcagct | 3960 |
| cactcaaagg cggtaatacg gttatccaca gaatcagggg ataacgcagg aaagaacatg | 4020 |
| tgagcaaaag gccagcaaaa ggccaggaac cgtaaaaagg ccgcgttgct ggcgtttttc | 4080 |
| cataggctcc gcccccctga cgagcatcac aaaaatcgac gctcaagtca gaggtggcga | 4140 |
| aacccgacag gactataaag ataccaggcg tttccccctg gaagctccct cgtgcgctct | 4200 |
| cctgttccga ccctgccgct taccggatac ctgtccgcct ttctcccttc gggaagcgtg | 4260 |
| gcgctttctc atagctcacg ctgtaggtat ctcagttcgg tgtaggtcgt tcgctccaag | 4320 |
| ctgggctgtg tgcacgaacc ccccgttcag cccgaccgct gcgccttatc cggtaactat | 4380 |
| cgtcttgagt ccaacccggt aagacacgac ttatcgccac tggcagcagc cactggtaac | 4440 |
| aggattagca gagcgaggta tgtaggcggt gctacagagt tcttgaagtg gtggcctaac | 4500 |
| tacggctaca ctagaagaac agtatttggt atctgcgctc tgctgaagcc agttaccttc | 4560 |
| ggaaaaagag ttggtagctc ttgatccggc aaacaaacca ccgctggtag cggtttttttt | 4620 |
| gtttgcaagc agcagattac gcgcagaaaa aaggatctc aagaagatcc tttgatcttt | 4680 |
| tctacggggt ctgacgctca gtggaacgaa aactcacgtt aagggatttt ggtcatgaga | 4740 |
| ttatcaaaaa ggatcttcac ctagatcctt ttaaattaaa aatgaagttt taaatcaatc | 4800 |
| taaagtatat atgagtaaac ttggtctgac agttaccaat gcttaatcag tgaggcacct | 4860 |
| atctcagcga tctgtctatt tcgttcatcc atagttgcct gactccccgt cgtgtagata | 4920 |
| actacgatac gggagggctt accatctggc cccagtgctg caatgatacc gcgagaccca | 4980 |
| cgctcaccgg ctccagattt atcagcaata aaccagccag ccggaagggc cgagcgcaga | 5040 |
| agtggtcctg caactttatc cgcctccatc cagtctatta attgttgccg ggaagctaga | 5100 |
| gtaagtagtt cgccagttaa tagtttgcgc aacgttgttg ccattgctac aggcatcgtg | 5160 |
| gtgtcacgct cgtcgtttgg tatggcttca ttcagctccg gttcccaacg atcaaggcga | 5220 |
| gttacatgat cccccatgtt gtgcaaaaaa gcggttagct ccttcggtcc tccgatcgtt | 5280 |
| gtcagaagta agttggccgc agtgttatca ctcatggtta tggcagcact gcataattct | 5340 |
| cttactgtca tgccatccgt aagatgcttt tctgtgactg gtgagtactc aaccaagtca | 5400 |
| ttctgagaat agtgtatgcg gcgaccgagt tgctcttgcc cggcgtcaat acgggataat | 5460 |
| accgcgccac atagcagaac tttaaaagtg ctcatcattg gaaaacgttc ttcggggcga | 5520 |
| aaactctcaa ggatcttacc gctgttgaga tccagttcga tgtaacccac tcgtgcaccc | 5580 |
| aactgatctt cagcatcttt tactttcacc agcgtttctg ggtgagcaaa aacaggaagg | 5640 |
| caaaatgccg caaaaaaggg aataagggcg acacggaaat gttgaatact catactcttc | 5700 |
| cttttttcaat attattgaag catttatcag ggttattgtc tcatgagcgg atacatattt | 5760 |
| gaatgtattt agaaaaataa acaaataggg gttccgcgca catttccccg aaaagtgcca | 5820 |
| cctgacgtc | 5829 |

<210> SEQ ID NO 67
<211> LENGTH: 6592
<212> TYPE: DNA
<213> ORGANISM: Artificial Sequence
<220> FEATURE:
<223> OTHER INFORMATION: Construct

<400> SEQUENCE: 67

```
gacggatcgg gagatctccc gatccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca     600
tcgctattac catggtgatg cggttttggc agtacatcaa tgggcgtgga tagcggtttg     660
actcacgggg atttccaagt ctccacccca ttgacgtcaa tgggagtttg ttttggcacc     720
aaaatcaacg ggactttcca aaatgtcgta acaactccgc cccattgacg caaatgggcg     780
gtaggcgtgt acggtgggag gtctatataa gcagagctct ctggctaact agagaaccca     840
ctgcttactg gcttatcgaa attaatacga ctcactatag ggagacccaa gctggctagc     900
gtttaaactt aagcttggta ccgagctcgg atccatggtc ttcacactcg aagatttcgt     960
tggggactgg gaacagacag ccgcctacaa cctggaccaa gtccttgaac agggaggtgt    1020
gtccagtttg ctgcagaatc tcgccgtgtc cgtaactccg atccaaagga ttgtccggag    1080
cggtgaaaat gccctgaaga tcgacatcca tgtcatcatc ccgtatgaag gtctgagcgc    1140
cgaccaaatg gcccagatcg aagaggtgtt taaggtggtg taccctgtgg atgatcatca    1200
ctttaaggtg atcctgccct atggcacact ggtaatcgac ggggttacgc cgaacatgct    1260
gaactatttc ggacggccgt atgaaggcat cgccgtgttc gacggcaaaa agatcactgt    1320
aacagggacc ctgtggaacg caacaaaat tatcgacgag cgcctgatca ccccgacgg     1380
ctccatgctg ttccgagtaa ccatcaacag tgggagttcc ggtggtggcg ggagcggagg    1440
tggaggctcg agcggttgag cctgcatcgg ccccagctcc ctcagtccct gcctggcaag    1500
gtcgctccat tggcacaacc aagcttcgcc tggtggaatt ttcagctttt ctcgagcagc    1560
agcgagaccc agactcgtac aacaaacacc tcttcgtgca cattgggcat gccaaccatt    1620
cttacagtga cccattgctt gaatcagtgg acattcgtca gatttatgac aaatttcctg    1680
aaaagaaagg tggcttaaag gaactgtttg gaaagggccc tcaaaatgcc ttcttcctcg    1740
taaaattctg ggctgattta aactgcaata ttcaagatga tgctggggct ttttatggtg    1800
taaccagtca gtacgagagt tctgaaaata tgacagtcac ctgttccacc aaagtttgct    1860
cctttgggaa gcaagtagta gaaaaagtag agacggagta tgcaaggttt gagaatggcc    1920
gatttgtata ccgaataaac cgctcccaa tgtgtgaata tatgatcaac ttcatccaca    1980
agctcaaaca cttaccagag aaatatatga tgaacagtgt tttggaaaac ttcacaattt    2040
tattggtggt aacaaacagg gatacacaag aaactctact ctgcatgcc tgtgtgtttg    2100
aagtttcaaa tcagatcctc ttctgagatg agttttttgtt cgcggccgct cgagtctaga    2160
gggcccgttt aaacccgctg atcagcctcg actgtgcctt ctagttgcca gccatctgtt    2220
gtttgcccct ccccgtgcc ttccttgacc ctggaaggtg ccactcccac tgtcctttcc    2280
```

```
taataaaatg aggaaattgc atcgcattgt ctgagtaggt gtcattctat tctgggggt    2340
ggggtggggc aggacagcaa gggggaggat tgggaagaca atagcaggca tgctggggat    2400
gcggtgggct ctatggcttc tgaggcggaa agaaccagct ggggctctag ggggtatccc    2460
cacgcgccct gtagcggcgc attaagcgcg gcggtgtgg tggttacgcg cagcgtgacc    2520
gctacacttg ccagcgccct agcgcccgct cctttcgctt tcttcccttc ctttctcgcc    2580
acgttcgccg gctttccccg tcaagctcta atcggggg tcccttagg gttccgattt      2640
agtgctttac ggcacctcga ccccaaaaaa cttgattagg gtgatggttc acgtagtggg   2700
ccatcgccct gatagacggt ttttcgccct tgacgttgg agtccacgtt ctttaatagt    2760
ggactcttgt tccaaactgg aacaacactc aaccctatct cggtctattc ttttgattta   2820
taagggattt tgccgatttc ggcctattgg ttaaaaatg agctgattta acaaaaattt    2880
aacgcgaatt aattctgtgg aatgtgtgtc agttaggggtg tggaaagtcc ccaggctccc  2940
cagcaggcag aagtatgcaa agcatgcatc tcaattagtc agcaaccagg tgtggaaagt   3000
ccccaggctc cccagcaggc agaagtatgc aaagcatgca tctcaattag tcagcaacca   3060
tagtcccgcc cctaactccg cccatcccgc cctaactccg cccagttccg cccattctc    3120
cgccccatgg ctgactaatt ttttttattt atgcagaggc cgaggccgcc tctgcctctg   3180
agctattcca gaagtagtga ggaggctttt ttggaggcct aggcttttgc aaaaagctcc   3240
cgggagcttg tatatccatt ttcggatctg atcaagagac aggatgagga tcgtttcgca   3300
tgattgaaca agatggattg cacgcaggtt ctccggccgc ttgggtggag aggctattcg   3360
gctatgactg ggcacaacag acaatcggct gctctgatgc cgccgtgttc cggctgtcag   3420
cgcaggggcg cccggttctt tttgtcaaga ccgacctgtc cggtgccctg aatgaactgc   3480
aggacgagga gcgcggcta tcgtggctgg ccacgacggg cgttccttgc gcagctgtgc   3540
tcgacgttgt cactgaagcg ggaagggact ggctgctatt gggcgaagtg ccggggcagg   3600
atctcctgtc atctcacctt gctcctgccg agaaagtatc catcatggct gatgcaatgc   3660
ggcggctgca tacgcttgat ccggctacct gcccattcga ccaccaagcg aaacatcgca   3720
tcgagcgagc acgtactcgg atggaagccg gtcttgtcga tcaggatgat ctggacgaag   3780
agcatcaggg gctcgcgcca gccgaactgt tcgccaggct caaggcgcgc atgcccgacg   3840
gcgaggatct cgtcgtgacc catggcgatg cctgcttgcc gaatatcatg gtggaaaatg   3900
gccgcttttc tggattcatc gactgtggcc ggctgggtgt ggcggaccgc tatcaggaca   3960
tagcgttggc tacccgtgat attgctgaag agcttggcgg cgaatgggct gaccgcttcc   4020
tcgtgcttta cggtatcgcc gctcccgatt cgcagcgcat cgccttctat cgccttcttg   4080
acgagttctt ctgagcggga ctctggggtt cgaaatgacc gaccaagcga cgcccaacct   4140
gccatcacga gatttcgatt ccaccgccgc cttctatgaa aggttgggct tcggaatcgt   4200
tttccgggac gccggctgga tgatcctcca gcgcgggat ctcatgctgg agttcttcgc    4260
ccaccccaac ttgtttattg cagcttataa tggttacaaa taaagcaata gcatcacaaa   4320
tttcacaaat aaagcatttt tttcactgca ttctagttgt ggtttgtcca aactcatcaa   4380
tgtatcttat catgtctgta taccgtcgac ctctagctag agcttggcgt aatcatggtc   4440
atagctgttt cctgtgtgaa attgttatcc gctcacaatt ccacacaaca tacgagccgg   4500
aagcataaag tgtaaagcct ggggtgccta atgagtgagc taactcacat taattgcgtt   4560
gcgctcactg cccgctttcc agtcgggaaa cctgtcgtgc cagctgcatt aatgaatcgg   4620
ccaacgcgcg gggagaggcg gtttgcgtat tgggcgctct tccgcttcct cgctcactga   4680
```

```
ctcgctgcgc tcggtcgttc ggctgcggcg agcggtatca gctcactcaa aggcggtaat    4740
acggttatcc acagaatcag gggataacgc aggaaagaac atgtgagcaa aaggccagca    4800
aaaggccagg aaccgtaaaa aggccgcgtt gctggcgttt ttccataggc tccgcccccc    4860
tgacgagcat cacaaaaatc gacgctcaag tcagaggtgg cgaaacccga caggactata    4920
aagataccag gcgtttcccc ctggaagctc cctcgtgcgc tctcctgttc cgaccctgcc    4980
gcttaccgga tacctgtccg cctttctccc ttcgggaagc gtggcgcttt ctcatagctc    5040
acgctgtagg tatctcagtt cggtgtaggt cgttcgctcc aagctgggct gtgtgcacga    5100
accccccgtt cagcccgacc gctgcgcctt atccggtaac tatcgtcttg agtccaaccc    5160
ggtaagacac gacttatcgc cactggcagc agccactggt aacaggatta gcagagcgag    5220
gtatgtaggc ggtgctacag agttcttgaa gtggtggcct aactacggct acactagaag    5280
aacagtattt ggtatctgcg ctctgctgaa gccagttacc ttcggaaaaa gagttggtag    5340
ctcttgatcc ggcaaacaaa ccaccgctgg tagcggtttt tttgtttgca agcagcagat    5400
tacgcgcaga aaaaaggat ctcaagaaga tcctttgatc ttttctacgg ggtctgacgc    5460
tcagtggaac gaaaactcac gttaagggat tttggtcatg agattatcaa aaaggatctt    5520
cacctagatc cttttaaatt aaaaatgaag ttttaaatca atctaaagta tatatgagta    5580
aacttggtct gacagttacc aatgcttaat cagtgaggca cctatctcag cgatctgtct    5640
atttcgttca tccatagttg cctgactccc cgtcgtgtag ataactacga tacgggaggg    5700
cttaccatct ggccccagtg ctgcaatgat accgcgagac ccacgctcac cggctccaga    5760
tttatcagca ataaaccagc cagccggaag ggccgagcgc agaagtggtc ctgcaacttt    5820
atccgcctcc atccagtcta ttaattgttg ccgggaagct agagtaagta gttcgccagt    5880
taatagtttg cgcaacgttg ttgccattgc tacaggcatc gtggtgtcac gctcgtcgtt    5940
tggtatggct tcattcagct ccggttccca acgatcaagg cgagttacat gatccccat     6000 gttgtgcaaa aaagcggtta gctccttcgg tcctccgatc gttgtcagaa gtaagttggc    6060
cgcagtgtta tcactcatgg ttatggcagc actgcataat tctcttactg tcatgccatc    6120
cgtaagatgc ttttctgtga ctggtgagta ctcaaccaag tcattctgag aatagtgtat    6180
gcggcgaccg agttgctctt gcccggcgtc aatacgggat aataccgcgc cacatagcag    6240
aactttaaaa gtgctcatca ttggaaaacg ttcttcgggg cgaaaactct caaggatctt    6300
accgctgttg agatccagtt cgatgtaacc cactcgtgca cccaactgat cttcagcatc    6360
ttttactttc accagcgttt ctgggtgagc aaaaacagga aggcaaaatg ccgcaaaaaa    6420
gggaataagg gcgacacgga aatgttgaat actcatactc ttcctttttc aatattattg    6480
aagcatttat cagggttatt gtctcatgag cggatacata tttgaatgta tttagaaaaa    6540
taaacaaata ggggttccgc gcacatttcc ccgaaaagtg ccacctgacg tc             6592
```

<210> SEQ ID NO 68
<211> LENGTH: 6559
<212> TYPE: DNA
<213> ORGANISM: Artificial Sequence
<220> FEATURE:
<223> OTHER INFORMATION: Construct

<400> SEQUENCE: 68

```
gacggatcgg gagatctccc gatccctat ggtgcactct cagtacaatc tgctctgatg     60
ccgcatagtt aagccagtat ctgctccctg cttgtgtgtt ggaggtcgct gagtagtgcg    120
```

-continued

```
cgagcaaaat ttaagctaca acaaggcaag gcttgaccga caattgcatg aagaatctgc      180
ttagggttag gcgttttgcg ctgcttcgcg atgtacgggc cagatatacg cgttgacatt      240
gattattgac tagttattaa tagtaatcaa ttacggggtc attagttcat agcccatata      300
tggagttccg cgttacataa cttacggtaa atggcccgcc tggctgaccg cccaacgacc      360
cccgcccatt gacgtcaata atgacgtatg ttcccatagt aacgccaata gggactttcc      420
attgacgtca atgggtggag tatttacggt aaactgccca cttggcagta catcaagtgt      480
atcatatgcc aagtacgccc cctattgacg tcaatgacgg taaatggccc gcctggcatt      540
atgcccagta catgacctta tgggactttc ctacttggca gtacatctac gtattagtca      600
tcgctattac catggtgatg cggttttggc agtacatcaa tgggcgtgga tagcggtttg      660
actcacgggg atttccaagt ctccacccca ttgacgtcaa tgggagtttg ttttggcacc      720
aaaatcaacg ggactttcca aaatgtcgta acaactccgc cccattgacg caaatgggcg      780
gtaggcgtgt acggtgggag gtctatataa gcagagctct ctggctaact agagaaccca      840
ctgcttactg gcttatcgaa attaatacga ctcactatag ggagacccaa gctggctagc      900
gtttaaactt aagcttggta ccgagctcgg atcctgagcc tgcatcggcc ccagctccct      960
cagtccctgc ctggcaaggt cgctccattg cacaaccaga gcttcgcctg gtggaatttt     1020
cagcttttct cgagcagcag cgagacccag actcgtacaa caaacacctc ttcgtgcaca     1080
ttgggcatgc caaccattct tacagtgacc cattgcttga atcagtggac attcgtcaga     1140
tttatgacaa atttcctgaa aagaaggtg gcttaaagga actgtttgga aagggccctc     1200
aaaatgcctt cttcctcgta aaattctggg ctgatttaaa ctgcaatatt caagatgatg     1260
ctggggcttt ttatggtgta accagtcagt acgagagttc tgaaaatatg acagtcacct     1320
gttccaccaa agtttgctcc tttgggaagc aagtagtaga aaaagtagag acggagtatg     1380
caaggtttga aatggccga tttgtatacc gaataaaccg ctccccaatg tgtgaatata     1440
tgatcaactt catccacaag ctcaaacact taccagagaa atatatgatg aacagtgttt     1500
tggaaaactt cacaatttta ttggtggtaa caaacaggga tacacaagaa actctactct     1560
gcatggcctg tgtgtttgaa gtttcaaatg gctcgagcgg tggtggcggg agcggaggtg     1620
gagggtcgtc aggtgtcttc acactcgaag atttcgttgg ggactgggaa cagacagccg     1680
cctacaacct ggaccaagtc cttgaacagg gaggtgtgtc cagtttgctg cagaatctcg     1740
ccgtgtccgt aactccgatc caaaggattg tccggagcgg tgaaaatgcc ctgaagatcg     1800
acatccatgt catcatcccg tatgaaggtc tgagcgccga ccaaatggcc cagatcgaag     1860
aggtgtttaa ggtggtgtac cctgtggatg atcatcactt taaggtgatc ctgcccttatg    1920 gcacactggt aatcgacggg gttacgccga acatgctgaa ctatttcgga cggccgtatg    1980
aaggcatcgc cgtgttcgac ggcaaaaaga tcactgtaac agggaccctg tggaacggca     2040
acaaaattat cgacgagcgc ctgatcaccc ccgacggctc catgctgttc cgagtaacca     2100
tcaacagcgc ggccgctcga gtctagaggg cccgtttaaa cccgctgatc agcctcgact     2160
gtgccttcta gttgccagcc atctgttgtt tgcccctccc ccgtgccttc cttgaccctg     2220
gaaggtgcca ctcccactgt cctttcctaa taaaatgagg aaattgcatc gcattgtctg     2280
agtaggtgtc attctattct ggggggtggg gtggggcagg acagcaaggg ggaggattgg     2340
gaagacaata gcaggcatgc tggggatgcg gtgggctcta tggcttctga ggcggaaaga     2400
accagctggg gctctagggg gtatccccac gcgccctgta gcggcgcatt aagcgcggcg     2460
ggtgtggtgg ttacgcgcag cgtgaccgct acacttgcca gcgccctagc gcccgctcct     2520
```

```
ttcgctttct tcccttcctt tctcgccacg ttcgccggct ttccccgtca agctctaaat    2580
cgggggctcc ctttagggtt ccgatttagt gctttacggc acctcgaccc caaaaaactt    2640
gattagggtg atggttcacg tagtgggcca tcgccctgat agacggtttt tcgccctttg    2700
acgttggagt ccacgttctt taatagtgga ctcttgttcc aaactggaac aacactcaac    2760
cctatctcgg tctattcttt tgatttataa gggattttgc cgatttcggc ctattggtta    2820
aaaaatgagc tgatttaaca aaaatttaac gcgaattaat tctgtggaat gtgtgtcagt    2880
tagggtgtgg aaagtcccca ggctccccag caggcagaag tatgcaaagc atgcatctca    2940
attagtcagc aaccaggtgt ggaaagtccc caggctcccc agcaggcaga agtatgcaaa    3000
gcatgcatct caattagtca gcaaccatag tcccgcccct aactccgccc atcccgcccc    3060
taactccgcc cagttccgcc cattctccgc cccatggctg actaattttt tttatttatg    3120
cagaggccga ggccgcctct gcctctgagc tattccagaa gtagtgagga ggcttttttg    3180
gaggcctagg cttttgcaaa aagctcccgg gagcttgtat atccattttc ggatctgatc    3240
aagagacagg atgaggatcg tttcgcatga ttgaacaaga tggattgcac gcaggttctc    3300
cggccgcttg ggtggagagg ctattcggct atgactgggc acaacagaca atcggctgct    3360
ctgatgccgc cgtgttccgg ctgtcagcgc agggggcgccc ggttcttttt gtcaagaccg    3420
acctgtccgg tgccctgaat gaactgcagg acgaggcagc gcggctatcg tggctggcca    3480
cgacgggcgt tccttgcgca gctgtgctcg acgttgtcac tgaagcggga agggactggc    3540
tgctattggg cgaagtgccg gggcaggatc tcctgtcatc tcaccttgct cctgccgaga    3600
aagtatccat catggctgat gcaatgcggc ggctgcatac gcttgatccg gctacctgcc    3660
cattcgacca ccaagcgaaa catcgcatcg agcgagcacg tactcggatg gaagccggtc    3720
ttgtcgatca ggatgatctg gacgaagagc atcaggggct cgcgccagcc gaactgttcg    3780
ccaggctcaa ggcgcgcatg cccgacgcg aggatctcgt cgtgacccat ggcgatgcct    3840
gcttgccgaa tatcatggtg gaaaatggcc gcttttctgg attcatcgac tgtggccggc    3900
tgggtgtggc ggaccgctat caggacatag cgttggctac ccgtgatatt gctgaagagc    3960
ttggcggcga atgggctgac cgcttcctcg tgctttacgg tatcgccgct cccgattcgc    4020
agcgcatcgc cttctatcgc cttcttgacg agttcttctg agcgggactc tggggttcga    4080
aatgaccgac caagcgacgc ccaacctgcc atcacgagat ttcgattcca ccgccgcctt    4140
ctatgaaagg ttgggcttcg gaatcgtttt ccgggacgcc ggctggatga tcctccagcg    4200
cggggatctc atgctggagt tcttcgccca ccccaacttg tttattgcag cttataatgg    4260
ttacaaataa agcaatagca tcacaaattt cacaaataaa gcatttttt cactgcattc    4320 tagttgtggt ttgtccaaac tcatcaatgt atcttatcat gtctgtatac cgtcgacctc    4380
tagctagagc ttggcgtaat catggtcata gctgtttcct gtgtgaaatt gttatccgct    4440
cacaattcca cacaacatac gagccggaag cataaagtgt aaagcctggg gtgcctaatg    4500
agtgagctaa ctcacattaa ttgcgttgcg ctcactgccc gctttccagt cgggaaacct    4560
gtcgtgccag ctgcattaat gaatcggcca acgcgcgggg agaggcggtt tgcgtattgg    4620
gcgctcttcc gcttcctcgc tcactgactc gctgcgctcg gtcgttcggc tgcggcgagc    4680
ggtatcagct cactcaaagg cggtaatacg gttatccaca gaatcagggg ataacgcagg    4740
aaagaacatg tgagcaaaag gccagcaaaa ggccaggaac cgtaaaaagg ccgcgttgct    4800
ggcgtttttc cataggctcc gcccccctga cgagcatcac aaaaatcgac gctcaagtca    4860
```

```
gaggtggcga aacccgacag gactataaag ataccaggcg tttccccctg gaagctccct    4920
cgtgcgctct cctgttccga ccctgccgct taccggatac ctgtccgcct ttctcccttc    4980
gggaagcgtg gcgctttctc atagctcacg ctgtaggtat ctcagttcgg tgtaggtcgt    5040
tcgctccaag ctgggctgtg tgcacgaacc ccccgttcag cccgaccgct gcgccttatc    5100
cggtaactat cgtcttgagt ccaacccggt aagacacgac ttatcgccac tggcagcagc    5160
cactggtaac aggattagca gagcgaggta tgtaggcgt gctacagagt tcttgaagtg     5220
gtggcctaac tacggctaca ctagaagaac agtatttggt atctgcgctc tgctgaagcc    5280
agttaccttc ggaaaaagag ttggtagctc ttgatccggc aaacaaacca ccgctggtag    5340
cggtttttt gtttgcaagc agcagattac gcgcagaaaa aaggatctc aagaagatcc      5400
tttgatcttt tctacggggt ctgacgctca gtggaacgaa aactcacgtt aagggatttt    5460
ggtcatgaga ttatcaaaaa ggatcttcac ctagatcctt ttaaattaaa aatgaagttt    5520
taaatcaatc taaagtatat atgagtaaac ttggtctgac agttaccaat gcttaatcag    5580
tgaggcacct atctcagcga tctgtctatt tcgttcatcc atagttgcct gactcccgt     5640
cgtgtagata actacgatac gggagggctt accatctggc cccagtgctg caatgatacc    5700
gcgagaccca cgctcaccgg ctccagattt atcagcaata aaccagccag ccggaagggc    5760
cgagcgcaga agtggtcctg caactttatc cgcctccatc cagtctatta attgttgccg    5820
ggaagctaga gtaagtagtt cgccagttaa tagtttgcgc aacgttgttg ccattgctac    5880
aggcatcgtg gtgtcacgct cgtcgtttgg tatggcttca ttcagctccg gttcccaacg    5940
atcaaggcga gttacatgat ccccatgtt gtgcaaaaaa gcggttagct ccttcggtcc      6000
tccgatcgtt gtcagaagta agttggccgc agtgttatca ctcatggtta tggcagcact    6060
gcataattct cttactgtca tgccatccgt aagatgcttt tctgtgactg gtgagtactc    6120
aaccaagtca ttctgagaat agtgtatgcg gcgaccgagt tgctcttgcc cggcgtcaat    6180
acgggataat accgcgccac atagcagaac tttaaaagtg ctcatcattg gaaaacgttc    6240
ttcggggcga aaactctcaa ggatcttacc gctgttgaga tccagttcga tgtaacccac    6300
tcgtgcaccc aactgatctt cagcatcttt tactttcacc agcgtttctg ggtgagcaaa    6360
aacaggaagg caaaatgccg caaaaaaggg aataagggcg acacggaaat gttgaatact    6420
catactcttc ctttttcaat attattgaag catttatcag ggttattgtc tcatgagcgg    6480
atacatattt gaatgtattt agaaaaataa acaaataggg gttccgcgca catttccccg    6540
aaaagtgcca cctgacgtc                                                 6559
```

<210> SEQ ID NO 69
<211> LENGTH: 6151
<212> TYPE: DNA
<213> ORGANISM: Artificial Sequence
<220> FEATURE:
<223> OTHER INFORMATION: Construct

<400> SEQUENCE: 69

```
gacggatcgg gagatctccc gatccccta t ggtgcactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
```

```
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccatggtg accggctacc ggctgttcga    960
ggagattctc gggagttccg gtggtggcgg gagcggaggt ggaggctcga gcggttgagc    1020
ctgcatcggc cccagctccc tcagtcctgc cctggcaagg tcgctccatt ggcacaacca    1080
agcttcgcct ggtggaattt tcagcttttc tcgagcagca gcgagaccca gactcgtaca    1140
acaaacacct cttcgtgcac attgggcatg ccaaccattc ttacagtgac ccattgcttg    1200
aatcagtgga cattcgtcag atttatgaca aatttcctga aaagaaaggt ggcttaaagg    1260
aactgtttgg aaagggccct caaaatgcct tcttcctcgt aaaattctgg gctgatttaa    1320
actgcaatat tcaagatgat gctggggctt tttatggtgt aaccagtcag tacgagagtt    1380
ctgaaaatat gacagtcacc tgttccacca aagtttgctc cttgggaaag caagtagtag    1440
aaaaagtaga gacggagtat gcaaggtttg agaatggccg atttgtatac cgaataaacc    1500
gctccccaat gtgtgaatat atgatcaact tcatccacaa gctcaaacac ttaccagaga    1560
aatatatgat gaacagtgtt ttggaaaact tcacaatttt attggtggta acaaacaggg    1620
atacacaaga aactctactc tgcatggcct gtgtgtttga gtttcaaat cagatcctct    1680 tctgagatga gttttgttc gcggccgctc gagtctagag ggcccgttta aacccgctga    1740
tcagcctcga ctgtgccttc tagttgccag ccatctgttg tttgcccctc ccccgtgcct    1800
tccttgaccc tggaaggtgc cactcccact gtcctttcct aataaaatga ggaaattgca    1860
tcgcattgtc tgagtaggtg tcattctatt ctggggggtg gggtggggca ggacagcaag    1920
ggggaggatt gggaagacaa tagcaggcat gctggggatg cggtgggctc tatggcttct    1980
gaggcggaaa gaaccagctg gggctctagg gggtatcccc acgcgccctg tagcggcgca    2040
ttaagcgcgg cgggtgtggt ggttacgcgc agcgtgaccg ctacacttgc cagcgcccta    2100
gcgcccgctc ctttcgcttt cttcccttcc tttctcgcca cgttcgccgg ctttccccgt    2160
caagctctaa atcgggggct ccctttaggg ttccgattta gtgctttacg gcacctcgac    2220
cccaaaaaac ttgattaggg tgatggttca cgtagtgggc catcgccctg atagacggtt    2280
tttcgccctt tgacgttgga gtccacgttc tttaatagtg gactcttgtt ccaaactgga    2340
acaacactca accctatctc ggtctattct tttgatttat aagggatttt gccgatttcg    2400
gcctattggt taaaaaatga gctgatttaa caaaaattta acgcgaatta attctgtgga    2460
atgtgtgtca gttagggtgt ggaaagtccc caggctcccc agcaggcaga agtatgcaaa    2520
gcatgcatct caattagtca gcaaccaggt gtggaaagtc cccaggctcc ccagcaggca    2580
gaagtatgca aagcatgcat ctcaattagt cagcaaccat agtcccgccc ctaactccgc    2640
ccatcccgcc cctaactccg cccagttccg cccattctcc gccccatggc tgactaattt    2700
```

```
tttttattta tgcagaggcc gaggccgcct ctgcctctga gctattccag aagtagtgag    2760
gaggcttttt tggaggccta ggcttttgca aaaagctccc gggagcttgt atatccattt    2820
tcggatctga tcaagagaca ggatgaggat cgtttcgcat gattgaacaa gatggattgc    2880
acgcaggttc tccggccgct tgggtggaga ggctattcgg ctatgactgg gcacaacaga    2940
caatcggctg ctctgatgcc gccgtgttcc ggctgtcagc gcaggggcgc ccggttcttt    3000
ttgtcaagac cgacctgtcc ggtgccctga atgaactgca ggacgaggca gcgcggctat    3060
cgtggctggc cacgacgggc gttccttgcg cagctgtgct cgacgttgtc actgaagcgg    3120
gaagggactg gctgctattg ggcgaagtgc cggggcagga tctcctgtca tctcaccttg    3180
ctcctgccga gaaagtatcc atcatggctg atgcaatgcg gcggctgcat acgcttgatc    3240
cggctacctg cccattcgac caccaagcga aacatcgcat cgagcgagca cgtactcgga    3300
tggaagccgg tcttgtcgat caggatgatc tggacgaaga gcatcagggg ctcgcgccag    3360
ccgaactgtt cgccaggctc aaggcgcgca tgcccgacgg cgaggatctc gtcgtgaccc    3420
atggcgatgc ctgcttgccg aatatcatgg tggaaaatgg ccgcttttct ggattcatcg    3480
actgtggccg gctgggtgtg gcggaccgct atcaggacat agcgttggct acccgtgata    3540
ttgctgaaga gcttggcggc gaatgggctg accgcttcct cgtgctttac ggtatcgccg    3600
ctcccgattc gcagcgcatc gccttctatc gccttcttga cgagttcttc tgagcgggac    3660
tctgggttc gaaatgaccg accaagcgac gcccaacctg ccatcacgag atttcgattc    3720
caccgccgcc ttctatgaaa ggttgggctt cggaatcgtt ttccgggacg ccggctggat    3780
gatcctccag cgcggggatc tcatgctgga gttcttcgcc cacccaact tgtttattgc    3840
agcttataat ggttacaaat aaagcaatag catcacaaat ttcacaaata aagcattttt    3900
ttcactgcat tctagttgtg gtttgtccaa actcatcaat gtatcttatc atgtctgtat    3960
accgtcgacc tctagctaga gcttggcgta atcatggtca tagctgtttc ctgtgtgaaa    4020
ttgttatccg ctcacaattc cacacaacat acgagccgga agcataaagt gtaaagcctg    4080
gggtgcctaa tgagtgagct aactcacatt aattgcgttg cgctcactgc ccgctttcca    4140
gtcgggaaac ctgtcgtgcc agctgcatta atgaatcggc caacgcgcgg ggagaggcgg    4200
tttgcgtatt gggcgctctt ccgcttcctc gctcactgac tcgctgcgct cggtcgttcg    4260
gctgcggcga gcggtatcag ctcactcaaa ggcggtaata cggttatcca cagaatcagg    4320
ggataacgca ggaaagaaca tgtgagcaaa aggccagcaa aaggccagga accgtaaaaa    4380
ggccgcgttg ctggcgtttt tccataggct ccgcccccct gacgagcatc acaaaaatcg    4440
acgctcaagt cagaggtggc gaaacccgac aggactataa agataccagg cgtttccccc    4500
tggaagctcc ctcgtgcgct ctcctgttcc gaccctgccg cttaccggat acctgtccgc    4560
cttctccct tcgggaagcg tggcgctttc tcatagctca cgctgtaggt atctcagttc    4620
ggtgtaggtc gttcgctcca agctgggctg tgtgcacgaa ccccccgttc agcccgaccg    4680
ctgcgcctta tccggtaact atcgtcttga gtccaacccg gtaagacacg acttatcgcc    4740
actggcagca gccactggta acaggattag cagagcgagg tatgtaggcg gtgctacaga    4800
gttcttgaag tggtggccta actacggcta cactagaaga acagtatttg gtatctgcgc    4860
tctgctgaag ccagttacct tcggaaaaag agttggtagc tcttgatccg gcaaacaaac    4920
caccgctggt agcggttttt tgttttgcaa gcagcagatt acgcgcagaa aaaaaggatc    4980
tcaagaagat cctttgatct tttctacggg gtctgacgct cagtggaacg aaaactcacg    5040
ttaagggatt ttggtcatga gattatcaaa aaggatcttc acctagatcc ttttaaatta    5100
```

```
aaaatgaagt tttaaatcaa tctaaagtat atatgagtaa acttggtctg acagttacca    5160
atgcttaatc agtgaggcac ctatctcagc gatctgtcta tttcgttcat ccatagttgc    5220
ctgactcccc gtcgtgtaga taactacgat acgggagggc ttaccatctg gccccagtgc    5280
tgcaatgata ccgcgagacc cacgctcacc ggctccagat ttatcagcaa taaaccagcc    5340
agccggaagg gccgagcgca gaagtggtcc tgcaacttta tccgcctcca tccagtctat    5400
taattgttgc cgggaagcta gagtaagtag ttcgccagtt aatagtttgc gcaacgttgt    5460
tgccattgct acaggcatcg tggtgtcacg ctcgtcgttt ggtatggctt cattcagctc    5520
cggttcccaa cgatcaaggc gagttacatg atcccccatg ttgtgcaaaa aagcggttag    5580
ctccttcggt cctccgatcg ttgtcagaag taagttggcc gcagtgttat cactcatggt    5640
tatggcagca ctgcataatt ctcttactgt catgccatcc gtaagatgct tttctgtgac    5700
tggtgagtac tcaaccaagt cattctgaga atagtgtatg cggcgaccga gttgctcttg    5760
cccggcgtca atacgggata ataccgcgcc acatagcaga actttaaaag tgctcatcat    5820
tggaaaacgt tcttcggggc gaaaactctc aaggatctta ccgctgttga tccagttc     5880 gatgtaaccc actcgtgcac ccaactgatc ttcagcatct tttactttca ccagcgtttc    5940
tgggtgagca aaaacaggaa ggcaaaatgc cgcaaaaaag gaataagggc gacacggaa     6000 atgttgaata ctcatactct tcctttttca atattattga agcatttatc agggttattg    6060
tctcatgagc ggatacatat ttgaatgtat ttagaaaaat aaacaaatag gggttccgcg    6120
cacatttccc cgaaaagtgc cacctgacgt c                                   6151
```

<210> SEQ ID NO 70
<211> LENGTH: 6118
<212> TYPE: DNA
<213> ORGANISM: Artificial Sequence
<220> FEATURE:
<223> OTHER INFORMATION: Construct

<400> SEQUENCE: 70

```
gacggatcgg gagatctccc gatccccat  ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
ttagggttag gcgttttgcg ctgcttcgcg atgtacgggc cagatatacg cgttgacatt     240
gattattgac tagttattaa tagtaatcaa ttacggggtc attagttcat agcccatata     300
tggagttccg cgttacataa cttacggtaa atggcccgcc tggctgaccg cccaacgacc     360
cccgcccatt gacgtcaata atgacgtatg ttcccatagt aacgccaata gggactttcc     420
attgacgtca atgggtggag tatttacggt aaactgccca cttggcagta catcaagtgt     480
atcatatgcc aagtacgccc cctattgacg tcaatgacgg taaatggccc gcctggcatt     540
atgcccagta catgacctta tgggactttc ctacttggca gtacatctac gtattagtca    600
tcgctattac catggtgatg cggttttggc agtacatcaa tgggcgtgga tagcggtttg     660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atcctgagcc tgcatcggcc ccagctccct    960
```

```
cagtccctgc ctggcaaggt cgctccattg gcacaaccaa gcttcgcctg gtggaatttt    1020
cagcttttct cgagcagcag cgagacccag actcgtacaa caaacacctc ttcgtgcaca    1080
ttgggcatgc caaccattct tacagtgacc cattgcttga atcagtggac attcgtcaga    1140
tttatgacaa atttcctgaa aagaaaggtg gcttaaagga actgtttgga aagggccctc    1200
aaaatgcctt cttcctcgta aaattctggg ctgatttaaa ctgcaatatt caagatgatg    1260
ctggggcttt ttatggtgta accagtcagt acgagagttc tgaaaatatg acagtcacct    1320
gttccaccaa agtttgctcc tttgggaagc aagtagtaga aaaagtagag acggagtatg    1380
caaggtttga aatggccga tttgtatacc gaataaaccg ctccccaatg tgtgaatata    1440
tgatcaactt catccacaag ctcaaacact taccagagaa atatatgatg aacagtgttt    1500
tggaaaactt cacaatttta ttggtggtaa caaacaggga tacacaagaa actctactct    1560
gcatggcctg tgtgtttgaa gtttcaaatg gctcgagcgg tggtggcggg agcggaggtg    1620
gagggtcgtc aggtgtgacc ggctaccggc tgttcgagga gattctggcg gccgctcgag    1680
tctagagggc ccgtttaaac ccgctgatca gcctcgactg tgccttctag ttgccagcca    1740
tctgttgttt gcccctcccc cgtgccttcc ttgaccctgg aaggtgccac tcccactgtc    1800
ctttcctaat aaaatgagga aattgcatcg cattgtctga gtaggtgtca ttctattctg    1860
gggggtgggg tggggcagga cagcaagggg gaggattggg aagacaatag caggcatgct    1920
ggggatgcgg tgggctctat ggcttctgag gcggaaagaa ccagctgggg ctctagggggg   1980 tatccccacg cgccctgtag cggcgcatta agcgcggcgg gtgtggtggt tacgcgcagc    2040
gtgaccgcta cacttgccag cgccctagcg cccgctcctt tcgctttctt cccttccttt    2100
ctcgccacgt tcgccggctt tccccgtcaa gctctaaatc gggggctccc tttagggttc    2160
cgatttagtg ctttacggca cctcgacccc aaaaaacttg attagggtga tggttcacgt    2220
agtgggccat cgccctgata cggttttt cgcccttga cgttggagtc cacgttcttt    2280
aatagtggac tcttgttcca aactggaaca acactcaacc ctatctcggt ctattctttt    2340
gatttataag ggattttgcc gatttcggcc tattggttaa aaaatgagct gatttaacaa    2400
aaatttaacg cgaattaatt ctgtggaatg tgtgtcagtt agggtgtgga aagtccccag    2460
gctccccagc aggcagaagt atgcaaagca tgcatctcaa ttagtcagca accaggtgtg    2520
gaaagtcccc aggctcccca gcaggcagaa gtatgcaaag catgcatctc aattagtcag    2580
caaccatagt cccgccccta actccgccca tcccgcccct aactccgccc agttccgccc    2640
attctccgcc ccatggctga ctaattttt ttatttatgc agaggccgag gccgcctctg    2700
cctctgagct attccagaag tagtgaggag gcttttttgg aggcctaggc ttttgcaaaa    2760
agctcccggg agcttgtata tccatttttcg gatctgatca agagacagga tgaggatcgt    2820
ttcgcatgat tgaacaagat ggattgcacg caggttctcc ggccgcttgg gtggagaggc    2880
tattcggcta tgactgggca caacagacaa tcggctgctc tgatgccgcc gtgttccggc    2940
tgtcagcgca ggggcgcccg gttcttttg tcaagaccga cctgtccggt gccctgaatg    3000
aactgcagga cgaggcagcg cggctatcgt ggctggccac gacgggcgtt ccttgcgcag    3060
ctgtgctcga cgttgtcact gaagcgggaa gggactggct gctattgggc gaagtgccgg    3120
ggcaggatct cctgtcatct caccttgctc ctgccgagaa agtatccatc atggctgatg    3180
caatgcggcg gctgcatacg cttgatccgg ctacctgccc attcgaccac caagcgaaac    3240
atcgcatcga gcgagcacgt actcggatgg aagccggtct tgtcgatcag gatgatctgg    3300
acgaagagca tcaggggctc gcgccagccg aactgttcgc caggctcaag gcgcgcatgc    3360
```

```
ccgacggcga ggatctcgtc gtgacccatg gcgatgcctg cttgccgaat atcatggtgg    3420
aaaatggccg ctttctgga ttcatcgact gtggccggct gggtgtggcg gaccgctatc    3480
aggacatagc gttggctacc cgtgatattg ctgaagagct tggcggcgaa tgggctgacc    3540
gcttcctcgt gctttacggt atcgccgctc ccgattcgca gcgcatcgcc ttctatcgcc    3600
ttcttgacga gttcttctga gcgggactct ggggttcgaa atgaccgacc aagcgacgcc    3660
caacctgcca tcacgagatt tcgattccac cgccgccttc tatgaaaggt tgggcttcgg    3720
aatcgttttc cgggacgccg gctggatgat cctccagcgc ggggatctca tgctggagtt    3780
cttcgcccac cccaacttgt ttattgcagc ttataatggt tacaaataaa gcaatagcat    3840
cacaaatttc acaaataaag catttttttc actgcattct agttgtggtt tgtccaaact    3900
catcaatgta tcttatcatg tctgtatacc gtcgacctct agctagagct tggcgtaatc    3960
atggtcatag ctgtttcctg tgtgaaattg ttatccgctc acaattccac acaacatacg    4020
agccggaagc ataaagtgta aagcctgggg tgcctaatga gtgagctaac tcacattaat    4080
tgcgttgcgc tcactgcccg ctttccagtc gggaaacctg tcgtgccagc tgcattaatg    4140
aatcggccaa cgcgcgggga gaggcggttt gcgtattggg cgctcttccg cttcctcgct    4200
cactgactcg ctgcgctcgg tcgttcggct gcggcgagcg gtatcagctc actcaaaggc    4260
ggtaatacgg ttatccacag aatcagggga taacgcagga agaacatgt gagcaaaagg    4320 ccagcaaaag gccaggaacc gtaaaaaggc cgcgttgctg gcgttttttcc ataggctccg    4380 cccccctgac gagcatcaca aaaatcgacg ctcaagtcag aggtggcgaa acccgacagg    4440
actataaaga taccaggcgt ttccccctgg aagctccctc gtgcgctctc ctgttccgac    4500
cctgccgctt accggatacc tgtccgcctt tctcccttcg ggaagcgtgg cgctttctca    4560
tagctcacgc tgtaggtatc tcagttcggt gtaggtcgtt cgctccaagc tgggctgtgt    4620
gcacgaaccc cccgttcagc ccgaccgctg cgccttatcc ggtaactatc gtcttgagtc    4680
caacccggta agacacgact tatcgccact ggcagcagcc actggtaaca ggattagcag    4740
agcgaggtat gtaggcggtg ctacagagtt cttgaagtgg tggcctaact acggctacac    4800
tagaagaaca gtatttggta tctgcgctct gctgaagcca gttaccttcg gaaaaagagt    4860
tggtagctct tgatccggca aacaaaccac cgctggtagc ggtttttttg tttgcaagca    4920
gcagattacg cgcagaaaaa aaggatctca agaagatcct ttgatctttt ctacggggtc    4980
tgacgctcag tggaacgaaa actcacgtta agggattttg gtcatgagat tatcaaaaag    5040
gatcttcacc tagatccttt taaattaaaa atgaagtttt aaatcaatct aaagtatata    5100
tgagtaaact tggtctgaca gttaccaatg cttaatcagt gaggcaccta tctcagcgat    5160
ctgtctattt cgttcatcca tagttgcctg actccccgtc gtgtagataa ctacgatacg    5220
ggagggctta ccatctggcc ccagtgctgc aatgataccg cgagacccac gctcaccggc    5280
tccagattta tcagcaataa accagccagc cggaagggcc gagcgcagaa gtggtcctgc    5340
aactttatcc gcctccatcc agtctattaa ttgttgccgg gaagctagag taagtagttc    5400
gccagttaat agtttgcgca acgttgttgc cattgctaca ggcatcgtgg tgtcacgctc    5460
gtcgtttggt atggcttcat tcagctccgg ttcccaacga tcaaggcgag ttacatgatc    5520
ccccatgttg tgcaaaaaag cggttagctc cttcggtcct ccgatcgttg tcagaagtaa    5580
gttggccgca gtgttatcac tcatggttat ggcagcactg cataattctc ttactgtcat    5640
gccatccgta agatgctttt ctgtgactgg tgagtactca accaagtcat tctgagaata    5700
```

```
gtgtatgcgg cgaccgagtt gctcttgccc ggcgtcaata cgggataata ccgcgccaca    5760
tagcagaact ttaaaagtgc tcatcattgg aaaacgttct tcggggcgaa aactctcaag    5820
gatcttaccg ctgttgagat ccagttcgat gtaacccact cgtgcaccca actgatcttc    5880
agcatctttt actttcacca gcgtttctgg gtgagcaaaa acaggaaggc aaaatgccgc    5940
aaaaaaggga ataagggcga cacggaaatg ttgaatactc atactcttcc tttttcaata    6000
ttattgaagc atttatcagg gttattgtct catgagcgga tacatatttg aatgtattta    6060
gaaaaataaa caaataggg ttccgcgcac atttccccga aaagtgccac ctgacgtc      6118
```

```
<210> SEQ ID NO 71
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 71

His Xaa Arg Xaa Xaa Ser
1               5

<210> SEQ ID NO 72
<211> LENGTH: 6
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(5)
<223> OTHER INFORMATION: Xaa can be any naturally occurring amino acid

<400> SEQUENCE: 72

His Xaa Arg Xaa Xaa Thr
1               5

<210> SEQ ID NO 73
<211> LENGTH: 5
<212> TYPE: PRT
<213> ORGANISM: Homo sapiens

<400> SEQUENCE: 73

Gly Gly Ala Gly Gly
1               5

<210> SEQ ID NO 74
<211> LENGTH: 10
<212> TYPE: PRT
<213> ORGANISM: Homo sapiens

<400> SEQUENCE: 74

Gly Gly Ser Gly Gly Gly Gly Ser Gly Gly
1               5                   10
```